US012435321B2

(12) United States Patent
Lai et al.

(10) Patent No.: US 12,435,321 B2
(45) Date of Patent: Oct. 7, 2025

(54) CRISPR/CAS12J ENZYME AND SYSTEM

(71) Applicant: China Agricultural University, Beijing (CN)

(72) Inventors: Jinsheng Lai, Beijing (CN); Yingsi Zhou, Beijing (CN); Yingnan Li, Beijing (CN); Jihong Zhang, Beijing (CN); Yingying Wang, Beijing (CN); Menglu Lyu, Beijing (CN); Xiangbo Zhang, Beijing (CN); Haiming Zhao, Beijing (CN); Weibin Song, Beijing (CN)

(73) Assignee: China Agricultural University, Beijing (CN)

( * ) Notice: Subject to any disclaimer, the term of this patent is extended or adjusted under 35 U.S.C. 154(b) by 64 days.

(21) Appl. No.: 17/294,175

(22) PCT Filed: Nov. 15, 2019

(86) PCT No.: PCT/CN2019/118702

§ 371 (c)(1),
(2) Date: May 14, 2021

(87) PCT Pub. No.: WO2020/098772

PCT Pub. Date: May 22, 2020

(65) Prior Publication Data

US 2022/0002691 A1 Jan. 6, 2022

(30) Foreign Application Priority Data

Nov. 15, 2018 (CN) ......................... 201811355943.0

(51) Int. Cl.

| | |
|---|---|
| ***C12N 9/22*** | (2006.01) |
| ***A61K 31/7088*** | (2006.01) |
| ***A61K 38/46*** | (2006.01) |
| ***A61K 47/62*** | (2017.01) |
| ***A61K 48/00*** | (2006.01) |
| ***C12N 15/11*** | (2006.01) |
| ***C12N 15/90*** | (2006.01) |

(52) U.S. Cl.

CPC ............ *C12N 9/22* (2013.01); *A61K 31/7088* (2013.01); *A61K 38/465* (2013.01); *A61K 47/62* (2017.08); *C12N 15/11* (2013.01); *C12N 15/907* (2013.01); *A61K 48/00* (2013.01); *C07K 2319/00* (2013.01); *C12N 2310/20* (2017.05); *C12N 2800/80* (2013.01)

(58) Field of Classification Search

None

See application file for complete search history.

(56) References Cited

PUBLICATIONS

Yan et al., Functionally diverse type V CRISPR-Cas systems. Science (2019), 363: 88-91 (Year: 2019).*
Koonin et al., Diversity, classification and evolution of CRISPR-Cas systems. Current Opinion in Microbiology (2017), 37: 67-78 (Year: 2017).*
Zetsche et al., Cpf1 is a single RNA-guided endonuclease of a class 2 CRISPR-Cas system. Cell (2015), 163: 759-771 (Year: 2015 ).*
Dastjerdi et al., The expanding class 2 CRISPR toolbox: diversity, applicability, and targeting drawbacks. BioDrugs (2019), 33: 503-5113 (Year: 2019).*
Knott and Doudna, CRISPR-Cas guides the future of genetic engineering. Science (2018), 361: 866-869 (Year: 2018).*

* cited by examiner

*Primary Examiner* — Abigail Vanhorn
*Assistant Examiner* — Catherine Konopka
(74) *Attorney, Agent, or Firm* — Bayramoglu Law Offices LLC

(57) ABSTRACT

Provided are a Cas effector protein, a fusion protein containing said protein, and a nucleic acid molecule coding same. Also provided are a complex and a composition for nucleic acid editing, for example, a complex and a composition for gene or genome editing, containing the Cas effector protein or the fusion protein, or the nucleic acid molecule encoding same. Also provided is a method for nucleic acid editing, for example, a method for gene or genome editing, using the Cas effector protein or the fusion protein.

29 Claims, 6 Drawing Sheets

Specification includes a Sequence Listing.

Spacer Sequence (SEQ ID NO: 121) 28 CUUCCAUCAGAGAACCUCACUGCGAGAC
(SEQ ID NO: 122) 26 CUUCCAUCAGAGAACCUCACUGCGAG
(SEQ ID NO: 123) 24 CUUCCAUCAGAGAACCUCACUGCG
(SEQ ID NO: 124) 22 CUUCCAUCAGAGAACCUCACUG
(SEQ ID NO: 125) 20 CUUCCAUCAGAGAACCUCAC
(SEQ ID NO: 126) 18 CUUCCAUCAGAGAACCUC
(SEQ ID NO: 127) 16 CUUCCAUCAGAGAACC
(SEQ ID NO: 128) 14 CUUCCAUCAGAGAA Repeat Sequence (SEQ ID NO: 129) WT GUGCUGCUGUCUCCCAGACGGGAGGCAGAACUGCAC (SEQ ID NO: 130) 34 GCUGCUGUCUCCCAGACGGGAGGCAGAACUGCAC (SEQ ID NO: 131) 32 UGCUGUCUCCCAGACGGGAGGCAGAACUGCAC (SEQ ID NO: 132) 30 CUGUCUCCCAGACGGGAGGCAGAACUGCAC (SEQ ID NO: 133) 28 GUCUCCCAGACGGGAGGCAGAACUGCAC (SEQ ID NO: 134) 26 CUCCCAGACGGGAGGCAGAACUGCAC (SEQ ID NO: 135) 24 CCCAGACGGGAGGCAGAACUGCAC

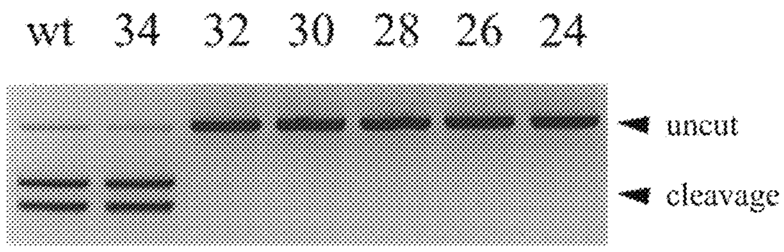

FIG. 7

Spacer Sequence (SEQ ID NO: 105) WT 5' CUUCCAUCAGAGAACCUCACUGCG3'
(SEQ ID NO: 136) C1A 5' AUUCCAUCAGAGAACCUCACUGCG3'
(SEQ ID NO: 137) U3A 5' CUACCAUCAGAGAACCUCACUGCG3'
(SEQ ID NO: 138) C5A 5' CUUCAAUCAGAGAACCUCACUGCG3'
(SEQ ID NO: 139) U7G 5' CUUCCAGCAGAGAACCUCACUGCG3'
(SEQ ID NO: 140) A9G 5' CUUCCAUCGGAGAACCUCACUGCG3'
(SEQ ID NO: 141) A11U 5' CUUCCAUCAGUGAACCUCACUGCG3'
(SEQ ID NO: 142) A13G 5' CUUCCAUCAGAGGACCUCACUGCG3'
(SEQ ID NO: 143) C15U 5' CUUCCAUCAGAGAAUCUCACUGCG3'
(SEQ ID NO: 144) U17A 5' CUUCCAUCAGAGAACCACACUGCG3'

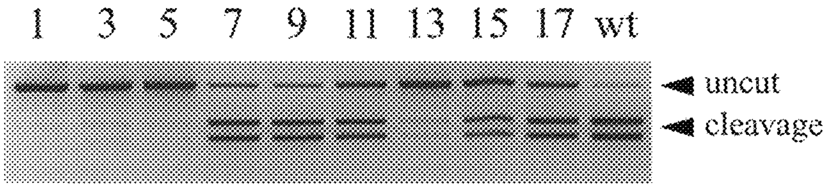

FIG. 8

CRISPR/CAS12J ENZYME AND SYSTEM

CROSS-REFERENCE TO RELATED APPLICATIONS

This application is a Section 371 of International Application No. PCT/CN2019/118702, filed Nov. 15, 2019, which was published in the Chinese language on May 22, 2020 under International Publication No. WO 2020/098772 A1, which claims priority under 35 U.S.C. § 119(b) to Chinese Application No. 201811355943.0, filed Nov. 15, 2018, the disclosures of which are incorporated herein by reference in their entirety.

REFERENCE TO SEQUENCE LISTING SUBMITTED ELECTRONICALLY

This application contains a sequence listing, which is submitted electronically as an ASCII formatted sequence listing with a file name "Substitute_Sequence_Listing_688457_84US", creation date of Oct. 25, 2024, and having a size of 436,164 bytes. The sequence listing submitted electronically is part of the specification and is herein incorporated by reference in its entirety.

TECHNICAL FIELD

The present invention relates to the field of nucleic acid editing, in particular to the technical field of Clustered Regularly Interspaced Short Palindromic Repeats (CRISPR). Specifically, the present invention relates to Cas effector proteins, fusion proteins containing such proteins, and nucleic acid molecules encoding them. The present invention also relates to complexes and compositions for nucleic acid editing (for example, gene or genome editing), which comprise the protein or fusion protein of the present invention, or nucleic acid molecules encoding them. The present invention also relates to a method for nucleic acid editing (for example, gene or genome editing), which uses that comprising the protein or fusion protein of the present invention.

BACKGROUND

CRISPR/Cas technology is a widely used gene editing technology. It uses RNA guidance to specifically bind target sequences on the genome and cut DNA to produce double-strand breaks and uses biological non-homologous end joining or homologous recombination for site-directed gene editing.

The CRISPR/Cas9 system is the most commonly used type II CRISPR system. It recognizes the PAM motif of 3'-NGG and cuts the target sequence with blunt ends. The CRISPR/Cas Type V system is a type of CRISPR system newly discovered in the past two years. It has a 5'-TTN motif and cuts the target sequence with sticky ends, such as Cpf1, C2c1, CasX, and CasY. However, the currently existing different CRISPR/Cas have different advantages and disadvantages. For example, Cas9, C2c1 and CasX all require two RNAs for guide RNA, while Cpf1 only requires one guide RNA and can be used for multiple gene editing. CasX has a size of 980 amino acids, while the common Cas9, C2c1, CasY and Cpf1 are usually around 1300 amino acids in size. In addition, the PAM sequences of Cas9, Cpf1, CasX, and CasY are more complex and diverse, and C2c1 recognizes the rigorous 5'-TTN, so that its target site is easier to be predicted than other systems, thereby reducing potential off-target effects.

In a word, given that the currently available CRISPR/Cas systems are limited by some shortcomings, the development of a more robust new CRISPR/Cas system with good performance in many aspects is of great significance to the development of biotechnology.

SUMMARY OF THE INVENTION

After a lot of experiments and repeated explorations, the inventor of the present invention has unexpectedly discovered a new type of RNA-guided endonuclease. Based on this discovery, the present inventor has developed a new CRISPR/Cas system and a gene editing method based on the system.

Cas Effector Protein

Therefore, in the first aspect, the present invention provides a variety of proteins, which have the amino acid sequence as shown in any one of SEQ ID NOs: 1-20, 107, 108 or an ortholog, a homolog, a variant or a functional fragment thereof; wherein the ortholog, homolog, variant or functional fragment substantially retains the biological function of the sequence from which it is derived.

In the present invention, the biological functions of the above sequences include, but are not limited to, the activity of binding to the guide RNA, the endonuclease activity, and the activity of binding to and cleaving a specific site of the target sequence under the guidance of the guide RNA.

In certain embodiments, the ortholog, homolog, or variant has at least 80%, at least 85%, at least 90%, at least 91%, at least 92%, at least 93%, at least 94%, at least 95%, at least 96%, at least 97%, at least 98%, or at least 99% sequence identity compared to the sequence from which it is derived.

In certain embodiments, the ortholog, homolog, variant has at least 80%, at least 85%, at least 90%, at least 91%, at least 92%, at least 93%, at least 94%, at least 95%, at least 96%, at least 97%, at least 98%, or at least 99% sequence identity compared with the sequence as shown in any one of SEQ ID NOs: 1-20, 107, 108, and substantially retains the biological functions of the sequence from which it is derived (for example, the activity of binding to the guide RNA, endonuclease activity, and the activity of binding to and cleaving a specific site of the target sequence under the guidance of the guide RNA).

In certain embodiments, the protein is an effector protein in the CRISPR/Cas system.

In certain embodiments, the protein of the present invention comprises a sequence selected from the following, or consists of a sequence selected from the following:

(i) a sequence as shown in any one of SEQ ID NOs: 1-20, 107, 108;

(ii) compared with the sequence as shown in any one of SEQ ID NOs: 1-20, 107, 108, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%. %, at least 96%, at least 97%, at least 98%, or at least 99% sequence identity with the sequence as shown in any one of SEQ ID NOs: 1-20, 107, and 108.

In certain embodiments, the protein of the present invention comprises a sequence selected from the following, or consists of a sequence selected from the following:

(i) a sequence as shown in SEQ ID No: 1;

(ii) compared with the sequence as shown in SEQ ID NO: 1, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 1.

In certain embodiments, the protein of the present invention has an amino acid sequence as shown in SEQ ID No: 2.

In certain embodiments, the protein of the present invention comprises a sequence selected from the following, or consists of a sequence selected from the following:

(i) a sequence as shown in SEQ ID NO: 2;

(ii) compared with the sequence as shown in SEQ ID NO: 2, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 2.

In certain embodiments, the protein of the present invention has an amino acid sequence as shown in SEQ ID No: 2.

In certain embodiments, the protein of the present invention comprises a sequence selected from the following, or consists of a sequence selected from the following:

(i) a sequence as shown in SEQ ID NO: 3;

(ii) compared with the sequence as shown in SEQ ID NO: 3, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 3.

In certain embodiments, the protein of the invention has an amino acid sequence as shown in SEQ ID No: 3.

In certain embodiments, the protein of the present invention comprises a sequence selected from the following, or consists of a sequence selected from the following:

(i) a sequence as shown in SEQ ID NO: 4;

(ii) compared with the sequence as shown in SEQ ID NO: 4, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 4.

In certain embodiments, the protein of the present invention has an amino acid sequence as shown in SEQ ID No: 4.

In certain embodiments, the protein of the present invention comprises a sequence selected from the following, or consists of a sequence selected from the following:

(i) a sequence as shown in SEQ ID NO: 5;

(ii) compared with the sequence as shown in SEQ ID NO: 5, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 5.

In certain embodiments, the protein of the present invention has an amino acid sequence as shown in SEQ ID No: 5.

In certain embodiments, the protein of the present invention comprises a sequence selected from the following, or consists of a sequence selected from the following:

(i) a sequence as shown in SEQ ID NO: 6;

(ii) compared with the sequence as shown in SEQ ID NO: 6, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 6.

In certain embodiments, the protein of the present invention has an amino acid sequence as shown in SEQ ID No: 6.

In certain embodiments, the protein of the present invention comprises a sequence selected from the following, or consists of a sequence selected from the following:

(i) a sequence as shown in SEQ ID NO: 7;

(ii) compared with the sequence as shown in SEQ ID NO: 7, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 7.

In certain embodiments, the protein of the present invention has an amino acid sequence as shown in SEQ ID No: 7.

In certain embodiments, the protein of the present invention comprises a sequence selected from the following, or consists of a sequence selected from the following:

(i) a sequence as shown in SEQ ID NO: 8;

(ii) compared with the sequence as shown in SEQ ID NO: 8, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 8.

In certain embodiments, the protein of the invention has an amino acid sequence as shown in SEQ ID No: 8.

In certain embodiments, the protein of the present invention comprises a sequence selected from the following, or consists of a sequence selected from the following:

(i) a sequence as shown in SEQ ID NO: 9;

(ii) compared with the sequence as shown in SEQ ID NO: 9, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 9.

In certain embodiments, the protein of the present invention has an amino acid sequence as shown in SEQ ID No: 9.

In certain embodiments, the protein of the present invention comprises a sequence selected from the following, or consists of a sequence selected from the following:

(i) a sequence as shown in SEQ ID NO: 10;

(ii) compared with the sequence as shown in SEQ ID NO: 10, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 10.

In certain embodiments, the protein of the present invention has an amino acid sequence as shown in SEQ ID No: 10.

In certain embodiments, the protein of the present invention comprises a sequence selected from the following, or consists of a sequence selected from the following:

(i) a sequence as shown in SEQ ID NO: 11;

(ii) compared with the sequence as shown in SEQ ID NO: 11, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 11.

In certain embodiments, the protein of the present invention has an amino acid sequence as shown in SEQ ID No: 11.

In certain embodiments, the protein of the present invention comprises a sequence selected from the following, or consists of a sequence selected from the following:

(i) a sequence as shown in SEQ ID NO: 12;

(ii) compared with the sequence as shown in SEQ ID NO: 12, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 12.

In some embodiments, the protein of the present invention has an amino acid sequence as shown in SEQ ID No: 12.

In certain embodiments, the protein of the present invention comprises a sequence selected from the following, or consists of a sequence selected from the following:

(i) a sequence as shown in SEQ ID NO: 13;

(ii) compared with the sequence as shown in SEQ ID NO: 13, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 13.

In certain embodiments, the protein of the present invention has an amino acid sequence as shown in SEQ ID No: 13.

In certain embodiments, the protein of the present invention comprises a sequence selected from the following, or consists of a sequence selected from the following:

(i) a sequence as shown in SEQ ID NO: 14;

(ii) compared with the sequence as shown in SEQ ID NO: 14, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 14.

In certain embodiments, the protein of the present invention has an amino acid sequence as shown in SEQ ID No: 14.

In certain embodiments, the protein of the present invention comprises a sequence selected from the following, or consists of a sequence selected from the following:

(i) a sequence as shown in SEQ ID NO: 15;

(ii) compared with the sequence as shown in SEQ ID NO: 15, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 15.

In certain embodiments, the protein of the present invention has an amino acid sequence as shown in SEQ ID No: 15.

In certain embodiments, the protein of the present invention comprises a sequence selected from the following, or consists of a sequence selected from the following:

(i) a sequence as shown in SEQ ID NO: 16;

(ii) compared with the sequence as shown in SEQ ID NO: 16, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 16.

In certain embodiments, the protein of the present invention has an amino acid sequence as shown in SEQ ID No: 16.

In certain embodiments, the protein of the present invention comprises a sequence selected from the following, or consists of a sequence selected from the following:

(i) a sequence as shown in SEQ ID NO: 17;

(ii) compared with the sequence as shown in SEQ ID NO: 17, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 17.

In certain embodiments, the protein of the present invention has an amino acid sequence as shown in SEQ ID No: 17.

In certain embodiments, the protein of the present invention comprises a sequence selected from the following, or consists of a sequence selected from the following:

(i) a sequence as shown in SEQ ID NO: 18;

(ii) compared with the sequence as shown in SEQ ID NO: 18, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 18.

In some embodiments, the protein of the invention has an amino acid sequence as shown in SEQ ID No: 18.

In certain embodiments, the protein of the present invention comprises a sequence selected from the following, or consists of a sequence selected from the following:

(i) a sequence as shown in SEQ ID NO: 19;

(ii) compared with the sequence as shown in SEQ ID NO: 19, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 19.

In certain embodiments, the protein of the present invention has an amino acid sequence as shown in SEQ ID No: 19.

In certain embodiments, the protein of the present invention comprises a sequence selected from the following, or consists of a sequence selected from the following:

(i) a sequence as shown in SEQ ID NO: 20;

(ii) compared with the sequence as shown in SEQ ID NO: 20, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in SEQ ID NO: 20.

In certain embodiments, the protein of the present invention has an amino acid sequence as shown in SEQ ID No: 20.

Derived Protein

The protein of the present invention can be subjected to derivatization, for example, linked to another molecule (for example, another polypeptide or protein). Generally, the derivatization of the protein (for example, labeling) will not adversely affect the desired activity of the protein (for example, the activity of binding to the guide RNA, endonuclease activity, the activity of binding to and cleaving a specific site of the target sequence guided by the guide RNA). Therefore, the protein of the present invention is also intended to include such derivatized forms. For example, the protein of the present invention can be functionally linked (through chemical coupling, gene fusion, non-covalent linkage or other means) to one or more other molecular groups, such as another protein or polypeptide, detection reagent, pharmaceutical reagent and the like.

In particular, the protein of the present invention can be connected to other functional units. For example, it can be linked to a nuclear localization signal (NLS) sequence to improve the ability of the protein of the present invention to enter the cell nucleus. For example, it can be connected to a targeting moiety to make the protein of the present invention have the targeting property. For example, it can be linked to a detectable label to facilitate detection of the protein of the present invention. For example, it can be linked to an epitope tag to facilitate the expression, detection, tracing and/or purification of the protein of the present invention.

Conjugate

Therefore, in a second aspect, the present invention provides a conjugate comprising the above-mentioned protein and a modified portion.

In certain embodiments, the modified portion is selected from an additional protein or polypeptide, a detectable label, and any combinations thereof.

In certain embodiments, the additional protein or polypeptide is selected from an epitope tag, a reporter gene sequence, a nuclear localization signal (NLS) sequence, a targeting moiety, a transcription activation domain (such as, VP64), a transcription repression domain (for example, KRAB domain or SID domain), a nuclease domain (for example, Fok 1), a domain having an activity selected from: nucleotide deaminase, methylase activity, demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity, and nucleic acid binding activity; and any combinations thereof.

In certain embodiments, the conjugate of the present invention comprises one or more NLS sequences, such as the NLS of the SV40 virus large T antigen. In certain exemplary embodiments, the NLS sequence is shown in SEQ ID NO: 81. In certain embodiments, the NLS sequence is located at, near, or close to the end (such as, N-terminal or C-terminal) of the protein of the present invention. In certain exemplary embodiments, the NLS sequence is located at, near, or close to the C-terminus of the protein of the present invention.

In certain embodiments, the conjugate of the present invention comprises an epitope tag. Such epitope tags are well known to those skilled in the art, examples of which include, but are not limited to, His, V5, FLAG, HA, Myc, VSV-G, Trx, etc., and those skilled in the art know how to select a suitable epitope tag according to the desired purpose (for example, purification, detection or tracing).

In certain embodiments, the conjugate of the present invention comprises a reporter gene sequence. Such reporter genes are well known to those skilled in the art, and examples thereof include but are not limited to GST, HRP, CAT, GFP, HcRed, DsRed, CFP, YFP, BFP and the like.

In certain embodiments, the conjugate of the present invention comprises a domain capable of binding to DNA molecules or intracellular molecules, such as maltose binding protein (MBP), DNA binding domain (DBD) of Lex A, DBD of GAL4, etc.

In certain embodiments, the conjugate of the invention comprises a detectable label, such as a fluorescent dye, such as FITC or DAPI.

In certain embodiments, the protein of the present invention is optionally coupled, conjugated or fused to the modified portion via a linker.

In certain embodiments, the modified portion is directly connected to the N-terminus or C-terminus of the protein of the present invention.

In some embodiments, the modified portion is connected to the N-terminus or C-terminus of the protein of the present invention through a linker. Such linkers are well known in the art, examples of which include, but are not limited to, a linker containing one or more (for example, 1, 2, 3, 4, or 5) amino acids (such as, Glu or Ser) or amino acid derivatives (such as, Ahx, β-Ala, GABA or Ava) or PEG and the like.

Fusion Protein

In a third aspect, the present invention provides a fusion protein comprising the protein of the present invention and an additional protein or polypeptide.

In certain embodiments, the additional protein or polypeptide is selected from an epitope tag, a reporter gene sequence, a nuclear localization signal (NLS) sequence, a targeting moiety, a transcription activation domain (such as, VP64), a transcription repression domain (for example, KRAB domain or SID domain), a nuclease domain (for example, Fok 1), a domain having an activity selected from: a nucleotide deaminase, methylase activity, a demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity, and nucleic acid binding activity; and any combinations thereof.

In certain embodiments, the fusion protein of the present invention comprises one or more NLS sequences, such as the NLS of the SV40 virus large T antigen. In certain embodiments, the NLS sequence is located at, near, or close to the end (such as, N-terminal or C-terminal) of the protein of the present invention. In certain exemplary embodiments, the NLS sequence is located at, near, or close to the C-terminus of the protein of the present invention.

In certain embodiments, the fusion protein of the present invention comprises an epitope tag.

In certain embodiments, the fusion protein of the present invention comprises a reporter gene sequence.

In certain embodiments, the fusion protein of the present invention contains a domain capable of binding to DNA molecules or intracellular molecules.

In certain embodiments, the protein of the present invention is optionally fused to the additional protein or polypeptide via a linker.

In certain embodiments, the additional protein or polypeptide is directly linked to the N-terminus or C-terminus of the protein of the present invention.

In certain embodiments, the additional protein or polypeptide is connected to the N-terminus or C-terminus of the protein of the present invention via a linker.

In certain exemplary embodiments, the fusion protein of the present invention has an amino acid sequence selected from the group consisting of SEQ ID NOs: 82-101.

The protein of the present invention, the conjugate of the present invention, or the fusion protein of the present invention is not limited by the manner in which it is produced. For example, it can be produced by genetic engineering methods (recombinant technology), or can be produced by chemical synthesis methods.

Direct repeat In a fourth aspect, the present invention provides an isolated nucleic acid molecule comprising a sequence selected from the following or consisting of a sequence selected from the following:

(i) a sequence as shown in any one of SEQ ID NOs: 41-60;
(ii) compared with the sequence as shown in any one of SEQ ID NOs: 41-60, a sequence having one or more base substitutions, deletions or additions (for example, 1, 2, 3, 4, 5, 6, 7, 8, 9 or 10 base substitutions, deletions or additions);
(iii) a sequence having at least 20%, at least 30%, at least 40%, at least 50%, at least 60%, at least 70%, at least 80%, at least 90%, at least 95% sequence identity with the sequence as shown in any one of SEQ ID NOs: 41-60; or
(iv) a sequence that hybridizes to the sequence as described in any one of (i) to (iii) under stringent conditions; or
(v) a complementary sequence of the sequence as described in any one of (i)-(iii);

In addition, the sequence as described in any one of (ii)-(v) substantially retains the biological function of the sequence from which it is derived, and the biological function of the sequence refers to its activity as a direct repeat sequence in the CRISPR-Cas system.

In certain embodiments, the isolated nucleic acid molecule is a direct repeat sequence in the CRISPR-Cas system.

In certain embodiments, the nucleic acid molecule comprises a sequence selected from the following, or consists of a sequence selected from the following:

(a) a nucleotide sequence as shown in any one of SEQ ID NOs: 41;
(b) a sequence that hybridizes to the sequence as described in (a) under stringent conditions; or
(c) a complementary sequence of the sequence as described in (a).

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 41;
(ii) compared with the sequence as shown in SEQ ID NO: 41, a sequence having one or more base substitutions, deletions or additions (for example, 1, 2, 3, 4, 5, 6, 7, 8, 9 or 10 base substitutions, deletions or additions);
(iii) a sequence having at least 20%, at least 30%, at least 40%, at least 50%, at least 60%, at least 70%, at least 80%, at least 90%, at least 95% sequence identity with the sequence as shown in SEQ ID NO: 41; or
(iv) a sequence that hybridizes to the sequence as described in any one of (i) to (iii) under stringent conditions; or
(v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 41;
(b) a sequence that hybridizes to the sequence as described in (a) under stringent conditions; or
(c) a complementary sequence of the nucleotide sequence as shown in SEQ ID No: 41.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 42;

(ii) compared with the sequence as shown in SEQ ID NO: 42, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 42; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 42;

(b) a sequence that hybridizes to the sequence as described in (a) under stringent conditions; or (c) a complementary sequence of the nucleotide sequence as shown in SEQ ID No: 42.

In certain embodiments, the isolated nucleic acid molecule is RNA.

In some embodiments, the isolated nucleic acid molecule comprises a sequence selected from the following, or consists of a sequence selected from the following:

(i) The sequence shown in SEQ ID NO: 43;

(ii) compared with the sequence as shown in SEQ ID NO: 43, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 43; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 43;

(b) a sequence that hybridizes to the sequence as described in (a) under stringent conditions; or (c) a complementary sequence of the nucleotide sequence as shown in SEQ ID No: 43.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 44;

(ii) compared with the sequence as shown in SEQ ID NO: 44, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 44; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 44;

(b) a sequence that hybridizes to the sequence as described in (a) under stringent conditions; or (c) a complementary sequence of the nucleotide sequence as shown in SEQ ID No: 44.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 45;

(ii) compared with the sequence as shown in SEQ ID NO: 45, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 45; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 45;

(b) a sequence that hybridizes to the sequence as described in (a) under stringent conditions; or (c) a complementary sequence of the nucleotide sequence as shown in SEQ ID No: 45.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 46;

(ii) compared with the sequence as shown in SEQ ID NO: 46, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 46; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 46;

(b) a sequence that hybridizes to the sequence as described in (a) under stringent conditions; or (c) a complementary sequence of the nucleotide sequence as shown in SEQ ID No: 46.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 47;

(ii) compared with the sequence as shown in SEQ ID NO: 47, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 47; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 47;

(b) a sequence that hybridizes to the sequence as described in (a) under stringent conditions; or (c) a complementary sequence of the nucleotide sequence as shown in SEQ ID No: 47.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 48;

(ii) compared with the sequence as shown in SEQ ID NO: 48, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 48; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 48;

(b) a sequence that hybridizes to the sequence as described in (a) under stringent conditions; or (c) a complementary sequence of the nucleotide sequence as shown in SEQ ID No: 48.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 49;

(ii) compared with the sequence as shown in SEQ ID NO: 49, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 49; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 49;

(b) a sequence that hybridizes to the sequence as described in (a) under stringent conditions; or (c) a complementary sequence of the nucleotide sequence as shown in SEQ ID No: 49.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 50;

(ii) compared with the sequence as shown in SEQ ID NO: 50, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 50; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 50;

(b) a sequence that hybridizes to the sequence as described in (a) under stringent conditions; or (c) a complementary sequence of the nucleotide sequence as shown in SEQ ID No: 50.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 51;

(ii) compared with the sequence as shown in SEQ ID NO: 51, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID No: 51; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 51;

(b) a sequence that hybridizes to the sequence as described in (a) under stringent conditions; or (c) a complementary sequence of the nucleotide sequence as shown in SEQ ID No: 51.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 52;

(ii) compared with the sequence as shown in SEQ ID NO: 52, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 52; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 52;

(b) a sequence that hybridizes to the sequence as described in (a) under stringent conditions; or (c) a complementary sequence of the nucleotide sequence as shown in SEQ ID No: 52.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 53;

(ii) compared with the sequence as shown in SEQ ID NO: 53, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 53; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 53;

(b) a sequence that hybridizes to the sequence as described in (a) under stringent conditions; or (c) a complementary sequence of the nucleotide sequence as shown in SEQ ID No: 53.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 54;

(ii) compared with the sequence as shown in SEQ ID NO: 54, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 54; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 54;

(b) a sequence that hybridizes to the sequence as described in (a) under stringent conditions; or (c) a complementary sequence of the nucleotide sequence as shown in SEQ ID No: 54.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 55;

(ii) compared with the sequence as shown in SEQ ID NO: 55, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 55; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 55;

(b) a sequence that hybridizes to the sequence as described in (a) under stringent conditions; or (c) a complementary sequence of the nucleotide sequence as shown in SEQ ID No: 55.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 56;

(ii) compared with the sequence as shown in SEQ ID NO: 56, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 56; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 56;

(b) a sequence that hybridizes to the sequence as described in (a) under stringent conditions; or (c) a complementary sequence of the nucleotide sequence as shown in SEQ ID No: 56.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 57;

(ii) compared with the sequence as shown in SEQ ID NO: 57, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 57; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 57;

(b) a sequence that hybridizes to the sequence as described in (a) under stringent conditions; or (c) a complementary sequence of the nucleotide sequence as shown in SEQ ID No: 57.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 58;

(ii) compared with the sequence as shown in SEQ ID NO: 58, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 58; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 58;

(b) a sequence that hybridizes to the sequence as described in (a) under stringent conditions; or (c) a complementary sequence of the nucleotide sequence as shown in SEQ ID No: 58.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 59;

(ii) compared with the sequence as shown in SEQ ID NO: 59, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 59; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 59;

(b) a sequence that hybridizes to the sequence as described in (a) under stringent conditions; or (c) a complementary sequence of the nucleotide sequence as shown in SEQ ID No: 59.

In certain embodiments, the isolated nucleic acid molecule is RNA.

In some embodiments, the isolated nucleic acid molecule comprises a sequence selected from the following, or consists of a sequence selected from the following:

(i) a sequence as shown in SEQ ID NO: 60;

(ii) compared with the sequence as shown in SEQ ID NO: 60, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO: 60; or (iv) a sequence that hybridizes to the sequence as described in any one of (i) to (iii) under stringent conditions; or (v) a complementary sequence of the sequence as described in any one of (i)-(iii).

In some embodiments, the isolated nucleic acid molecule comprises a sequence selected from the following, or consists of a sequence selected from the following:

(a) a nucleotide sequence as shown in SEQ ID NO: 60;

(b) a sequence that hybridizes to the sequence as described in (a) under stringent conditions; or (c) a complementary sequence of the nucleotide sequence as shown in SEQ ID No: 60.

CRISPR/Cas Complex

In a fifth aspect, the present invention provides a complex comprising:

(i) a protein component, which is selected from: the protein, conjugate or fusion protein of the present invention, and any combinations thereof; and (ii) a nucleic acid component, which comprises the isolated nucleic acid molecule as described above and a targeting sequence capable of hybridizing to the target sequence from the 5' to 3', wherein the protein component and the nucleic acid component combine with each other to form a complex.

In certain embodiments, the targeting sequence is attached to the 3' end of the nucleic acid molecule.

In certain embodiments, the targeting sequence comprises the complementary sequence of the target sequence.

In certain embodiments, the nucleic acid component is a guide RNA in the CRISPR-Cas system.

In certain embodiments, the nucleic acid molecule is RNA.

In certain embodiments, the complex does not comprise trans-acting crRNA (tracrRNA).

In certain embodiments, the targeting sequence is at least 5, at least 10, or at least 14 in length. In certain embodiments, the targeting sequence is 10-30, or 15-25, or 15-22, or 19-25, 19-22 nucleotides, or 14-28 nucleotides in length.

In certain embodiments, the isolated nucleic acid molecule is 55-70 nucleotides in length, such as 55-65 nucleotides, such as 60-65 nucleotides, such as 62-65 nucleosides, such as 63-64 nucleotides. In certain embodiments, the isolated nucleic acid molecule is 15-30 nucleotides in length, such as 15-25 nucleotides, such as 20-25 nucleotides, such as 22-24 nucleotides, such as 23 nucleotides.

Encoding Nucleic Acid, Vector and Host Cell

In a sixth aspect, the present invention provides an isolated nucleic acid molecule comprising:

(i) a nucleotide sequence encoding the protein or fusion protein of the present invention;

(ii) encoding the isolated nucleic acid molecule as described in the fourth aspect; or (iii) a nucleotide sequence containing (i) and (ii).

In certain embodiments, the nucleotide sequence described in any one of (i) to (iii) is codon optimized for expression in prokaryotic cells. In certain embodiments, the nucleotide sequence as described in any one of (i) to (iii) is codon optimized for expression in eukaryotic cells.

In a seventh aspect, the present invention also provides a vector comprising the isolated nucleic acid molecule as described in the sixth aspect. The vector of the present invention can be a cloning vector or an expression vector. In certain embodiments, the vector of the present invention can be, for example, a plasmid, a cosmid, a bacteriophage, a cosmid and the like. In certain preferred embodiments, the vector is capable of expressing the protein, fusion protein of the present invention, isolated nucleic acid molecule according to the fourth aspect or the complex according to the fifth aspect in a subject (for example, a mammal, such as a human).

In an eighth aspect, the present invention also provides a host cell containing the isolated nucleic acid molecule or vector as described above. Such host cells include, but are not limited to, prokaryotic cells such as *E. coli* cells, and eukaryotic cells such as yeast cells, insect cells, plant cells and animal cells (such as mammalian cells, such as mouse cells, human cells, etc.). The cells of the present invention can also be cell lines, such as 293T cells.

Composition and Vector Composition

In a ninth aspect, the present invention also provides a composition, which comprises:

(i) a first component, which is selected from: the protein, conjugate, fusion protein of the present invention, nucleotide sequence encoding the protein or fusion protein, and any combinations thereof; and (ii) a second component, which is a nucleotide sequence containing a guide RNA, or a nucleotide sequence encoding the nucleotide sequence containing a guide RNA;

wherein the guide RNA includes a direct repeat sequence and a guide sequence from the 5' to 3', and the guide sequence can hybridize with the target sequence;

the guide RNA can form a complex with the protein, conjugate or fusion protein as described in (i).

In certain embodiments, the direct repeat sequence is an isolated nucleic acid molecule as defined in the fourth aspect.

In certain embodiments, the guide sequence is connected to the 3' end of the direct repeat sequence. In certain embodiments, the guide sequence comprises the complementary sequence of the target sequence.

In certain embodiments, the composition does not include tracrRNA.

In certain embodiments, the composition is non-naturally occurring or modified. In certain embodiments, at least one component of the composition is non-naturally occurring or modified. In certain embodiments, the first component is non-naturally occurring or modified; and/or, the second component is non-naturally occurring or modified.

In some embodiments, when the target sequence is DNA, the target sequence is located at the 3' end of the original spacer sequence adjacent motif (PAM), and the PAM has the sequence shown by 5'-ATG.

In certain embodiments, when the target sequence is DNA, the target sequence is located at the 3' end of the original spacer sequence adjacent motif (PAM), and the PAM has a sequence shown by 5'-TTN, wherein N is selected from A, G, T, C.

In some embodiments, when the target sequence is DNA, the target sequence is located at the 3' end of the original spacer sequence adjacent motif (PAM), and the PAM has the sequence shown by 5'-KTR.

In certain embodiments, when the target sequence is RNA, the target sequence does not have PAM domain restrictions.

In certain embodiments, the target sequence is a DNA or RNA sequence derived from a prokaryotic cell or a eukaryotic cell. In certain embodiments, the target sequence is a non-naturally occurring DNA or RNA sequence.

In certain embodiments, the target sequence is present in the cell. In certain embodiments, the target sequence is present in the cell nucleus or in the cytoplasm (such as, organelles). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminus or C-terminus of the protein. In certain embodiments, the NLS sequence is fused to the N-terminus or C-terminus of the protein.

In a tenth aspect, the present invention also provides a composition comprising one or more vectors, the one or more vectors comprising:

(i) a first nucleic acid, which is a nucleotide sequence encoding a protein or fusion protein of the present invention; optionally, the first nucleic acid is operably linked to a first regulatory element; and (ii) a second nucleic acid, which encodes a nucleotide sequence comprising a guide RNA; optionally the second nucleic acid is operably linked to a second regulatory element;

wherein:

the first nucleic acid and the second nucleic acid are present on the same or different vectors;

the guide RNA includes a direct repeat sequence and a guide sequence from the 5' to 3', and the guide sequence can hybridize with the target sequence;

the guide RNA can form a complex with the effector protein or fusion protein as described in (i).

In certain embodiments, the direct repeat sequence is an isolated nucleic acid molecule as defined in the fourth aspect.

In certain embodiments, the guide sequence is connected to the 3' end of the direct repeat sequence. In certain embodiments, the guide sequence comprises the complementary sequence of the target sequence.

In certain embodiments, the composition does not include tracrRNA.

In certain embodiments, the composition is non-naturally occurring or modified. In certain embodiments, at least one component of the composition is non-naturally occurring or modified.

In certain embodiments, the first regulatory element is a promoter, such as an inducible promoter.

In certain embodiments, the second regulatory element is a promoter, such as an inducible promoter.

In some embodiments, when the target sequence is DNA, the target sequence is located at the 3' end of the original spacer sequence adjacent motif (PAM), and the PAM has the sequence shown by 5'-ATG.

In certain embodiments, when the target sequence is DNA, the target sequence is located at the 3' end of the original spacer sequence adjacent motif (PAM), and the PAM has a sequence shown by 5'-TTN, wherein N is selected from A, G, T, C.

In some embodiments, when the target sequence is DNA, the target sequence is located at the 3' end of the original spacer sequence adjacent motif (PAM), and the PAM has the sequence shown by 5'-KTR.

In certain embodiments, when the target sequence is RNA, the target sequence does not have PAM domain restrictions.

In certain embodiments, the target sequence is a DNA or RNA sequence derived from a prokaryotic cell or a eukaryotic cell. In certain embodiments, the target sequence is a non-naturally occurring DNA or RNA sequence.

In certain embodiments, the target sequence is present in the cell. In certain embodiments, the target sequence is present in the cell nucleus or in the cytoplasm (such as, organelles). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminus or C-terminus of the protein. In certain embodiments, the NLS sequence is fused to the N-terminus or C-terminus of the protein.

In certain embodiments, one type of vector is a plasmid, which refers to a circular double-stranded DNA loop into which additional DNA fragments can be inserted, for example, by standard molecular cloning techniques. Another type of vector is a viral vector, in which virus-derived DNA or RNA sequences are present in the vector used to package the virus (for example, retrovirus, replication-defective retrovirus, adenovirus, replication-defective adenovirus, and adeno-associated virus). Viral vectors also contain polynucleotides carried by the virus used for transfection into a host cell. Certain vectors (for example, bacterial vectors with a bacterial origin of replication and episomal mammalian vectors) are capable of autonomous replication in the host cell into which they are introduced. Other vectors (e.g., non-episomal mammalian vectors) are integrated into the host cell's genome after being introduced into the host cell, and thus replicate with the host genome. Moreover, certain vectors can direct the expression of genes to which they are operably linked. Such vectors are referred to herein as "expression vectors". Common expression vectors used in recombinant DNA technology are usually in the form of plasmids.

Recombinant expression vectors may contain the nucleic acid molecule of the present invention in a form suitable for expression of the nucleic acid in a host cell, which means that these recombinant expression vectors contain one or more regulatory elements selected based on the host cell to be used for expression. The regulatory element is operably linked to the nucleic acid sequence to be expressed.

Delivery and Delivery Composition

The protein, conjugate, fusion protein of the present invention, the isolated nucleic acid molecule as described in the fourth aspect, the complex of the present invention, the isolated nucleic acid molecule as described in the sixth aspect, the vector as described in the seventh aspect, the composition according to the ninth and tenth aspects can be delivered by any method known in the art. Such methods include, but are not limited to, electroporation, lipofection, nuclear transfection, microinjection, sonoporation, gene gun, calcium phosphate-mediated transfection, cationic transfection, liposome transfection, dendritic transfection, heat shock transfection, nuclear transfection, magnetic transfection, lipofection, puncture transfection, optical transfection, reagent-enhanced nucleic acid uptake, and delivery via liposome, immunoliposome, viral particle, artificial virosome etc.

Therefore, in another aspect, the present invention provides a delivery composition comprising a delivery vehicle and one or more selected from the following: the protein, conjugate, fusion protein of the present invention, the isolated nucleic acid molecule according to the fourth aspect, the complex of the present invention, the isolated nucleic acid molecule according to the sixth aspect, the vector according to the seventh aspect, the composition as described in the ninth and tenth aspects.

In certain embodiments, the delivery vehicle is a particle.

In certain embodiments, the delivery vehicle is selected from a lipid particle, sugar particle, metal particle, protein particle, liposome, exosome, microvesicle, gene gun, or viral vector (e.g., replication defective retrovirus, lentivirus, adenovirus or adeno-associated virus).

Kit

In another aspect, the present invention provides a kit comprising one or more of the components as described above. In certain embodiments, the kit includes one or more components selected from the following: the protein, conjugate, fusion protein of the present invention, the isolated nucleic acid molecule as described in the fourth aspect, the complex of the present invention, the isolated nucleic acid molecule as described in the sixth aspect, the vector as described in the seventh aspect, and the composition as described in the ninth and tenth aspects.

In certain embodiments, the kit of the present invention comprises the composition as described in the ninth aspect. In certain embodiments, the kit further includes instructions for using the composition.

In certain embodiments, the kit of the present invention comprises a composition as described in the tenth aspect. In certain embodiments, the kit further includes instructions for using the composition.

In certain embodiments, the component contained in the kit of the present invention may be provided in any suitable container.

In certain embodiments, the kit further includes one or more buffers. The buffer can be any buffer, including but not limited to sodium carbonate buffer, sodium bicarbonate buffer, borate buffer, Tris buffer, MOPS buffer, HEPES buffer, and combinations thereof. In certain embodiments, the buffer is alkaline. In certain embodiments, the buffer has a pH of from about 7 to about 10.

In certain embodiments, the kit further includes one or more oligonucleotides corresponding to a guide sequence for insertion into the vector so as to operably link the guide sequence and regulatory element. In certain embodiments, the kit includes a homologous recombination template polynucleotide.

Method and Use

In another aspect, the present invention provides a method for modifying a target gene, which comprises: contacting the complex according to the fifth aspect, the composition according to the ninth aspect, or the composition according to the tenth aspect with the target gene, or delivering that to a cell containing the target gene; the target sequence is present in the target gene.

In certain embodiments, the target gene is present in the cell. In certain embodiments, the cell is a prokaryotic cell. In certain embodiments, the cell is a eukaryotic cell. In certain embodiments, the cell is a mammalian cell. In certain embodiments, the cell is a human cell. In certain embodiments, the cell is selected from a non-human primate, bovine, pig, or rodent cell. In certain embodiments, the cell is a non-mammalian eukaryotic cell, such as poultry or fish and the like. In certain embodiments, the cell is a plant cell, such as a cell possessed by a cultivated plant (such as cassava, corn, sorghum, wheat, or rice), algae, tree, or vegetable.

In certain embodiments, the target gene is present in a nucleic acid molecule (e.g., a plasmid) in vitro. In certain embodiments, the target gene is present in a plasmid.

In some embodiments, the modification refers to a break in the target sequence, such as a double-strand break in DNA or a single-strand break in RNA.

In certain embodiments, the break results in decreased transcription of the target gene.

In some embodiments, the method further comprises: contacting the editing template with the target gene, or delivering it to the cell containing the target gene. In such embodiments, the method repairs the broken target gene by homologous recombination with an exogenous template polynucleotide, wherein the repair results in a mutation including the insertion, deletion, or substitution of one or more nucleotides of the target gene. In certain embodiments, the mutation results in one or more amino acid changes in the protein expressed from the gene containing the target sequence.

Therefore, in certain embodiments, the modification further includes inserting an editing template (for example, an exogenous nucleic acid) into the break.

In certain embodiments, the protein, conjugate, fusion protein, isolated nucleic acid molecule, complex, vector or composition is contained in a delivery vehicle.

In some embodiments, the delivery vehicle is selected from a lipid particle, sugar particle, metal particle, protein particle, liposome, exosome, viral vector (such as replication-defective retrovirus, lentivirus, adenovirus or adeno-associated virus).

In certain embodiments, the method is used to change one or more target sequences in a target gene or a nucleic acid molecule encoding a target gene product to modify a cell, cell line, or organism.

In another aspect, the present invention provides a method for altering the expression of a gene product, which comprises: contacting the complex according to the fifth aspect, the composition according to the ninth aspect or the composition according to the tenth aspect with a nucleic acid molecule encoding the gene product, or delivering that to a cell containing the nucleic acid molecule in which the target sequence is present.

In certain embodiments, the nucleic acid molecule is present in a cell. In certain embodiments, the cell is a prokaryotic cell. In certain embodiments, the cell is a eukaryotic cell. In certain embodiments, the cell is a mammalian cell. In certain embodiments, the cell is a human cell. In certain embodiments, the cell is selected from a non-human primate, bovine, pig, or rodent cell. In certain embodiments, the cell is a non-mammalian eukaryotic cell, such as poultry or fish and the like. In certain embodiments, the cell is a plant cell, such as a cell possessed by a cultivated plant (such as cassava, corn, sorghum, wheat, or rice), algae, tree, or vegetable.

In certain embodiments, the nucleic acid molecule is present in a nucleic acid molecule (e.g., a plasmid) in vitro. In certain embodiments, the nucleic acid molecule is present in a plasmid.

In certain embodiments, the expression of the gene product is altered (e.g., enhanced or decreased). In certain embodiments, the expression of the gene product is enhanced. In certain embodiments, the expression of the gene product is reduced.

In certain embodiments, the gene product is a protein.

In certain embodiments, the protein, conjugate, fusion protein, isolated nucleic acid molecule, complex, vector or composition is contained in a delivery vehicle.

In some embodiments, the delivery vehicle is selected from a lipid particle, sugar particle, metal particle, protein particle, liposome, exosome, viral vector (such as replication-defective retrovirus, lentivirus, adenovirus or adeno-associated virus).

In certain embodiments, the method is used to change one or more target sequences in a target gene or a nucleic acid molecule encoding a target gene product to modify a cell, cell line, or organism.

In another aspect, the present invention relates to a use of the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention for the nucleic acid editing.

In certain embodiments, the nucleic acid editing includes gene or genome editing, such as modifying genes, knocking out genes, altering the expression of gene products, repairing mutations, and/or inserting polynucleotides.

In another aspect, the present invention relates to a use of the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention in the preparation of a formulation, which is used for:

(i) the in vitro gene or genome editing;

(ii) the detection of an isolated single-stranded DNA;

(iii) editing the target sequence in the target locus to modify a biological or non-human organism;

(iv) the treatment of the disease caused by defects in the target sequence in the target locus.

Cells and Cell Progeny

In some cases, the modifications introduced into the cell by the method of the present invention can cause the cell and its progeny to be altered to improve the production of its biological products (such as antibodies, starch, ethanol, or other desired cell output). In some cases, the modifications introduced into the cell by the methods of the present invention can cause the cell and its progeny to include changes that alter the biological product produced.

Therefore, in another aspect, the present invention also relates to a cell or its progeny obtained by the method as described above, wherein the cell contains a modification that is not present in its wild type.

The present invention also relates to the cell product of the cell or its progeny as described above.

The present invention also relates to an in vitro, isolated or in vivo cell or cell line or their progeny, the cell or cell line or their progeny comprises: the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention.

In certain embodiments, the cell is a prokaryotic cell.

In certain embodiments, the cell is a eukaryotic cell. In certain embodiments, the cell is a mammalian cell. In certain embodiments, the cell is a human cell. In certain embodiments, the cell is a non-human mammalian cell, such as a cell of a non-human primate, cow, sheep, pig, dog, monkey, rabbit, rodent (such as rat or mouse). In certain embodiments, the cell is a non-mammalian eukaryotic cell, such as a poultry bird (e.g. chicken), fish, or crustacean (e.g. clam, shrimp) cell. In certain embodiments, the cell is a plant cell, such as a cell possessed by a monocot or dicot or a cultivated plant or a food crop such as cassava, corn, sorghum, soybean, wheat, oats or rice, for example Algae, trees or production plants, fruits or vegetables (for example, trees such as citrus trees, nut trees; nightshades, cotton, tobacco, tomatoes, grapes, coffee, cocoa, etc.).

In certain embodiments, the cell is a stem cell or stem cell line.

Definition of Terms

In the present invention, unless otherwise specified, the scientific and technical terms used herein have the meanings commonly understood by those skilled in the art. In addition, the molecular genetics, nucleic acid chemistry, chemistry, molecular biology, biochemistry, cell culture, microbiology, cell biology, genomics and recombinant DNA and other procedures used in this article are all routine procedures widely used in the corresponding fields. At the same time, in order to better understand the present invention, definitions and explanations of related terms are provided below.

In the present invention, the expression "Cas12j" refers to a Cas effector protein discovered and identified for the first time by the present inventors, which has an amino acid sequence selected from the following:

(i) a sequence as shown in any one of SEQ ID NOs: 1-20, 107, 108;

(ii) compared with the sequence as shown in any one of SEQ ID NOs: 1-20, 107, 108, a sequence having one or more amino acid substitutions, deletions or additions (for example, 1, 2, 3, 4, 5, 6, 7, 8, 9 or 10 amino acid substitutions, deletions or additions); or (iii) a sequence having at least 80%, at least 85%, at least 90%, at least 91%, at least 92%, at least 93%, at least 94%, at least 95%, at least 96%, at least 97%, at least 98%, or at least 99% sequence identity with the sequence as shown in any one of SEQ ID NOs: 1-20, 107, 108.

The Cas12j of the present invention is an endonuclease that binds to and cuts a specific site of a target sequence under the guidance of a guide RNA, and has DNA and RNA endonuclease activities at the same time.

As used herein, the terms "Clustered Regularly Interspaced Short Palindromic Repeats (CRISPR)-CRISPR-associated (Cas) (CRISPR-Cas) system" or "CRISPR system" are used interchangeably and have the meaning commonly understood by those skilled in the art, it usually contains transcription products or other elements related to the expression of CRISPR-associated ("Cas") genes, or transcription products or other elements capable of directing the activity of the Cas gene. Such transcription products or other elements may include sequences encoding Cas effector proteins and guide RNAs including CRISPR RNA (crRNA), as well as trans-activating crRNA (tracrRNA) sequences contained in the CRISPR-Cas9 system, or other sequences or transcription products from the CRISPR locus.

As used herein, the terms "Cas effector protein" and "Cas effector enzyme" are used interchangeably and refer to any protein present in the CRISPR-Cas system that is greater than 800 amino acids in length. In some cases, this type of protein refers to a protein identified from the Cas locus.

As used herein, the terms "guide RNA" and "mature crRNA" can be used interchangeably and have meanings commonly understood by those skilled in the art. Generally speaking, a guide RNA can contain a direct repeat and a guide sequence (targeting sequence), or it essentially consists of or consists of a direct repeat sequence and a guide sequence (also called a spacer in the context of an endogenous CRISPR system). In some cases, the guide sequence is any polynucleotide sequence that has sufficient complementarity with the target sequence to hybridize to the target sequence and guide the specific binding of the CRISPR/Cas complex to the target sequence. In certain embodiments, when optimally aligned, the degree of complementarity between the guide sequence and its corresponding target sequence is at least 50%, at least 60%, at least 70%, at least 80%, at least 90%, at least 95%, or at least 99%. Determining the best alignment is within the ability of a person of ordinary skill in the art. For example, there are published and commercially available alignment algorithms and programs, such as but not limited to Smith-Waterman, Bowtie, Geneious, Biopython and SeqMan in ClustalW, matlab.

In some cases, the guide sequence is at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 nucleotides in length. In some cases, the guide sequence is no more than 50, 45, 40, 35, 30, 25, 24, 23, 22, 21, 20, 15, 10 or fewer nucleotides in length. In certain embodiments, the guide sequence is 10-30, or 15-25, or 15-22, or 19-25, or 19-22 nucleotides in length.

In some cases, the direct repeat sequence is at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 56, at least 57, at least 58, at least 59, at least 60, at least 61, at least 62, at least 63, at least 64, at least 65, or at least 70 nucleotides in length. In some cases, the direct repeat sequence is no more than 70, 65, 64, 63, 62, 61, 60, 59, 58, 57, 56, 55, 50, 45, 40, 35, 30, 29, 28, 27, 26, 25, 24, 23, 22, 21, 20, 15, 10 or fewer nucleotides in length. In certain embodiments, the direct repeat sequence is 55-70 nucleotides in length, such as 55-65 nucleotides, such as 60-65 nucleotides, such as 62-65 nucleotides, such as 63-64 nucleotides. In certain embodiments, the direct repeat sequence is 15-30 nucleotides in length, such as 15-25 nucleotides, such as 20-25 nucleotides, such as 22-24 nucleosides, such as 23 nucleotides. In some embodiments, the direct repeat sequence is no less than 32 nt in length, for example, 32 nt-37 nt.

As used herein, the term "CRISPR/Cas complex" refers to a ribonucleoprotein complex formed by the combination of guide RNA or mature crRNA and Cas protein, which contains a guide sequence that hybridizes to the target sequence and binds to the Cas protein. The ribonucleoprotein complex can recognize and cleave polynucleotides that can hybridize with the guide RNA or mature crRNA.

Therefore, in the case of forming a CRISPR/Cas complex, the "target sequence" refers to a polynucleotide that is targeted by a guide sequence designed to have targeting, for example, a sequence that is complementary to the guide sequence, wherein the hybridization between the target sequence and the guide sequence will promote the formation of the CRISPR/Cas complex. Complete complementarity is not necessary, as long as there is sufficient complementarity to cause hybridization and promote the formation of a CRISPR/Cas complex. The target sequence can comprise any polynucleotide, such as DNA or RNA. In some cases, the target sequence is located in the nucleus or cytoplasm of the cell. In some cases, the target sequence may be located in an organelle of a eukaryotic cell such as mitochondria or chloroplast. The sequence or template that can be used to be recombined into the target locus containing the target sequence is referred to as "editing template" or "editing polynucleotide" or "editing sequence". In certain embodiments, the editing template is an exogenous nucleic acid. In certain embodiments, the recombination is a homologous recombination.

In the present invention, the expression "target sequence" or "target polynucleotide" can be any endogenous or exogenous polynucleotide for a cell (for example, a eukaryotic cell). For example, the target polynucleotide may be a polynucleotide present in the nucleus of a eukaryotic cell. The target polynucleotide may be a sequence encoding a gene product (e.g., protein) or a non-coding sequence (e.g., regulatory polynucleotide or useless DNA). In some cases, it is believed that the target sequence should be related to the protospacer adjacent motif (PAM). The exact sequence and length requirements for PAM vary depending on the Cas effector enzyme used, but PAM is typically a 2-5 base pair sequence adjacent to the protospacer (i.e., the target sequence). Those skilled in the art are able to identify the PAM sequence to be used with a given Cas effector protein.

In some cases, the target sequence or target polynucleotide may include multiple disease-related genes and polynucleotides and signal transduction biochemical pathway-related genes and polynucleotides. Non-limiting examples of such target sequences or target polynucleotides include those listed in U.S. Provisional Patent Applications 61/736,527 and 61/748,427 filed on Dec. 12, 2012 and Jan. 2, 2013 respectively, and the international application PCT/US2013/074667 filed on Dec. 12, 2013, which are all incorporated herein by reference.

In some cases, examples of a target sequence or a target polynucleotide includes a sequence related to signal transduction biochemical pathways, such as a signal transduction biochemical pathway related gene or polynucleotide. Examples of a target polynucleotide includes a disease-related gene or polynucleotide. The "disease-related" gene or polynucleotide refers to any gene or polynucleotide that produces transcription or translation products at abnormal levels or in abnormal forms in cells derived from tissues affected by the disease, compared with non-disease control tissues or cells. In the case where the altered expression is related to the appearance and/or progression of the disease, it may be a gene expressed at an abnormally high level; or, it may be a gene expressed at an abnormally low level. The disease-related gene also refers to genes that have one or more mutations or genetic variations that are directly responsible for or genetic linkage disequilibrium with one or more genes responsible for the etiology of the disease. The transcribed or translated product can be known or unknown, and can be at normal or abnormal levels.

As used herein, the term "wild-type" has the meaning commonly understood by those skilled in the art, which means a typical form of organisms, strains, genes, or features that distinguishes it from mutants or variant forms when it exists in nature, it can be isolated from natural sources and has not been deliberately modified.

As used herein, the terms "non-naturally occurring" or "engineered" can be used interchangeably and refer to artificial involvement. When these terms are used to describe a nucleic acid molecule or polypeptide, it means that the nucleic acid molecule or polypeptide is at least substantially free from at least another component that they bind to in nature or as found in nature.

As used herein, the term "orthologue (ortholog)" has the meaning commonly understood by those skilled in the art. As a further guidance, the "orthologue" of the protein as described herein refers to proteins belonging to different species, which perform the same or similar functions as the proteins that act as their orthologs.

As used herein, the term "identity" is used to refer to the matching of sequences between two polypeptides or between two nucleic acids. When a certain position in the two sequences to be compared is occupied by the same base or amino acid monomer subunit (for example, a certain position in each of the two DNA molecules is occupied by adenine, or a certain position in each of the two peptides is occupied by lysine), then the molecules are identical at that position. The "percent identity" between two sequences is a function of the number of matching positions shared by the two sequences divided by the number of positions to be compared×100. For example, if 6 out of 10 positions in two sequences match, then the two sequences have 60% identity. For example, the DNA sequences CTGACT and CAGGTT share 50% identity (3 out of 6 total positions match). Generally, the comparison is made when two sequences are aligned to produce maximum identity. Such alignment can be achieved by using, for example, the method of Needleman et al. (1970) J. Mol. Biol. 48:443-453, which can be conveniently performed by a computer program such as the Align program (DNAstar, Inc.). It is also possible to use the algorithm of E. Meyers and W. Miller (Comput. Appl Biosci., 4:11-17 (1988)) integrated into the ALIGN program (version 2.0), using the PAM120 weight residue table, a gap length penalty of 12, and a gap penalty of 4 to determine the percent identity between two amino acid sequences. In addition, the Needleman and Wunsch (J MoI Biol. 48:444-453 (1970)) algorithm in the GAP program integrated into the GCG software package (available on www.gcg.com) can be used, the Blossum 62 matrix or PAM250 matrix and gap weights of 16, 14, 12, 10, 8, 6, or 4 and length weights of 1, 2, 3, 4, 5 or 6 to determine the percent identity between two amino acid sequences.

As used herein, the term "vector" refers to a nucleic acid delivery vehicle into which a polynucleotide can be inserted. When the vector can express the protein encoded by the inserted polynucleotide, the vector is called an expression vector. The vector can be introduced into the host cell through transformation, transduction or transfection, so that the genetic material elements which it carries can be expressed in the host cell. Vector is well-known to those skilled in the art, including but not limited to: a plasmid; phagemid; cosmid; artificial chromosome, such as yeast artificial chromosome (YAC), bacterial artificial chromosome (BAC) or P1 derived artificial chromosome (PAC); bacteriophage such as a lambda bacteriophage or M13 bacteriophage and animal virus. An animal virus that can be used as a vector includes, but is not limited to, a retrovirus (including a lentivirus), adenovirus, adeno-associated virus, herpes virus (such as herpes simplex virus), poxvirus, baculovirus, papilloma virus, and papovaviruses (such as SV40). A vector can contain a variety of elements that control expression, including but not limited to a promoter sequence, transcription initiation sequence, enhancer sequence, selection element, and reporter gene. In addition, the vector may also contain an origin of replication.

As used herein, the term "host cell" refers to a cell that can be used to introduce a vector, which includes, but is not limited to, a prokaryotic cell such as *Escherichia coli* or *Bacillus subtilis* and the like, a fungal cell such as a yeast cell or *Aspergillus*, etc., an insect cell such as a S2 Drosophila cell or Sf9, etc., or an animal cell such as a fibroblast, CHO cell, COS cell, NSO cell, HeLa cell, BHK cell, HEK 293 cell or human cell, etc.

Those skilled in the art will understand that the design of the expression vector may depend on factors such as the selection of the host cell to be transformed, the desired expression level, and the like. A vector can be introduced into a host cell to thereby produce transcripts, proteins, or peptides, including proteins, fusion proteins, isolated nucleic acid molecules, etc. as described herein (for example, CRISPR transcripts, such as nucleic acid transcripts, proteins, or enzymes).

As used herein, the term "regulatory element" is intended to include a promoter, enhancer, internal ribosome entry site (IRES), and other expression control elements (e.g., transcription termination signals, such as polyadenylation signals and Poly U sequence), for a detailed description, please refer to Goeddel, "GENE EXPRESSION TECHNOLOGY: METHOD IN ENZYMOLOGY" 185, Academic Press, San Diego, California (1990). In some cases, the regulatory element includes those that direct the constitutive expression of a nucleotide sequence in many types of host cells and those that direct the expression of the nucleotide sequence only in certain host cells (for example, tissue-specific regulatory sequence). A tissue-specific promoter may mainly direct expression in desired tissues of interest, such as muscles, neurons, bone, skin, blood, specific organs (such as liver, pancreas), or specific cell types (such as lymphocytes). In some cases, the regulatory element may also direct expression in a time-dependent manner (such as in a cell cycle-dependent or developmental stage-dependent manner), which may be or may not be tissue or cell type specific. In some cases, the term "regulatory element" encompasses an enhancer element, such as WPRE; CMV enhancer; R-U5' fragment in the LTR of HTLV-I ((Mol.Cell.Biol., Volume 8(1), Pages 466-472, 1988); SV40 enhancer; and the intron sequence between exons 2 and 3 of rabbit β-globin (Proc. Natl. Acad. Sci. USA., Vol. 78(3), pp. 1527-31, 1981).

As used herein, the term "promoter" has the meaning well known to those skilled in the art, which refers to a non-coding nucleotide sequence located upstream of a gene and capable of promoting downstream gene expression. A constitutive promoter is such a nucleotide sequence: when it is operationally linked to a polynucleotide encoding or defining a gene product, it leads to the production of a gene product in the cell under most or all physiological conditions of the cell. An inducible promoter is such a nucleotide sequence that, when operationally linked to a polynucleotide encoding or defining a gene product, basically only when an inducer corresponding to the promoter is present in the cell, it leads to the gene product to be produced in the cell. A tissue-specific promoter is such a nucleotide sequence that, when operationally linked to a polynucleotide encoding or defining a gene product, basically only when the cell is a cell of the tissue type corresponding to the promoter, it leads to the production of gene products in the cell.

As used herein, the term "operationally linked" is intended to mean that the nucleotide sequence of interest is linked to the one or more regulatory elements in a manner that allows the expression of the nucleotide sequence (e.g., in an in vitro transcription/translation system or when the vector is introduced into the host cell, it is in the host cell).

As used herein, the term "complementarity" refers to the ability of a nucleic acid to form one or more hydrogen bonds with another nucleic acid sequence by means of traditional Watson-Crick or other non-traditional types. The percentage of complementarity represents the percentage of residues in a nucleic acid molecule that can form hydrogen bonds (e.g., Watson-Crick base pairing) with a second nucleic acid sequence (e.g., 5, 6, 7, 8, 9, 10 out of 10 are 50%, 60%, 70%, 80%, 90%, and 100% complementary). "Completely complementary" means that all consecutive residues of a nucleic acid sequence form hydrogen bonds with the same number of consecutive residues in a second nucleic acid sequence. As used herein, "substantially complementary" means that there are at least 60%, 65%, 70%, 75%, 80%, 85%, 90%, 95%, 97%, 98%, 99%, or 100% degree of complementarity in a region of 8, 9, 10, 11, 12, 13, 14, 15, 16, 17, 18, 19, 20, 21, 22, 23, 24, 25, 30, 35, 40, 45, 50 or more nucleotides, or refers to two nucleic acids that hybridize under stringent conditions.

As used herein, "stringent conditions" for hybridization refer to conditions under which a nucleic acid having complementarity with a target sequence mainly hybridizes to the target sequence and substantially does not hybridize to a non-target sequence. Stringent conditions are usually sequence-dependent and vary depending on many factors. Generally speaking, the longer the sequence, the higher the temperature at which the sequence specifically hybridizes to its target sequence. Non-limiting examples of stringent conditions are described in "Laboratory Techniques In Biochemistry And Molecular Biology-Hybridization With Nucleic Acid Probes" by Tijssen (1993), Part I, Chapter 2, "Overview of principles of hybridization and the strategy of nucleic acid probe assay", Elsevier, New York.

As used herein, the term "hybridization" refers to a reaction in which one or more polynucleotides react to form a complex that is stabilized by hydrogen bonding of bases between these nucleotide residues. Hydrogen bonding can occur by means of Watson-Crick base pairing, Hoogstein binding, or in any other sequence-specific manner. The complex may comprise two strands forming a duplex, three or more strands forming a multi-strand complex, a single self-hybridizing strand, or any combination of these. The hybridization reaction can constitute a step in a broader process (such as the beginning of PCR, or the cleavage of polynucleotides by an enzyme). A sequence that can hybridize to a given sequence is called the "complement" of the given sequence.

As used herein, the term "expression" refers to the process by which the DNA template is transcribed into polynucleotides (such as mRNA or other RNA transcripts) and/or the process by which the transcribed mRNA is subsequently translated into peptides, polypeptides or proteins. The transcript and the encoded polypeptide can be collectively referred to as a "gene product". If the polynucleotide is derived from a genomic DNA, the expression can include splicing of mRNA in eukaryotic cells.

As used herein, the term "linker" refers to a linear polypeptide formed by multiple amino acid residues connected by peptide bonds. The linker of the present invention may be an artificially synthesized amino acid sequence, or a naturally-occurring polypeptide sequence, such as a polypeptide having the function of a hinge region. Such linker polypeptides are well known in the art (see, for example, Holliger, P. et al. (1993) Proc. Natl. Acad. Sci. USA 90: 6444-6448; Poljak, R. J. et al. (1994) Structure 2: 1121-1123).

As used herein, the term "treatment" refers to treating or curing a disorder, delaying the onset of symptoms of the disorder, and/or delaying the development of the disorder.

As used herein, the term "subject" includes, but is not limited to, various animals, such as mammals, e.g., bovines, equines, caprids, swines, canines, felines, leporidae animals, rodents (for example, mice or rats), non-human primates (for example, macaques or cynomolgus), or humans. In certain embodiments, the subject (e.g., human) has a disorder (e.g., a disorder caused by a disease-related gene defect).

The Beneficial Effects of the Present Invention

Compared with the prior art, the Cas protein and system of the present invention have significant advantages. For example, the Cas effector protein of the present invention has a strict mismatch tolerance, which makes it possible to have a lower off-target rate. For example, the Cas effector protein of the present invention has a more rigorous PAM recognition method, thereby significantly reducing off-target effects.

DESCRIPTION OF THE DRAWINGS

FIG. 7 shows a result of the effect of different repeat lengths on the enzyme cleavage activity in the CRISPR/Cas12j. 19 system. WT represents a repeat sequence without truncation.

FIG. 8 shows a result of CRISPR/Cas12j.19 system's tolerance to spacer mismatches. WT represents a spacer sequence without mutation.

SEQUENCE INFORMATION

Figure 1:
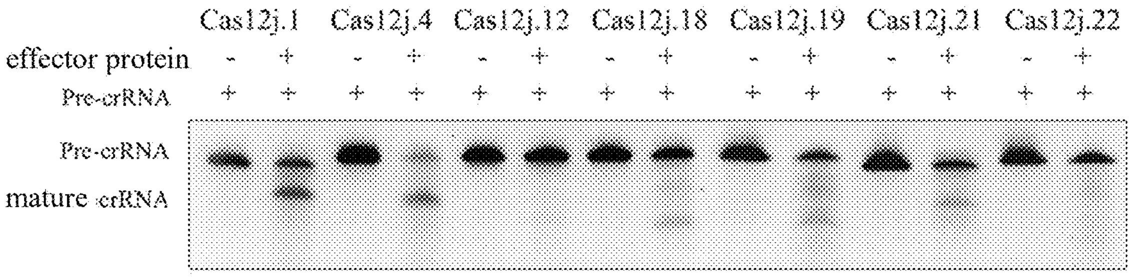
FIG. 1 shows a gel electrophoresis result of pre-crRNA processing by cas12j protein.

Partial sequence information involved in the present invention is provided in Table 1 below.

TABLE 1

Description of the sequence

| SEQ ID NO: | Description |
|---|---|
| 1 | amino acid sequence of Cas12j.3 |
| 2 | amino acid sequence of Cas12j.4 |
| 3 | amino acid sequence of Cas12j.5 |
| 4 | amino acid sequence of Cas12j.6 |
| 5 | amino acid sequence of Cas12j.7 |
| 6 | amino acid sequence of Cas12j.8 |
| 7 | amino acid sequence of Cas12j.9 |
| 8 | amino acid sequence of Cas12j.10 |
| 9 | amino acid sequence of Cas12j.11 |
| 10 | amino acid sequence of Cas12j.12 |
| 11 | amino acid sequence of Cas12j.13 |
| 12 | amino acid sequence of Cas12j.14 |
| 13 | amino acid sequence of Cas12j.15 |
| 14 | amino acid sequence of Cas12j.16 |
| 15 | amino acid sequence of Cas12j.17 |
| 16 | amino acid sequence of Cas12j.18 |
| 17 | amino acid sequence of Cas12j.19 |
| 18 | amino acid sequence of Cas12j.20 |
| 19 | amino acid sequence of Cas12j.21 |
| 20 | amino acid sequence of Cas12j.22 |
| 21 | an encoding nucleic acid sequence of Cas12j.3 |
| 22 | an encoding nucleic acid sequence of Cas12j.4 |
| 23 | an encoding nucleic acid sequence of Cas12j.5 |
| 24 | an encoding nucleic acid sequence of Cas12j.6 |
| 25 | an encoding nucleic acid sequence of Cas12j.7 |
| 26 | an encoding nucleic acid sequence of Cas12j.8 |
| 27 | an encoding nucleic acid sequence of Cas12j.9 |
| 28 | an encoding nucleic acid sequence of Cas12j.10 |
| 29 | an encoding nucleic acid sequence of Cas12j.11 |
| 30 | an encoding nucleic acid sequence of Cas12j.12 |
| 31 | an encoding nucleic acid sequence of Cas12j.13 |
| 32 | an encoding nucleic acid sequence of Cas12j.14 |
| 33 | an encoding nucleic acid sequence of Cas12j.15 |
| 34 | an encoding nucleic acid sequence of Cas12j.16 |
| 35 | an encoding nucleic acid sequence of Cas12j.17 |
| 36 | an encoding nucleic acid sequence of Cas12j.18 |
| 37 | an encoding nucleic acid sequence of Cas12j.19 |
| 38 | an encoding nucleic acid sequence of Cas12j.20 |
| 39 | an encoding nucleic acid sequence of Cas12j.21 |
| 40 | an encoding nucleic acid sequence of Cas12j.22 |
| 41 | Cas12j.3 prototype direct repeat sequence |
| 42 | Cas12j.4 prototype direct repeat sequence |
| 43 | Cas12j.5 prototype direct repeat sequence |
| 44 | Cas12j.6 prototype direct repeat sequence |
| 45 | Cas12j.7 prototype direct repeat sequence |
| 46 | Cas12j.8 prototype direct repeat sequence |
| 47 | Cas12j.9 prototype direct repeat sequence |
| 48 | Cas12j.10 prototype direct repeat sequence |
| 49 | Cas12j.11 prototype direct repeat sequence |
| 50 | Cas12j.12 prototype direct repeat sequence |
| 51 | Cas12j.13 prototype direct repeat sequence |
| 52 | Cas12j.14 prototype direct repeat sequence |
| 53 | Cas12j.15 prototype direct repeat sequence |
| 54 | Cas12j.16 prototype direct repeat sequence |
| 55 | Cas12j.17 prototype direct repeat sequence |
| 56 | Cas12j.18 prototype direct repeat sequence |
| 57 | Cas12j.19 prototype direct repeat sequence |
| 58 | Cas12j.20 prototype direct repeat sequence |
| 59 | Cas12j.21 prototype direct repeat sequence |

TABLE 1-continued

| Description of the sequence | |
|---|---|
| SEQ ID NO: | Description |
| 60 | Cas12j.22 prototype direct repeat sequence |
| 61 | a coding nucleic acid sequence of Cas12j.3 prototype direct repeat sequence |
| 62 | a coding nucleic acid sequence of Cas12j.4 prototype direct repeat sequence |
| 63 | a coding nucleic acid sequence of Cas12j.5 prototype direct repeat sequence |
| 64 | a coding nucleic acid sequence of Cas12j.6 prototype direct repeat sequence |
| 65 | a coding nucleic acid sequence of Cas12j.7 prototype direct repeat sequence |
| 66 | a coding nucleic acid sequence of Cas12j.8 prototype direct repeat sequence |
| 67 | a coding nucleic acid sequence of Cas12j.9 prototype direct repeat sequence |
| 68 | a coding nucleic acid sequence of Cas12j.10 prototype direct repeat sequence |
| 69 | a coding nucleic acid sequence of Cas12j.11 prototype direct repeat sequence |
| 70 | a coding nucleic acid sequence of Cas12j.12 prototype direct repeat sequence |
| 71 | a coding nucleic acid sequence of Cas12j.13 prototype direct repeat sequence |
| 72 | a coding nucleic acid sequence of Cas12j.14 prototype direct repeat sequence |
| 73 | a coding nucleic acid sequence of Cas12j.15 prototype direct repeat sequence |
| 74 | a coding nucleic acid sequence of Cas12j.16 prototype direct repeat sequence |
| 75 | a coding nucleic acid sequence of Cas12j.17 prototype direct repeat sequence |
| 76 | a coding nucleic acid sequence of Cas12j.18 prototype direct repeat sequence |
| 77 | a coding nucleic acid sequence of Cas12j.19 prototype direct repeat sequence |
| 78 | a coding nucleic acid sequence of Cas12j.20 prototype direct repeat sequence |
| 79 | a coding nucleic acid sequence of Cas12j.21 prototype direct repeat sequence |
| 80 | a coding nucleic acid sequence of Cas12j.22 prototype direct repeat sequence |
| 81 | NLS sequence |
| 82 | an amino acid sequence of Cas12j.3-NLS fusion protein |
| 83 | an amino acid sequence of Cas12j.4-NLS fusion protein |
| 84 | an amino acid sequence of Cas12j.5-NLS fusion protein |
| 85 | an amino acid sequence of Cas12j.6-NLS fusion protein |
| 86 | an amino acid sequence of Cas12j.7-NLS fusion protein |
| 87 | an amino acid sequence of Cas12j.8-NLS fusion protein |
| 88 | an amino acid sequence of Cas12j.9-NLS fusion protein |
| 89 | an amino acid sequence of Cas12j.10-NLS fusion protein |
| 90 | an amino acid sequence of Cas12j.11-NLS fusion protein |
| 91 | an amino acid sequence of Cas12j.12-NLS fusion protein |
| 92 | an amino acid sequence of Cas12j.13-NLS fusion protein |
| 93 | an amino acid sequence of Cas12j.14-NLS fusion protein |
| 94 | an amino acid sequence of Cas12j.15-NLS fusion protein |
| 95 | an amino acid sequence of Cas12j.16-NLS fusion protein |
| 96 | an amino acid sequence of Cas12j.17-NLS fusion protein |
| 97 | an amino acid sequence of Cas12j.18-NLS fusion protein |
| 98 | an amino acid sequence of Cas12j.19-NLS fusion protein |
| 99 | an amino acid sequence of Cas12j.20-NLS fusion protein |
| 100 | an amino acid sequence of Cas12j.21-NLS fusion protein |
| 101 | an amino acid sequence of Cas12j.22-NLS fusion protein |
| 102 | Plasmid expressing Cas12j.3 system |
| 103 | PAM library sequence |
| 104 | Pre-crRNA processing and PAM consumption guide RNA |
| 105 | Cas12j.19 guide RNA |
| 106 | targeted double-stranded DNA sequence |
| 107 | Cas12j.1 amino acid sequence |
| 108 | Cas12j.2 amino acid sequence |

DETAILED DESCRIPTION

The invention will now be described with reference to the following examples which are intended to illustrate the present invention rather than limit the present invention.

Unless otherwise specified, the experiments and methods described in the examples are basically performed according to conventional methods well known in the art and described in various references. For example, conventional techniques such as immunology, biochemistry, chemistry, molecular biology, microbiology, cell biology, genomics, and recombinant DNA used in the present invention can be found in Sambrook, Fritsch and Maniatis, "MOLECULAR CLONING: A LABORATORY MANUAL", 2nd edition (1989); "CURRENT PROTOCOLS IN MOLECULAR BIOLOGY" (edited by F. M. Ausubel et al., (1987)); "METHODS IN ENZYMOLOGY" series (Academic Publishing Company): "PCR 2: A PRACTICAL APPROACH" (edited by M. J. MacPherson, BD Hames and G. R. Taylor (1995)), "ANTIBODIES, A LABORATORY MANUAL", edited by Harlow and Lane (1988), and "ANIMAL CELL CULTURE" (edited by R. I. Freshney (1987)).

In addition, if the specific conditions are not specified in the examples, it shall be carried out in accordance with the conventional conditions or the conditions recommended by the manufacturer. The reagents or instruments used without the manufacturer's indication are all conventional products that can be purchased commercially. Those skilled in the art know that the embodiments describe the present invention by way of example, and are not intended to limit the scope of protection claimed by the present invention. All publications and other references mentioned in this article are incorporated into this article by reference in their entirety.

The sources of some reagents involved in the following examples are as follows:

LB liquid medium: 10 g Tryptone, 5 g Yeast Extract, 10 g NaCl, diluted to 1 L, and sterilized. If antibiotics are needed, they are added at a final concentration of 50 μg/ml after cooling the medium.

Chloroform/isoamyl alcohol: adding 240 ml of chloroform to 10 ml of isoamyl alcohol and mixing them well.

RNP buffer: 100 mM sodium chloride, 50 mM Tris-HCl, 10 mM $MgCl_2$, 100 μg/ml BSA, pH 7.9.

The prokaryotic expression vectors pACYC-Duet-1 and pUC19 are purchased from Genscript Biotech Corporation.

*E. coli* competence EC100 is purchased from Epicentre company.

Example 1. Acquisition of Cas12j Gene and Cas12j Guide RNA

1. CRISPR and gene annotation: using Prodigal to perform gene annotation on the microbial genome and metagenomic data of NCBI and JGI databases to obtain all proteins. At the same time, using Piler-CR to annotate CRISPR locus. The parameters are the default parameters.

2. Protein filtering: Eliminating redundancy of annotated proteins by sequence identity, removing proteins with exactly identical sequence, and at the same time classifying proteins longer than 800 amino acids into macromolecular proteins. Since all the effector proteins of the second type of CRISPR/Cas system discovered so far are more than 900 amino acids in length, in order to reduce the computational complexity, when we are mining CRISPR effector proteins, we only consider macromolecular proteins larger than 800 amino acids.

3. Obtaining CRISPR-associated macromolecular proteins: extending each CRISPR locus by 10 Kb upstream and downstream, and identifying non-redundant macromolecular proteins in the adjacent interval of CRISPR.

4. Clustering of CRISPR-associated macromolecular proteins: using BLASTP to perform internal pairwise comparisons of non-redundant macromolecular CRISPR-associated proteins, and output the comparison result of Evalue<1E-10. Using MCL to perform cluster analysis on the output result of BLASTP, CRISPR-associated protein family.

5. Identification of CRISPR-enriched macromolecular protein family: using BLASTP to compare the proteins of the CRISPR-associated protein family to the non-redundant macromolecular protein database that removes the CRISPR-associated proteins and output the comparison result of Evalue<1E-10. If the homologous protein found in a non-CRISPR-associated protein database is less than 100%, it means that the proteins of this family are enriched in the CRISPR region. In this way, we identify the CRISPR-enriched macromolecular protein family. 6. Annotation of protein functions and domains: using the Pfam database, NR database and Cas protein collected from NCBI to annotate the CRISPR-enriched macromolecular protein family to obtain a new CRISPR/Cas protein family. Using Mafft to perform multiple sequence alignments for each CRISPR/Cas family protein, and then using JPred and HHpred to perform conserved domain analysis to identify protein families containing RuvC domains.

On this basis, the present inventors have obtained a new Cas effector protein, namely Cas12j, named Cas12j.3 (SEQ ID NO: 1), Cas12j.4 (SEQ ID NO: 2), Cas12j.5 (SEQ ID NO: 3), Cas12j.6 (SEQ ID NO: 4), Cas12j.7 (SEQ ID NO: 5), Cas12j.8 (SEQ ID NO: 6), Cas12j.9 (SEQ ID NO: 7), Cas12j.10 (SEQ ID NO: 8), Cas12j.11 (SEQ ID NO: 9), Cas12j.12 (SEQ ID NO: 10), Cas12j.13 (SEQ ID NO: 11), Cas12j.14 (SEQ ID NO: 12), Cas12j.15 (SEQ ID NO: 13), Cas12j.16 (SEQ ID NO: 14), Cas12j.17 (SEQ ID NO: 15), Cas12j.18 (SEQ ID NO: 16), Cas12j.19 (SEQ ID NO: 17), Cas12j.20 (SEQ ID NO: 18), Cas12j.21 (SEQ ID NO: 19), Cas12j.22 (SEQ ID NO: 20), Cas12j.1 (SEQ ID NO: 107), Cas12j.2 (SEQ ID NO: 108), respectively with its 22 active homologue sequences. The coding DNA of 20 homologues are shown in SEQ ID NOs: 21-40, respectively.

The prototype direct repeat sequences (repeat sequences contained in pre-crRNA) corresponding to Cas12j.3, Cas12j.4, Cas12j.5, Cas12j.6, Cas12j.7, Cas12j.8, Cas12j.9, Cas12j.10, Cas12j.11, Cas12j.12, Cas12j.13, Cas12j.14, Cas12j. 15, Cas12j.16, Cas12j.17, Cas12j.18, Cas12j.19, Cas12j.20 are shown in SEQ ID NOs: 41-60, respectively.

Example 2. Processing of Pre-crRNA by Cas12j Gene

I. In Vitro Expression and Purification of Cas12j Protein

The specific steps of in vitro expression and purification of Cas12j protein were as follows:

1. Artificially synthesizing DNA sequence encoding Cas12j protein (SEQ ID NO: 82-101) with nuclear localization signal.

2. Connecting the double-stranded DNA molecule synthesized in step 1 with the prokaryotic expression vector pET-30a (+) to obtain a recombinant plasmid pET-30a-CRISPR/Cas12j.

3. Introducing the recombinant plasmid pET-30a-CRISPR/Cas12j into *E. coli* EC100 to obtain a recombinant bacteria, which is named EC100-CRISPR/Cas12j.

Taking a single clone of EC100-CRISPR/Cas12j, inoculating it into 100 mL LB liquid medium (containing 50 μg/mL ampicillin), culturing it with shaking at 37° C. and 200 rpm for 12 h to obtain a culture bacteria liquid.

4. Taking the culture bacteria liquid, inoculated to 50 mL LB liquid medium (containing 50 μg/mL ampicillin) at a volume ratio of 1:100, cultured with shaking at 37° C. and 200 rpm until the $OD_{600nm}$ value is 0.6, then adding IPTG and making the concentration 1 mM, cultured with shaking at 28° C., 220 rpm for 4 h, centrifuged at 4° C., 10000 rpm for 10 min, and the bacterial precipitation was collected.

5. Taking the bacterial precipitation, adding 100 mL of pH 8.0, 100 mM Tris-HCl buffer, subjected to ultrasonication after resuspension (ultrasonic power 600 W, cycle program: broken for 4 s, stopped for 6 s, 20 min in total), then centrifuged at 4° C., 10000 rpm for 10 min, collecting the supernatant A.

6. Taking the supernatant A, centrifuged at 12000 rpm at 4° C. for 10 min, and the supernatant B was collected.

7. Using the nickel column produced by GE to purify the supernatant B (refer to the instructions of the nickel column for the specific purification steps), and then using the protein quantification kit produced by Thermo Fisher to quantify the Cas12j protein.

II. Transcription and Purification of Cas12j Protein Guide RNA:

1. Designing a template for guide RNA transcription. The structure of the transcription template is: T7 promoter+Cas12j prototype repeat (SEQ ID NO: 41-60)+spacer (SEQ ID NO: 104), primer design uses Primer5.0 software to ensure that the forward primer and reverse primer have at least 18 bp overlapping sequence.

2. Configuring the following reaction system, gently pipetted to mix, centrifuged briefly, and annealed slowly in a PCR machine:

PCR amplification reaction

| component | volume (μl) |
|---|---|
| Forward primer (100 nM) | 7.5 |
| Reverse primer (100 nM) | 7.5 |
| 2 * KAPA Mix | 25 |
| $ddH_2O$ | 10 |
| total volume | 50 |

Primer annealing PCR reaction procedure

| Temperature (° C.) | Time | ramp at(° C./s) |
|---|---|---|
| 98° C. | 5 min | 2° C./s |
| 85° C./95° C. | 0.05 s | — |
| 85° C. | 1 min | 0.03° C./s |
| 75° C./85° C. | 0.05 s | — |
| 75° C. | 1 min | 0.03° C./s |
| 72° C./75° C. | 0.05 s | — |
| 72° C. | 1 min | 0.03° C./s |
| 55° C./65° C. | 0.05 s | — |
| 55° C. | 1 min | 0.03° C./s |
| 45° C./55° C. | 0.05 s | — |
| 45° C. | 1 min | 0.03° C./s |
| 35° C./45° C. | 0.05 s | — |
| 35° C. | 1 min | 0.03° C./s |
| 30° C./35° C. | 0.05 s | — |
| 30° C. | 1 min | 0.03° C./s |
| 25° C. | 1 min | — |
| 10° C. | forever | — |

3. Using the MinElute PCR Purification Kit to purify the template. The steps are as follows:

1) Adding 5 times the volume of PB to the PCR product, putting a MinElute column on a 2 ml collection tube, and placing it at room temperature for 2 min, 12000 g/2 min;

2) Discarding the waste liquid and adding 750 µl Buffer PE (remember to add ethanol before use), 12000 g/2 min;

3) Discarding the waste liquid, adding 3541 Buffer PE, 12000 g/2 min, discarding the waste liquid, 12000 g, and vacuum centrifuged for 2 min;

4) Changing the MinElute column to a new 1.5 ml centrifuge tube, opening the cap, and placing it at 65° C. for 2 minutes;

5) Adding 20 µl of preheated EB solution and placing it for 2 min, 12000 g/2 min, in order to improve the recovery rate, the contents of the centrifuge tube can be passed through the MinElute spin column for 2-3 times;

6) Measuring the concentration with Nanodrop and stored at −20° C., ready for use.

4. Purification of guide RNA: phenol:chloroform:isoamyl alcohol (25:24:1) extraction to remove DNAseI in the system 1) Adding 80 µl RNA free $H_2O$ to the post-transcription reaction system and adjusting the volume to 100 µl;

2) Taking out 2 ml Phase Lock Gel (PLG) Heavy, 15000 g, centrifuged for 2 min, adding 100 µl phenol:chloroform:isoamyl alcohol (25:24:1), 100 µl RNA digested with DNAseI, gently flicking the Phase-Lock tube 5-10 times by hand to make it evenly mixed, then centrifuged at 15° C./16000 g for 12 min;

3) Taking a new RNA-free 1.5 ml centrifuge tube and aspirating the supernatant from the previous centrifugation into the centrifuge tube. Be careful not to absorb the gel, adding isopropanol equal to the volume of the supernatant and one-tenth volume of sodium acetate solution, mixed well with pipette tip, putting it in the refrigerator at −20° C. for 1 h or overnight;

4) Centrifuged at 4° C./16000 g for 30 min, discarding the supernatant, adding 75% of pre-cooled ethanol, mixing the precipitate well by pipetting, centrifuged at 4° C./16000 g for 12 min, discarding the supernatant, and placed for 2-3 min in a fume cupboard. Drying the ethanol on the surface of the RNA, adding 100 µl of RNA free $H_2O$, and mixed by pipetting.

5) Measuring the purified crRNA concentration with Nanodrop, and uniformly diluted to 250 ng/µl, dispensed into 200 µl of PCR centrifuge tubes, and stored at −80° C., ready for use.

4. The precrRNA transcription of Cas12f uses NEB's HiScribe T7 high-efficiency RNA synthesis kit. The reaction system is shown in the following table:

DNA transcription system

| Component | Volume (µl) |
|---|---|
| ATP (100 mM) | 2 |
| GTP (100 nM) | 2 |
| CTP (100 nM) | 2 |
| UTP (100 nM) | 2 |
| 10 * Reaction buffer | 2 |
| T7 RNA Polymerase Mix | 2 |
| DNA template | 8 |
| total | 20 |

Setting the PCR reaction procedure as: 37° C./3 h or 31° C./forever, adding DNAseI, 37° C./45 min 5. Purification of PrecrRNA:

(1) Phenol:chloroform:isoamyl alcohol (25:24:1) extraction to remove DNAseI in the system 1) Adding 80 µl of RNA free $H_2O$ to the post-transcription reaction system and adjusting the volume to 100 µl;

2) Taking out 2 ml of Phase Lock Gel (PLG) Heavy, 15000 g, centrifuged for 2 min, adding 100 µl of phenol:chloroform:isoamyl alcohol (25:24:1), 100 µl of RNA digested with DNAseI, gently flicking the Phase-Lock tube by hand 5-10 times to make it evenly mixed, then centrifuged at 15° C./16000 g for 12 min;

3) Taking a new RNA-free of 1.5 ml centrifuge tube and aspirating the supernatant from step 0 into the centrifuge tube. Be careful not to get the gel, adding isopropanol equal to the volume of the supernatant and one-tenth volume of sodium acetate solution, mixed well with pipette tip, putting it in the refrigerator at −20° C. for 1 h or overnight;

4) Centrifuged at 4° C./16000 g for 30 min, discarding the supernatant, adding 75% of pre-cooled ethanol, mixing the precipitate well by pipetting, centrifuged at 4° C./16000 g for 12 min, discarding the supernatant, and placed for 2-3 min in a fume cupboard. Drying the ethanol on the surface of the RNA, adding 100 µl of RNA free $H_2O$, and mixed by pipetting.

(2) Running the gel and purifying the precrRNA from the polyacrylamide gel, using ZR Small-RNA™ PAGE Recovery Kit from ZYMO RESEARCH to purify and recover the precrRNA. Steps are shown as follows:

1) The size of the precrRNA band is about 90 bp, cutting the RNA fragment of the corresponding band, and transferring it to a 1.5 ml RNA-free centrifuge tube;

2) Using Squisher™-single to completely mash the gel, adding 400 µl of RNA Recovery Buffer, and heated in a 65° C. water bath for 15 minutes;

3) Quick freezing in liquid nitrogen for 5 minutes, immediately taking it out and putting it in a 65° C. water bath to heat for 5 minutes;

4) Taking out the Zymo-Spin™ IV column on the collection tube, then adding the dissolved gel to it, centrifuged at 12000 g for 5 minutes, and retaining the liquid in the collection tube;

5) Taking out the Zymo-Spin™ IIIC column on a new collection tube, adding the liquid collected in the previous step to it, centrifuged at 2000 g for 2 minutes, and retaining the liquid in the collection tube;

6) Estimating the volume of liquid in the collection tube, adding 2 times the volume of RNA MAX Buffer, and mixed upside down;

7) Taking out the Zymo-Spin™ IC column in a new collection tube, adding the liquid in the collection tube of step ⑥ into it, placed for 2 minutes, and centrifuged at 12000 g for 2 minutes;

8) Adding 800 μl RNA Wash Buffer (note that adding a certain volume of absolute ethanol according to the instructions before use), centrifuged at 12000 g for 2 min, and discarding the liquid in the collection tube;

9) Adding 400 μl RNA Wash Buffer, centrifuged at 12000 g for 2 min, discarding the liquid in the collection tube, and then vacuum centrifuged for 2 min;

10) Placed in a 65° C. oven for 1 min, adding 20 μl RNA-free $H_2O$, measuring the concentration of the collected precrRNA with nanodrop, and uniformly adjusting the concentration to 200 ng/μl, dispensed into PCR centrifuge tubes, and stored frozen at minus 80° C., ready for use.

6. Establishment of an In Vitro Pre-crRNA Digestion System (1) Configuring the following reaction system, mixed gently by pipetting and centrifuged briefly. Placed at 37° C., 1 hour;

In vitro pre-crRNA digestion system

| Reagent | Dosage |
|---|---|
| pre-crRNA | 400 ng |
| Cas protein | 1 μg |
| RNA Cleavage Buffer | 1 μL |
| RNA-free $H_2O$ | make up to 10 μL |

(2) Adding 10 μl 2×RNA loading dye to the above reaction system and placed at 98° C. for 3 min. Placed on ice for 2 min immediately after the reaction is completed;

(3) Loading 10 μl in the sample well of 10% TBE-Urea polyacrylamide gel, 150V/40 min;

(4) Adding SYBR Gold nucleic acid gel stain dye to the 1×TBE electrophoresis buffer, placed in the gel, stained at room temperature for 10-15 minutes, and then scanning the gel.

The gel scanning results are shown in FIG. 1. The result shows that Cas12j.1, Cas12j.4, Cas12j.18, Cas12j.19, Cas12j.21, and Cas12j.22 have pre-crRNA cleavage activity in vitro.

Example 3. Identification of the PAM Domain of Cas12j Protein

1. Construction of the recombinant plasmid pACYC-Duet-1+CRISPR/Cas12j and sequencing According to the sequencing results, the structure of the recombinant plasmid pACYC-Duet-1+CRISPR/Cas12j is described as follows: replacing the small fragment between the restriction endonuclease of Pml I and Kpn I recognition sequences of the vector pACYC-Duet-1 with the Cas12j gene (in the sequence as shown in SEQ ID NO: 21-40, double-stranded DNA molecules from the 1st position from the 5' end to the last position at the 3' end). The recombinant plasmid pACYC-Duet-1+CRISPR/Cas12j expresses the Cas12j protein (SEQ ID NO: 1-20, 107, 108) and the Cas12j guide RNA as shown in SEQ ID NO: 104.

2. The recombinant plasmid pACYC-Duet-1+CRISPR/Cas12j contains an expression cassette, and the nucleotide sequence of the expression cassette is composed of Cas12j gene connected to SEQ ID NO: 104 respectively. For example, as shown in SEQ ID No: 102. In the sequence as shown in SEQ ID NO: 102, positions 1 to 44 from the 5' end is the nucleotide sequence of the pLacZ promoter, positions 45 to 3056 is the nucleotide sequence of the Cas12j.3 gene, and positions 3057 to 3143 is the nucleotide sequence of the rrnB T1 terminator (used to terminate transcription). From the 5' end, positions 3144 to 3178 is the nucleotide sequence of the J23119 promoter, positions 3179 to 3241 is the nucleotide sequence of the CRISPR array, and positions 3244 to 3268 is the nucleotide sequence of the rrnB-T2 terminator (used to terminate transcription).

3. Obtaining recombinant *Escherichia coli*: the recombinant plasmid pACYC-Duet-1+CRISPR/Cas12j was introduced into *Escherichia coli* EC100 to obtain recombinant *Escherichia coli*, named EC100/pACYC-Duet-1+CRISPR/Cas12j. The recombinant plasmid pACYC-Duet-1 was introduced into *E. coli* EC100 to obtain a recombinant *E. coli* named EC100/pACYC-Duet-1.

4. Construction of the PAM library: the sequence as shown in SEQ ID NO: 103 is artificially synthesized and connected to the pUC19 vector, wherein the sequence as shown in SEQ ID NO: 103 includes eight random bases at the 5' end and the target sequence. Eight random bases were designed in front of the 5' end of the target sequence of the PAM library to construct a plasmid library. The plasmids were transferred into *Escherichia coli* containing the Cas12j locus and *Escherichia coli* without the Cas.12j locus, respectively. After treatment at 37° C. for 1 hour, we extracted the plasmid, and performed PCR amplification and sequencing on the sequence of the PAM region.

Figure 2A:
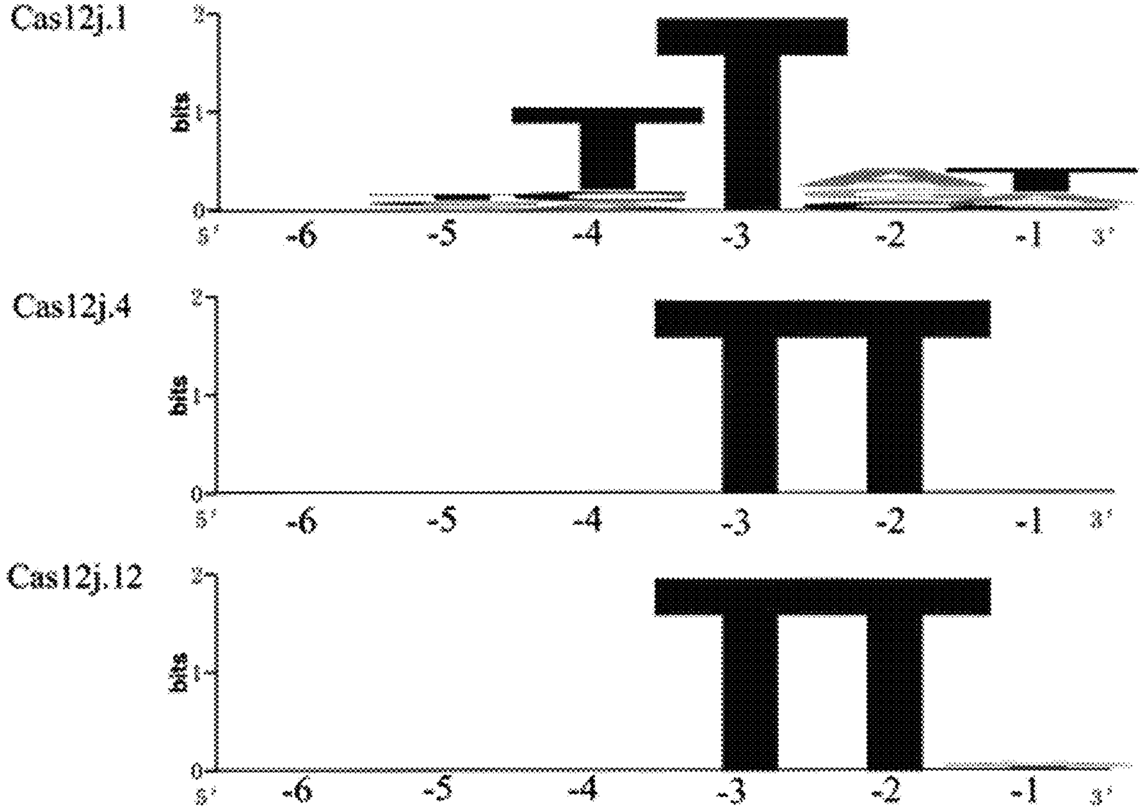
FIGS. 2A-2B show a result of the analysis of the PAM domain of the cas12j protein.
Figure 2B:
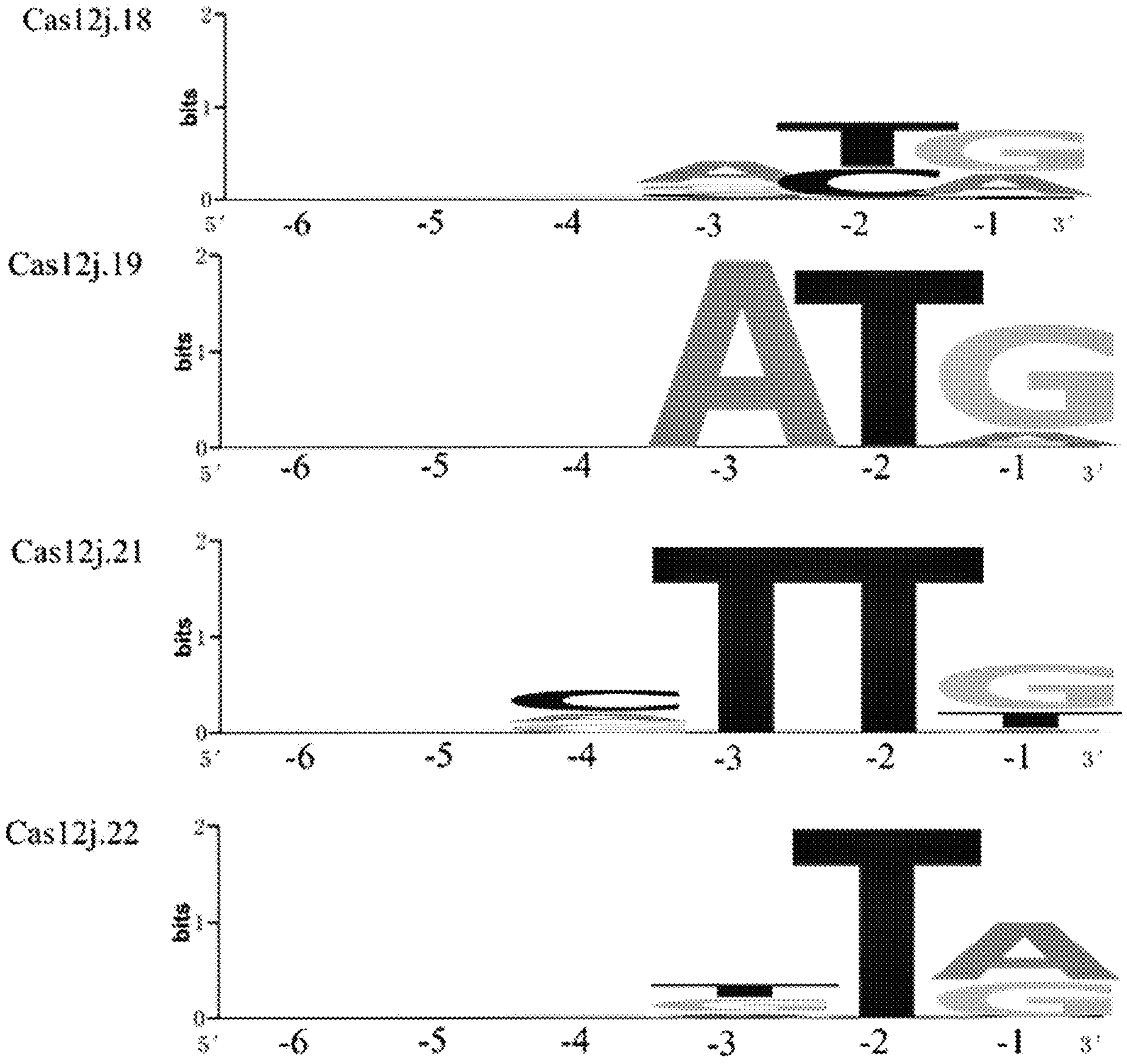

5. The acquisition of the PAM library domain: counting the number of appearances of 65,536 combinations of PAM sequences in the experimental group and the control group, respectively, and the number of PAM sequences in each group was subjected to normalization. For any PAM sequence, when log 2 (Normalized value of control group/normalized value of experimental group) is greater than 3.5, we consider this PAM to be significantly consumed. We used Weblogo to predict the PAM sequence that was significantly consumed, and have found the PAM domain of each protein. Among them, Cas12j.1 is 5'-TTVW, Cas12j.4 and Cas12j.12 are 5'-TTN, and Cas12j.18 is 5'.-AYR, Cas12j.19 is 5'-ATG, Cas12j.21 is 5'-VTTG, Cas12j.22 is 5'-KTR. The PAM domain analysis results are shown in FIGS. 2A-2B.

Example 4. Identification of DNA Cutting Method of CRISPR/Cas12j System

I. In Vitro Expression and Purification of Cas12j Protein

The specific steps of in vitro expression and purification of Cas12j protein are as follows:

1. Artificially synthesizing DNA sequence encoding Cas12j protein (SEQ ID NO: 82-101) with nuclear localization signal.

2. Connecting the double-stranded DNA molecule synthesized in step 1 with the prokaryotic expression vector pET-30a (+) to obtain a recombinant plasmid pET-30a-CRISPR/Cas12j.

3. Introducing the recombinant plasmid pET-30a-CRISPR/Cas12j into *E. coli* EC100 to obtain a recombinant bacteria, which is named EC100-CRISPR/Cas12j.

Taking a single clone of EC100-CRISPR/Cas12j, inoculated into 100 mL LB liquid medium (containing 50 μg/mL ampicillin), cultured with shaking at 37° C. and 200 rpm for 12 h to obtain a culture bacteria solution.

4. Taking the culture bacteria solution, inoculated to 50 mL LB liquid medium (containing 50 μg/mL ampicillin) at a volume ratio of 1:100, cultured with shaking at 37° C. and 200 rpm until the $OD_{600nm}$ value is 0.6, then adding IPTG and making the concentration 1 mM, cultured with shaking at 28° C. and 220 rpm for 4 hours, and centrifuged at 4° C. and 10000 rpm for 10 minutes to collect the bacteria precipitation.

5. Taking the bacteria precipitation, adding 100 mL pH 8.0, 100 mM Tris-HCl buffer solution, subjected to ultrasonication after resuspension (ultrasonic power 600 W, cycle program: broken for 4 s, stopped for 6 s, 20 min in total), then centrifuged at 4° C., 10000 rpm for 10 min, collecting the supernatant A.

6. Taking the supernatant A, centrifuged at 12000 rpm at 4° C. for 10 min, and collecting the supernatant B.

7. Using the nickel column produced by GE to purify the supernatant B (refer to the instructions of the nickel column for the specific steps of purification), and then using the protein quantification kit produced by Thermo Fisher to quantify the Cas12j protein.

II. Transcription and Purification of Cas12j Protein Guide RNA:

1. Designing a template for guide RNA transcription. The structure of the transcription template is: T7 promoter+ Cas12j prototype repeat (SEQ ID NO: 41-60)+spacer (SEQ ID NO: 105), primer design uses Primer 5.0 software to ensure that the forward primer and reverse primer have at least 18 bp overlapping sequence.

2. Configuring the following reaction system, gently pipetted to mix, centrifuged briefly, and annealed slowly in a PCR machine:

PCR amplification reaction

| component | Volume (μl) |
|---|---|
| Forward primer (100 nM) | 7.5 |
| Reverse primer (100 nM) | 7.5 |
| 2 * KAPA Mix | 25 |
| $ddH_2O$ | 10 |
| total volume | 50 |

3. Using the MinElute PCR Purification Kit to purify the template. The steps are as follows:

1) Adding 5 times the volume of PB to the PCR product, putting a MinElute column on a 2 ml collection tube, and placed at room temperature for 2 min, 12000 g/2 min;
2) Discarding the waste liquor and adding 750 μl Buffer PE (remember to add ethanol before use), 12000 g/2 min;
3) Discarding the waste liquor, adding 3541 Buffer PE, 12000 g/2 min, discarding the waste liquor, 12000 g, and vacuum centrifuged for 2 min;
4) Changing the MinElute column to a new 1.5 ml centrifuge tube, opening the cap, and placed at 65° C. for 2 minutes;
5) Adding 20 μl of preheated EB solution and placed for 2 min, 12000 g/2 min. In order to improve the recovery rate, the contents of the centrifuge tube can be passed through the MinElute spin column 2-3 times;
6) Measuring the concentration with Nanodrop and frozen stored at −20° C., ready for use.

4. Purification of guide RNA: phenol:chloroform:isoamyl alcohol (25:24:1) extraction to remove DNAseI in the system 1) Adding 80 μl RNA free $H_2O$ to the post-transcription reaction system and adjusting the volume to 100 μl;
2) Taking out 2 ml Phase Lock Gel (PLG) Heavy, 15000 g, centrifuged for 2 min, adding 100 μl phenol:chloroform:isoamyl alcohol (25:24:1), 100 μl RNA digested with DNAseI, gently flicking the Phase-Lock tube by hand 5-10 times to make it evenly mixed, then centrifuged at 15° C./16000 g for 12 min;
3) Taking a new RNA-free 1.5 ml centrifuge tube and aspirating the supernatant from the previous centrifugation into the centrifuge tube. Be careful not to get the gel, adding isopropanol equal to the volume of the supernatant and one-tenth volume of sodium acetate solution, mixed well with pipette tip, putting it in the refrigerator at −20° C. for 1 h or overnight;
4) Centrifuged at 4° C./16000 g for 30 min, discarding the supernatant, adding 75% pre-cooled ethanol, mixed the precipitate by pipetting, centrifuged at 4° C./16000 g for 12 min, discarding the supernatant, and placed for 2-3 min in a fume cupboard. Drying the ethanol on the surface of the RNA, adding 100 μl of RNA free $H_2O$, and mixed by pipetting.

5. Measuring the purified crRNA concentration with Nanodrop, and uniformly diluted to 250 ng/μl, dispensed into 200 μl PCR centrifuge tubes, and frozen stored at −80° C., ready for use.

6. the Establishment of Double-Stranded DNA Digestion System:

(1) Configuring the following reaction system, mixed gently by pipetting and centrifuged briefly. Placed at 37° C. for 15 min;

DNA cleavage reaction system

| component | Sample volume |
|---|---|
| 12j-crRNA (250 ng/μl) | 600 ng |
| 12j protein (0.5 μg/μl) | 0.5 μg |
| 10 * DNA Cleavage buffer | 1 μl |
| RNA-Free $H_2O$ | Make up to 7 μl |

(2) Adding 300 ng substrate DNA (SEQ ID NO: 106) (100 ng/μl), 3 μL, gently pipetted to mix, and centrifuged briefly. Placed at 37° C., 8 hours;
(3) Adding RNase and placed at 37° C. for 15 minutes to fully digest the RNA impurities in the system;
(4) Adding proteinase K, placed at 58° C. for 15 minutes, and digesting Cas12j protein;
(5) Agarose running gel for the detection.

Figure 3:
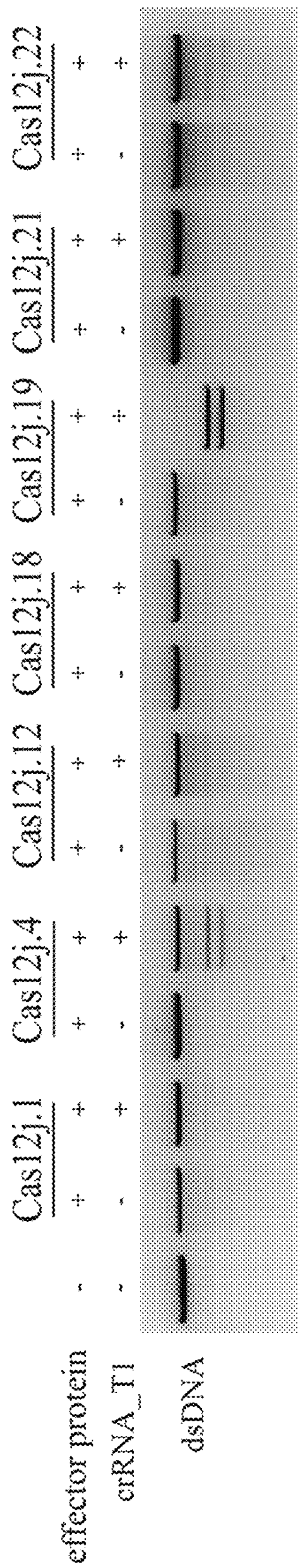
FIG. 3 shows an identification result of the DNA cutting method of the CRISPR/Cas12j system.

The result of the running gel is shown in FIG. 3. Cas12j.4, Cas12j.19 and Cas12j.22 can cut double-stranded DNA effectively. However, the cleavage activity of Cas12j.22 is very weak.

III. The Results of In Vitro Cleavage Site Analysis of Cas12j.4, Cas12j.19, and Cas12j.22

Figure 4:
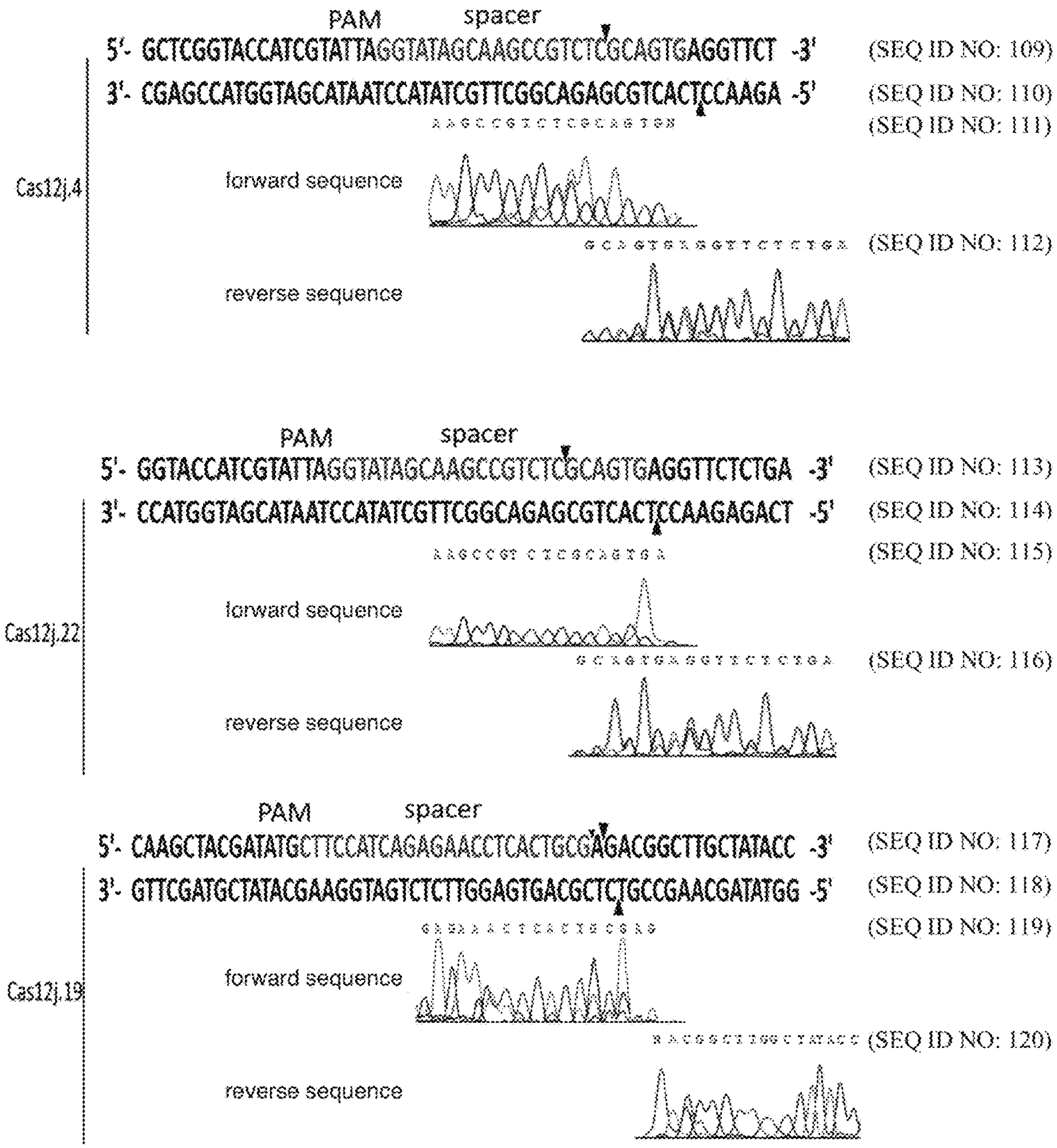
FIG. 4 shows a result of in vitro cleavage site analysis of Cas12j.4, Cas12j.19 and Cas12j.22.

Next, we analyzed the in vitro cleavage active sites of these three proteins with DNA double-strand cleavage activity. We recovered the strips cut in the previous step and sent them to the company for Sanger sequencing. Sequencing results are compared with seqman software. The comparison results are shown in FIG. 4. From the peak diagram we can see: Cas12j.4, Cas12j.19, Cas12j.22 have different cleavage methods, the cleavage sites of Cas12j.4 and Cas12j.22 are located at 18 nt and 25 nt at the end of PAM. After cutting, a Int sticky end is formed. Cas12j.19 has a cleavage site 25 nt away from the distal end of PAM, forming an end of about 1 nt.

Figure 5:
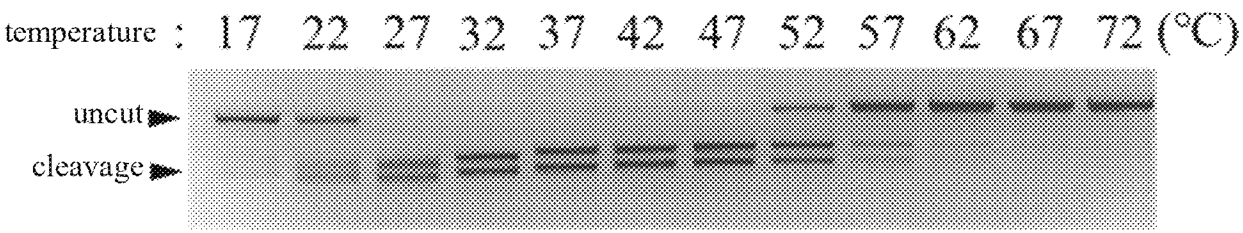
FIG. 5 shows a result of in vitro digestion activity of Cas12j.19 at different temperatures.

Example 5. The Results of In Vitro Enzyme Cleavage Activity Detection of Cas12j.19 at Different Temperatures Incubating Cas12j.19 (SEQ ID NO: 17) and guide RNA (SEQ ID NO: 105) at 25° C. for 15 minutes to form a mixture of RNA and protein, usually called RNP, and then adding double-stranded DNA (SEQ ID NO: 106) to the reaction system, and placed in different temperature settings, the set temperatures are: 17° C., 22° C., 27° C., 32° C., 37° C., 42° C., 47° C., 52° C., 62° C., 67° C., 72° C., reacted for 8 h, adding RNase after the reaction is completed, digesting RNA for 15 minutes at 37° C., and proteinase K, reacted at 58° C. for 15 minutes to digest the protein, and the result of DNA consumption was detected by agarose gel electrophoresis. The results are shown in FIG. 5. The result shows that Cas12j.19 has double-stranded DNA cleavage activity between 27° C. and 42° C.

Figure 6:
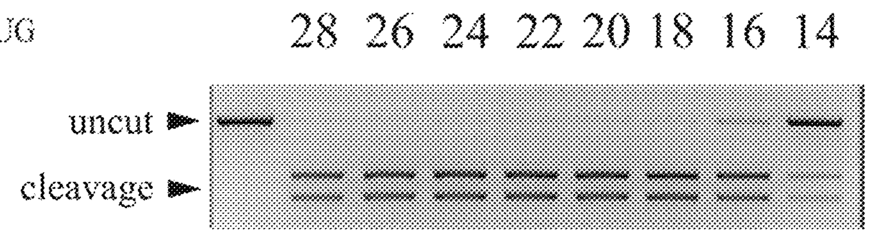
FIG. 6 shows a result of the effect of different spacer lengths on the enzyme cleavage activity in the CRISPR/Cas12j.19 system.

Example 6. Results of the Effect of Different Spacer Lengths of Cas12j.19 on Enzyme Cleavage Activity Since the cleavage site of Cas12j.19 is outside the target sequence, we further tested the Cas12j.19 guide RNA (SEQ ID NO: 105) containing the sequence of the target site, also commonly referred to the influence of the length of the spacer sequence on the cleavage activity. The guide RNA containing the target site sequence was truncated (14-28 nt) to obtain the truncation as shown in FIG. 6. Cas12j.19 and the truncated guide RNA were incubated at 25° C. for 15 minutes to form RNP, and then adding double-stranded DNA (SEQ ID NO: 106) to the reaction system, and reacted at 37° C. for 8 hours. After the reaction was completed, RNase was added, the RNA was digested at 37° C. for 15 minutes, and the proteinase K was reacted at 58° C. for 15 minutes to digest the protein, and the digestion results were detected by agarose gel electrophoresis. The results are shown in FIG. 6. The result shows that the spacer length required for Cas12j.19 to exert its cleavage activity is at least 14 nt.

Example 7. Results of the Effect of Different Repeat Lengths of Cas12j.19 on Enzyme Cleavage Activity Similarly, we tested the effect of the length of the direct repeat sequence of the guide RNA on the cleavage activity of Cas12j.19 double-stranded DNA. We truncated the direct repeat sequence in the guide RNA (SEQ ID NO: 105) to 2434 nt to obtain the truncation in FIG. 7. The Cas12j.19 and the corresponding guide RNA with different repeat lengths were incubated at 25° C. for 15 minutes to form RNP, then adding double-stranded DNA to the reaction system, and reacted at 37° C. for 8 hours. After the reaction, RNase was added, the RNA was digested at 37° C. for 15 minutes, and the proteinase K was reacted at 58° C. for 15 minutes to digest the protein, and the digestion results were detected by agarose gel electrophoresis. The result is shown in FIG. 7. The result shows that the shortest direct repeat sequence required for detection has a length of 32 nt.

Example 8. Results of Cas12j.19's Tolerance to Spacer Mismatch

The complementary pairing between the sequence containing the target site in the guide RNA and the original target sequence is of great significance for DNA recombination and cleavage. The part of the guide RNA (SEQ ID NO: 105) that contains the target sequence was subjected to point mutations successively (that is, the bases at positions 1, 3, 5, 7, 9, 11, 13, 15, 17 starting from the 5' end of the spacer) to obtain the mutant in FIG. 8, thereby forming a mismatch with the target sequence. Incubating Cas12j.19 with the corresponding guide RNA containing the mutation site at 25° C. for 15 minutes to form RNP, and then adding double-stranded DNA (SEQ ID NO: 106) to the reaction system at 37° C. and reacted for 8 hours. After the reaction, RNase was added, the RNA was digested at 37° C. for 15 minutes, and the proteinase K was reacted at 58° C. for 15 minutes to digest the protein, and the digestion results were detected by agarose gel electrophoresis. The results are shown in FIG. 8. The results show that within 5 nt before the 5' end of the spacer sequence, the mutation of the target sequence base has an important effect on the cleavage of Cas12j.19 double-stranded DNA. In addition, the mispairing of the 13th nt target sequence greatly affects the cleavage activity of Cas12j.19 double-stranded DNA. Cas12j.19's strict mismatch tolerance makes it possible to have a lower off-target rate.

Although the specific embodiments of the present invention have been described in detail, those skilled in the art will understand that various modifications and changes can be made to the details according to all the teachings that have been published, and these changes are within the protection scope of the present invention. All of the present invention is given by the appended claims and any equivalents thereof.

What is claimed is:

1. A protein, or a polynucleotide encoding the protein, where in the protein comprises an amino acid sequence of any one of SEQ ID NOs: 17, 2, or 20 with one or more amino acid substitutions, deletions or additions, and of at least 95%, at least 96%, at least 97%, at least 98%, or at least 99% sequence identity compared to a full-length sequence of any one of SEQ ID NOs: 17, 2, or 20.

2. A kit comprising the protein of claim 1 and instructions for using the protein.

3. A delivery composition comprising a delivery vehicle and the protein of claim 1, wherein the delivery vehicle is selected from a particle, a lipid particle, a sugar particle, a metal particle, a protein particle, a liposome, an exosome, a microvesicle, a gene gun, or a viral vector.

4. An in vitro, isolated or in vivo cell or cell line or its progeny, wherein the cell or cell line or its progeny comprises the protein of claim 1.

5. A method for nucleic acid editing comprising contacting the protein of claim 1 with a nucleic acid.

6. A method for in vitro gene or genome editing comprising contacting the protein of claim 1 with a gene or genome.

7. The method of claim 5, wherein the nucleic acid editing comprises a gene or genome editing; and the gene or genome editing includes modifying genes, knocking out genes, altering the expression of gene products, repairing mutations, and/or inserting polynucleotides.

8. A method for editing a target sequence in a target locus to modify a biological or non-human organism comprising contacting the protein of claim 1 with a gene or genome.

9. A conjugate or a fusion protein comprising (I) a protein having at least 95% sequence identity compared to a full-length sequence of any one of SEQ ID NOs: 17, 2 or 20, and (II) an additional polypeptide; wherein the additional polypeptide is selected from, a detectable label, an epitope tag, a reporter polypeptide, a nuclear localization signal (NLS) sequence, a targeting moiety, a transcription activation domain, a transcription repression domain, a nuclease domain, a domain having an activity selected from: nucleotide deaminase, methylase activity, demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combinations thereof; and/or wherein the additional polypeptide is connected to the N-terminus or C-terminus of the protein through a linker.

10. The conjugate or fusion protein of claim 9, wherein the conjugate or the fusion protein comprises an NLS sequence, and wherein the NLS sequence as shown in SEQ ID NO: 81, and/or wherein the NLS sequence is located at the N-terminal and/or C-terminal end of the protein; or wherein the fusion protein has an amino acid sequence selected from SEQ ID NOs: 98, 83, and 101.

11. An isolated nucleic acid molecule comprising a sequence as shown in any one of SEQ ID NOs: 57, 42, or 60, with one or more base substitutions, deletions or additions and of at least 95% sequence identity with the sequence as shown in any one of SEQ ID NO: 57, 42, or 60.

12. An isolated nucleic acid molecule comprising:

(i) a nucleotide sequence encoding a protein having at least 95% sequence identity compared to a full-length sequence of any one of SEQ ID NOs: 17, 2 or 20, and (ii) a nucleotide sequence encoding the nucleic acid component of claim 11.

13. A vector comprising the isolated nucleic acid molecule of claim 12.

14. A host cell comprising the isolated nucleic acid molecule of claim 12.

15. A complex comprising:
(i) a protein component comprising an amino acid sequence of any one of SEQ ID NOs: 17, 2, or 20; or an amino acid sequence of any one of SEQ ID NOs: 17, 2, or 20 with one or more amino acid substitutions, deletions or additions and of at least 95%, at least 96%, at least 97%, at least 98%, or at least 99% sequence identity compared to a full-length sequence of any one of SEQ ID NOs: 17, 2, or 20; and
(ii) a nucleic acid component, which comprises the isolated nucleic acid molecule of claim 11 and a guide sequence capable of hybridizing to a target sequence from the 5' to 3',
wherein the protein component and the nucleic acid component combine with each other to form a complex.

16. A method for modifying a target gene, comprising contacting the complex of claim 15 with the target gene, or delivering that to a cell containing the target gene;
wherein the target sequence is present in the target gene;
wherein the target gene is present in a cell selected from a prokaryotic cell, a eukaryotic cell, a mammalian cell, a human cell, and a plant cell; and/or
wherein the target gene is present in a nucleic acid molecule in vitro; and/or
wherein, the modification refers to a double-strand break in DNA or a single-strand break in RNA; wherein
the modification further includes inserting an exogenous nucleic acid into the break.

17. A method for altering the expression of a gene product, comprising:
(I) contacting the complex of claim 15 with a nucleic acid molecule encoding the gene product, wherein the nucleic acid molecule is present in a nucleic acid molecule in vitro, or
(II) delivering the complex of claim 15 to a cell containing a nucleic acid molecule comprising the target sequence; wherein the cell is selected from a prokaryotic cell, a eukaryotic cell, a mammalian cell, a human cell, and a plant cell, and/or
wherein the protein, nucleic acid molecule, or complex is contained in a delivery vehicle selected from a lipid particle, a sugar particle, a metal particle, a protein particle, a liposome, an exosome, and a viral vector;
wherein the expression of the gene product is altered; and/or wherein the method is used to change one or more target sequences in a target gene or a nucleic acid molecule encoding a target gene product to modify a cell, cell line, or organism.

18. A composition comprising:
(i) a first component which is selected from:
(a) a protein component comprising
an amino acid sequence of any one of SEQ ID NOs: 17, 2, or 20 with one or more amino acid substitutions, deletions or additions and of at least 95%, at least 96%, at least 97%, at least 98%, or at least 99% sequence identity compared to a full-length sequence of any one of SEQ ID NOs: 17, 2, or 20; or
(b) a fusion protein comprising a protein having at least 95% sequence identity compared to a full-length sequence of any one of SEQ ID NOs: 17, 2 or 20, and an additional polypeptide; or
(c) a nucleotide sequence encoding (a) or (b); and
(ii) a second component, which is a nucleotide sequence containing a guide RNA, or a nucleotide sequence encoding the nucleotide sequence containing a guide RNA; wherein the guide RNA includes a direct repeat sequence and a guide sequence from the 5' to 3', wherein the guide sequence can hybridize with a target sequence; and wherein the guide RNA can form a complex with the protein of (i)(a) or the fusion protein of (i)(b).

19. The composition of claim 18, wherein the additional polypeptide is selected from, a detectable label, an epitope tag, a reporter polypeptide, a nuclear localization signal (NLS) sequence, a targeting moiety, a transcription activation domain, a transcription repression domain, a nuclease domain, a domain having an activity selected from: nucleotide deaminase, methylase activity, demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combinations thereof.

20. The composition of claim 18, wherein when the target sequence is DNA, the target sequence is located at the 3' end of the original spacer sequence adjacent motif (PAM), and the PAM has a sequence shown by 5'-ATG, 5'-TTN, or 5'-KTR.

21. The composition of claim 18,
wherein when the target sequence is RNA, the target RNA sequence does not have PAM domain restrictions; and/or
wherein the target sequence is a DNA or RNA sequence derived from a prokaryotic cell or a eukaryotic cell or the target sequence is a non-naturally occurring DNA or RNA sequence; and/or
wherein the target sequence is present in a cell; and/or
wherein the protein or fusion protein is linked to one or more NLS sequences.

22. A composition comprising one or more vectors, the one or more vectors comprising:
(i) a first nucleic acid, which is a nucleotide sequence encoding a protein comprising an amino acid sequence of any one of SEQ ID NOs: 17, 2, or 20; or an amino acid sequence of any one of SEQ ID NOs: 17, 2, or 20 with one or more amino acid substitutions, deletions or additions and of at least 95%, at least 96%, at least 97%, at least 98%, or at least 99% sequence identity compared to a full-length sequence of any one of SEQ ID NOs: 17, 2, or 20; wherein, the first nucleic acid is operably linked to a first regulatory element; and
(ii) a second nucleic acid, which encodes a nucleotide sequence comprising a guide RNA comprising a direct repeat sequence and a guide sequence from 5' to 3', wherein the second nucleic acid is operably linked to a second regulatory element;
wherein:
the first nucleic acid and the second nucleic acid are present on the same or different vectors;
the guide sequence can hybridize with a target sequence;
the guide RNA can form a complex with the protein described in (i); and
the direct repeat sequence comprises a sequence as shown in any one of SEQ ID NOs: 57, 42 or 60 with one or more base substitution, deletions of additions and of at least 95% sequence identity with the sequence identity with the sequence as shown in any one of SEQ ID NO: 57, 42 or 60.

23. The composition of claim 22, wherein:
when the target sequence is DNA, the target sequence is located at the 3' end of the original spacer sequence adjacent motif (PAM), and the PAM has the sequence shown by 5'-ATG, 5'-TTN, or 5'-KTR.

24. A composition comprising one or more vectors, the one or more vectors comprising:

(i) a first nucleic acid, which is a nucleotide sequence encoding a protein comprising an amino acid sequence of any one of SEQ ID NOs: 17, 2, or 20 with one or more amino acid substitutions, deletions or additions and of at least 95%, at least 96%, at least 97%, at least 98%, or at least 99% sequence identity compared to a full-length sequence of any one of SEQ ID NOs: 17, 2, or 20; wherein, the first nucleic acid is operably linked to a first regulatory element; and (ii) a second nucleic acid, which encodes a nucleotide sequence comprising a guide RNA comprising a direct repeat sequence and a guide sequence from 5' to 3', wherein the direct repeat sequence comprises a sequence that is at least 95% identical to SEQ ID NOs: 57, 42 or 60; wherein the guide sequence can hybridize with a target sequence; wherein the guide RNA can form a complex with the protein described in (i), and wherein the second nucleic acid is operably linked to a second regulatory element;

wherein: the first nucleic acid and the second nucleic acid are present on the same or different vectors.

25. A non-naturally occurring composition comprising:

(i) a first component, which is selected from:

(a) a protein component comprising the amino acid sequence of any one of SEQ ID NOS:

17, 2, or 20; or (b) a nucleotide sequence encoding (a);

(ii) a second component, which is a nucleotide sequence containing a guide RNA, or a nucleotide sequence encoding the nucleotide sequence containing a guide RNA; wherein the guide RNA includes a direct repeat sequence and a guide sequence from the 5' to 3'; wherein the guide sequence can hybridize with a target sequence; wherein the target sequence is derived from a eukaryotic cell; and wherein the guide RNA can form a complex with the protein of (i)(a).

26. A non-naturally occurring complex comprising:

(i) a protein component comprising the amino acid sequence of any one of SEQ ID NOs: 17, 2, or 20; or an amino acid sequence of any one of SEQ ID NOs: 17, 2, or 20 with one or more amino acid substitutions, deletions or additions, and of at least 95%, at least 96%, at least 97%, at least 98%, or at least 99% sequence identity compared to a full-length sequence of any one of SEQ ID NOs: 17, 2, or 20; and (ii) a nucleic acid component, which is a nucleotide sequence containing a guide RNA, or a nucleotide sequence encoding the nucleotide sequence containing a guide RNA;

wherein the guide RNA includes a direct repeat sequence and a guide sequence from the 5' to 3', and wherein the guide sequence can hybridize with a target sequence;

wherein the target sequence is derived from a eukaryotic cell;

wherein the protein component and the nucleic acid component combine with each other to form a complex.

27. A method for eukaryotic nucleic acid editing, comprising contacting a protein with a eukaryotic nucleic acid, wherein the protein is an effector protein in the CRISPR/Cas system, wherein the protein comprises the amino acid sequence of any one of SEQ ID NOs: 17, 2, or 20.

28. The method of claim 27, wherein the eukaryotic nucleic acid editing comprises eukaryotic gene or genome editing; and the eukaryotic gene or genome editing includes modifying genes, knocking out genes, altering the expression of gene products, repairing mutations, and/or inserting polynucleotides.

29. A method for editing a eukaryotic target sequence in a eukaryotic target locus to modify a biological comprising contacting a protein with a eukaryotic gene or genome, wherein the protein is an effector protein in the CRISPR/Cas system, wherein the protein comprises the amino acid sequence of any one of SEQ ID NOs: 17, 2, or 20.

* * * * *

SEQUENCE LISTING

```
<160> NUMBER OF SEQ ID NOS: 144

<210> SEQ ID NO 1
<211> LENGTH: 1003
<212> TYPE: PRT
<213> ORGANISM: artificial sequence
<220> FEATURE:
<223> OTHER INFORMATION: amino acid sequence of Cas12j.3

<400> SEQUENCE: 1

Met Thr Lys Glu Lys Ile Lys Lys Thr Lys Lys Ala Lys Val Glu Lys
1               5                   10                  15

Asp Ser Val Thr Arg Ala Gly Ile Leu Arg Ile Leu Leu Asn Pro Asp
            20                  25                  30

Gln His Gln Glu Leu Asp Thr Leu Ile Ser Asp His Gln Glu Ala Ala
        35                  40                  45
```

```
Arg Glu Ile Gln Thr Ala Thr Tyr Lys Leu Ser Gly Leu Lys Leu Tyr
    50                  55                  60

Asp Lys Thr Asn Asn Met Val Val Asp Gly Ser Lys Ala Thr Pro Glu
65                  70                  75                  80

Glu Gln Glu Ala Tyr Tyr Lys Ile Ile Asn Trp Glu Gly Gln Pro Ile
                85                  90                  95

Ser Ile Ser Asn Pro Met Val Arg Ala Thr Phe Lys Ser Ile Ala Lys
            100                 105                 110

Val Lys Glu Asp Ile Arg Arg Lys Gln Glu Glu Tyr Ala Lys Leu Glu
        115                 120                 125

Glu Ala Asp Leu Thr Lys Met Ser Thr Gly Asp Val Lys Lys His Lys
    130                 135                 140

Asn Glu Leu Arg Lys Ala Ala Asn Arg Ile Lys His Ser Glu Glu Ile
145                 150                 155                 160

Leu Gln Phe Ala Lys Trp Arg Leu Ala Asp Ile Phe Pro Leu Pro Leu
                165                 170                 175

Ser His Asn Ser Gln Leu His Leu Lys Asn Asn Tyr His Gln Asn Val
            180                 185                 190

Phe Ser Gly Phe His Ala Arg Val Lys Gly Trp Asn Ala Cys Asp Ile
        195                 200                 205

Ala Ala Gln Ala Asn Tyr Ala Glu Ile Asp Asn Arg Leu Thr Glu Leu
    210                 215                 220

Ser Ser Glu Leu Ser Gly Asp Tyr Gly Ser Glu Val Ile Thr Asp Leu
225                 230                 235                 240

Met Gly Leu Leu Gln Tyr Thr Lys Glu Leu Gly Glu Gly Tyr Thr Asp
                245                 250                 255

Thr Ser Tyr Leu Asn Tyr Lys Phe Leu Ser Phe Phe Lys Glu Cys Trp
            260                 265                 270

Arg Pro Asn Ala Ile Ala Asn Asn Thr Gly Leu Leu Glu Gly Phe Trp
        275                 280                 285

Leu Ala Asn Asn Lys His Thr Asn Lys Lys Asn Gln Val Ala Tyr Ser
    290                 295                 300

Phe Asn Pro Lys Ile Ser Glu Glu Leu Phe Arg Arg Arg Ser Leu Trp
305                 310                 315                 320

Glu Ser Asp Lys Cys Leu Leu Ser Asp Pro Arg Phe Glu Lys Tyr Val
                325                 330                 335

Glu Leu Phe Asp Lys His Gly Arg Tyr Arg Lys Gly Ala Ser Leu Thr
            340                 345                 350

Leu Ile Ser Lys Glu Ser Pro Ile Pro Ile Gly Phe Ser Met Asp Arg
        355                 360                 365

Asn Ala Ala Lys Leu Val Arg Ile Asp Asn Asp Thr Ala Asn Arg Gln
    370                 375                 380

Leu Thr Ile Thr Ile Glu Leu Pro Asn Lys Glu Glu Arg Ser Tyr Val
385                 390                 395                 400

Ala Ala Tyr Gly Arg Lys His Glu Thr Lys Cys Tyr Tyr Asn Gly Leu
                405                 410                 415

Thr Thr Arg Leu Pro Arg Ser Glu Lys Glu Leu Leu Ala Leu Ala Lys
            420                 425                 430

Ala Glu Asn Arg Glu Leu Thr Asp Lys Glu Ile His Glu Ala Ser Leu
        435                 440                 445

Glu Lys Cys Tyr Ile Phe Glu Tyr Ala Arg Ala Gly Lys Ile Pro Val
    450                 455                 460

Phe Ala Val Val Lys Thr Leu Tyr Phe Arg Arg Asn Pro Ser Asn Gly
```

```
465                 470                 475                 480

Glu Tyr Tyr Val Ile Leu Pro Thr Asn Ile Phe Val Glu Tyr His Ala
                485                 490                 495

Asn Asn Glu Phe Asn Ser Lys Glu Leu Phe Lys Ile Arg Ser Glu Leu
            500                 505                 510

Gln Lys Ala Trp Asp Glu Val Arg Thr Pro Lys Arg Asn Val Gln Ser
        515                 520                 525

Cys Val Leu Asp Lys Asp Leu Ser Lys Arg Phe Ala Gly Arg Thr Leu
    530                 535                 540

Lys Tyr Ala Gly Ile Asp Leu Gly Tyr Ser Asn Pro Tyr Thr Val Ser
545                 550                 555                 560

Tyr Tyr Asn Val Val Gly Thr Glu Glu Gly Ile Gln Ile Lys Glu Thr
                565                 570                 575

Gly Asn Glu Ile Val Ser Thr Val Phe Asn Glu Gln Tyr Ile Gln Leu
            580                 585                 590

Lys Gly Asn Ile Tyr Gln Leu Ile Asn Ile Ile Arg Ala Ser Arg Arg
        595                 600                 605

Tyr Leu Gln Glu Ser Gly Glu Leu Lys Leu Ser Lys Asp Asp Ile Lys
    610                 615                 620

Ser Phe Asp Gln Leu Met Glu Leu Leu Pro Ser Glu Gln Arg Ile Thr
625                 630                 635                 640

Ile Asp Gln Phe Ile Lys Asp Ile Lys Lys Ala Lys Gln Glu Gly Lys
                645                 650                 655

Leu Ile Arg Asp Ile Lys Gly Lys Leu Pro Val Glu Gly Lys Lys Lys
            660                 665                 670

Glu Tyr Trp Val Ile Ser Asn Leu Met Tyr Val Ile Thr Gln Thr Met
        675                 680                 685

Asn Gly Ile Arg Gly Asn Arg Asp Ser Asn Asn His Leu Thr Glu Lys
    690                 695                 700

Lys Asn Trp Leu Ser Ala Pro Pro Leu Ile Glu Leu Ile Asp Ala Tyr
705                 710                 715                 720

Tyr Asn Leu Lys Lys Thr Phe Asn Asp Ser Gly Asp Gly Ile Lys Met
                725                 730                 735

Leu Pro Lys Asp His Val Tyr Ala Glu Gly Glu Lys Gln Arg Cys Thr
            740                 745                 750

Leu Arg Glu Glu Asn Phe Cys Lys Gly Ile Leu Glu Trp Arg Asp Asn
        755                 760                 765

Val Lys Asp Tyr Phe Ile Lys Lys Leu Phe Ser Gln Ile Ala His Arg
    770                 775                 780

Cys Tyr Glu Leu Gly Ile Gly Ile Val Ala Met Glu Asn Leu Asp Ile
785                 790                 795                 800

Met Gly Ser Ser Lys Asn Thr Lys Gln Ser Asn Arg Met Phe Asn Ile
                805                 810                 815

Trp Pro Arg Gly Gln Met Lys Lys Ser Ala Glu Asp Ala Phe Ser Tyr
            820                 825                 830

Met Gly Ile Leu Ile Gln Tyr Val Asp Glu Asn Gly Thr Ser Arg His
        835                 840                 845

Asp Ala Asp Ser Gly Ile Tyr Gly Cys Arg Asp Gly Ala Asn Leu Trp
    850                 855                 860

Leu Pro Asn Lys Lys Leu His Ala Asp Val Asn Ala Ser Arg Met Ile
865                 870                 875                 880

Ala Leu Arg Gly Leu Thr His His Thr Asn Leu Tyr Cys Arg Ser Leu
                885                 890                 895
```

```
Thr Glu Ile Glu Asn Gly Lys Tyr Val Asn Thr Tyr Glu Leu Phe Asp
            900                 905                 910

Thr Thr Lys Asn Asp Gln Ser Gly Ala Ala Lys Arg Leu Arg Gly Ala
        915                 920                 925

Glu Thr Leu Leu His Gly Tyr Ser Ala Thr Val Tyr Gln Ile His Thr
    930                 935                 940

Thr Asn Thr Gly Ala Gly Val Ala Leu Leu Pro Asp Leu Thr Ala Thr
945                 950                 955                 960

Asp Val Ile Lys Asn Lys Lys Ile Thr Ala Thr Lys Glu Asn Thr Ala
                965                 970                 975

Lys Tyr Tyr Lys Leu Asp Asn Thr Asn Thr Tyr Tyr Pro Trp Ser Val
            980                 985                 990

Cys Glu Lys Leu His Lys Asn Trp  Lys Leu Ser
        995                 1000


<210> SEQ ID NO 2
<211> LENGTH: 874
<212> TYPE: PRT
<213> ORGANISM: artificial sequence
<220> FEATURE:
<223> OTHER INFORMATION: amino acid sequence of Cas12j.4

<400> SEQUENCE: 2

Met Lys Lys Lys Lys Asn Phe Ser Val Ser Ala Thr Gly Val Phe Ser
1               5                   10                  15

Phe Pro Thr Thr Glu Ala Lys Met Asp Phe Phe His Arg Phe Ile Glu
            20                  25                  30

Leu Asn Gly Leu Ala Ala Glu Ile Glu Thr His Phe Leu Asn Leu Lys
        35                  40                  45

Asn Asp Lys Asn Gly Glu Ser Val Tyr Asn Lys Val Leu Ser Asn Ser
    50                  55                  60

Asn His Ser Arg Pro Phe Ser Thr Pro Leu Leu Gly Thr Met Thr Gly
65                  70                  75                  80

Ser Thr Lys Val Thr Asp Lys Asn Ala Leu Tyr Gly Asn Asp Leu Asp
                85                  90                  95

His Cys Arg Lys Lys Lys Ile Val Pro Phe Ser Ser Ser Ser Pro Leu
            100                 105                 110

Ser Ser Gln Glu Lys Phe Phe Cys Ile Glu Ala Val Phe Arg Arg Ala
        115                 120                 125

Lys Ser His Met Glu Cys Lys Lys Leu Phe Gln Asp Glu Thr Asn Arg
    130                 135                 140

Met Asp Ser Gln Ile Asn Gly Ile Leu Asn Glu Leu Pro Tyr Gly Val
145                 150                 155                 160

Glu Leu Ser Asn Met Leu Ser Glu Leu Ile Ala Ile Pro Phe Ala Ile
                165                 170                 175

Gly Trp Lys Leu Glu Gly Tyr Leu Gly Gln Val Phe Phe Pro Ser Ile
            180                 185                 190

Ala Glu Gly Leu Thr Pro Pro Lys Ser Ala Lys Ile Lys Gly Arg Arg
        195                 200                 205

Arg Ser Ile Asp Tyr Ser Val Thr Asp Glu Ala Tyr Asp Ile Leu Met
    210                 215                 220

Lys Tyr Ser Asn Leu His Ser Ser Phe Glu Thr Gly Leu Lys Met Ser
225                 230                 235                 240

Asn Leu Phe Ser Ala Phe Tyr Lys Lys Ser Asn Arg Lys Asp Glu Ile
                245                 250                 255
```

-continued

```
Gln Phe Thr Pro Ile Ser Met Glu Ser Arg Cys Asp Leu Leu Leu Gly
            260                 265                 270

Lys Asn Phe Leu Lys Phe Asp Leu Lys Asn Cys Asp His Arg Ser Gly
        275                 280                 285

Ser Leu Met Leu Thr Ile Asn Asp Lys Asn Arg Leu Asn Gly Asp Tyr
    290                 295                 300

Glu Ile Arg Val Gly Ser Asp Lys Lys Asp Ser Tyr Leu Thr Gly Val
305                 310                 315                 320

Asn Val Thr Asn Leu Gly Asp Asn Val Phe Asn Leu Asn Tyr Lys Val
                325                 330                 335

Asn Gly Lys Arg Glu Tyr Asn Met Leu Leu Lys Glu Pro Ser Ile His
            340                 345                 350

Ile Lys Met His Arg Met Arg Asp Asp Gly Asn Tyr Leu Ser Ser Asp
        355                 360                 365

Phe Asp Phe Tyr Met Ile Phe Ser Met Ser Ser Glu Lys Asp Glu Glu
    370                 375                 380

Lys Leu Ala Arg Ser Trp Asp Met Arg Ala Ala Met Ser Thr Ala Tyr
385                 390                 395                 400

Gly Thr Asp Ile Lys Lys Tyr His Ser Ser Phe Pro Cys Arg Ile Leu
                405                 410                 415

Ala Cys Asp Leu Gly Val Lys His Pro Tyr Ser Ala Ala Val Met Asp
            420                 425                 430

Ile Gly Gln Leu Asn Glu Asn Gly Met Pro Val Ser Val Asp Lys Val
        435                 440                 445

His Cys Met His Ser Glu Gly Val Ser Glu Ile Gly Gln Gly Tyr Asn
    450                 455                 460

His Leu Ile Gln Lys Ile Leu Ala Leu Asn Tyr Ile Leu Ala Tyr Cys
465                 470                 475                 480

Arg Glu Phe Val Ser Gly Thr Val Asp Asp Phe Asp Lys Ile Asp Tyr
                485                 490                 495

Lys Leu Ser Gln Leu Ser Tyr Lys Gln Glu Asp Leu Leu Ile Asn Leu
            500                 505                 510

Gln Glu Met Lys Asp His Phe Gly Asn Asp Met Gln Ala Trp Lys Lys
        515                 520                 525

Ser Arg Thr Trp Val Val Ser Thr Leu Phe Phe Glu Leu Arg Gln Glu
    530                 535                 540

Phe Asn Gln Leu Arg Asn Gln Arg Pro Gly Lys Lys Thr Val Ser Leu
545                 550                 555                 560

Ala Asp Glu Phe Gln Tyr Ile Asp Met Arg Arg Lys Phe Ile Ser Leu
                565                 570                 575

Ser Arg Ser Tyr Thr Asn Val Gly Arg Gln Ser Ser Lys His Arg His
            580                 585                 590

Asp Ser Tyr Gln Thr His Tyr Asp Val Ile Asn Arg Cys Lys Lys Asn
        595                 600                 605

Leu Leu Arg Asn Ile Cys Arg Arg Met Ile Asp Met Ala Val Gln Asn
    610                 615                 620

Lys Cys Asp Ile Ile Val Val Glu Asp Leu Ser Phe Gln Leu Ser Ser
625                 630                 635                 640

His Asn Ser Arg Arg Asp Asn Val Phe Asn Ala Leu Trp Ser Cys Lys
                645                 650                 655

Ser Ile Lys Asn Met Leu Gly Ile Met Ala Glu Gln His Asn Ile Ile
            660                 665                 670
```

```
Ile Ser Glu Val Asp Pro Asn His Thr Ser Lys Ile Asp Cys Glu Thr
        675                 680                 685

Gly Asn Phe Gly Tyr Arg Tyr Ser Ser Asp Phe Tyr Ser Val Ile Asp
    690                 695                 700

Gly Gln Leu Val Arg Arg His Ala Asp Glu Asn Ala Ala Ile Asn Ile
705                 710                 715                 720

Gly Asn Arg Trp Ala Ser Arg His Thr Asp Leu Lys Ser Phe Asn Cys
                725                 730                 735

Arg Gln Ile Ser Ile Asp Gly Arg Lys Val Ala Phe Pro Tyr Ala Lys
            740                 745                 750

Gly Lys Arg Lys Ser Ala Leu Phe Gly Tyr Leu Phe Gly Asn Cys Lys
        755                 760                 765

Thr Val Phe Val Ser Asp Asp Gly Asp Ser Tyr Thr Pro Ile Pro Tyr
    770                 775                 780

Ser Lys Phe Arg Lys Ser Ile Ser Lys Asp Asp His Asp Val Val Asn
785                 790                 795                 800

Tyr Leu His Asp Leu Thr Met Asn Lys Asn Val Ile Arg Val Glu Tyr
                805                 810                 815

Asn Lys Ser Ile Lys Ser Ala Ser Val Glu Leu Tyr Leu Asn Asp Asp
            820                 825                 830

Arg Val Ile Ser Arg Ser Leu Arg Asp Lys Glu Val Asp Ala Ile Glu
        835                 840                 845

Lys Leu Val Ser Arg Gly Ser Leu Ile Asn Glu Ser Gly Pro Ser Leu
    850                 855                 860

Glu His Asp Glu Val Lys Ser Val Thr His
865                 870


<210> SEQ ID NO 3
<211> LENGTH: 870
<212> TYPE: PRT
<213> ORGANISM: artificial sequence
<220> FEATURE:
<223> OTHER INFORMATION: amino acid sequence of Cas12j.5

<400> SEQUENCE: 3

Met Lys Val His Glu Ile Pro Arg Ser Gln Leu Leu Lys Ile Lys Gln
1               5                   10                  15

Tyr Glu Gly Ser Phe Val Glu Trp Tyr Arg Asp Leu Gln Glu Asp Arg
            20                  25                  30

Lys Lys Phe Ala Ser Leu Leu Phe Arg Trp Ala Ala Phe Gly Tyr Ala
        35                  40                  45

Ala Arg Glu Asp Asp Gly Ala Thr Tyr Ile Ser Pro Ser Gln Ala Leu
    50                  55                  60

Leu Glu Arg Arg Leu Leu Leu Gly Asp Ala Glu Asp Val Ala Ile Lys
65                  70                  75                  80

Phe Leu Asp Val Leu Phe Lys Gly Gly Ala Pro Ser Ser Ser Cys Tyr
                85                  90                  95

Ser Leu Phe Tyr Glu Asp Phe Ala Leu Arg Asp Lys Ala Lys Tyr Ser
            100                 105                 110

Gly Ala Lys Arg Glu Phe Ile Glu Gly Leu Ala Thr Met Pro Leu Asp
        115                 120                 125

Lys Ile Ile Glu Arg Ile Arg Gln Asp Glu Gln Leu Ser Lys Ile Pro
    130                 135                 140

Ala Glu Glu Trp Leu Ile Leu Gly Ala Glu Tyr Ser Pro Glu Glu Ile
145                 150                 155                 160
```

-continued

```
Trp Glu Gln Val Ala Pro Arg Ile Val Asn Val Asp Arg Ser Leu Gly
                165                 170                 175

Lys Gln Leu Arg Glu Arg Leu Gly Ile Lys Cys Arg Arg Pro His Asp
            180                 185                 190

Ala Gly Tyr Cys Lys Ile Leu Met Glu Val Val Ala Arg Gln Leu Arg
        195                 200                 205

Ser His Asn Glu Thr Tyr His Glu Tyr Leu Asn Gln Thr His Glu Met
    210                 215                 220

Lys Thr Lys Val Ala Asn Asn Leu Thr Asn Glu Phe Asp Leu Val Cys
225                 230                 235                 240

Glu Phe Ala Glu Val Leu Glu Glu Lys Asn Tyr Gly Leu Gly Trp Tyr
                245                 250                 255

Val Leu Trp Gln Gly Val Lys Gln Ala Leu Lys Glu Gln Lys Lys Pro
            260                 265                 270

Thr Lys Ile Gln Ile Ala Val Asp Gln Leu Arg Gln Pro Lys Phe Ala
        275                 280                 285

Gly Leu Leu Thr Ala Lys Trp Arg Ala Leu Lys Gly Ala Tyr Asp Thr
    290                 295                 300

Trp Lys Leu Lys Lys Arg Leu Glu Lys Arg Lys Ala Phe Pro Tyr Met
305                 310                 315                 320

Pro Asn Trp Asp Asn Asp Tyr Gln Ile Pro Val Gly Leu Thr Gly Leu
                325                 330                 335

Gly Val Phe Thr Leu Glu Val Lys Arg Thr Glu Val Val Val Asp Leu
            340                 345                 350

Lys Glu His Gly Lys Leu Phe Cys Ser His Ser His Tyr Phe Gly Asp
        355                 360                 365

Leu Thr Ala Glu Lys His Pro Ser Arg Tyr His Leu Lys Phe Arg His
    370                 375                 380

Lys Leu Lys Leu Arg Lys Arg Asp Ser Arg Val Glu Pro Thr Ile Gly
385                 390                 395                 400

Pro Trp Ile Glu Ala Ala Leu Arg Glu Ile Thr Ile Gln Lys Lys Pro
                405                 410                 415

Asn Gly Val Phe Tyr Leu Gly Leu Pro Tyr Ala Leu Ser His Gly Ile
            420                 425                 430

Asp Asn Phe Gln Ile Ala Lys Arg Phe Phe Ser Ala Ala Lys Pro Asp
        435                 440                 445

Lys Glu Val Ile Asn Gly Leu Pro Ser Glu Met Val Val Gly Ala Ala
    450                 455                 460

Asp Leu Asn Leu Ser Asn Ile Val Ala Pro Val Lys Ala Arg Ile Gly
465                 470                 475                 480

Lys Gly Leu Glu Gly Pro Leu His Ala Leu Asp Tyr Gly Tyr Gly Glu
                485                 490                 495

Leu Ile Asp Gly Pro Lys Ile Leu Thr Pro Asp Gly Pro Arg Cys Gly
            500                 505                 510

Glu Leu Ile Ser Leu Lys Arg Asp Ile Val Glu Ile Lys Ser Ala Ile
        515                 520                 525

Lys Glu Phe Lys Ala Cys Gln Arg Glu Gly Leu Thr Met Ser Glu Glu
    530                 535                 540

Thr Thr Thr Trp Leu Ser Glu Val Glu Ser Pro Ser Asp Ser Pro Arg
545                 550                 555                 560

Cys Met Ile Gln Ser Arg Ile Ala Asp Thr Ser Arg Arg Leu Asn Ser
                565                 570                 575

Phe Lys Tyr Gln Met Asn Lys Glu Gly Tyr Gln Asp Leu Ala Glu Ala
```

```
            580                 585                 590

Leu Arg Leu Leu Asp Ala Met Asp Ser Tyr Asn Ser Leu Leu Glu Ser
        595                 600                 605

Tyr Gln Arg Met His Leu Ser Pro Gly Glu Gln Ser Pro Lys Glu Ala
    610                 615                 620

Lys Phe Asp Thr Lys Arg Ala Ser Phe Arg Asp Leu Leu Arg Arg Arg
625                 630                 635                 640

Val Ala His Thr Ile Val Glu Tyr Phe Asp Asp Cys Asp Ile Val Phe
                645                 650                 655

Phe Glu Asp Leu Asp Gly Pro Ser Asp Ser Asp Ser Arg Asn Asn Ala
            660                 665                 670

Leu Val Lys Leu Leu Ser Pro Arg Thr Leu Leu Leu Tyr Ile Arg Gln
        675                 680                 685

Ala Leu Glu Lys Arg Gly Ile Gly Met Val Glu Val Ala Lys Asp Gly
    690                 695                 700

Thr Ser Gln Asn Asn Pro Ile Ser Gly His Val Gly Trp Arg Asn Lys
705                 710                 715                 720

Gln Asn Lys Ser Glu Ile Tyr Phe Tyr Glu Asp Lys Glu Leu Leu Val
                725                 730                 735

Met Asp Ala Asp Glu Val Gly Ala Met Asn Ile Leu Cys Arg Gly Leu
            740                 745                 750

Asn His Ser Val Cys Pro Tyr Ser Phe Val Thr Lys Ala Pro Glu Lys
        755                 760                 765

Lys Asn Asp Glu Lys Lys Glu Gly Asp Tyr Gly Lys Arg Val Lys Arg
    770                 775                 780

Phe Leu Lys Asp Arg Tyr Gly Ser Ser Asn Val Arg Phe Leu Val Ala
785                 790                 795                 800

Ser Met Gly Phe Val Thr Val Thr Thr Lys Arg Pro Lys Asp Ala Leu
                805                 810                 815

Val Gly Lys Arg Leu Tyr Tyr His Gly Gly Glu Leu Val Thr His Asp
            820                 825                 830

Leu His Asn Arg Met Lys Asp Glu Ile Lys Tyr Leu Val Glu Lys Glu
        835                 840                 845

Val Leu Ala Arg Arg Val Ser Leu Ser Asp Ser Thr Ile Lys Ser Tyr
    850                 855                 860

Lys Ser Phe Ala His Val
865                 870


<210> SEQ ID NO 4
<211> LENGTH: 964
<212> TYPE: PRT
<213> ORGANISM: artificial sequence
<220> FEATURE:
<223> OTHER INFORMATION: amino acid sequence of Cas12j.6

<400> SEQUENCE: 4

Met Ser Ala Asn Arg Val Ser Ala Asn Ser Gln Phe Glu Leu Gly Tyr
1               5                   10                  15

Pro Met Ser Leu Ser Leu Arg Gly Lys Val Phe Asn Ser Arg Glu Met
            20                  25                  30

Met Lys Glu Ile Leu Pro Val Met Asn Asn Ile Val His Tyr Gln Asn
        35                  40                  45

Asn Leu Leu Lys Leu Met Leu Ile Leu Arg Gly Glu Lys Tyr Thr Leu
    50                  55                  60

Asp Gly Gln Phe Phe Ser Gln Lys Asp Val Asp Arg Gln Phe Gly Asp
```

```
65                  70                  75                  80

Leu Cys Lys Glu His Asn Ile Lys Gly Ser Ile Cys Ser Leu Lys Glu
                85                  90                  95

Lys Ser Arg Lys Leu Tyr Glu Val Phe Ser Cys Tyr Ile Asp Lys Lys
            100                 105                 110

Gly Asn Leu Lys Thr Asn Ser Lys Ala Arg Ser Phe Ala Gly Val Leu
        115                 120                 125

Leu Asn Pro Lys Asp Val Lys Leu Pro Pro Gln Ile Asp Ser Ile Ser
    130                 135                 140

Ser Phe Val Val Glu Leu Arg Ala Lys Gly Val Leu Pro Ile Lys His
145                 150                 155                 160

Glu Gly Asn Tyr Leu Ser Gly His Pro Ser Leu Lys Tyr Ser Val Ala
                165                 170                 175

Gln Asn Val Leu Val Lys Leu Thr Ser Met Glu Lys Leu Gln Lys Ile
            180                 185                 190

Tyr Ser Asp Glu Lys Ala Gly Trp Glu Asn Ile Val Ser Glu Val Arg
        195                 200                 205

Ser Asp Leu Pro Lys Ile Glu Arg Tyr Glu Arg Met Leu Leu Ser Ile
    210                 215                 220

Lys Ala Val Lys Glu Met Glu Lys Phe Gly Ile Asn Asn Tyr Arg His
225                 230                 235                 240

Leu Leu Asn Asn Trp Arg Asp Glu Val Asp Lys Asp Ser Gly Lys Val
                245                 250                 255

Leu Lys Gln Gly Met Arg Thr Tyr Phe Val Asn Met Leu Glu Ser Lys
            260                 265                 270

Lys Asp Tyr Arg Phe Glu Glu Ser Asp Arg Tyr Leu Phe Gly Tyr Ala
        275                 280                 285

Pro Glu Val Met Asn Leu Val Tyr His Asp Phe Arg Asp Leu Trp Gln
    290                 295                 300

Gly Glu Asp Ile Ile Gly Ser Gln Ser Pro Glu Lys Lys Asp Arg Asp
305                 310                 315                 320

Tyr Val Asp Val Ile Phe Asn Tyr Phe Asn Trp Arg Lys Glu Ser Ile
                325                 330                 335

Asn Ile Ser Ser Phe Asp Ser Tyr Gly Lys Thr Ala Gln Ile Lys Leu
            340                 345                 350

Gly Asp Asn Tyr Val Pro Phe Ser Asn Phe Gln Tyr Asp Lys Ile Leu
        355                 360                 365

Asp Ala Trp Thr Leu Glu Ile Ala Asn Val Ser Gly Glu Gly Asp Asn
    370                 375                 380

His Lys Leu Val Ile Ala Arg Ser Pro Gln Phe Asp Ser His Ser Ser
385                 390                 395                 400

Val Lys Asp Ile Val Met Lys Asn Leu Lys Gly Lys Glu Ala Ser Lys
                405                 410                 415

Thr Thr Leu Glu Phe Arg Tyr Ser Gly Asp Ser Lys Lys Ser Thr Trp
            420                 425                 430

Tyr Arg Gly Thr Leu Lys Glu Pro Thr Leu Arg Tyr Ser Ser Ser Lys
        435                 440                 445

Asn Cys Leu Tyr Val Asp Phe Ala Leu Ser Asn His Ile Val Glu Gly
    450                 455                 460

Leu Ile Ser Asp Asn Leu Gly Ile Ser Asp Lys Met Tyr Lys Phe Arg
465                 470                 475                 480

Gly Glu Phe Met Lys Ala Ser Pro Ser Ser Gly Lys Gln Ser Asn Ser
                485                 490                 495
```

```
Ile Asn Leu Pro Ile Lys Lys Leu Arg Ala Met Gly Val Asp Phe Asn
            500                 505                 510

Leu Arg Arg Pro Phe Gln Ala Ser Ile Tyr Asp Val Glu Asn Lys Asn
        515                 520                 525

Gly Asn Leu Glu Phe Ser Phe Val Lys His Val Gln Ser Phe Ser Asn
    530                 535                 540

Glu Asn Asp Glu Glu Arg Ala Lys Glu Leu Leu Asn Ile Glu Arg Asn
545                 550                 555                 560

Ile Leu Ala Leu Lys Ile Leu Ile Trp Gln Thr Val Gly Tyr Val Thr
                565                 570                 575

Gly Lys Asn Asp Thr Ile Asp Gly Val Val Thr Arg Lys Asn Asn Ala
            580                 585                 590

Val Asp Ile Glu Lys Thr Leu Gly Ile Asn Met Lys Glu Tyr Met Ala
        595                 600                 605

Tyr Leu Asn Gln Phe Arg Ser Tyr Glu Asp Lys Asn Lys Ala Phe Met
    610                 615                 620

Asp Leu Arg Lys Arg Glu Tyr Ala Trp Ile Val Pro Pro Leu Ile Phe
625                 630                 635                 640

Gln Cys Arg Ser Arg Leu Ile Ser Phe Arg Ser Glu Tyr Phe Asn Thr
                645                 650                 655

Pro Lys Asp Glu Lys Ser His Tyr Cys Gln His Arg Asn Phe Val Asp
            660                 665                 670

Tyr Ser Thr Phe Leu Lys Lys Asn Val Val Lys Lys Met Met Glu Leu
        675                 680                 685

Arg Arg Ser Tyr Ser Thr Phe Gly Met Ser Ser Glu Gln Ser Ile Trp
    690                 695                 700

Val Thr Asn Asn Asp His Ala Lys Asp Gly Ser Lys Lys Asn Gly Asn
705                 710                 715                 720

Met Phe Asp Asp Asp Leu His Gln Trp Tyr Asn Gly Leu Val Arg Lys
                725                 730                 735

Cys Ser Ser Leu Ala Ser Ser Ile Ile Asn Val Ala Arg Asp Asn Gly
            740                 745                 750

Ala Ile Leu Val Phe Ile Glu Asp Leu Asp Cys His Pro Ser Ala Phe
        755                 760                 765

Asp Ser Glu Glu Asp Asn Ser Leu Lys Ser Ile Trp Gly Trp Gly Ser
    770                 775                 780

Ile Lys Ala Ser Leu Ala His Gln Ala Arg Lys His Asn Ile Ala Val
785                 790                 795                 800

Val Ala Asn Asp Pro His Leu Thr Ser Leu Val Ser Ser Thr Thr Gly
                805                 810                 815

Glu Leu Gly Ile Ala Lys Gly Arg Asp Val Leu Phe Phe Asp Ser Lys
            820                 825                 830

Gly Lys Leu Thr Ser Lys Val Asn Arg Asp Glu Asn Ala Ala Gln Asn
        835                 840                 845

Ile Ala Ile Arg Gly Phe Val Arg His Ser Asp Leu Arg Glu Phe Val
    850                 855                 860

Ala Glu Lys Ile Glu Glu Asn Arg Tyr Arg Val Val Val Asn Lys Thr
865                 870                 875                 880

His Lys Arg Lys Ala Gly Ala Ile Tyr Arg His Ile Gly Ser Thr Glu
                885                 890                 895

Cys Ile Met Ser Lys Gln Ala Asp Gly Ser Leu Lys Ile Asp Lys Thr
            900                 905                 910
```

```
Glu Leu Thr Pro Leu Glu Ile Lys Met Glu Lys Lys Asn Asp Lys Lys
        915                 920                 925

Met Tyr Val Ile Leu His Gly Lys Thr Trp Arg Leu Arg His Glu Leu
    930                 935                 940

Asn Glu Lys Leu Glu Lys Asp Leu Asp Asn His Leu Lys Ser Lys Ser
945                 950                 955                 960

Ser Val Ile Ser


<210> SEQ ID NO 5
<211> LENGTH: 962
<212> TYPE: PRT
<213> ORGANISM: artificial sequence
<220> FEATURE:
<223> OTHER INFORMATION: amino acid sequence of Cas12j.7

<400> SEQUENCE: 5

Met Ser Ser Ala Asn Asp Gln Leu Gly Leu Gly Tyr Pro Leu Thr Leu
1               5                   10                  15

Thr Leu Arg Gly Lys Val Tyr Asn His Asp Thr Ala Met Glu Ala Phe
            20                  25                  30

Ala Pro Val Met Lys Gly Met Val Pro Tyr Ala Asn Asn Leu Met Arg
        35                  40                  45

Ile Leu Leu Thr Leu Arg Leu Glu Lys Tyr Thr Leu Asp Gly Ile His
    50                  55                  60

His Thr Lys Glu Glu Val Glu Lys Asp Leu Arg Gly Leu Met Lys Glu
65                  70                  75                  80

Tyr Gly Ile Asn Leu Ser Phe Ala Lys Phe Ser Glu Met Ala Gly Glu
                85                  90                  95

Val Tyr Arg Val Phe Val Cys Tyr Val Asp Ala Lys Gly Lys Leu Lys
            100                 105                 110

Val Asn Gly Lys Ala Arg Gly Phe Ala Asn Val Phe Phe Ser Glu Asp
        115                 120                 125

Asp Ala Thr Ile Pro Glu Asn Cys Pro Ser Met Glu Leu Leu Arg Lys
    130                 135                 140

Lys Gly Met Phe Pro Ile Leu Val Asp Gly Lys Pro Ile Ser Ser Ile
145                 150                 155                 160

Ser Arg Glu Lys Thr Pro Leu Lys Tyr Ser Val Ala Gln Asp Val Leu
                165                 170                 175

Thr Lys Leu Thr Ser Met Glu Glu Ile Ser Lys Glu Tyr Glu Lys Ala
            180                 185                 190

Lys Thr Asp Trp Glu Asn Glu Cys Gln Lys Val Ile Ser Gln Leu Pro
        195                 200                 205

Leu Ile Gly Arg Tyr Glu Ala Leu Leu Thr Thr Ile Pro Leu Ile Pro
    210                 215                 220

Glu Met Arg Gly Phe Asp Gly Asp Asn Tyr Arg Lys Met Leu Asn Arg
225                 230                 235                 240

Trp Arg Asp Tyr Val Asn Glu Asp Gly Glu Leu Val Arg Gly Gly Met
                245                 250                 255

Lys Thr Tyr Phe Leu Asp Leu Leu Ser Lys Asp Thr Ser His Lys Phe
            260                 265                 270

Asn Glu Glu Glu Arg Tyr Leu Phe Gly Tyr Cys Pro Glu Phe Met Asn
        275                 280                 285

Leu Ile Tyr His Asp Phe Arg Asp Leu Trp Ser Lys Glu Asp Ile Ile
    290                 295                 300

Gly Ser Gln Arg Lys Gly Lys Gly Leu Lys Gly Lys Asp Tyr Val Asp
```

-continued 305 310 315 320

Val Ile Phe Asn Cys Phe His Trp Arg Arg Glu Ser Ile Asn Ile Ser
325 330 335

Ser Phe Gly Asn Asn Asp Lys Val Met Asn Ile His Leu Gly Asp Asn
340 345 350

Phe Val Pro Phe Glu Leu Lys Ser Gln Asn Gly Ile Trp Glu Val His
355 360 365

Val Gln Asn Leu His Gly Gln Asn Asp Pro His Arg Val Ile Val Cys
370 375 380

Arg Cys Pro Gln Phe Asn Glu Asp Ser Ser Met Lys Met Val His Pro
385 390 395 400

Leu Ala Lys Asn Gly Glu Glu Ser Asp Lys Glu Asn Ile Glu Phe Arg
405 410 415

Tyr Ser Gly Asp Ser Lys Arg Glu Thr Trp Tyr Thr Gly Leu Leu Lys
420 425 430

Glu Pro Thr Leu Arg Tyr Asp Val Glu Arg Lys Ser Leu Tyr Val Asp
435 440 445

Phe Ile Leu Ser Asn His Arg Val Glu Gly Val Val Thr Asn Glu Tyr
450 455 460

Leu Lys Asp Pro Arg Asp Leu Phe Gly Val Arg Gly Tyr Phe Leu Ser
465 470 475 480

Ser Ser Val Ser Asn Pro Arg Gln Lys Asp Lys Thr Ser Leu Pro Asp
485 490 495

Gly Lys Phe Asn Val Met Gly Val Asp Leu Gly Leu Lys Cys Pro Tyr
500 505 510

Glu Cys Ala Ile Tyr Gly Ile Thr Val Lys Asn Gly Lys Met Gln His
515 520 525

Lys Trp Ser His Asn Val Ser Ala Glu Asp Asn Asn Asn Val Ser Glu
530 535 540

Arg Leu Ala Asn Leu Lys Lys Ile Asp Glu Lys Ile Leu Ala Thr Gln
545 550 555 560

Val Leu Ile Ser Leu Thr Lys Met Cys Val Val Lys Asp Glu Glu Ile
565 570 575

Pro Asp Ser Tyr Thr Leu Arg Glu His Arg Val Asp Ile Ala Lys Ser
580 585 590

Leu Asp Leu Asp Met Asp Lys Tyr Arg Arg Tyr Val Glu Lys Cys Lys
595 600 605

Lys Asn Pro Asp Lys Ile Gln Ala Leu Lys Asp Ile Arg Lys Ser Glu
610 615 620

Asn Asn Trp Ile Val Ala Glu Lys Ile Asn Glu Ile Arg Ser Leu Ile
625 630 635 640

Ser Glu Ile Arg Ser Glu Tyr Tyr Ala Ser Lys Asp Lys Arg Asn Tyr
645 650 655

Cys Arg Asn Leu Asn Gly Val Asp Leu Ser Val Phe Leu Lys Lys Lys
660 665 670

Val Val Lys Asn Trp Ile Ser Leu Leu Arg Ser Phe Ser Thr Phe Gly
675 680 685

Met Thr Pro Gln Glu Ser Ala Tyr Ile Arg Lys Asp Phe Ala Lys Asn
690 695 700

Leu Ser Lys Trp Tyr Lys Gly Leu Val Arg Lys Cys Gly Ser Ile Ala
705 710 715 720

Ala His Ile Val Asn Ile Ala Arg Asp Asn Lys Val Met Val Ile Phe
725 730 735

Ile Glu Asp Leu Asp Ala Arg Thr Ser Ala Phe Asp Ser Lys Glu Asp
740 745 750

Asn Glu Leu Lys Ile Leu Trp Gly Trp Gly Glu Ile Lys Lys Trp Ile
755 760 765

Gly His Gln Ala Arg Lys His Asn Ile Ala Val Val Ala Val Asp Pro
770 775 780

His Leu Thr Ser Leu Val Asn His Glu Ser Gly Leu Leu Gly Ile Ala
785 790 795 800

Gly Ser Gly Asn Asp Arg Asn Ile Tyr Thr Phe Gln Lys Asn Lys Lys
805 810 815

Tyr Val Val Ile Asn Arg Asp Asn Asn Ala Ala His Asn Ile Ala Leu
820 825 830

Arg Gly Leu Ser Lys His Thr Asp Ile Arg Glu Phe Tyr Val Glu Gln
835 840 845

Ile Asp Val Asp His Tyr Arg Leu Met Tyr Gly Pro Glu Ala Glu Asn
850 855 860

Gly Lys Arg Arg Ser Gly Ala Ile Tyr Lys His Ile Gly Ser Thr Glu
865 870 875 880

Cys Val Phe Ser Lys Gln Lys Asn Gly Thr Leu Lys Val Glu Lys Thr
885 890 895

Ser Leu Thr Lys Asp Glu Lys Glu Met Pro Lys Ile Asn Gly Lys Gly
900 905 910

Val Tyr Ala Ile Leu His Gly Asn Glu Trp Arg Leu Arg His Glu Leu
915 920 925

Asn Glu Glu Leu Gly Ala Lys Leu Asp Gly Ile Ser Val Lys Arg Val
930 935 940

Val Ser Glu Pro Asn Lys Val Lys Thr Ser Leu Val Lys Gly Ser Val
945 950 955 960

Arg Ala

<210> SEQ ID NO 6
<211> LENGTH: 907
<212> TYPE: PRT
<213> ORGANISM: artificial sequence
<220> FEATURE:
<223> OTHER INFORMATION: amino acid sequence of Cas12j.8

<400> SEQUENCE: 6

Met Lys Lys Gln Thr Ile Val Lys Lys Asp Ser Lys Ala Glu Thr Lys
1 5 10 15

Glu Asn Lys Met Tyr Pro Asp Lys Asp Thr Asp Phe Pro Val Asn Ser
20 25 30

Gln Phe Ser Arg Ser Ile Ser Ile Arg Ala Asn Val Asp Pro Lys Asp
35 40 45

Leu Leu Val Leu Lys Arg Thr Phe Glu Glu Thr Thr Lys Ile Ser Asp
50 55 60

Glu Leu Leu Ser Thr Leu Leu Met Leu Arg Gly Lys Asp Tyr Cys Leu
65 70 75 80

Asp Asn Val Val Cys Lys Gly Glu Glu Val Leu Glu Asn Leu Tyr Lys
85 90 95

Lys Leu Ser Lys Asn Ala Thr Val Asn Arg Asp Lys Phe Ile Ser Thr
100 105 110

Ala Lys Ala Phe Tyr Glu Tyr Phe His Gly Cys Ser Tyr His Lys Gly
115 120 125

```
Phe Lys Ser Phe Phe Phe Ser Ser Lys Glu Ile Asp Ser Ile Gln Ser
    130                 135                 140

Glu Lys Phe Gly Tyr Leu Arg Glu Ile Gly Leu Phe Pro Ile Lys Ile
145                 150                 155                 160

Asp Ala Gln Ile Ser Asn Asp Leu Gln Tyr Ser Ile Val Ala Ser Asn
                165                 170                 175

His Ala Lys Ile Lys Gly Phe Glu Lys Ile Asp Lys Glu Tyr Gln Ala
            180                 185                 190

Asn Lys Glu Lys Trp Asn Lys Thr Ile Gly Glu Ser Thr Leu Lys His
        195                 200                 205

Leu Asn Arg Tyr Gly Glu Met Leu Lys Gly Leu Ser Asp Leu Gly Thr
    210                 215                 220

Met Gly Asn Phe Asn Gly Lys Lys Tyr Asp Arg Phe Met Gly His Trp
225                 230                 235                 240

Arg Asn Glu Gln Lys Ile Pro Asp His Ile Ser Met Leu Asp Phe Phe
                245                 250                 255

Arg Lys Ile Tyr Gln Glu Lys Gly Lys Ser His Arg Phe Thr Ala Ile
            260                 265                 270

Asp Asn Phe Thr Tyr Gly Tyr Glu Ser Glu Phe Met Asn His Ile Tyr
        275                 280                 285

Leu Asn Phe Ser Asp Leu Trp Leu Lys Glu Asp Val Ile Gly Asp Glu
    290                 295                 300

Glu Tyr Val Ser Leu Ile Arg Gly Ala Tyr His Trp Gln Lys Asp Val
305                 310                 315                 320

Val Gly Ile Ala Ser Phe Ser Gly Tyr Asn Lys Tyr Glu Lys Leu Phe
                325                 330                 335

Met Gly Asp Asn Lys Ile Asn Tyr Ala Leu Asp Phe Ser Asn Lys Asp
            340                 345                 350

Gln Trp Leu Met Lys Phe Asn Asn Val Ile Ser Lys Glu Pro Glu Thr
        355                 360                 365

Ile Thr Leu Arg Leu Cys Lys Asn Gly Tyr Phe Asn Asn Leu Ser Val
    370                 375                 380

Leu Glu Lys Asn Asp Glu Asn Gly Arg Tyr Lys Ile Arg Phe Ser Thr
385                 390                 395                 400

Glu Lys Gln Gly Lys Tyr Phe Tyr Glu Ala Phe Ile Arg Glu Pro Phe
                405                 410                 415

Leu Arg Tyr Asn Lys Asp Asn Asp Lys Ile Tyr Val His Phe Cys Leu
            420                 425                 430

Ser Glu Glu Ile Lys Glu Asn Cys Pro Asn His Leu Asp Thr Arg Ser
        435                 440                 445

Asp Lys Tyr Leu Phe Lys Ser Ala Leu Leu Thr Asn Ser Arg Gln Lys
    450                 455                 460

Leu Gly Lys Leu His Tyr Arg Asp Phe His Ile Val Gly Val Asp Leu
465                 470                 475                 480

Gly Ile Asn Pro Val Ala Lys Ile Thr Val Cys Lys Val His Val Asp
                485                 490                 495

Lys Asn Glu Asn Leu Lys Ile Thr Lys Ile Ile Thr Glu Glu Thr Arg
            500                 505                 510

Lys Asn Ile Asp Thr Asn Tyr Leu Asp Gln Leu Asn Leu Leu Tyr Lys
        515                 520                 525

Lys Ile Val Ser Leu Lys Arg Leu Ile Arg Ala Thr Val Ala Phe Lys
    530                 535                 540

Lys Asp Gly Glu Glu Ile Pro Lys Met Phe Lys Met Gly Lys Lys Ser
```

```
545                 550                 555                 560

Pro Tyr Phe Leu Asn Trp Thr Glu Val Leu Asn Val Asn Tyr Asp Asp
                565                 570                 575

Tyr Ile Lys Glu Ile Ser Thr Phe Ser Val Asp Arg Leu Ser Gly Leu
            580                 585                 590

Thr Leu Pro Met Gln Trp Ala Arg Ser Gln Asn Lys Trp Val Val Lys
        595                 600                 605

Asp Leu Thr Lys Met Val Arg Lys Gly Ile Ser Asp Leu Ile Tyr Ala
    610                 615                 620

Arg Tyr Phe Asn Cys Ser Asp Lys Thr Gln Tyr Val Thr Glu Asn Asn
625                 630                 635                 640

Ala Val Asp Ile Thr Thr Phe Lys Lys His Asp Ile Ile Ser Glu Ile
                645                 650                 655

Ile Gly Leu Gln Lys Met Phe Ser Gly Gly Gly Lys Asp Val Ala Lys
            660                 665                 670

Lys Asp Tyr Leu Tyr Leu Arg Gly Leu Arg Lys His Ile Gly Asn Tyr
        675                 680                 685

Thr Ala Ser Ala Ile Val Ser Ile Ala Gln Lys Tyr Asn Ala Val Phe
    690                 695                 700

Ile Phe Ile Glu Asp Leu Asp Leu Lys Ile Ser Gly Met Asn Gly Lys
705                 710                 715                 720

Lys Glu Asn Lys Val Lys Ile Leu Trp Gly Val Gly Gln Leu Lys Lys
                725                 730                 735

Arg Leu Ser Glu Lys Ala Glu Lys Phe Gly Ile Gly Ile Val Pro Val
            740                 745                 750

Asn Pro Glu Leu Thr Ser Gln Met Asp Arg Glu Thr Phe Leu Leu Gly
        755                 760                 765

Tyr Arg Asn Pro Thr Asn Lys Lys Glu Leu Tyr Val Lys Arg Asp Asp
    770                 775                 780

Lys Ile Glu Ile Leu Asp Ala Asp Glu Thr Ala Ser Tyr Asn Val Ala
785                 790                 795                 800

Leu Arg Gly Leu Gly His His Ala Asn Leu Ile Gln Phe Arg Ala Asp
                805                 810                 815

Lys Met Pro Asn Gly Cys Phe Arg Val Met Pro Asp Arg Lys Tyr Lys
            820                 825                 830

Gln Gly Ala Leu Tyr Gly Tyr Leu Asn Ser Thr Ala Val Leu Phe Lys
        835                 840                 845

Asp Lys Gly Asp Gly Val Leu Thr Ile His Lys Ser Lys Leu Thr Lys
    850                 855                 860

Lys Glu Arg Asp Ser Arg Pro Ile Lys Gly Lys Lys Thr Phe Val Val
865                 870                 875                 880

Lys Asn Gly Lys Arg Trp Ile Leu Arg His Val Leu Asp Glu Glu Val
                885                 890                 895

Lys Lys Tyr Pro Glu Met Tyr Asn Ser Gln Asn
            900                 905


<210> SEQ ID NO 7
<211> LENGTH: 912
<212> TYPE: PRT
<213> ORGANISM: artificial sequence
<220> FEATURE:
<223> OTHER INFORMATION: amino acid sequence of Cas12j.9

<400> SEQUENCE: 7

Met Ser Asp Tyr Lys Phe Ser Asn Asn Gly Val Thr Asn Thr Gly Ser
```

-continued

```
1               5                   10                  15

Ala His Ile Gly Leu Ser Pro Glu Asn Ser Ser Thr Val Met Asp Met
            20                  25                  30

Phe Lys Val Ile Thr Lys Asp Ala Asp Phe Leu Leu Lys Asn Leu Leu
        35                  40                  45

Ile Met Glu Gly Gly Glu Tyr Met Leu Asn Arg Glu Ile His Asn Gly
    50                  55                  60

Asp Lys Glu Phe Asp Lys Ile Ile Ser Lys Leu Gly Leu Ser Lys Lys
65                  70                  75                  80

Glu Lys Glu Asn Leu Lys Met Lys Cys Lys Asp Phe Phe Phe Asp Phe
                85                  90                  95

Val Lys Leu Gln Asn Gly Arg Ser Leu Ala Asn Ile Leu Phe Glu Thr
            100                 105                 110

Lys Gly Thr Thr Leu Ile Gly Cys Gly Lys Asp Lys Lys Gly Glu Lys
        115                 120                 125

Val Asp Gly Glu Tyr Pro Thr Ile Tyr His Asp His Glu Thr Leu Arg
    130                 135                 140

Ser Thr Gly Leu Leu Pro Leu Lys Phe Ser Lys Asn Ile Asp Asp Val
145                 150                 155                 160

Asp Tyr Lys Tyr Leu Ile Cys Tyr Leu Val His Asn Val Leu Ser Ser
                165                 170                 175

Phe Ile Glu Lys Arg Asp Ala Tyr Asn Asp Asn Lys Lys Glu Trp Glu
            180                 185                 190

Ser Lys Leu Ser Asn Ser Asn Leu Pro Gln Leu Glu Arg Met Ser Glu
        195                 200                 205

Phe Leu Asn Gly Ile Asn His Leu Gly Asn Ile Ile Gly Trp Asn Gly
    210                 215                 220

Lys Lys Tyr Ile Gly Phe Ile Lys Lys Trp Thr Asp Glu Glu Ser Ser
225                 230                 235                 240

Met Tyr Asp Phe Phe Val Gln Lys Leu Gln Asp Asn Pro Lys Tyr Lys
                245                 250                 255

Phe Gly Lys Lys Asp Gln Phe Leu Tyr Gly Tyr Glu Pro Glu Phe Leu
            260                 265                 270

Asn Tyr Leu Phe His Asp Phe Arg Asp Leu Trp His Pro Asp Asn Leu
        275                 280                 285

Ile Gly Lys Asp Glu Tyr Val Asp Leu Ile Ser Gly Lys Asn Asn Thr
    290                 295                 300

Asp Ala Glu Thr Ala Asn Lys Gly Ala Tyr His Trp Leu Lys Asp Phe
305                 310                 315                 320

Ile Asn Ile Ser Ser Phe Asp Ala Tyr Gly Lys Met Ala Thr Ile Gly
                325                 330                 335

Met Gly Asn Asn Leu Ile Asn Tyr Ser Met Asn Ile Asp Lys Asp Gly
            340                 345                 350

Lys Ile Ile Val Asn Met Asp Asn Ile Phe Asp Arg Ser Lys Pro Ile
        355                 360                 365

Val Phe Asn Val Tyr Arg Asn Ser Tyr Phe Arg Asn Phe Lys Ile Ile
    370                 375                 380

Glu Ser Asp Asp Lys Lys Gly Ile Tyr Lys Val Glu Phe Ser Thr Ser
385                 390                 395                 400

Asn Asn Gly Val Ile Tyr Glu Gly Tyr Ile Lys Ser Pro Ser Leu Arg
                405                 410                 415

Phe Ala Thr Lys Gly Gly Thr Ile Lys Ile Asp Phe Pro Ile Ser Asp
            420                 425                 430
```

```
Lys Arg Ile Lys Gly Gly Arg Glu Met Asn Thr Asp Leu Met Trp Phe
        435                 440                 445

Leu Asn Arg Ala Ser Pro Cys Ser Thr Lys Asn Lys Glu Val Asn Ser
    450                 455                 460

Phe Ile Gly Lys Asn Phe Val Gly Leu Ala Ile Asp Arg Gly Ile Asn
465                 470                 475                 480

Pro Leu Met Ala Trp Tyr Val Ala Glu Trp Thr Tyr Asp Lys Asp Gly
                485                 490                 495

Lys Ala Lys Ile Val Arg Ser Ile Ala Asn Gly Arg Val Asp Ser Gly
            500                 505                 510

His Asn Glu Ser Glu Val Lys Phe Val Arg Glu Thr Thr Asn Arg Ile
        515                 520                 525

Val Gly Ile Lys Ser Leu Val Trp Asn Thr Val Lys Tyr Arg Thr Gly
    530                 535                 540

Gly Ser Glu Gly Ile Asp Arg Cys Arg Lys Ser Gln Asn Gly Gln Val
545                 550                 555                 560

Asp Leu Phe Glu Met Phe Asp Ile Asp Tyr Asn Asn Tyr Leu Lys Glu
                565                 570                 575

Val Asn Asn Leu Pro Tyr Asp Pro Asn Ser Glu Arg Ser Ile Ile Gln
            580                 585                 590

Thr Trp Val Ser Ser Pro Trp Lys Val Lys Asp Leu Val Lys Asp Ala
        595                 600                 605

Lys Asn Arg Met Val Gln Ile Lys Thr Gln Tyr His Asn Ala Lys Asp
    610                 615                 620

Lys Glu Lys Tyr Ile Thr Thr Gln Asn Arg Ala Gly Phe Tyr Asp Phe
625                 630                 635                 640

Leu Lys Ile Glu Met Glu Lys Gln Phe Thr Ser Leu Gln Arg Met Phe
                645                 650                 655

Ser Gly Gly Gln Lys Asp Ile Cys Lys Asn Asn Glu Glu Tyr Arg Arg
            660                 665                 670

Gly Leu Arg Arg Arg Ile Asn Leu Tyr Thr Ser Ser Val Ile Met Ser
        675                 680                 685

Leu Ala Arg Lys Phe Asn Val Asp Cys Ile Phe Leu Glu Asp Leu Asp
    690                 695                 700

Ser Ser Lys Ser Ser Trp Asp Asp Ala Lys Lys Asn Ser Leu Lys Asp
705                 710                 715                 720

Leu Trp Ser Thr Gly Gly Ala Asp Asp Ile Leu Gly Lys Met Ala Asn
                725                 730                 735

Lys Tyr Lys Tyr Pro Ile Val Lys Val Asn Ser His Leu Thr Ser Leu
            740                 745                 750

Val Asp Asn Lys Thr Gly Lys Ile Gly Tyr Arg Asp Pro Lys Lys Lys
        755                 760                 765

Ser Asn Leu Tyr Val Glu Arg Gly Lys Lys Ile Glu Ile Ile Asp Ser
    770                 775                 780

Asp Glu Asn Ala Ala Ile Asn Ile Leu Lys Arg Gly Ile Ser Lys His
785                 790                 795                 800

Ile Asp Ile Arg Glu Phe Phe Ala Glu Lys Ile Glu Val Ser Gly Lys
                805                 810                 815

Thr Leu Tyr Arg Ile Ser Asn Lys Leu Gly Lys Gln Arg Met Gly Ser
            820                 825                 830

Leu Tyr Tyr Leu Glu Gly Asn Lys Glu Ile Leu Phe Gly Leu Gly Lys
        835                 840                 845
```

Asn Gly Glu Pro Ile Val Cys Lys Arg Gly Leu Cys Lys Lys Glu Arg
850 855 860

Leu Ala Pro Arg Ile Ala Glu Lys Lys Ser Thr Tyr Leu Ile Met Asn
865 870 875 880

Gly Ser Lys Trp Met Phe Arg His Glu Ala Lys Lys Ile Val Glu Thr
885 890 895

Tyr Lys Asp Arg Tyr Cys Ala Asn His Lys Val Ala Ser Lys Asp Gly
900 905 910

<210> SEQ ID NO 8
<211> LENGTH: 1119
<212> TYPE: PRT
<213> ORGANISM: artificial sequence
<220> FEATURE:
<223> OTHER INFORMATION: amino acid sequence of Cas12j.10

<400> SEQUENCE: 8

Met Met Asn Ile Asn Glu Met Val Lys Leu Met Lys Ser Glu Tyr Leu
1 5 10 15

Phe Glu Asp Asp Gly Ile Val Thr Lys Asn Lys Ile Gln Glu Arg Leu
20 25 30

Arg Asn Gly Phe Ser Asp Ile Gly Val Asp Pro Ser Leu Val Ser Tyr
35 40 45

Ala Ser Lys Phe Leu Asp Ser Met Phe Ile Cys Phe Ser Arg Val Lys
50 55 60

Gly Glu Lys Asn Phe Lys Ala Lys Asn Val Arg Lys Asn Met Ser Ser
65 70 75 80

Ala Glu Lys Lys Ala Gln Lys Lys Lys Glu Tyr Gln Glu Tyr Tyr Gln
85 90 95

Gly Val Met Ala Gln Gln Asp Ala Tyr Ala Gln Leu Leu Ser Asp Pro
100 105 110

Thr Gln Glu Asn Leu Asp Lys Leu Asn Glu Leu Ile Ser Met Ser Val
115 120 125

Asn Gly Ser Leu Val Glu Asp Phe Phe Pro Ala Leu Lys Asn Met Ile
130 135 140

Gln Lys Ala Asp Tyr Ser Ile Asp Lys Lys Gly Leu Leu Asp Phe Ser
145 150 155 160

Cys Cys Met Met Asp Arg Tyr Glu Asp Arg Ser Leu Thr Arg Ala Ile
165 170 175

Ser Ile Ser Ala Phe Asn Ile His Ser Gly Gly Leu Arg Lys Ala Leu
180 185 190

Ser Asp Ile Ser Glu Lys Val Gln Asp Leu Ser Asn Thr Leu Leu Ile
195 200 205

Arg Ile Leu Tyr Met Lys Gly Glu Glu Leu Ser Ile Asp Gly Glu Lys
210 215 220

Ile Ser Lys Glu Glu Val Gln Arg Gln Leu Lys Ala Asp Tyr Glu Glu
225 230 235 240

His Lys Glu Tyr Phe Glu Asp Phe Glu Asp Phe Ala Lys Lys Cys Arg
245 250 255

Phe Phe Tyr Asn Lys Phe Ser Lys Lys Lys Lys Thr Arg Gly Phe Gly
260 265 270

Thr Tyr Phe Phe Gly Asp Lys Lys Lys Glu Ile Ser Ser Ala Glu Tyr
275 280 285

Lys Ala His Lys Glu Leu Arg Asp Ser Gly Tyr Leu Trp Phe Asp Ile
290 295 300

```
Gly Trp Ser Glu Ser Ser Asp Phe Lys Tyr Val Ile Val Gly Asn Val
305                 310                 315                 320

Ser Gly Lys Leu Lys Ser Phe Glu Glu Thr Ser Glu Glu Tyr Gln Lys
                325                 330                 335

Ser Lys Asn Cys Trp Glu Ala Glu Arg Val Lys Leu Tyr Glu Gln Asp
            340                 345                 350

Ser Asp Phe Val Leu Phe Val Glu Asp Met Ile Glu Ser Lys Tyr Gly
        355                 360                 365

Pro Ile Glu Lys Met Lys Leu Arg Thr Phe Lys Thr Ile Val Lys Lys
    370                 375                 380

Leu Asp Lys Glu Phe Gly Lys Arg Gly Asp Lys Thr Pro Ser Ile His
385                 390                 395                 400

Asp Tyr Phe Glu Ser Leu Asp Pro Asn His Thr Phe Ser Gln Ser Glu
                405                 410                 415

Gln Phe Met Tyr Gly Leu Asp Val Thr Leu Met Gln Phe Leu Phe Asn
            420                 425                 430

Asn Lys Lys Gln Phe Tyr Lys Leu Cys Lys Asp His Asp Gly Lys Arg
        435                 440                 445

Thr Phe Ala Lys Val Val Glu Glu Ser Tyr His Trp Gly Lys Asn Ser
    450                 455                 460

Ile Asn Val Ser Thr Phe Gln Asn Ser Thr Ser Ile Leu Leu Gly Gly
465                 470                 475                 480

Asn Tyr Leu Asn Tyr Ser Met Ser Ile Glu Gly Glu Gly Leu Val Ile
                485                 490                 495

Lys Phe Asp Asn Pro Leu Ser Gly Lys Glu Val His Phe Val Val Cys
            500                 505                 510

Asn Asn Lys Tyr Leu Ser Asp Leu Glu Ile Leu Ser Gly Asn Pro Asn
        515                 520                 525

Arg Lys Asp Asn Asn Tyr Thr Ile Ser Tyr Ser Thr Gly Gly Lys Ala
    530                 535                 540

Arg Phe Ile Ala Lys Ser Lys Glu Pro Arg Ile Phe Phe Asn Arg Lys
545                 550                 555                 560

Thr Lys Lys Trp Glu Ile Ala Phe Gln Leu Ser Asp Val Ser Pro Leu
                565                 570                 575

Asn Gly Lys Phe Gly Lys Gln Gly Glu Phe Leu Ser Asn Leu Arg Lys
            580                 585                 590

Phe Val Tyr Asn His Val Ala Lys Ser Pro Ser Lys Leu Asn Ile Ser
        595                 600                 605

Asp Asn Asn Cys Arg Ala Val Ala Tyr Asp Leu Gly Ile Arg Asn Val
    610                 615                 620

Gly Ala Trp Ser Ser Phe Asp Phe Ser Tyr Lys Asp Gly Val Leu Gly
625                 630                 635                 640

Gly Tyr Lys Tyr Leu Thr Ser Gly Ser Leu Arg Ser Lys Ser Glu Ser
                645                 650                 655

Ser Glu Met Asp Gln Gly Tyr Tyr Phe Val Leu Asn Leu Lys Lys Ile
            660                 665                 670

Val Lys Leu Ile Pro Val Val Lys Lys Ser Ile Ile Asp Asp Pro Glu
        675                 680                 685

Leu Lys Arg Gln Phe Ile Gly Val Leu Asn Glu Asn Gly Asn Thr Val
    690                 695                 700

Gly Leu Gly Asn Ile Gly Lys Leu Asp Ile Ala Ser Arg Lys Ala Val
705                 710                 715                 720

Gln Ser Phe His Asn Cys Ile Gln Gln Ile Asn Tyr Tyr Val Asp Thr
```

```
                725                 730                 735

Tyr Ala Asp His Ile Asp Lys Ile Ser Ala Lys Asp Phe Val Asp Asp
            740                 745                 750

Ile Asp Gly Ile Lys Val Leu Asp Glu Asp Asp Pro Tyr Val Val Lys
        755                 760                 765

Ile Leu Ser His Leu Pro Glu Asp Val Glu Gly Asn Gln Asp Asp Ile
    770                 775                 780

Leu Asn Ile Ser Leu Leu Lys Trp Lys Thr Ser Asn Ala Gln Phe Val
785                 790                 795                 800

Pro Pro Leu Ile Gln Glu Ala Lys Ala Ile Met Ser Arg Ile Lys Arg
                805                 810                 815

Glu Asn Leu Asp Asn Ile Arg Gly Lys Lys Thr Gln Val Val Thr Gln
            820                 825                 830

Lys Thr Phe His Lys Ile Lys Phe Ala Lys Ala Leu Leu Ser Leu Met
        835                 840                 845

Lys Ser Trp Ser Ser Ile Gly Thr Val Arg Val Val Lys Thr Asp Gln
    850                 855                 860

Ile Tyr Gly Lys Lys Ile Trp Asp Tyr Ile Asn Gly Leu Arg Arg Asn
865                 870                 875                 880

Val Leu Thr Tyr Leu Ser Ser Ala Ile Val Asn Asn Ala Leu Asp Leu
                885                 890                 895

Gly Ala His Met Ile Ile Leu Glu Asp Leu Asp Ser Ser Val Ser Lys
            900                 905                 910

Tyr Arg Glu Lys Asp Lys Asn Ala Ile Gln Ser Leu Trp Gly Ser Gly
        915                 920                 925

Glu Leu Lys Lys Arg Ile Glu Glu Lys Ala Glu Lys His Arg Val Val
    930                 935                 940

Val Gln Tyr Val Ser Pro Tyr Leu Thr Ser Gln Leu Asp Asn Glu Thr
945                 950                 955                 960

Lys Asp Ile Gly Tyr Arg Lys Gly Gly Arg Leu Tyr Val Val Arg Asn
                965                 970                 975

Gly Lys Ile Lys Ser Ile Asp Ala Asp Ile Asn Ala Ser Lys Asn Ile
            980                 985                 990

Gly Glu Arg Phe Phe Asp Arg Asp  Leu Ile Gln Thr Leu  Ser Gly Val
        995                 1000                1005

Val Val  Glu Asp Gln Ser Thr  Val Tyr Ile Leu Gln  Lys Arg Asn
    1010                1015                1020

Val Ser  Ser Asp Asn Arg Lys  Arg Phe Tyr Lys Lys  Phe Leu Glu
    1025                1030                1035

Asp Val  Gly Gly Lys Ser Lys  Lys Asp Ala Val Leu  Lys Met Gly
    1040                1045                1050

Asp His  Gly Glu Leu Glu Val  Glu Arg Leu Ile Asp  Gly Lys Lys
    1055                1060                1065

Leu Asp  Ile Asp Gly Lys Lys  Ile Leu Val Asp Gly  Glu Lys Val
    1070                1075                1080

Pro Phe  Arg Asn Thr Ser Val  Tyr Tyr Ser Pro Lys  Lys Lys Lys
    1085                1090                1095

Trp Val  Ser Lys Glu Leu Arg  Cys Asn His Ile Lys  Leu Thr Val
    1100                1105                1110

Glu Glu  Gln Asp Ile Lys
    1115

<210> SEQ ID NO 9
```

<211> LENGTH: 1135
<212> TYPE: PRT
<213> ORGANISM: artificial sequence
<220> FEATURE:
<223> OTHER INFORMATION: amino acid sequence of Cas12j.11

<400> SEQUENCE: 9

```
Met Asn Asn Tyr Asp Asn Tyr Leu Ser Asp Tyr Leu Ala Met Leu Pro
1               5                   10                  15

His Thr Lys Arg Thr Glu Ile Lys Lys Thr Ala Ser Lys Ile Ser Arg
            20                  25                  30

Lys Leu Asn Gln Lys Glu Val Lys Lys Gln Ile Glu Arg Ser Glu Tyr
        35                  40                  45

Ile Arg Ser Asn Cys Gly Tyr Ile Asn Ile Glu Arg Pro Gln Lys Ser
    50                  55                  60

Leu Ser Phe Leu Ser Tyr Ser Thr Ile Lys Ser Ala Cys Met Ser Val
65                  70                  75                  80

Asn Phe Arg Ala Phe Gln Asn Pro Ile Asn Asp Tyr Glu Thr Ala Ile
                85                  90                  95

Cys Asn Gly Ile Asn Glu Cys Glu Arg Phe Phe Tyr Gln Gln Ile Asp
            100                 105                 110

Ser Ile Tyr Met Ser Gln Ile Ile Glu Gln Leu Phe Asp Phe Tyr Ile
        115                 120                 125

Ala Ser Arg Gln His Asp Met Phe Ile Asn Asn Thr Val Val Pro Tyr
    130                 135                 140

Asp Val Asn Lys Leu Lys Ser Tyr Tyr Thr Ala Asn Glu Lys Tyr Ser
145                 150                 155                 160

Phe Glu Gln Phe Cys Asp Asp Ile Lys Glu Phe Thr Asn Lys Gly Phe
                165                 170                 175

Thr Ser Gly Gly Val Ser Cys Ile Leu Asn Leu Phe Tyr Lys Gly Ser
            180                 185                 190

Val Lys Asp Ser Lys Asn Lys Lys Asp Tyr Ile Lys Ser Val Lys Arg
        195                 200                 205

Leu Glu Thr Asn Gly Leu Phe Lys Lys Leu Asn Ile Phe Glu Lys Asn
    210                 215                 220

Gly Ile Ser Lys Tyr Phe Ala Ala Ser Thr Leu Ser Thr Phe Phe Ala
225                 230                 235                 240

Thr Ile Ser Ser Trp Lys Lys Gln Asn Asp Asp Trp Thr Gly Val Ala
                245                 250                 255

Lys Asp Gly Thr Ser Leu Leu Ser Lys Leu Glu Asn Lys Thr Ile Thr
            260                 265                 270

Leu Gln Ser Ile Ile Lys His His Arg Val Ile Asn Glu Leu Ala Val
        275                 280                 285

Leu Ile Val Lys Ala Tyr Lys Asp Pro Val Lys Thr Leu Asn Asn Leu
    290                 295                 300

Phe Glu Glu Arg Ser Asp Asn Asn Asn Asp Phe Lys Tyr Thr Cys Ser
305                 310                 315                 320

Asp Asp Glu Asp Lys Tyr Pro Met Tyr Ile Lys Arg Glu Ile Ala Glu
                325                 330                 335

Phe Val Lys Lys His Lys Thr Val Trp Glu Glu Ile Arg Tyr Phe Asp
            340                 345                 350

Glu Ser Asp Thr Lys Lys Lys Lys Arg Asp Lys Lys Glu Ser Ser Ser
        355                 360                 365

Asp Asp Lys Ser Tyr Leu Cys Cys Gly Asp Ser Trp Asp Tyr Leu Lys
    370                 375                 380
```

```
Thr Trp Val Arg Leu Tyr Gly Glu Tyr Tyr Phe Phe Asp Asn Ala Leu
385                 390                 395                 400

Asn Gln Phe Leu Arg Lys Pro Ser Ala Ser Met His Leu Tyr Thr Ser
                405                 410                 415

Leu Asp Trp Ile Asn Lys Lys Thr Ile Cys Ile Val Gly Ala Asn Tyr
            420                 425                 430

Tyr Lys Ile Gly Lys Val Glu Val Val Glu Arg Asn Asn Gln Arg Phe
        435                 440                 445

Leu Leu Val Tyr Val Ser Val Pro Glu Met Glu Asn Tyr Ile Ile Ile
    450                 455                 460

Pro Leu Gln Leu Asn Lys Tyr Phe Gly Asn Phe Gln Cys Lys Ile Phe
465                 470                 475                 480

Glu Gly Arg Leu Gln Ala Ile Phe Lys Arg Tyr Ala Asn Phe Asn Ala
                485                 490                 495

Leu Lys Asn Asn Lys Pro Gln Pro Ser Pro Asn Ile Ser Val Arg Ile
            500                 505                 510

Asn Glu Phe His Phe Ala Leu Arg Ser Tyr Arg Lys Gln Gln Ile Ser
        515                 520                 525

Ala Glu Asp Phe Ser Lys Gly Arg Phe Ser Leu Ile Ser Lys Ile Gly
    530                 535                 540

Phe Gln Met Thr Asn Asp Glu Val Phe Gly Arg Thr Pro Arg Glu Ile
545                 550                 555                 560

Ala Leu Val Lys Asp His Leu Ser Lys Gly Tyr Val His Phe Gly Ser
                565                 570                 575

Gln Ile Ile Glu Asp Ser Arg Lys Glu Val Glu Gln Val Leu Lys Lys
            580                 585                 590

Pro Met Ile Leu Met Gly Val Asp Phe Gly Tyr Ser Pro Leu Ala Ser
        595                 600                 605

Tyr Asn Ile Lys Pro Leu Gln Thr Gly Lys Pro Ala Thr Asp Trp Val
    610                 615                 620

Lys Asn Leu His Gly Asn Phe Leu Cys Gln Asn Val Ser Leu Gly Glu
625                 630                 635                 640

Thr Ile Thr Glu Gly Glu Ile Gly Asp Val Pro Thr Asp Thr Tyr Thr
                645                 650                 655

Ser Ser Asn Glu Ile Tyr Ser Ile Ala Thr Leu Thr Phe Arg Asn Ala
            660                 665                 670

Asp Gly Lys Leu Glu Asn Arg Ser Phe Ser Arg Phe Tyr His Glu Leu
        675                 680                 685

Asn Asn Thr Leu Asn Ile Ile Glu Gln Ile Lys Gly Thr Phe Asn Phe
    690                 695                 700

Ile His Ser Ile Asn Thr Gln Phe Lys Glu Ile Lys Ala Leu Lys Thr
705                 710                 715                 720

Thr Glu Glu Phe Ser Ser Tyr Val Ser Thr Leu Thr Trp Asp Gln Phe
                725                 730                 735

Ile Glu Asp Ser Arg Lys Thr Ala Arg Tyr Ser Lys Tyr Trp Ile His
            740                 745                 750

Ile Ile Asn Glu Asn Pro Lys Arg Arg Thr Ile Ala Thr Leu Asn Glu
        755                 760                 765

Thr Leu Lys Leu Val Asp Glu Lys His Arg Phe Thr Val Thr Ile Gln
    770                 775                 780

Glu Ile Phe Asp Leu Val Lys Tyr Cys Gln Gln His Gly Tyr Tyr Pro
785                 790                 795                 800
```

```
Lys Ser Asn Val Met Ser Lys Leu Arg Asn Leu Ala Ile Lys Leu Ile
                805                 810                 815

Asn Asp Leu Ile Arg Tyr Gln Lys Ile Gly Ile His Ser Cys Tyr Leu
            820                 825                 830

Asp Phe Cys Val Leu Ile Lys Asn His Ile Ala Leu Leu Asn Ser Ser
        835                 840                 845

Thr Ala Phe Ile Ile Asn Phe Ser Arg Asn Lys Glu Asn Ile Ile Arg
    850                 855                 860

Asn Asn Thr Ser Lys Ile His Ser Leu Trp Val Tyr Arg Asp Asn Phe
865                 870                 875                 880

Arg Arg Gln Met Ile Lys Asn Leu Cys Ser Gln Ile Leu Lys Ile Ala
                885                 890                 895

Ala Lys Asn Lys Val His Ile Val Val Val Glu Lys Leu Asn Asn Met
            900                 905                 910

Arg Thr Asn Asn Arg Asn Asn Glu Asp Lys Asn Asn Met Ile Asp Leu
        915                 920                 925

Leu Ala Thr Gly Gln Phe Arg Lys Gln Leu Ser Asp Gln Ala Lys Trp
    930                 935                 940

Tyr Gly Ile Ala Val Val Asp Thr Ala Glu Tyr Asn Thr Ser Lys Val
945                 950                 955                 960

Asp Phe Met Thr Gly Glu Tyr Gly Tyr Arg Asp Glu Asn Asn Lys Arg
                965                 970                 975

His Phe Tyr Cys Arg Lys Gln Asp Lys Thr Val Leu Leu Asp Cys Asp
            980                 985                 990

Lys Lys Ala Ser Glu Asn Ile Leu  Leu Ala Phe Val Thr  Gln Ser Leu
        995                 1000                1005

Leu Leu  Asn His Leu Lys Val  Leu Ile Thr Glu Asp  Gly Lys Thr
    1010                1015                1020

Ala Val  Ile Asp Leu Ser Glu  Arg Thr Thr Glu Pro  Gln Lys Ile
    1025                1030                1035

Arg Ser  Lys Ile Trp Thr Asn  Ser Asp Val Gln Lys  Ile Ile Phe
    1040                1045                1050

Cys Lys  Gln Glu Asn Gly Ser  Tyr Val Leu Lys Lys  Gly Ser Thr
    1055                1060                1065

Asp Ile  Lys Glu Lys Met His  Lys Ala Val Leu His  Arg His Gly
    1070                1075                1080

Ser Leu  Trp Tyr Asp Tyr Leu  Asn His Lys Asn Met  Ile Glu Asp
    1085                1090                1095

Ile Lys  Asn Leu His Leu Ser  Asn Cys Ser Leu Thr  Thr Ser Thr
    1100                1105                1110

Asn Ser  Asp Val Ile Asn Ser  His Ser Gly Ser Ser  Arg Ser Leu
    1115                1120                1125

Asp Lys  Thr Lys Thr Tyr Ala
    1130                1135


<210> SEQ ID NO 10
<211> LENGTH: 1013
<212> TYPE: PRT
<213> ORGANISM: artificial sequence
<220> FEATURE:
<223> OTHER INFORMATION: amino acid sequence of Cas12j.12

<400> SEQUENCE: 10

Met Ala Ser Ser Asp Ala Gln Lys Phe Pro Gln Thr His Asn Lys Val
1               5                   10                  15
```

```
Met Ser Phe Arg Leu Thr Ala Ser Asn Ile Gly Ser Val Leu Ser Leu
            20                  25                  30

His Ser Asn Leu His Asp Ala Ala Glu Ile Gly Ile Asn Glu Cys Arg
        35                  40                  45

Trp Trp Ile Gly Asp Gly Glu Ile Tyr Glu Arg Asp Pro Ala Cys Arg
    50                  55                  60

Ser Ile Lys Lys Gly Asn Asp Ile Arg Thr Val Thr Ser Glu Lys Ile
65                  70                  75                  80

Lys Glu Leu Trp Thr Lys His Thr Asp His Ser Val Pro Leu Val Asp
                85                  90                  95

Phe Ile Asp Met Leu Lys Phe Val Ala Gln Cys Ala Ile Tyr Gly Asp
            100                 105                 110

Ser Arg Ala Leu Ala Ser Thr Leu Phe Gly Lys Ser Lys Ala Glu Thr
        115                 120                 125

Arg Gly Val Ser Thr Glu Asp Met Thr Val Ile Arg Ala Trp Ile Ala
    130                 135                 140

Glu Thr Asp Ala Val Leu Ala Ser Gly Leu Ser Pro Lys Lys Lys Lys
145                 150                 155                 160

Lys Lys Glu Lys Glu Ala Gly Lys Lys Glu Arg Lys Pro Asp Val Lys
                165                 170                 175

Met Glu Met Cys Arg Arg Ile Arg Cys Thr Met Val Gln Cys Gly Tyr
            180                 185                 190

Phe Arg Arg Phe Pro Phe Glu Ala Lys Ile Asp Asn Gly Gly Glu Arg
        195                 200                 205

Gly Lys Met Asp Ser Glu Leu Ser Tyr Val Ser Ala Arg Asn Leu Leu
    210                 215                 220

Arg Cys Leu Ser Thr Trp Arg Ala Ser Ser Val Met Arg Arg Asp Ser
225                 230                 235                 240

Tyr Leu Ile Glu Glu Glu Arg Ile Lys Glu Ala Glu Ser Lys Met Thr
                245                 250                 255

Pro Glu Ile Ile Asp Gly Leu Arg Arg Leu Tyr Arg Tyr Cys Ala Val
            260                 265                 270

Asp His Asp Phe Leu Lys Trp Phe Gly Gly Arg Ile Ile Arg His Ile
        275                 280                 285

Asp Ser Cys Leu Ala Pro Ala Ile Ala Gly Asn Thr Gly Arg Pro Thr
    290                 295                 300

Gly Gly Glu Ser Phe Thr Val Ile Tyr Asp Arg Arg Lys Lys Arg Asp
305                 310                 315                 320

Val Lys Ile Thr Tyr Ser Val Pro Glu Glu Ile Tyr Gly Tyr Leu Ser
                325                 330                 335

Ser His Pro Glu Leu Val Ala Ile Gly Lys Asp Gly Met Thr Pro Ile
            340                 345                 350

Ser Arg His Ala Asp Tyr Leu Glu Met Ile Ala Ser His Glu Lys His
        355                 360                 365

Arg Trp Tyr Ala Thr Phe Pro Thr Val Gly Lys Glu Asp Gly Tyr Arg
    370                 375                 380

Thr Ser Val Leu Leu Gly Lys Asn Tyr Leu Thr Tyr Asp Leu Ser Tyr
385                 390                 395                 400

Asp Gly Glu Ser Val Pro Asp Lys Lys Ile Asn Val Ile Ser Lys Gly
                405                 410                 415

Gln Pro Val Cys Leu Asp Leu His Asp Gly Arg Arg Val Ser Ser Leu
            420                 425                 430

Tyr Leu Thr Val Gly Glu Ser Ala Ala Tyr Asp Ile Ala Val Arg Lys
```

```
        435                 440                 445

Asn Lys Arg His His Gly Lys Pro Ala Asp Tyr Cys Arg Met Arg Val
    450                 455                 460

His Leu Thr Gln Glu Arg Glu Asp Lys Thr Tyr Asn Asp Pro Tyr Phe
465                 470                 475                 480

Ser Asn Met Glu Ile Trp Arg Ala Gly Asp Gln Val Tyr Ala Ile Glu
                485                 490                 495

Phe Asp Arg His Gly Ala Arg Tyr Thr Ala Ile Val Lys Glu Pro Ser
            500                 505                 510

Val Glu Tyr Arg Asn Lys Lys Leu Tyr Leu Arg Val Asn Met Val Leu
        515                 520                 525

Asp Ser Pro Ser Arg Gln Asp Asp Lys Asp Met Tyr Tyr Ala Tyr Met
    530                 535                 540

Thr Ala Tyr Pro Ser Ser Asn Pro Pro Val Glu Thr Ser Asp Asn Lys
545                 550                 555                 560

Lys Arg Phe Glu Arg Leu Gly Pro Gly Arg Arg Ala Ile Gly Gly Ile
                565                 570                 575

Asp Ile Gly Ile Gly Arg Pro Tyr Val Ala Val Val Ala Ser Tyr Glu
            580                 585                 590

Val Gly Pro Ala Gly Thr Glu Gln Lys Phe Gln Ile Glu Asp Arg Leu
        595                 600                 605

Ile Glu Asp Asp Gly Ser Ser Pro Tyr Asp Ser Leu Tyr Asn Asp Phe
    610                 615                 620

Leu Thr Asp Ile Arg Thr Val Ser Arg Ile Ile Glu Ala Ala Lys Lys
625                 630                 635                 640

Ile Ser Glu Gly Asp Leu Glu Asp Ile Pro Ser Asp Met Ser Val Asp
                645                 650                 655

Glu Asp Gly Ser Ile Ala Ala Thr Met Lys Arg Met Ser Ala Arg Ile
            660                 665                 670

Ala Glu Arg His His Leu Tyr Gly Glu Arg Lys Ser Glu Ala Tyr Ala
        675                 680                 685

Thr Phe Leu Lys Met Asn His Lys Gln Arg Leu Asp Ile Leu Leu Thr
    690                 695                 700

Gln Lys Ala Ser Asn Ala Thr Leu Lys Gln Leu Val Glu Glu Asp Pro
705                 710                 715                 720

Ser Phe Leu Pro Arg Ile Cys Val Tyr Tyr Val Ile Ser Val Glu Arg
                725                 730                 735

Glu Leu Lys Asn Lys His Arg Asn Ala Tyr Leu Asp Gly Leu Thr Val
            740                 745                 750

Asp Glu Lys Tyr Ser Gly Glu Thr Lys Arg Gly Tyr Ala Gln Lys Arg
        755                 760                 765

Leu Asn Ser Met Leu Arg Ala Tyr Ser Ala Leu Gly Glu Glu Glu Thr
    770                 775                 780

Asp Glu Val Arg Thr Phe Ser Thr Arg Ser Glu Lys Val Arg Asn Met
785                 790                 795                 800

Ala Lys Asn Ala Ile Lys Arg Asn Ala Arg Lys Leu Val Asn Phe Tyr
                805                 810                 815

Val Gly Lys Gly Ile Arg Thr Ile Val Ala Glu Asp Thr Asp Pro Thr
            820                 825                 830

Lys Ser Arg Asn Asp Gly Lys Lys Ser Asn Arg Ile Lys Ala Ala Trp
        835                 840                 845

Ser Pro Lys Gln Phe Leu Ala Ala Val Lys Asn Ala Ala Gln Trp His
    850                 855                 860
```

Gly Leu Glu Ile Ala Glu Val Asp Pro Arg Met Thr Ser Gln Val His
865 870 875 880

Pro Glu Thr Gly Leu Ile Gly Tyr Arg Asp Gly Asp Thr Leu His Cys
885 890 895

Pro Asp Gly Ser Lys Ile Asp Ala Asp Val Ala Gly Ala Ala Asn Val
900 905 910

Cys Arg Val Phe Ala Gly Arg Gly Leu Trp Arg Phe Ser Ile Asn Thr
915 920 925

Asn Ile Asp Ile Ser Asn Lys Asp Glu Lys Lys Arg Leu Arg Ala Tyr
930 935 940

Ile Val His His Phe Gly Ser Glu Ser Asn Trp Glu Lys Phe Arg Lys
945 950 955 960

Gln Tyr Pro Ser Gly Thr Thr Leu Tyr Leu His Gly Arg Glu Trp Leu
965 970 975

Thr Ala Glu Glu His Lys Ser Ala Ile Asp Arg Ile Arg Asp Asp Val
980 985 990

Gly Arg Asp Ala Glu Asn Asp His Val Ala Ile Val Thr Ala Ala Glu
995 1000 1005

Lys Val Glu Ile Phe
1010

<210> SEQ ID NO 11
<211> LENGTH: 1052
<212> TYPE: PRT
<213> ORGANISM: artificial sequence
<220> FEATURE:
<223> OTHER INFORMATION: amino acid sequence of Cas12j.13

<400> SEQUENCE: 11

Met Ser His Asp Leu Lys Pro Gln Arg Leu Ile Arg Ser Asn Ile Thr
1 5 10 15

Lys Thr His Ser Asp Gln Asn Ala Lys Gln Val Ala Glu Glu Val Lys
20 25 30

Lys Glu His Leu Asn Tyr Leu Leu Ile Lys Asn Glu Met Leu Ile Ser
35 40 45

Ile Val Pro Glu Ala Lys Asp Asp Asp Gly Asn Asp Ile Asp Phe Lys
50 55 60

Lys Gln Leu Lys Ser Leu Tyr Lys Glu Thr Asp Gln Ser Val Ser Phe
65 70 75 80

Ser Val Phe Cys Gln Met Met Lys Phe Arg Asn Ile Ala Leu Leu Tyr
85 90 95

Ala Lys Gly Gln Ser Arg Trp Ala Val Ser Ser Tyr Phe Thr Gly Asn
100 105 110

Arg Arg Lys Asp Asp Tyr Ala Lys Asp Leu Ser Leu Leu Asp Glu Ala
115 120 125

Ile Glu Leu Leu Glu Cys Lys Arg Arg Lys Lys Ala Glu Glu Glu Asn
130 135 140

Glu Glu Glu Asn Glu Thr Pro Lys Lys Lys Glu Asp Asn Pro Ser Asn
145 150 155 160

Ile Ser Glu Glu Gln Ile Met Lys Leu Phe Tyr Ala Val Asn Lys Lys
165 170 175

Leu Lys Glu Ile Gly Tyr Leu Asp Arg Tyr Ser His Ile Glu Lys Gln
180 185 190

Glu Gln Tyr Ala Ile Ile Gly Val Thr Ser Arg Thr Val Lys Ala Trp
195 200 205

```
Asp Tyr Ala Asn Phe Ala Thr Arg Asn His Tyr Gln Ser Val Gln Asn
    210                 215                 220

Glu Tyr Gln Lys Lys Leu Lys Ala Leu Pro Gly Thr Lys Lys Asp Lys
225                 230                 235                 240

Val Cys Leu Glu Lys Phe Phe Asp His Leu Asn Glu Asn Asn Ile Ala
                245                 250                 255

Ala Asp Trp Asp Lys Trp Arg Leu Lys Lys His Ile Leu Gln Cys Ile
            260                 265                 270

Ile Pro Ala Ala Lys Ile Gly Leu Lys Glu Leu Lys Gln Ser Phe Tyr
        275                 280                 285

Val Asp Asn Lys Gly Asn Lys His Asn Tyr Phe Val Asn Gly Leu Tyr
    290                 295                 300

Glu Glu Ile Leu Lys Arg Pro Phe Leu Tyr Ser Ala Glu Asp Pro Glu
305                 310                 315                 320

Glu Ser Ile Leu Tyr Leu Gly Val Glu Val Ala Ser Leu His Ser Lys
                325                 330                 335

Leu Asn His Leu Arg Ser Glu Ala Arg Phe Ser Phe Glu Thr Pro Asp
            340                 345                 350

Asp Ile Cys Lys Tyr Met Thr Ile Cys Gly Asp Asn Tyr His Asn Phe
        355                 360                 365

Thr Met Ser Ala Ile Gly Glu Asp Val Glu Asp Ile Glu Val Glu Val
    370                 375                 380

Tyr Asp Tyr Asn His Ser Lys Lys Tyr Glu Thr Met Arg Phe Ile Asn
385                 390                 395                 400

Gly Lys Arg Thr Thr Asp Leu Ser Leu Asn Phe Lys Gly Ile Pro Val
                405                 410                 415

Arg Leu Cys Leu Glu Gly Lys Arg Asn Asn Ser Tyr Phe Ala Asp Ala
            420                 425                 430

Ile Val Trp Glu Leu Asp Asn Lys Asp Lys Thr Gly Tyr Leu Ile Glu
        435                 440                 445

Tyr Gly Lys Ser Asn Asn Arg Leu Tyr Met Leu Val Lys Glu Pro Leu
    450                 455                 460

Ile Gly Cys Arg Arg Lys Phe Gly Lys Asp Val Leu Phe Val Ser Leu
465                 470                 475                 480

Ser Gly Thr Leu Val Asn Lys Tyr Ile Glu Asp Asp Ile Val Ser Ala
                485                 490                 495

Arg Tyr Leu Met Gln Thr Ala Ala Pro Ile Phe Lys Thr Ser Arg Ala
            500                 505                 510

Lys Lys Gln Asp Lys Ile Gly Asp Lys Trp Phe Glu His Cys Gln Gly
        515                 520                 525

Ser Thr Ile Lys Ile Ala Gly Ile Asp Ile Gly Ile Asn Pro Ile Ala
    530                 535                 540

Ala Ile Thr Val Ala Asn Val Thr Phe Asp Arg Ala Leu Gly Asn Lys
545                 550                 555                 560

Ile Lys Asn Gln Lys Gln Ile Val Ile Asp Cys Tyr Ala Glu Asp Tyr
                565                 570                 575

Lys Ile Asp Pro Val Val Val Lys Arg Met Glu Asp Ile Arg His Ile
            580                 585                 590

Lys Tyr Thr Ile Asn Ser Trp Tyr His Leu Ala Asp Cys Cys Arg Leu
        595                 600                 605

Lys Ala Ala Asn Lys Glu Tyr Val Val Asn Glu Arg Lys Gln Gly Phe
    610                 615                 620
```

```
Phe Arg Glu Asn Ile Glu Tyr Leu Lys Glu Val Ala Lys Lys Ala Ile
625                 630                 635                 640

Thr Glu Ser Asp Gln Gln Ile Lys Glu Gln Lys Ala Ala Leu Lys Arg
                645                 650                 655

Phe Asp Gly Glu Lys Lys Lys Glu Ile Gln Ala Thr Ile Asn Gly Phe
            660                 665                 670

Asn Leu Lys Ile Lys Ile Leu Lys Lys Phe Val Arg Gln Ser Ala Lys
        675                 680                 685

Lys Ile Phe Asp Ser Thr Leu Glu Thr Leu Glu Lys Tyr Asp Asn Asn
    690                 695                 700

Ile Glu Gln Ala Lys Arg Asp Arg Glu Phe Gly Leu Lys Ile Ile Tyr
705                 710                 715                 720

Asp Leu Ile Ile Lys Tyr Tyr Lys Arg Ser Lys Lys Glu Arg Glu Met
                725                 730                 735

Asn Gln Arg Ile Tyr Val Asp Asp Tyr Asn Gln Glu Glu Ile Asp Thr
            740                 745                 750

Glu Arg Thr Lys Lys Ile Arg Lys Glu Thr Ile Thr Phe Cys Asp Asn
        755                 760                 765

Asp Trp Asn Ser Leu Thr Lys Arg Ile His Asp Leu Glu Lys Lys Met
    770                 775                 780

Lys Lys Ile Gly Ile Ser Glu Pro Gly Arg Val Glu Gln Glu Ile Asn
785                 790                 795                 800

Asp Arg Asp Tyr Tyr Asn Asn Ile Gln Asp Asn Thr Lys Lys Arg Gln
                805                 810                 815

Ala Lys Ile Ile Val Asp Ala Leu Lys Glu Glu Gly Val Ser Ile Ile
            820                 825                 830

Val Val Glu Asp Leu Thr Gly Gly Gly Ser Glu Asn Thr Lys Glu Ile
        835                 840                 845

Asn Lys Ser Phe Asp Ala Phe Ala Pro Ile Arg Phe Leu Asn Ala Leu
    850                 855                 860

Lys Asn Cys Ala Glu Thr Asn Gly Ile Gln Val Thr Glu Val Leu Ser
865                 870                 875                 880

Pro Met Ser Ser Lys Met Val Pro Ser Thr Gly Glu Ile Gly His Arg
                885                 890                 895

Asp Lys Arg Asp Lys Gln Leu Tyr Tyr Lys Asp Gly Glu Glu Leu Lys
            900                 905                 910

Ser Ile Asp Gly Asp Ile Ser Ala Ser Glu Ile Leu Leu Arg Arg Gly
        915                 920                 925

Val Ser Arg His Thr Glu Leu Ile Gly Thr Met Asn Val Glu Asp Val
    930                 935                 940

Leu Asp Lys Asn Asn Asn Lys Asn Lys Cys Ile Lys Gly Tyr Val Cys
945                 950                 955                 960

Asn Arg Trp Gly Asn Ile Gln Asn Phe Glu Lys Ile Leu Lys Glu Lys
                965                 970                 975

Gly Ile Gly Glu Arg Glu Ile Ile Tyr Leu His Gly Asp Lys Ile Leu
            980                 985                 990

Thr Met Asp Glu Lys Arg Thr Leu  Gln Ala Ser Ile Arg  Lys Glu Leu
        995                 1000                 1005

Lys Glu  Met Arg Glu Arg Glu  Ser Gly Glu Glu Asn  Ala Gly Thr
    1010                 1015                 1020

Ala Arg  Lys Lys Ser Lys Pro  Lys Lys Lys Lys Lys  Ile Lys Arg
    1025                 1030                 1035

Asn Asn  Asp Gln Asp Leu Ser  Asn Asn Arg Pro Ala  Ala Ser
```

1040 1045 1050

<210> SEQ ID NO 12
<211> LENGTH: 1045
<212> TYPE: PRT
<213> ORGANISM: artificial sequence
<220> FEATURE:
<223> OTHER INFORMATION: amino acid sequence of Cas12j.14

<400> SEQUENCE: 12

Met Lys Glu Asn Lys Met Lys Glu Asn Gly Ser Met Thr Thr His Ser
1 5 10 15

Lys Val Ile Ala Leu Lys Met Lys Ser Glu Asn Val Glu Phe Asp Thr
20 25 30

Phe Tyr Lys Glu Ser Phe Glu Leu Phe Lys Gln Phe Thr Asn Glu Phe
35 40 45

Val Ala Trp Gly Asn Asp Glu Ile Tyr Gln Tyr Gly Ser Ser Lys Arg
50 55 60

Lys Lys Asp Asp Gln Lys Ile Ser Leu Ile Pro Val Ile Glu Asp Ile
65 70 75 80

Tyr Lys Ser Val Glu Lys Lys Ala Thr Ala Glu Gly Ile Ser Lys Thr
85 90 95

Asp Phe Arg Ala Val Leu Lys Tyr Leu Tyr His Gln Ile Ile Asn Val
100 105 110

Gly Asn Ser Gly Arg Ser Tyr Gly Thr Ser Leu Phe Gly Gly Cys Glu
115 120 125

Val Lys Glu Lys Leu Ser Lys Gln Asp Ile Ser Asn Ile Val Glu Cys
130 135 140

Val Lys Glu Leu Glu Leu Cys Lys Ser Lys Gln Glu Glu Ser Asp Ala
145 150 155 160

Tyr Asp Lys Ile Leu Leu Lys Glu Lys Ile Thr His Ile Val Lys Ser
165 170 175

Gly Glu Thr Ala Gly Asp Ile Thr Lys Lys Tyr Asn Gln Ala Thr Thr
180 185 190

Gly Arg Lys Thr Ser Ser Lys Gly Phe Phe Asp Lys Ser Thr Lys Thr
195 200 205

Glu Val Lys Tyr Lys Asp Ile Lys Asp Asp Thr Leu Leu Gln Asp Gly
210 215 220

Ser Thr Ile Phe Ile Lys Ser Ser Val Asp Leu Phe Val Lys Lys Val
225 230 235 240

Cys Asn Thr Leu Arg Glu Ile Asn Phe Phe Asp Arg Leu Pro Phe Lys
245 250 255

Asn Asn His Ser Asn Asn Tyr Gly Leu Leu Phe Ser Met Leu Ser Gln
260 265 270

Ile Glu Ser Trp Lys Thr Ile Ser Glu Thr Thr Lys Lys Ser His Glu
275 280 285

Glu His Gly Glu Lys Ile Ala Ser Met Val Lys Lys Leu Asp Leu Thr
290 295 300

Gln Thr Glu Leu Met Lys Asp Phe Ala Ala Phe Cys Ile Glu Asn Asn
305 310 315 320

Ile Thr Lys Lys Phe Asp His Lys Phe Lys Arg His Met Glu Asp Cys
325 330 335

Val Ile Pro Ser Phe Lys Asn Gly Lys Ile Pro Asp Lys Leu Phe Tyr
340 345 350

Phe Asn Ile Ile Leu Ala Lys Lys Thr Asp Glu Gln Ile Asp Tyr Ser

```
        355                 360                 365

Leu Ser Ser Glu Phe Tyr Thr Lys Leu Phe Ser Met Pro Asn Leu Trp
    370                 375                 380

Gln Glu Glu Glu Ala Phe Ile Val Lys Asn Ile Asn Leu Ile Glu Glu
385                 390                 395                 400

Ile Thr Ile Phe Asn Lys Arg Arg Asn Tyr Ala Cys Cys Pro Leu Ile
                405                 410                 415

Lys Glu Lys Glu Tyr Asp Arg Phe Gln Ile Gln Leu Asn Glu Thr Asn
            420                 425                 430

Phe Leu Lys Phe Gln Phe Asp Pro Lys Asn Val Val Asn Ile Asp Glu
        435                 440                 445

Asn Thr Thr Glu Ala Thr Val Gly Phe Asp Glu Lys Leu Lys Leu Val
    450                 455                 460

Val Cys Ala Asp Lys Lys Tyr Ala Phe Ser Ile Phe Thr Gln Cys Lys
465                 470                 475                 480

Tyr His Gly Asn Lys His Lys Pro Asn Thr Tyr Phe Asn Asn Leu Lys
                485                 490                 495

Ile Ile Lys Val Ile Glu Ser Lys Ser Asn Ser Val Lys Ser Met Lys
            500                 505                 510

Tyr Thr Phe Glu Phe Thr Lys Arg Asn Glu Leu Lys Arg Ala Glu Ile
        515                 520                 525

Lys Gln Pro Ser Ile Val Tyr Lys Asn Asn Asn Tyr Tyr Ile Arg Ile
    530                 535                 540

Asn Met Asn Val Ile Leu Asp Ala Asp Gln Thr Ser Tyr Lys Ile Ile
545                 550                 555                 560

Asn Asn Asn Gln Thr Ala Ser Leu Pro Ser Tyr Phe Gln Ser Ser Leu
                565                 570                 575

Pro Phe Glu Asn Asn Arg Gly Lys Ile His Asp Lys Gly Ile Val His
            580                 585                 590

Trp Glu Lys Ile Lys Asn Arg Lys Ile Ile Ala Met Gly Val Asp Leu
        595                 600                 605

Gly Val Arg Arg Pro Phe Ser Tyr Ala Ile Gly Asn Phe Thr Leu Asn
    610                 615                 620

Lys Asp Ile Leu Asp Lys Asn Asp Val Asn Ile Val Ala Ser Gly Phe
625                 630                 635                 640

Asn Leu Cys Ser Asp Ser Asp Val Tyr Phe Gln Val Phe Asn Gln Ile
                645                 650                 655

Lys Thr Leu Ala Lys Phe Ile Gly Lys Leu Lys Ser His Asn Lys Gly
            660                 665                 670

Leu Lys Val Asp Phe Glu Lys Asp Lys Lys Tyr Ile Phe Asp Leu Val
        675                 680                 685

Asn Asp Ala Lys Ala Tyr Phe Lys Asp Met Ser Ala Lys Arg Ile Asn
    690                 695                 700

Asp Thr Lys Asp Asn Ile Ser Asn Thr Val Thr Asn Lys Glu Arg Ile
705                 710                 715                 720

Tyr Gly Ser Phe Val Ser Glu Ser Ala Glu Ser Ala Ile Gln Cys Ala
                725                 730                 735

Ile Asp Arg Ser Glu Lys Glu Ser Gly Leu Thr Leu Lys Lys Asp Ile
            740                 745                 750

Ser Trp Leu Val Asn Val Leu Ser Lys Tyr Leu Glu Arg Lys Phe Lys
        755                 760                 765

Glu Val Lys Asn Asn Arg Lys Tyr Thr Asn Val Asn Lys Cys Asp Asn
    770                 775                 780
```

Cys Phe Asn Trp Leu Arg Val Ile Glu Asn Ile Lys Arg Leu Lys Arg
785 790 795 800

Ser Ile Ser Tyr Leu Gly Glu Asp Leu Gln Lys Asn Pro Glu Leu Lys
805 810 815

Ile Glu Leu Lys Asn Leu Asn Glu Tyr Gly Asn Asn Val Lys Ser Asp
820 825 830

Phe Leu Lys Gln Ile Ala Ser Asn Ile Ile Lys Val Ala Ile Glu His
835 840 845

Lys Cys Asp Ile Val Phe Ile Glu Lys Leu Gly Lys Ala Asp Ser Arg
850 855 860

Ser Arg Lys Leu Asn Glu Met Phe Ser Phe Trp Ser Pro Lys Ala Ile
865 870 875 880

Lys Lys Ala Ile Glu Asn Ala Ala Ser Trp His Gly Ile Pro Val Val
885 890 895

Glu Val Asp Pro Ser Cys Thr Ser Lys Val His Tyr Glu Thr Asn Leu
900 905 910

Phe Gly His Arg Ile Gly Asn Asp Leu Tyr Tyr Val Glu Asp Gln Cys
915 920 925

Leu Lys Lys Val Asp Ala Asp Ile Asn Ala Ala Lys Gln Ile Leu Val
930 935 940

Arg Gly Ala Thr Arg His Gly Asn Ile Ser Ser Ile Asn Ile Lys Tyr
945 950 955 960

Leu Gln Ala Lys Ile Ala Glu Leu Asn Ser Glu Ala Asn Ser Glu Glu
965 970 975

Asp Lys Glu Glu Ile Lys Gln Gly Gly Lys Arg Ile Gln Gly Phe Leu
980 985 990

Trp Lys Lys Tyr Gly Asn Ile Thr Asn Ile Thr Asn Gln Leu Thr Ala
995 1000 1005

Ala His Lys Glu Arg Glu Ser Lys Phe Asp Tyr Ile Tyr Leu His
1010 1015 1020

Asn Asp Lys Trp Ile Ala Tyr Glu Asp Arg Asn Glu Ile Lys Lys
1025 1030 1035

Asp Ile Glu Lys Arg Leu Glu
1040 1045

<210> SEQ ID NO 13
<211> LENGTH: 895
<212> TYPE: PRT
<213> ORGANISM: artificial sequence
<220> FEATURE:
<223> OTHER INFORMATION: amino acid sequence of Cas12j.15

<400> SEQUENCE: 13

Met Thr Ala Lys Lys Thr Ala Lys Lys Tyr Phe Pro Pro Lys Cys Leu
1 5 10 15

Arg Ser Ser His Phe Lys Ile Tyr Gly Ile Pro Thr Ala Ile Arg Ala
20 25 30

Leu Glu Glu Thr Asn Thr Phe Val Asn Lys Ala Ala Ala Asp Leu Met
35 40 45

Glu Met Phe Phe Leu Met Arg Gly Gln Pro Tyr Arg Arg Arg Ile Gly
50 55 60

Ser Glu Glu Lys Gln Val Thr Gln Glu His Ile Asp Ala Arg Leu Arg
65 70 75 80

Val Leu Val Gly Asp Tyr Ser Leu Asn Glu Val Lys Pro Leu Leu Arg
85 90 95

```
Gln Leu Tyr Asp Gly Ile Lys Ala Lys Gln Asn Tyr Ala Pro Thr His
            100                 105                 110

Phe Val Arg Phe Phe Ile Gln Pro Thr Lys Gly Ala Ile Asp Lys Lys
        115                 120                 125

Ser Pro Val Ser Gln Arg Ala Lys Lys Ala Gly Gln Lys Leu Gln Lys
    130                 135                 140

Met Gly Val Leu Pro Ile Leu Pro Leu Ser Pro Gly Phe Lys Phe Trp
145                 150                 155                 160

Thr Ala Ala Met Met Met Ala Cys Ser Arg Met Asn Ser Trp Glu Ala
                165                 170                 175

Cys Asn Glu Lys Thr Ile Glu Asn His Lys Ala Phe Leu Glu Gly Ile
            180                 185                 190

Glu Asn Tyr Lys Lys Glu Ile Arg Phe Glu Asp Leu Cys Glu Glu Trp
        195                 200                 205

Ser Leu Phe Ser Asp Trp Leu Thr Glu Ala Glu Ser Asp Asn Glu Gly
    210                 215                 220

Gly Cys Lys Phe Lys Leu Thr Pro Arg Phe Leu Gln Arg Trp Glu Arg
225                 230                 235                 240

Ile Tyr Leu Lys Gln Met Arg Lys Gly Lys Ile Pro Ala Arg His Asn
                245                 250                 255

Leu Gly Pro Val Met Glu Ala Leu Ala Gly Asp Lys Tyr Arg Gln Leu
            260                 265                 270

Trp Asp Asn Gly Glu Glu Arg Asp Tyr Ile Thr Glu Leu Gly Asp Leu
        275                 280                 285

Val Thr Ser Gln Arg Lys Ala Val Arg Leu Ser Arg Asp Ser Ala Val
    290                 295                 300

Thr Phe Pro Asp Glu Glu Leu Ser Pro Val Gly Thr Glu Phe Gly His
305                 310                 315                 320

Asn Tyr Met Ser Phe Ser Ile Asp Gln Glu Asn Ser His Leu Val Thr
                325                 330                 335

Leu Glu Val Ile Gly Gly Lys Tyr Gln Phe Glu Ile Ser Lys Ser Asp
            340                 345                 350

Tyr Phe Arg Asp Leu Ile Val Glu Glu Ala Gly Lys Gln Ser Lys Phe
        355                 360                 365

Tyr Asn Val Ser Tyr Arg Lys Gly Asn Val Arg Glu Glu Asn Leu Ala
    370                 375                 380

Gly Asp Phe Lys Glu Ala Thr Val Arg Asn Arg Arg Ser Leu Lys Thr
385                 390                 395                 400

Gly Lys Arg Arg Leu Tyr Phe Tyr Met Ser His Ser Ile Pro Thr Arg
                405                 410                 415

Phe Asp Asp Asp Leu Tyr Ala Gln Phe Thr Glu Lys Gly Gln Pro Asp
            420                 425                 430

Phe Ser Lys Leu Tyr Lys Ala Val Thr Tyr Phe Gln Cys Ser Leu Gly
        435                 440                 445

Asn Lys Lys Ala Asp Thr Tyr Arg Val Tyr Val Lys Met Gly Thr Arg
    450                 455                 460

Phe Leu Gly Val Asp Ile Gly Val Ser Arg Leu Phe Gly Phe Ser Leu
465                 470                 475                 480

Phe Glu Leu Arg Glu Glu Lys Pro Glu Lys Asn Pro Phe Phe Glu Leu
                485                 490                 495

Pro Asp Asp Leu Gly Tyr Ala Val Cys Leu Glu Ser Trp Val Asp Gly
            500                 505                 510
```

Val Glu Lys Asn His Lys Val Ala Gln Glu Met Lys Asp Trp Arg Arg
515 520 525

Glu Cys Leu Ala Ala Gln Arg Leu Ile His Tyr Ala Lys Phe Leu Lys
530 535 540

Lys Arg Asp Lys Asn Glu Glu Ile Asp Tyr Lys His Glu Glu Ser Leu
545 550 555 560

Glu Thr Ile Ala Gly Leu Leu Gly Ile Glu Ile Asp Pro Glu Gln Ile
565 570 575

Ile Asp Val Pro Leu Lys Leu Leu Asp Leu Val Gly Gln Ala Ile Gly
580 585 590

Ala Leu Arg Lys Lys Tyr Leu Val Leu Lys Lys Asn Glu Val Arg Gln
595 600 605

Gly Arg Ile Thr Ser Glu Leu Phe Leu Trp Pro Glu Cys Val Asp Thr
610 615 620

Tyr Ile Arg Leu Leu Lys Ser Trp Thr Tyr Lys Asp Lys Lys Pro Tyr
625 630 635 640

Gln Lys Gly Glu Thr Asn Lys Asp Ala Phe Lys Lys Leu Lys Gly Tyr
645 650 655

Leu Ala Arg Leu Arg Lys Asp Leu Ala Pro Lys Tyr Ala Ala Val Ile
660 665 670

Ala Asp Ala Ala Ile Arg His Lys Val His Val Val Val Ala Glu Asn
675 680 685

Leu Glu Gln Phe Gly Leu Ser Met Lys Asn Glu Lys Asp Leu Asn Arg
690 695 700

Val Leu Ala His Trp Ser His Gln Lys Ile Trp Ser Met Val Glu Glu
705 710 715 720

Gln Leu Arg Pro Tyr Gly Ile Met Val Val Tyr Val Asp Pro Arg His
725 730 735

Thr Ser Lys Leu Asp Phe Ala Thr Asp Glu Phe Gly Gly Arg Cys Phe
740 745 750

Thr Ser Leu Tyr Val Met Arg Asp Gly Lys Lys Thr Thr Thr Asp Thr
755 760 765

Glu Lys Asn Ala Ser Gln Asn Ile Pro Lys Lys Phe Leu Thr Arg His
770 775 780

Arg Asn Val Ser Trp Leu Leu Ala Tyr Ala Val Asp Leu Ser Asp Ser
785 790 795 800

Gln Lys Lys Lys Leu Gly Ile Gly Asp Glu Lys Val Trp Leu Pro Asn
805 810 815

Met Gly Leu Met Ile Ser Gly Ala Leu Lys Ala Lys His Gly Lys Asn
820 825 830

Ser Ala Leu Leu Val Glu Asp Gly Glu Asn Tyr Arg Leu Leu Pro Ile
835 840 845

Thr Ala Ala Gln Ala Lys Lys Phe Val Val Lys Arg Lys Lys Glu Glu
850 855 860

Phe Tyr Arg His Gly Glu Ile Trp Leu Thr Lys Glu Ala His Lys Ala
865 870 875 880

Arg Ile Glu Tyr Leu Phe Pro Glu Ser Lys Lys Gly Arg Lys Ser
885 890 895

<210> SEQ ID NO 14
<211> LENGTH: 956
<212> TYPE: PRT
<213> ORGANISM: artificial sequence
<220> FEATURE:
<223> OTHER INFORMATION: amino acid sequence of Cas12j.16

<400> SEQUENCE: 14

```
Met Lys Lys Thr Asn Tyr Lys Thr Ser His Leu Leu Ile Asp Asn Pro
1               5                   10                  15

Pro Gln Ser Ile Ile Asp Leu His Arg Asp Val Ile Glu Ile Gly Ser
            20                  25                  30

Tyr Leu Thr Lys Phe Phe Leu Ala Cys Leu Gly Arg Pro Val Asp Ser
        35                  40                  45

Thr Ile Leu Ser Glu Pro Ala Leu His Phe Gln Phe Val Asn Gly Ile
    50                  55                  60

Leu Pro Val Lys Asn Gly Pro Gly Ala Asp Asp Ser Ser Trp Arg His
65                  70                  75                  80

Ser Glu Asn Cys Tyr Ser Met Leu Phe Glu Lys Asn Ser Lys Ser Gly
                85                  90                  95

Lys Ser Asp Gly Lys Val Arg Gln Val Arg Glu Leu Lys Val Ala Leu
            100                 105                 110

Phe Gly Lys Lys Glu Lys Gly Lys Gly Ile Val Gly Lys Lys Thr Trp
        115                 120                 125

Asp Glu Leu Lys Val Val Leu Glu Ala Leu Pro Glu Glu His Gln Ile
    130                 135                 140

Leu Ser Leu Glu Ile Cys Gln Arg His Tyr Glu Ser Arg Asp Val Lys
145                 150                 155                 160

Ala Phe Gly Lys Leu Ala Leu Ser Ser Lys Ser Arg Pro Ser Val Glu
                165                 170                 175

Ala Gly Leu Lys Leu Arg Glu Leu Gly Leu Leu Pro Leu Asp Ser Arg
            180                 185                 190

Gly Leu Asp Lys Asn Lys Leu Leu Gly Ile Leu Ala Ala Val Thr Gly
        195                 200                 205

Arg Leu Lys Ser Trp Arg Asp Arg Asp Cys Ala Cys Lys Ala Asp Lys
    210                 215                 220

Gln Ala Leu Arg Val Lys Phe Glu Glu Arg Leu Ser Lys Val Asp Gln
225                 230                 235                 240

Ser Ala Tyr Gln Gln Phe Lys Gln Phe Ala Asp Glu Leu Leu Thr Gln
                245                 250                 255

Glu Gly Tyr Arg Ile Ser Gly Arg Val Leu Arg Ala Val Glu Lys Lys
            260                 265                 270

Asp Ser Asp Tyr Ser Pro Val Leu Thr Val Leu Ala Lys Tyr Pro Asp
        275                 280                 285

Leu Gln Asp Asn Phe Glu Glu Leu Cys Arg Ala Cys Leu Ala Glu Gln
    290                 295                 300

Ala Phe Asn Lys Lys Lys Ala Asp Ala Arg Val Thr Val Cys Ser Glu
305                 310                 315                 320

Thr Ser Pro Leu Gln Phe Pro Phe Gly Met Thr Gly Asn Gly Tyr Pro
                325                 330                 335

Phe Thr Leu Ser Ala Cys Glu Gly Arg Ile Asn Ala Thr Ile His Phe
            340                 345                 350

Pro Gly Gly Asp Leu Pro Leu Arg Leu Arg Lys Ser Lys Tyr Phe Gln
        355                 360                 365

Asn Pro Glu Ile Leu Pro Val Lys Asp Gly Phe Gln Ile Thr Phe Thr
    370                 375                 380

Arg Gly Lys Thr Pro Leu Val Gly Thr Ile Lys Glu Pro Ser Leu Leu
385                 390                 395                 400

Lys Lys Asn Asn His Tyr Tyr Leu Ser Leu Arg Val Asn Val Pro Ser
```

```
                405                 410                 415

Val Lys Ile Pro Lys Glu Val Arg Asp Thr Arg Ala Tyr Tyr Ser Ser
            420                 425                 430

Ala Val Gly Gly Asp Glu Thr Thr Pro Val Pro Val Lys Ala Val Ala
        435                 440                 445

Ile Asp Leu Gly Val Thr Thr Leu Ala Asp Tyr Ser Ile Ile Asp Thr
    450                 455                 460

Cys Leu Pro Gly Asp Cys Lys Val Phe Gly Gly Glu Thr Ala Ala Phe
465                 470                 475                 480

Thr Ala His Gly Lys Ile Gly Gln Cys Ala Asn Lys Ser Leu Arg Asp
                485                 490                 495

Arg Leu Tyr Lys Asn Thr Glu Glu Ala Leu Phe Leu Gly Lys Phe Ile
            500                 505                 510

Arg Leu Ser Lys Lys Leu Arg Asp Gly Glu Gly Leu Asn Arg Trp Glu
        515                 520                 525

Val Glu Lys Leu Pro Gly Tyr Ala Glu Arg Leu Gly Ile Thr Gln His
    530                 535                 540

Leu Asp Asn Ala Tyr Thr Arg Lys Asp Glu Ile Ala Arg Lys Phe Lys
545                 550                 555                 560

Gln Ile Lys Gly Asn Phe Asp Lys Leu Val Ser Glu Phe Ala Leu Arg
                565                 570                 575

Asp His Pro Ser Lys Lys Gly Glu Ser Trp Glu Thr Ile Ser Ala Glu
            580                 585                 590

Thr Ile Gln Val Leu Ala Ala Leu Lys Arg Ile Gln Ser Leu Leu Lys
        595                 600                 605

Ser Trp Thr Tyr Tyr Ser Trp Thr Ala Glu Asp Tyr Val Leu Ala Leu
    610                 615                 620

Thr Ala Asp Gly Pro Val Cys Ile Asp Gly Glu His Val Lys Ala Val
625                 630                 635                 640

Thr Ala Thr Ser Arg Arg Ser Phe Ala Pro Cys Gly Lys Ala Ala Leu
                645                 650                 655

Leu Arg Leu Ile Glu Ser Gly Glu Ile Val Glu Thr Gly Gly Gln Tyr
            660                 665                 670

Gln Leu Ala Thr Gly Val Lys His Arg Asn His Pro Val Asn Phe Leu
        675                 680                 685

Ser Ser Tyr Ile Lys His Phe Asn Gly Leu Arg Arg Asp Leu Thr Asn
    690                 695                 700

Lys Leu Val Arg Ala Ile Val Asn Lys Ala Gln Glu Tyr Arg Val Gln
705                 710                 715                 720

Ile Val Ile Val Glu Asp Phe Gly Ile Ala Asp Leu Glu Asp Arg Ile
                725                 730                 735

Lys Asp Ala Tyr Glu Asn Tyr Arg Trp Asn Leu Phe Ala Pro Ala Thr
            740                 745                 750

Ile Val Lys Lys Leu Glu Ala Ala Leu Leu Glu Val Gly Ile Ala Met
        755                 760                 765

Ala Gln Val Asp Pro Arg His Thr Ser Gln Ile Ala Pro Thr Gly Ala
    770                 775                 780

Phe Gly Phe Arg Asp His Ala Phe Leu Tyr Tyr Gln Asp Asp Gly Leu
785                 790                 795                 800

Cys Arg Ile Asp Ala Asn Thr Asn Ala Ser Met Arg Ile Ala Glu Arg
                805                 810                 815

Phe Phe Met Arg His Ser Val Leu Thr Gln Leu Arg Ala Ala Lys Ile
            820                 825                 830
```

```
Gly Glu Thr Glu Tyr Leu Ile Pro Glu Ser Ala Ser Lys Arg Leu Asn
        835                 840                 845

Ala Phe Val Lys Leu Gln Thr Gly Lys Pro Phe Ala Lys Leu Ile Met
    850                 855                 860

Asn Cys Ser Gly Phe Val Leu Glu Gly Leu Thr Lys Lys Gln Tyr Ala
865                 870                 875                 880

Lys Leu Ala Glu Thr Ala Gly Lys Lys Glu Ser Phe Tyr Gln Tyr Asp
                885                 890                 895

Asp Arg Trp Phe Asp Lys Gly His His Phe Ala Cys Arg Ala Thr Leu
            900                 905                 910

Glu Asn Lys Val Gln Val Cys Leu Asn Gly Gly Gly Arg Ile Lys Asp
        915                 920                 925

Thr Thr Pro Asp Phe Asn Pro Lys Ser Leu Leu Arg Ser Asp Leu Gln
    930                 935                 940

Thr Pro Leu Asp Gln Leu Phe Gly Asn Ser Gly Ala
945                 950                 955


<210> SEQ ID NO 15
<211> LENGTH: 946
<212> TYPE: PRT
<213> ORGANISM: artificial sequence
<220> FEATURE:
<223> OTHER INFORMATION: amino acid sequence of Cas12j.17

<400> SEQUENCE: 15

Met Ser Asn Thr Thr Tyr Lys Thr Ser His Leu Leu Ile Asp Leu Pro
1               5                   10                  15

Gln Gln Glu Leu Ile Asp Leu His Arg Asp Ser Asn Glu Met Gly Ser
            20                  25                  30

Tyr Leu Thr Lys Phe Phe Leu Ala Ala Leu Gly Arg Pro Val Asp Asn
        35                  40                  45

Ser Ile Val Leu Pro Pro Glu Leu Ala Asp Leu Tyr Phe Gln Phe Ala
    50                  55                  60

Asn Gly Ile Leu Pro Val Asp Lys Gly Pro Gly Ser Asp Asp Pro Ser
65                  70                  75                  80

Trp Leu His Ser Glu Asn Cys Tyr Ser Met Phe Phe Glu Lys Asp Ser
                85                  90                  95

Met Ser Gly Asn Cys Thr Asn Lys Ile Lys Gln Tyr Gln Glu Leu Lys
            100                 105                 110

Thr Ala Leu Cys Gly Gln Lys Val Lys Gly Gln Lys Gly Leu Val Gly
        115                 120                 125

Lys Lys Thr Trp Ala Gln Leu Lys Lys Val Leu Thr Ala Leu Pro Gln
    130                 135                 140

Lys Tyr Gln Ile Leu Ser Pro Lys Ile Cys Gln Lys Tyr Phe Lys Ser
145                 150                 155                 160

Gly Asn Leu Glu Gly Phe Gly Lys Leu Ala Leu Ala Gly Lys Asn Arg
                165                 170                 175

Pro Ser Met Ser Ala Gly Leu Gln Leu Arg Glu Leu Gly Leu Leu Pro
            180                 185                 190

Leu Asp Ser Arg Gly Ile Asp Lys Asn Lys Leu Leu Gly Ile Leu Val
        195                 200                 205

Gly Ile Thr Gly Arg Leu Lys Ser Trp Arg Asp Arg Asp Trp Ala Cys
    210                 215                 220

Lys Thr Val Lys Glu Glu Leu Arg Val Thr Phe Glu Lys Gly Leu Gly
225                 230                 235                 240
```

```
Glu Val Asp Pro Thr Ala Tyr Pro Gln Phe Lys Gln Phe Ala Asp Gln
                245                 250                 255

Leu Phe Lys Gln Glu Gly Tyr Lys Ile Ser Gly Arg Val Leu Arg Ala
            260                 265                 270

Val Glu Gly Lys Asp Ala Asp Tyr Gln Pro Val Leu Ser Leu Leu Thr
        275                 280                 285

Gln Tyr Pro Asp Leu Gln Gly Asp Phe Glu Glu Leu Gly Arg Val Tyr
    290                 295                 300

Leu Ala Glu Ala Glu Tyr Leu Arg Lys Lys Val Asp Ala Arg Val Thr
305                 310                 315                 320

Val Cys Asp Ala Glu Thr Ser Pro Leu Gln Phe Pro Phe Gly Leu Thr
                325                 330                 335

Gly Asn Gly Tyr Ser Ile Thr Leu Thr Val Val Lys Gly Gln Ile Ala
            340                 345                 350

Ala Thr Leu His Leu Pro Gly Gly Asp Ile Thr Pro Arg Leu Arg Arg
        355                 360                 365

Ser Lys Tyr Phe Gln Asn Pro Glu Ile Ala Pro Val Lys Asp Gly Lys
    370                 375                 380

Gly Lys Val Asn Gly Phe Gln Ile Ser Phe Lys Arg Gly Lys Thr Pro
385                 390                 395                 400

Leu Val Gly Ile Ile Lys Glu Pro Lys Leu Leu Lys Lys Asn Gly Asn
                405                 410                 415

Tyr Tyr Leu Ser Leu Ala Val Gly Ile Asn Lys Thr Glu Ile Pro Lys
            420                 425                 430

Glu Ile Cys Asp Ala Arg Ala Tyr Tyr Ser Ser Thr Ser Arg Thr Asp
        435                 440                 445

Thr Pro Pro Ala Val Lys Ala Met Ser Ile Asp Leu Gly Val Thr Thr
    450                 455                 460

Leu Ala Asp Tyr Ser Ile Ile Asp Thr Gly Leu Pro Gly Asp Cys Gly
465                 470                 475                 480

Val Phe Gly Gly Ser Thr Ala Ala Phe Thr Glu His Gly Lys Ile Gly
                485                 490                 495

Arg Cys Gly Ser Lys Ser Leu Arg Asp Gly Leu Tyr Lys Asn Thr Glu
            500                 505                 510

Ala Gly Tyr Phe Leu Ala Lys Tyr Ile Arg Leu Ser Lys Asn Leu Arg
        515                 520                 525

Gly Gly Val Gly Leu Asn Lys Leu Glu Lys Glu Lys Leu Leu Glu His
    530                 535                 540

Val Glu Arg Leu Gly Ile Glu His Cys Ala Asp Asp Phe Ala Arg Lys
545                 550                 555                 560

Asp Glu Ile His Arg Lys Phe Ser Glu Ile Lys Ser Lys Leu Glu Lys
                565                 570                 575

Ser Ile Ser Glu Phe Ala Leu Arg Asp Arg Pro Asp Lys Lys Gly Ala
            580                 585                 590

Ser Trp Glu Gly Ile Cys Ala Glu Thr Val Gln Val Leu Gly Ala Val
        595                 600                 605

Lys Arg Trp Gln Ser Leu Ala Lys Ser Trp Thr Tyr Tyr Ser Trp Thr
    610                 615                 620

Ala Glu Asp Tyr Val Leu Ala Leu Thr Gly Glu Gly Arg Thr Arg Val
625                 630                 635                 640

Ser Asp Glu His Val Glu Ser Val Val Lys Thr Gly Arg Arg Gln Phe
                645                 650                 655
```

Ala Pro Cys Gly Lys Ala Ala Leu Leu Arg Leu Leu Glu Lys Gly Lys
660 665 670

Ile Val Glu Val Cys Pro Gly Gln Phe Gln Leu Ala Glu Gly Val Asp
675 680 685

Tyr Lys Arg His Pro Thr Glu Phe Leu Ala Ala His Ile Arg His Phe
690 695 700

Asn Gly Leu Arg Arg Asp Leu Thr Asn Lys Leu Val Arg Ala Ile Val
705 710 715 720

Glu Lys Ala Gln Gln His Arg Val Gln Ile Val Ile Val Glu Asp Phe
725 730 735

Gly Ile Pro Asp Ile Glu Gly Arg Ile Met Asp His Tyr Asp Asn Tyr
740 745 750

Arg Trp Asn Leu Phe Ala Pro Ala Lys Val Ile Glu Lys Leu Glu Glu
755 760 765

Ala Leu Ser Glu Val Gly Ile Ala Met Ala Glu Val Asp Pro Arg His
770 775 780

Thr Ser Gln Leu Ala Pro Thr Gly Asp Phe Gly Phe Arg Asp His Glu
785 790 795 800

Asn Leu Tyr Phe Trp Glu Lys Gly Leu Cys Arg Thr Asp Ala Asn Thr
805 810 815

Asn Ala Ser Met Arg Ile Ala Glu Arg Phe Phe Thr Arg His Ser Val
820 825 830

Leu Ser Gln Leu Arg Ala Val Lys Ile Ser Glu Thr Glu Phe Leu Ile
835 840 845

Pro Val Ser Thr Gly Lys Arg Glu Asn Ala Phe Ile Lys Ser Gln Thr
850 855 860

Gly Lys Leu Phe Ala Lys Leu Val Ala Asp Ser Asn Gly Phe Val Met
865 870 875 880

Val Gly Leu Thr Glu Lys Gln His Gly Ala Thr Val Thr Val Gly Lys
885 890 895

Lys Val Ser Phe Tyr Asn His Ala Gly Arg Trp Leu Gly Lys Ala His
900 905 910

His Ile Ala His Arg Asp Arg Ile Lys Asn Glu Val Asn Gln Val Leu
915 920 925

Thr Ser Gly Arg Gly Arg Ile Arg Asn Ile Ala Pro Glu Leu Ser Pro
930 935 940

Lys Thr
945

<210> SEQ ID NO 16
<211> LENGTH: 930
<212> TYPE: PRT
<213> ORGANISM: artificial sequence
<220> FEATURE:
<223> OTHER INFORMATION: amino acid sequence of Cas12j.18

<400> SEQUENCE: 16

Met Thr Asn Gln Lys Pro Lys Phe Lys Ser Ser Asp Ile Gln Ile Lys
1 5 10 15

His Ile Ser Pro Thr Asp Lys Lys Arg Leu Lys Thr Phe Tyr His Gln
20 25 30

Leu Tyr Glu Gln Val Asn Phe Ile Leu Glu Arg Met Ile Val Met Arg
35 40 45

Gly Arg Pro Arg Thr Ile Arg Asn Ile Asp Gly Thr Glu Ile Phe Val
50 55 60

```
Ser Gln Glu Glu Ala Asp Gln Gln Leu Leu Ser Leu Ala Gly Gly Ser
65                  70                  75                  80

His Glu Gly Val Lys Tyr Leu Lys Gln Tyr Tyr Glu Ser Cys Val Asp
                85                  90                  95

Ala Gly Lys Pro Ala Lys Tyr Ala Ala Asn Met Phe Leu Thr Lys Thr
            100                 105                 110

Ile Ser Gly Thr Asn Pro Leu Gln Cys His Thr Ala Val Tyr Lys Leu
        115                 120                 125

Tyr Lys Lys Val Gln Ala Lys Gln Ile Thr Lys Lys Glu Phe Ile Asp
    130                 135                 140

Lys Leu Tyr Ser Lys Thr Lys Lys Lys Lys Ser Leu Lys Pro Ala Tyr
145                 150                 155                 160

Lys Val Phe Thr Glu Asn Glu His Ile Glu Phe Tyr His Lys Val Arg
                165                 170                 175

Ser Gly Lys Leu Pro Ala Ser Glu Val Arg Leu Glu Glu Ser Arg Arg
            180                 185                 190

Ala Pro Asp Val Gly Leu Glu Val Gly Leu Leu Leu Arg Glu Leu Gly
        195                 200                 205

Ile Phe Pro Phe Asn Phe Pro His Phe Thr Glu Lys Lys Tyr Leu Asp
    210                 215                 220

Leu Ala Trp Thr Ile Ala Ile Arg Trp Leu Lys Asn Trp Asn Glu Asn
225                 230                 235                 240

Asn Lys Asn Thr Ala Lys Glu Lys Ala Lys Gln Lys Ala Ile Val Asp
                245                 250                 255

Lys Leu Arg Thr Ser Leu Asp Gln Lys Glu Val Asp Leu Phe Glu Glu
            260                 265                 270

Phe Ala Glu Glu Cys Ser Gln Glu Gln Phe Gly Ile Arg Glu Gly Phe
        275                 280                 285

Val Lys Ala Lys Lys Arg Leu Lys Ser Phe Pro Lys Gly Ile Glu Lys
    290                 295                 300

Ser Ser Tyr Lys Glu Gly Met Arg Ile Leu Val Gln Asn Lys His Gly
305                 310                 315                 320

Ser Ile Trp Asp Asn Phe Glu Asn Leu Ala Tyr His His Ile Ala Leu
                325                 330                 335

Asn Glu Tyr Asn Arg Leu Arg Asp Glu Ala Ser Phe Ser Phe Pro Asp
            340                 345                 350

Pro Ile Tyr His Pro Ile Arg Ala Glu Phe Gly Leu Thr Ser Leu Pro
        355                 360                 365

Lys Phe Asn Val Gly Leu Asn Asp Arg Gly Asn Tyr Glu Phe Thr Ile
    370                 375                 380

Asn Leu Pro Asp Gly Pro Leu Met Met Leu Gly Lys Lys Ser Arg Tyr
385                 390                 395                 400

Tyr Leu Lys Pro Ile Ile Gln Gly Pro Leu Asn Asn Ala Phe Ser Phe
                405                 410                 415

Glu Phe Ile Lys Gly Asn Lys Lys Arg Pro Lys Ile Ser Ala Lys Leu
            420                 425                 430

Lys Ser Ile Thr Val Val Phe Ala Lys Ser Ser Ile Tyr Val Gly Leu
        435                 440                 445

Pro Tyr Arg Pro Ile Ser Ile Pro Ile Pro Gln Ala Val Thr Asn Ser
    450                 455                 460

Thr Tyr Tyr Phe Lys Lys Asn Leu Ser Ser Thr Ser Lys Phe Asp Lys
465                 470                 475                 480

Asp Val Phe Met Gly Leu Thr Ala Val Ser Val Asp Leu Gly Leu Asn
```

```
                485                 490                 495

Pro Val Phe Ser Met Ser Ala Cys Arg Leu Asp Glu Met Lys Ala Asp
            500                 505                 510

Glu His Tyr Ser Cys Glu Val Pro Gly Phe Gly Trp Ala Asn Gln Ile
        515                 520                 525

Trp Ser Lys Arg Ala Gly Gly Val Trp Asn Arg Ser Phe Arg Asp Lys
    530                 535                 540

Ile Arg Gly Phe Val Pro Gly Asn Leu Ser Asp Arg Ile Phe Cys Cys
545                 550                 555                 560

Lys Lys Ser Ile Ile Val Ser Lys Lys Leu Arg Asp Glu Lys Pro Leu
                565                 570                 575

Thr Gln Tyr Glu Glu Glu Asn Phe Glu Arg Trp Met Gln Val Val Gly
            580                 585                 590

Val Asp Pro Asn Glu Asp His Tyr Lys Gln Leu Arg Ile Ala Ile Arg
        595                 600                 605

Asp Ile Lys Thr Glu Tyr Glu Thr Val Arg Ser Glu Phe Ala Leu Arg
    610                 615                 620

Asp His Pro Asn Asn Ser Asn Lys Thr Thr Glu Asn Ile Cys Thr Glu
625                 630                 635                 640

Cys Phe Asp Met Leu Phe Val Ile Lys Asn Leu Ile Ser Leu Leu Lys
                645                 650                 655

Ser Trp Asn Arg Trp His Arg Thr Thr Gly Asp Ile Glu Glu Arg Gly
            660                 665                 670

Lys Asp Pro Asn Glu Cys Ser Thr Tyr Trp Arg His Tyr Asn Gly Leu
        675                 680                 685

Lys Thr Asp Leu Leu Lys Lys Leu Thr Asn Ile Leu Ile Glu Ser Ala
    690                 695                 700

Lys Ser Ile Gly Ala His Ile Ile Ile Leu Glu Asp Leu Thr Leu Ser
705                 710                 715                 720

Gln Arg Ser Ser Arg Ser Arg Arg Glu Asn Ser Leu Val Ala Ile Phe
                725                 730                 735

Gly Ala Gln Thr Ile Ile Lys Thr Ile Ser Glu Glu Ala Glu Ile Asn
            740                 745                 750

Gly Ile Leu Val Tyr Leu Glu Asp Pro Arg His Ser Ser Gln Ile Ser
        755                 760                 765

Ile Val Thr Asn Glu Phe Gly Tyr Arg Pro Lys Glu Asp Lys Ala Lys
    770                 775                 780

Leu Tyr Phe Met Asp Glu Glu Thr Val Cys Val Thr Asn Cys Asp Asp
785                 790                 795                 800

Ser Ala Ala Leu Met Leu Gln Gln Ser Phe Trp Ser Arg His Lys Asp
                805                 810                 815

Val Val Lys Val Lys Gly Thr Lys Val Ser Asp Thr Glu Tyr Leu Val
            820                 825                 830

Ser Ser Glu Asp Lys Asp Gly Thr Lys Met Arg Leu Arg Ser Tyr Leu
        835                 840                 845

Lys Arg Asn Val Gly Thr Ala Asn Ala Ile Leu Gln Lys Asn Cys Asp
    850                 855                 860

Gly Tyr Asp Leu Lys Lys Ile Ser Pro Gln Lys Lys Lys Lys Ile Glu
865                 870                 875                 880

Glu Phe Gly Lys Asp Glu Tyr Phe Tyr Arg His Gly Glu Gln Trp Phe
                885                 890                 895

Thr Ala Asp Ala His Phe Asp Lys Leu Arg Glu Phe Gly Asn Gln Val
            900                 905                 910
```

```
Phe Leu Thr Pro Gln Ser Gln Ile Lys Arg Ile Asn Leu Gln Val Glu
        915                 920                 925

Gly Thr
    930


<210> SEQ ID NO 17
<211> LENGTH: 908
<212> TYPE: PRT
<213> ORGANISM: artificial sequence
<220> FEATURE:
<223> OTHER INFORMATION: amino acid sequence of Cas12j.19

<400> SEQUENCE: 17

Met Pro Ser Tyr Lys Ser Ser Arg Val Leu Val Arg Asp Val Pro Glu
1               5                   10                  15

Glu Leu Val Asp His Tyr Glu Arg Ser His Arg Val Ala Ala Phe Phe
            20                  25                  30

Met Arg Leu Leu Leu Ala Met Arg Arg Glu Pro Tyr Ser Leu Arg Met
        35                  40                  45

Arg Asp Gly Thr Glu Arg Glu Val Asp Leu Asp Glu Thr Asp Asp Phe
    50                  55                  60

Leu Arg Ser Ala Gly Cys Glu Glu Pro Asp Ala Val Ser Asp Asp Leu
65                  70                  75                  80

Arg Ser Phe Ala Leu Ala Val Leu His Gln Asp Asn Pro Lys Lys Arg
                85                  90                  95

Ala Phe Leu Glu Ser Glu Asn Cys Val Ser Ile Leu Cys Leu Glu Lys
            100                 105                 110

Ser Ala Ser Gly Thr Arg Tyr Tyr Lys Arg Pro Gly Tyr Gln Leu Leu
        115                 120                 125

Lys Lys Ala Ile Glu Glu Glu Trp Gly Trp Asp Lys Phe Glu Ala Ser
    130                 135                 140

Leu Leu Asp Glu Arg Thr Gly Glu Val Ala Glu Lys Phe Ala Ala Leu
145                 150                 155                 160

Ser Met Glu Asp Trp Arg Arg Phe Phe Ala Ala Arg Asp Pro Asp Asp
                165                 170                 175

Leu Gly Arg Glu Leu Leu Lys Thr Asp Thr Arg Glu Gly Met Ala Ala
            180                 185                 190

Ala Leu Arg Leu Arg Glu Arg Gly Val Phe Pro Val Ser Val Pro Glu
        195                 200                 205

His Leu Asp Leu Asp Ser Leu Lys Ala Ala Met Ala Ser Ala Ala Glu
    210                 215                 220

Arg Leu Lys Ser Trp Leu Ala Cys Asn Gln Arg Ala Val Asp Glu Lys
225                 230                 235                 240

Ser Glu Leu Arg Lys Arg Phe Glu Glu Ala Leu Asp Gly Val Asp Pro
                245                 250                 255

Glu Lys Tyr Ala Leu Phe Glu Lys Phe Ala Ala Glu Leu Gln Gln Ala
            260                 265                 270

Asp Tyr Asn Val Thr Lys Lys Leu Val Leu Ala Val Ser Ala Lys Phe
        275                 280                 285

Pro Ala Thr Glu Pro Ser Glu Phe Lys Arg Gly Val Glu Ile Leu Lys
    290                 295                 300

Glu Asp Gly Tyr Lys Pro Leu Trp Glu Asp Phe Arg Glu Leu Gly Phe
305                 310                 315                 320

Val Tyr Leu Ala Glu Arg Lys Trp Glu Arg Arg Arg Gly Gly Ala Ala
                325                 330                 335

Val Thr Leu Cys Asp Ala Asp Asp Ser Pro Ile Lys Val Arg Phe Gly
```

```
            340                 345                 350

Leu Thr Gly Arg Gly Arg Lys Phe Val Leu Ser Ala Ala Gly Ser Arg
        355                 360                 365

Phe Leu Ile Thr Val Lys Leu Pro Cys Gly Asp Val Gly Leu Thr Ala
    370                 375                 380

Val Pro Ser Arg Tyr Phe Trp Asn Pro Ser Val Gly Arg Thr Thr Ser
385                 390                 395                 400

Asn Ser Phe Arg Ile Glu Phe Thr Lys Arg Thr Thr Glu Asn Arg Arg
                405                 410                 415

Tyr Val Gly Glu Val Lys Glu Ile Gly Leu Val Arg Gln Arg Gly Arg
            420                 425                 430

Tyr Tyr Phe Phe Ile Asp Tyr Asn Phe Asp Pro Glu Glu Val Ser Asp
        435                 440                 445

Glu Thr Lys Val Gly Arg Ala Phe Phe Arg Ala Pro Leu Asn Glu Ser
    450                 455                 460

Arg Pro Lys Pro Lys Asp Lys Leu Thr Val Met Gly Ile Asp Leu Gly
465                 470                 475                 480

Ile Asn Pro Ala Phe Ala Phe Ala Val Cys Thr Leu Gly Glu Cys Gln
                485                 490                 495

Asp Gly Ile Arg Ser Pro Val Ala Lys Met Glu Asp Val Ser Phe Asp
            500                 505                 510

Ser Thr Gly Leu Arg Gly Gly Ile Gly Ser Gln Lys Leu His Arg Glu
        515                 520                 525

Met His Asn Leu Ser Asp Arg Cys Phe Tyr Gly Ala Arg Tyr Ile Arg
    530                 535                 540

Leu Ser Lys Lys Leu Arg Asp Arg Gly Ala Leu Asn Asp Ile Glu Ala
545                 550                 555                 560

Arg Leu Leu Glu Glu Lys Tyr Ile Pro Gly Phe Arg Ile Val His Ile
                565                 570                 575

Glu Asp Ala Asp Glu Arg Arg Arg Thr Val Gly Arg Thr Val Lys Glu
            580                 585                 590

Ile Lys Gln Glu Tyr Lys Arg Ile Arg His Gln Phe Tyr Leu Arg Tyr
        595                 600                 605

His Thr Ser Lys Arg Asp Arg Thr Glu Leu Ile Ser Ala Glu Tyr Phe
    610                 615                 620

Arg Met Leu Phe Leu Val Lys Asn Leu Arg Asn Leu Leu Lys Ser Trp
625                 630                 635                 640

Asn Arg Tyr His Trp Thr Thr Gly Asp Arg Glu Arg Arg Gly Gly Asn
                645                 650                 655

Pro Asp Glu Leu Lys Ser Tyr Val Arg Tyr Tyr Asn Asn Leu Arg Met
            660                 665                 670

Asp Thr Leu Lys Lys Leu Thr Cys Ala Ile Val Arg Thr Ala Lys Glu
        675                 680                 685

His Gly Ala Thr Leu Val Ala Met Glu Asn Ile Gln Arg Val Asp Arg
    690                 695                 700

Asp Asp Glu Val Lys Arg Arg Lys Glu Asn Ser Leu Leu Ser Leu Trp
705                 710                 715                 720

Ala Pro Gly Met Val Leu Glu Arg Val Glu Gln Glu Leu Lys Asn Glu
                725                 730                 735

Gly Ile Leu Ala Trp Glu Val Asp Pro Arg His Thr Ser Gln Thr Ser
            740                 745                 750

Cys Ile Thr Asp Glu Phe Gly Tyr Arg Ser Leu Val Ala Lys Asp Thr
        755                 760                 765
```

Phe Tyr Phe Glu Gln Asp Arg Lys Ile His Arg Ile Asp Ala Asp Val
770 775 780

Asn Ala Ala Ile Asn Ile Ala Arg Arg Phe Leu Thr Arg Tyr Arg Ser
785 790 795 800

Leu Thr Gln Leu Trp Ala Ser Leu Leu Asp Asp Gly Arg Tyr Leu Val
805 810 815

Asn Val Thr Arg Gln His Glu Arg Ala Tyr Leu Glu Leu Gln Thr Gly
820 825 830

Ala Pro Ala Ala Thr Leu Asn Pro Thr Ala Glu Ala Ser Tyr Glu Leu
835 840 845

Val Gly Leu Ser Pro Glu Glu Glu Leu Ala Gln Thr Arg Ile Lys
850 855 860

Arg Lys Lys Arg Glu Pro Phe Tyr Arg His Glu Gly Val Trp Leu Thr
865 870 875 880

Arg Glu Lys His Arg Glu Gln Val His Glu Leu Arg Asn Gln Val Leu
885 890 895

Ala Leu Gly Asn Ala Lys Ile Pro Glu Ile Arg Thr
900 905

<210> SEQ ID NO 18
<211> LENGTH: 821
<212> TYPE: PRT
<213> ORGANISM: artificial sequence
<220> FEATURE:
<223> OTHER INFORMATION: amino acid sequence of Cas12j.20

<400> SEQUENCE: 18

Met Ala Phe Gln Ser Lys Arg Arg Ile Val Gly Asn Phe Val Lys Glu
1 5 10 15

Gln Cys Leu Lys Ala Val Asp Gly Lys Val Ile Leu Thr Asp Gln Glu
20 25 30

Lys Arg Glu Leu Ile Lys Arg Tyr Glu Leu His Leu Glu Pro His Lys
35 40 45

Trp Leu Leu Arg Leu Phe Leu Ser Gly Tyr Glu Gly Arg Asp Asp Gly
50 55 60

Phe Tyr Glu Glu Leu Gly Asn Thr Asn Leu Asp Lys Glu Lys Phe Phe
65 70 75 80

Glu Val Thr Ala Gly Leu Arg Asp Ala Leu Leu Arg Gln Ser Gly Ser
85 90 95

Ser Arg Ala Leu Lys Ser Ser Met Leu Gly Lys Cys Pro Pro Ser Ala
100 105 110

Ala Val Gly Lys Ala Ala Lys His Ile Gln Thr Leu Arg Asp Ala Gly
115 120 125

Ile Leu Pro Phe Lys Thr Gly Leu Thr Ser Gly Glu Asp Tyr Asn Val
130 135 140

Leu Gln Gln Ala Val Gln Gln Leu Arg Ser Trp Val Ala Cys Asp His
145 150 155 160

Arg Thr Arg Glu Ala Tyr Ala Glu Gln Gln Glu Lys Thr Ser Gln Ala
165 170 175

Glu Glu Ala Ala Lys Lys Ala Ala Asn Glu Val Lys Pro Glu Asp Ala
180 185 190

Lys Ser Leu Glu Arg His Glu Arg Val Leu Thr Lys Leu Arg Lys Gln
195 200 205

Glu Arg Arg Leu Glu Arg Met Lys Ser His Ala Gln Phe Ser Leu Asp
210 215 220

```
Glu Met Asp Cys Thr Gly Tyr Ser Leu Cys Met Gly Ala Asn Tyr Leu
225                 230                 235                 240

Lys Asp Tyr Cys Leu Glu Lys Glu Gly Arg Gly Leu Arg Leu Thr Leu
                245                 250                 255

Lys Asn Ser Thr Met Ala Gly Ser Tyr Tyr Val Ser Val Gly Asp Gly
            260                 265                 270

Gln His Ala Gly Met Lys Asn Pro Gly Thr Pro Ala Gly Gly Ser Pro
        275                 280                 285

Glu Lys Gly Arg Arg Arg Asn Ile Leu Phe Asp Phe Thr Val Glu Lys
    290                 295                 300

Cys Gly Asp Asn Tyr Leu Phe Arg Tyr Asp Glu Asn Gly Lys Arg Pro
305                 310                 315                 320

Arg Ala Gly Val Val Lys Glu Pro Arg Phe Cys Trp Arg Arg Lys Gly
                325                 330                 335

Asn Ser Val Glu Leu Tyr Leu Ala Met Pro Ile Asn Ile Glu Asn Ser
            340                 345                 350

Met Arg Asn Ile Phe Val Gly Lys Gln Lys Ser Gly Lys His Ser Ala
        355                 360                 365

Phe Thr Arg Gln Trp Pro Lys Glu Val Glu Gly Leu Asp Glu Leu Arg
    370                 375                 380

Asp Ala Val Val Leu Gly Val Asp Ile Gly Ile Asn Arg Ala Ala Phe
385                 390                 395                 400

Cys Ala Ala Leu Lys Thr Ser Arg Phe Glu Asn Gly Leu Pro Ala Asp
                405                 410                 415

Val Gln Val Met Asp Thr Thr Cys Asp Ala Leu Thr Glu Lys Gly Gln
            420                 425                 430

Glu Tyr Arg Gln Leu Arg Lys Asp Ala Thr Cys Leu Ala Trp Leu Ile
        435                 440                 445

Arg Thr Thr Arg Arg Phe Lys Ala Asp Pro Gly Asn Lys His Asn Gln
    450                 455                 460

Ile Lys Glu Lys Asp Val Glu Arg Phe Asp Ser Ala Asp Gly Ala Tyr
465                 470                 475                 480

Arg Arg Tyr Met Asp Ala Ile Ala Glu Met Pro Ser Asp Pro Leu Gln
                485                 490                 495

Val Trp Glu Ala Ala Arg Ile Thr Gly Tyr Gly Glu Trp Ala Lys Glu
            500                 505                 510

Ile Phe Ala Arg Phe Asn His Tyr Lys His Glu His Ala Cys Cys Ala
        515                 520                 525

Val Ser Leu Ser Leu Ser Asp Arg Leu Val Trp Cys Arg Leu Ile Asp
    530                 535                 540

Arg Ile Leu Ser Leu Lys Lys Cys Leu His Phe Gly Gly Tyr Glu Ser
545                 550                 555                 560

Lys His Arg Lys Gly Phe Cys Lys Ser Leu Tyr Arg Leu Arg His Asn
                565                 570                 575

Ala Arg Asn Asp Val Arg Lys Lys Leu Ala Arg Phe Ile Val Asp Ala
            580                 585                 590

Ala Val Asp Ala Gly Ala Ser Val Ile Ala Met Glu Lys Leu Pro Ser
        595                 600                 605

Ser Gly Gly Lys Gln Ser Lys Asp Asp Asn Arg Ile Trp Asp Leu Met
    610                 615                 620

Ala Pro Asn Thr Leu Ala Thr Thr Val Cys Leu Met Ala Lys Val Glu
625                 630                 635                 640
```

```
Gly Ile Gly Phe Val Gln Val Asp Pro Glu Phe Thr Ser Gln Trp Val
                645                 650                 655

Phe Glu Gln Arg Val Ile Gly Asp Arg Glu Gly Arg Ile Val Ser Cys
            660                 665                 670

Leu Asp Ala Glu Gly Val Arg Arg Asp Tyr Asp Ala Asp Glu Asn Ala
        675                 680                 685

Ala Lys Asn Ile Ala Trp Leu Ala Leu Thr Arg Glu Ala Glu Pro Phe
    690                 695                 700

Cys Met Ala Phe Glu Lys Arg Asn Gly Val Val Glu Pro Lys Gly Leu
705                 710                 715                 720

Arg Phe Asp Ile Pro Glu Glu Pro Thr Arg Glu Gln Asp Glu Ser Asp
                725                 730                 735

Gln Asp Phe Lys Lys Arg Leu Glu Glu Arg Asp Lys Leu Ile Glu Arg
            740                 745                 750

Leu Gln Ala Lys Ala Asp Arg Met Gln Ala Ile Val Gln Arg Leu Phe
        755                 760                 765

Gly Asp Arg Arg Pro Trp Asp Ala Phe Ala Asp Arg Ile Pro Glu Gly
    770                 775                 780

Lys Ser Lys Arg Leu Phe Arg His Arg Asp Gly Leu Val Leu Asn Lys
785                 790                 795                 800

Pro Phe Lys Gly Leu Cys Gly Ser Glu Asn Ser Glu Gln Lys Ala Ser
                805                 810                 815

Ala Arg Asn Ser Arg
            820


<210> SEQ ID NO 19
<211> LENGTH: 837
<212> TYPE: PRT
<213> ORGANISM: artificial sequence
<220> FEATURE:
<223> OTHER INFORMATION: amino acid sequence of Cas12j.21

<400> SEQUENCE: 19

Met Gly Arg Phe Gly Lys Lys Lys Ile Ala Val Asn Gly Tyr Val Glu
1               5                   10                  15

Gln Asp Cys Ile Lys Thr Ile Ser Ala Lys Cys Leu Leu Thr Arg Ala
            20                  25                  30

Gln Ile Asp Glu Leu Arg Ala Lys Tyr Asp Ala Val Leu Asp Thr Met
        35                  40                  45

Arg Pro Leu Ile Arg Leu Ile Leu Ala Gly Tyr Glu Gly Arg Asp Asp
    50                  55                  60

Gly Ile Tyr Glu Glu Ile Ala Pro Glu Met Ser Lys Lys Lys Phe Phe
65                  70                  75                  80

Glu Ala Ala Thr Glu Trp Arg Glu Ser Ile Val Lys Asn Ala Ser Pro
                85                  90                  95

Arg Ala Met Lys Ala Ser Val Phe Gly Asp Lys Glu Pro Cys Lys Ser
            100                 105                 110

Thr Gly Gly Ala Arg Ala Val Ile Gly Lys Leu Arg Lys Ser Gly Val
        115                 120                 125

Phe Pro Ile Glu Thr Gly Leu Ser Gly Gly Asp Glu Tyr Asn Leu Ile
    130                 135                 140

Glu Gln Ala Ile Glu Tyr Ala Lys Ser Trp Leu Lys Ser Asp Glu Ala
145                 150                 155                 160

Thr Arg Glu Ala Tyr Ala Asp Gln Gln Lys Asp Ile Lys Arg Leu Ile
                165                 170                 175
```

-continued

```
Gly Glu Ala Lys Lys Leu Ala Leu Lys Ile Glu Lys Ala Glu Lys Lys
            180                 185                 190

Leu Glu Ala Thr Asn Pro Gln Thr Lys Ser Trp Lys Lys Thr Thr Glu
        195                 200                 205

Ile Ile Lys Lys Ser Lys Arg Glu Phe Gly Ser Val Thr Thr Lys Thr
    210                 215                 220

Glu Lys Ala Glu Lys Arg Phe Glu Arg Met Lys Pro Phe Ser Lys Leu
225                 230                 235                 240

Glu Leu Gln Asn Met Asp Cys Thr Lys Tyr Ser Thr Tyr Leu Gly Thr
                245                 250                 255

Asn Tyr Ser Pro Phe Lys Leu Lys Lys Glu Gly Asp Leu Leu Gln Ile
            260                 265                 270

Thr Val Thr Ser Ser Val Met Lys Gly Thr Tyr Leu Ala Ser Tyr Gly
        275                 280                 285

Asp Gly Gln Tyr Gly Ser Arg Arg Asn Asn Gly Gln Ser Arg Arg Asp
    290                 295                 300

Asp Phe Val Pro Asn Met Asn Gln Lys Arg Arg Arg Asn Leu Met Phe
305                 310                 315                 320

Asp Cys Thr Val Glu Pro Phe Gly Asp Gly Ser Leu Leu Arg Tyr Glu
                325                 330                 335

Glu Asn Gly Leu Arg Pro Arg Val Ala Glu Leu Lys Glu Pro Arg Leu
            340                 345                 350

Cys Trp Arg Arg Arg Asn Gly Asn Tyr Glu Leu Tyr Leu Met Met Pro
        355                 360                 365

Val Lys Met His Val Lys Ser Pro Glu Met Phe Ala Gly Asp His Leu
    370                 375                 380

Ala Phe Ser Arg Tyr Trp Pro Lys Glu Val Glu Gly Leu Asp Ser Asp
385                 390                 395                 400

Thr Lys Ile Thr Ala Leu Gly Val Asp Val Gly Ile Ile Arg Ser Ala
                405                 410                 415

Tyr Cys Val Ala Val Thr Ala Glu Arg Phe Val Asp Gly Leu Pro Thr
            420                 425                 430

Glu Met Thr Val Gly Lys Ala Ser Phe Asp Ala Gln Thr Glu Lys Gly
        435                 440                 445

Arg Glu Tyr Phe Glu Leu Gly Arg Arg Ala Thr Met Leu Gly Trp Leu
    450                 455                 460

Ile Lys Thr Thr Arg Arg Tyr Lys Lys Asp Pro Lys Asn Glu His Asn
465                 470                 475                 480

Gln Ile Lys Glu Ser Asp Val Ala Ala Phe Asp Gly Ser Pro Gly Ala
                485                 490                 495

Phe Glu His Tyr Ile Leu Ala Val Asp Glu Met Ser Asp Asp Pro Leu
            500                 505                 510

Asp Val Trp Gly His Ala Asn Ile Thr Gly Tyr Gly Lys Trp Thr Lys
        515                 520                 525

Gln Ile Phe Lys Glu Phe Asn Gln Leu Lys Arg Glu Arg Ala Glu Gly
    530                 535                 540

Gln Val Glu Pro Asn Met Thr Asp Asp Leu Thr Trp Cys Ser Leu Ile
545                 550                 555                 560

Asp Tyr Ile Ile Ser Leu Lys Lys Thr Leu His Phe Gly Gly Tyr Glu
                565                 570                 575

Thr Lys Glu Arg Glu Ser Phe Cys Pro Ala Leu Tyr Asn Glu Arg Ala
            580                 585                 590

Asn Cys Arg Asp Val Val Arg Lys Arg Leu Ala Arg Tyr Val Val Glu
```

595 600 605

Arg Ala Ile Ala Ala Glu Ala Gln Val Ile Ser Val Glu Asn Leu Ser
610 615 620

Lys Cys Arg Arg Asp Asp Lys Arg Lys Asn Arg Val Trp Asp Leu Met
625 630 635 640

Ser Gln Gln Ser Trp Ile Gly Val Leu Thr Asn Met Ala Arg Met Glu
645 650 655

Asn Ile Ala Val Val Ser Val Asn Pro Asp Leu Thr Ser Gln Trp Val
660 665 670

Glu Gln Cys Gly Ala Ile Gly Asp Arg Lys Ala Arg Thr Ile Ala Cys
675 680 685

Arg Asp Val Asn Gly Lys Phe Val Ser Leu Asp Ala Asp Leu Asn Ala
690 695 700

Ala Tyr Asn Ile Ala Ser Arg Ala Leu Thr Arg His Ala Glu Pro Phe
705 710 715 720

Ser Ile Thr Phe Lys Lys Lys Asp Gly Ile Leu Glu Gln Lys Asp Val
725 730 735

Cys Phe Asp Pro Gly Val Ile Pro Val Leu Glu Lys Asn Glu Asn Glu
740 745 750

Glu Lys Phe Arg Glu Arg Val Glu Lys Tyr Glu Lys Ser Leu Val Ile
755 760 765

Lys Gln Glu Arg Ala Val Arg Trp Arg Ala Ile Leu Gln His Leu Phe
770 775 780

Gly Asn Glu Arg Pro Trp Asp Glu Phe Thr Asp Glu Val Lys Glu Gly
785 790 795 800

Arg His Val Ser Leu Tyr Arg His His Gly Lys Leu Val Arg Thr Lys
805 810 815

Gln Tyr Ala Gly Leu Val Lys Glu Ala Asn Asn Glu Leu Val Pro Val
820 825 830

Cys Ala Val Ala Arg
835

<210> SEQ ID NO 20
<211> LENGTH: 968
<212> TYPE: PRT
<213> ORGANISM: artificial sequence
<220> FEATURE:
<223> OTHER INFORMATION: amino acid sequence of Cas12j.22

<400> SEQUENCE: 20

Met Ser Lys Ala Thr Arg Lys Thr Lys Thr Thr Val Pro Glu Ser Thr
1 5 10 15

Asp Thr Glu Ser Pro Ala Ala Asp Thr Gln Val Arg Val His Trp Leu
20 25 30

Ala Ala Ser His Arg Ala Ser Pro Gly Leu Gln Gln Val Lys Glu Met
35 40 45

Ile Gln Gln His Ala Asp Val Ala Ser Val Leu Phe Gln Gly Leu Val
50 55 60

Arg Thr Ala Pro Ile Val Phe Arg Asn Asp Asp Gly Ser Pro Val Lys
65 70 75 80

Pro Leu Asp Leu Leu Leu Ala Ser Leu Arg Pro Thr Tyr Lys Val Gln
85 90 95

Arg Asp Thr Glu Thr Val Leu Val Thr Lys Asp Asp Val Ile Arg Cys
100 105 110

Leu Thr Leu Ala Thr Thr Ala Val Asn Gly Gly Gln Ala Thr Asn Val

```
        115                 120                 125

Ala Val Phe Ala Ser Ala Asp Pro Ala Leu Ser Ala Pro Leu Ala Thr
    130                 135                 140

Leu Leu Ala Gln Leu Arg Ala Leu Glu Ser Val Asp Ser Ser Trp Ser
145                 150                 155                 160

Val Val Gly Lys Leu Asp Ile Asn Leu Arg Lys Phe Val Trp Leu Val
                165                 170                 175

Leu Ser Ala Ala Gly Val Leu Pro Ala Leu Ala Asp Leu Glu Gly Tyr
            180                 185                 190

Ala Ala Lys Ser Val Leu Ala Asn Val Gln Gly Lys Tyr Lys Ser Leu
        195                 200                 205

Gln Ala Cys Ala Asp Thr His Ala Ala Leu Tyr Lys Gln His Gln Thr
    210                 215                 220

Asn Lys Glu Gln Leu Glu Lys Leu Ile Ala Asp Pro Gly Phe Val Ala
225                 230                 235                 240

Leu Cys Ser Ala Leu Leu Gln Asp Pro Asp Leu Arg Ser Val Asp Ser
                245                 250                 255

Arg Arg Leu Ala Ala Leu Glu Glu Met Leu Gly Phe Val Ala Ala Asp
            260                 265                 270

Lys Asn Tyr Ser Glu Tyr Thr Ser Thr Arg Lys Cys Asp Gly Trp Ala
        275                 280                 285

Pro Pro Ala Asn Met Phe Asp Leu Leu Cys Glu His Lys Glu Ala Val
    290                 295                 300

Arg Arg Asn Ile Val Val Asp Asn Ser Lys Cys Leu Ser Arg Arg Ile
305                 310                 315                 320

Ser Leu Val Ala Asp Gly Asp Val Asn Glu Val Ser Val Phe Glu Leu
                325                 330                 335

Leu Asn Glu Met Arg Trp Leu Ser Val His Ser Ser Gly Ile Arg Met
            340                 345                 350

Pro Asn Tyr Pro Lys His Ala Tyr Ala Leu Lys Phe Gly Asp Asn Tyr
        355                 360                 365

Ile Ser Val Lys Ser Phe Glu Thr Val Val Asp Gly Gly Cys Ser Leu
    370                 375                 380

Leu Arg Met Thr Ala Arg Val Gly Lys Asn Asp Leu Val Cys Asp Phe
385                 390                 395                 400

Val Leu Gly Arg Gly Asn Glu Tyr Trp Asn Asn Leu Lys Ile Thr Pro
                405                 410                 415

Met Gly Lys Gly Ile Phe Ala Val Val Lys Thr Val Arg Arg Phe Thr
            420                 425                 430

Ala Thr Gly Ala Lys Leu Val Glu Leu Arg Gly Val Cys Lys Glu Pro
        435                 440                 445

Glu Ile Arg Tyr Glu Arg Gly Val Leu Gly Leu Arg Leu Pro Ile Ser
    450                 455                 460

Phe Asp Val Tyr Gly Lys Val Glu Glu Asp Ser Ile Ala Phe Gly Lys
465                 470                 475                 480

Asn Arg Val Ser Leu Arg Thr Thr Pro Phe Val Glu Lys Ala Asp Lys
                485                 490                 495

Phe Gln Gly Leu Leu Asp Tyr Arg Asn Thr Thr Ala Arg Asp Gly Tyr
            500                 505                 510

Ile Tyr Tyr Ala Gly Phe Asp Gln Gly Glu Asn Asp Gln Val Val Gly
        515                 520                 525

Ile Tyr Arg Thr Arg Thr Tyr Lys Asn Ala Thr Met Leu Glu Phe Phe
    530                 535                 540
```

-continued

```
Asn Val Ser Asp Thr Leu Glu Glu Val Ala Ser Cys Arg Phe Ser Asp
545                 550                 555                 560

Tyr Gln Glu Arg Lys Arg Arg Leu Arg Gly Asp Thr Gly Val Leu Asp
                565                 570                 575

Ile Asn Ser Ile Asn Val Leu Ala Asp Lys Val Gln Arg Leu Arg Arg
            580                 585                 590

Leu Ile Ser Thr Leu Arg Ala Cys Ala Ser His Thr Asp Trp Tyr Pro
        595                 600                 605

Lys Leu Lys Glu Arg Arg Arg Leu Glu Trp Ala Val Leu Ala Gln Gly
    610                 615                 620

Val Gly Val Ser Asp Phe Asp Thr Glu Ile Glu Arg Ala Glu Thr Ala
625                 630                 635                 640

Leu Ser Ala Val Ala Ala Val Asp Phe Val Arg Asp Pro Thr Cys Ile
                645                 650                 655

Ile Asn Val Met Asp Lys His Ile Tyr Ala Gln Phe Lys Gln Leu Arg
            660                 665                 670

Ser Glu Arg Asn Glu Lys Tyr Arg Ser Gln His Gln His Asp Tyr Lys
        675                 680                 685

Trp Leu Gln Leu Val Asp Ser Val Ile Ser Leu Arg Lys Ser Ile Tyr
    690                 695                 700

Arg Phe Gly Lys Ala Pro Glu Pro Arg Gly Ala Gly Glu Leu Tyr Pro
705                 710                 715                 720

Gln Asn Leu Tyr Thr Tyr Arg Asp Asn Leu Met Gln Gln Tyr Arg Lys
                725                 730                 735

Glu Val Ala Ala Phe Ile Arg Asp Val Cys Leu Glu His Gly Val Arg
            740                 745                 750

Gln Leu Ala Val Glu Ala Leu Asn Pro Thr Ser Tyr Ile Gly Glu Asp
        755                 760                 765

Ser Asp Ala Asn Arg Lys Arg Ala Leu Phe Ala Pro Ser Glu Leu His
    770                 775                 780

Asn Asp Ile Val Leu Ala Cys Ser Leu His Ser Ile Ala Val Val Ala
785                 790                 795                 800

Val Asp Glu Thr Met Thr Ser Arg Val Ala Pro Asn Asn Arg Leu Gly
                805                 810                 815

Phe Arg Ser His Gly Asp Tyr Gln Lys Phe Ser Glu Thr Ala Gln Gly
            820                 825                 830

Arg Phe Asn Trp Lys His Leu His Tyr Phe Gly Asp Asn Asp Val Ser
        835                 840                 845

Glu His Cys Asp Ala Asp Glu Asn Ala Cys Arg Asn Ile Val Leu Arg
    850                 855                 860

Ala Leu Thr Cys Gly Ala Ser Lys Pro Arg Phe Ser Arg Gln Ser Leu
865                 870                 875                 880

Leu Gly Lys Ile Lys Gly Pro Val Leu Arg Thr Gln Leu Ala Tyr Leu
                885                 890                 895

Ala His Lys Arg Gly Leu Leu Thr Ala Ser Thr Glu Pro Lys Lys Ala
            900                 905                 910

Ala Glu Thr Gly Phe Glu Leu Val Glu Ala Asp Leu Gly Gly Ala Leu
        915                 920                 925

Arg Val Gly Lys Gly Phe Ile Tyr Val Asp Ala Gly Ile Cys Ile Asn
    930                 935                 940

Ala Thr Thr Arg Lys Glu Arg Ser His Lys Val Gly Glu Ala Val Val
945                 950                 955                 960
```

Ser Arg Ser Leu Ala Ser Pro Phe
965

<210> SEQ ID NO 21
<211> LENGTH: 3012
<212> TYPE: DNA
<213> ORGANISM: artificial sequence
<220> FEATURE:
<223> OTHER INFORMATION: Cas12j.3 encoding nucleic acid sequence

<400> SEQUENCE: 21
atgaccaagg agaagatcaa gaagaccaag aaggccaagg tggagaagga ctccgtgacc 60
agggccggca tcctgaggat cctgctgaac ccggaccagc accaggagct ggacaccctg 120
atctccgacc accaggaggc cgccagggag atccagaccg ccacctacaa gctgtccggc 180
ctgaagctgt acgacaagac caacaacatg gtggtggacg gctccaaggc caccccggag 240
gagcaggagg cctactacaa gatcatcaac tgggagggcc agccgatctc catctccaac 300
ccgatggtga gggccacctt caagtccatc gccaaggtga aggaggacat caggaggaag 360
caggaggagt acgccaagct ggaggaggcc gacctgacca agatgtccac cggcgacgtg 420
aagaagcaca agaacgagct gaggaaggcc gccaacagga tcaagcactc cgaggagatc 480
ctgcagttcg ccaagtggag gctggccgac atcttcccgc tgccgctgtc ccacaactcc 540
cagctgcacc tgaagaacaa ctaccaccag aacgtgttct ccggcttcca cgccagggtg 600
aagggctgga acgcctgcga catcgccgcc caggccaact acgccgagat cgacaacagg 660
ctgaccgagc tgtcctccga gctgtccggc gactacggct ccgaggtgat caccgacctg 720
atgggcctgc tgcagtacac caaggagctg ggcgagggct acaccgacac ctcctacctg 780
aactacaagt tcctgtcctt cttcaaggag tgctggaggc cgaacgccat cgccaacaac 840
accggcctgc tggagggctt ctggctggcc aacaacaagc acaccaacaa gaagaaccag 900
gtggcctact ccttcaaccc gaagatctcc gaggagctgt tcaggaggag gtccctgtgg 960
gagtccgaca agtgcctgct gtccgacccg aggttcgaga agtacgtgga gctgttcgac 1020
aagcacggca ggtacaggaa gggcgcctcc ctgaccctga tctccaagga gtccccgatc 1080
ccgatcggct tctccatgga caggaacgcc gccaagctgg tgaggatcga caacgacacc 1140
gccaacaggc agctgaccat caccatcgag ctgccgaaca aggaggagag gtcctacgtg 1200
gccgcctacg gcaggaagca cgagaccaag tgctactaca acggcctgac caccaggctg 1260
ccgaggtccg agaaggagct gctggccctg gccaaggccg agaacaggga gctgaccgac 1320
aaggagatcc acgaggcctc cctggagaag tgctacatct tcgagtacgc cagggccggc 1380
aagatcccgg tgttcgccgt ggtgaagacc ctgtacttca ggaggaaccc gtccaacggc 1440
gagtactacg tgatcctgcc gaccaacatc ttcgtggagt accacgccaa caacgagttc 1500
aactccaagg agctgttcaa gatcaggtcc gagctgcaga aggcctggga cgaggtgagg 1560
accccgaaga ggaacgtgca gtcctgcgtg ctggacaagg acctgtccaa gaggttcgcc 1620
ggcaggaccc tgaagtacgc cggcatcgac ctgggctact ccaacccgta caccgtgtcc 1680
tactacaacg tggtgggcac cgaggagggc atccagatca aggagaccgg caacgagatc 1740
gtgtccaccg tgttcaacga gcagtacatc cagctgaagg gcaacatcta ccagctgatc 1800
aacatcatca gggcctccag gaggtacctg caggagtccg gcgagctgaa gctgtccaag 1860
gacgacatca agtccttcga ccagctgatg gagctgctgc cgtccgagca gaggatcacc 1920
atcgaccagt tcatcaagga catcaagaag gccaagcagg agggcaagct gatcagggac 1980
atcaagggca agctgccggt ggagggcaag aagaaggagt actgggtgat ctccaacctg 2040
atgtacgtga tcacccagac catgaacggc atcaggggca acagggactc caacaaccac 2100
ctgaccgaga agaagaactg gctgtccgcc ccgccgctga tcgagctgat cgacgcctac 2160
tacaacctga agaagacctt caacgactcc ggcgacggca tcaagatgct gccgaaggac 2220
cacgtgtacg ccgagggcga gaagcagagg tgcaccctga gggaggagaa cttctgcaag 2280
ggcatcctgg agtggaggga caacgtgaag gactacttca tcaagaagct gttctcccag 2340
atcgcccaca ggtgctacga gctgggcatc ggcatcgtgg ccatggagaa cctggacatc 2400
atgggctcct ccaagaacac caagcagtcc aacaggatgt tcaacatctg gccgaggggc 2460
cagatgaaga agtccgccga ggacgccttc tcctacatgg gcatcctgat ccagtacgtg 2520
gacgagaacg gcacctccag gcacgacgcc gactccggca tctacggctg cagggacggc 2580
gccaacctgt ggctgccgaa caagaagctg cacgccgacg tgaacgcctc caggatgatc 2640
gccctgaggg gcctgaccca ccacaccaac ctgtactgca ggtccctgac cgagatcgag 2700
aacggcaagt acgtgaacac ctacgagctg ttcgacacca ccaagaacga ccagtccggc 2760
gccgccaaga ggctgagggg cgccgagacc ctgctgcacg gctactccgc caccgtgtac 2820
cagatccaca ccaccaacac cggcgccggc gtggccctgc tgccggacct gaccgccacc 2880
gacgtgatca agaacaagaa gatcaccgcc accaaggaga acaccgccaa gtactacaag 2940
ctggacaaca ccaacaccta ctacccgtgg tccgtgtgcg agaagctgca caagaactgg 3000
aagctgtcct ga 3012

<210> SEQ ID NO 22
<211> LENGTH: 2625
<212> TYPE: DNA
<213> ORGANISM: artificial sequence
<220> FEATURE:
<223> OTHER INFORMATION: Cas12j.4 encoding nucleic acid sequence

<400> SEQUENCE: 22
atgaagaaga agaagaactt ctccgtgtcc gccaccggcg tgttctcctt cccgaccacc 60
gaggccaaga tggacttctt ccacaggttc atcgagctga acggcctggc cgccgagatc 120
gagacccact tcctgaacct gaagaacgac aagaacggcg agtccgtgta caacaaggtg 180
ctgtccaact ccaaccactc caggccgttc tccaccccgc tgctgggcac catgaccggc 240
tccaccaagg tgaccgacaa gaacgccctg tacggcaacg acctggacca ctgcaggaag 300
aagaagatcg tgccgttctc ctcctcctcc ccgctgtcct cccaggagaa gttcttctgc 360
atcgaggccg tgttcaggag ggccaagtcc cacatggagt gcaagaagct gttccaggac 420
gagaccaaca ggatggactc ccagatcaac ggcatcctga acgagctgcc gtacggcgtg 480
gagctgtcca acatgctgtc cgagctgatc gccatcccgt tcgccatcgg ctggaagctg 540
gagggctacc tgggccaggt gttcttcccg tccatcgccg agggcctgac cccgccgaag 600
tccgccaaga tcaagggcag gaggaggtcc atcgactact ccgtgaccga cgaggcctac 660
gacatcctga tgaagtactc caacctgcac tcctccttcg agaccggcct gaagatgtcc 720
aacctgttct ccgccttcta caagaagtcc aacaggaagg acgagatcca gttcaccccg 780
atctccatgg agtccaggtg cgacctgctg ctgggcaaga acttcctgaa gttcgacctg 840
aagaactgcg accacaggtc cggctccctg atgctgacca tcaacgacaa gaacaggctg 900
aacggcgact acgagatcag ggtgggctcc gacaagaagg actcctacct gaccggcgtg 960
aacgtgacca acctgggcga caacgtgttc aacctgaact acaaggtgaa cggcaagagg 1020
gagtacaaca tgctgctgaa ggagccgtcc atccacatca agatgcacag gatgagggac 1080
gacggcaact acctgtcctc cgacttcgac ttctacatga tcttctccat gtcctccgag 1140
aaggacgagg agaagctggc caggtcctgg gacatgaggg ccgccatgtc caccgcctac 1200
ggcaccgaca tcaagaagta ccactcctcc ttcccgtgca ggatcctggc ctgcgacctg 1260
ggcgtgaagc acccgtactc cgccgccgtg atggacatcg gccagctgaa cgagaacggc 1320
atgccggtgt ccgtggacaa ggtgcactgc atgcactccg agggcgtgtc cgagatcggc 1380
cagggctaca accacctgat ccagaagatc ctggccctga actacatcct ggcctactgc 1440
agggagttcg tgtccggcac cgtggacgac ttcgacaaga tcgactacaa gctgtcccag 1500
ctgtcctaca agcaggagga cctgctgatc aacctgcagg agatgaagga ccacttcggc 1560
aacgacatgc aggcctggaa gaagtccagg acctgggtgg tgtccaccct gttcttcgag 1620
ctgaggcagg agttcaacca gctgaggaac cagaggccgg gcaagaagac cgtgtccctg 1680
gccgacgagt tccagtacat cgacatgagg aggaagttca tctccctgtc caggtcctac 1740
accaacgtgg gcaggcagtc ctccaagcac aggcacgact cctaccagac ccactacgac 1800
gtgatcaaca ggtgcaagaa gaacctgctg aggaacatct gcaggaggat gatcgacatg 1860
gccgtgcaga acaagtgcga catcatcgtg gtggaggacc tgtccttcca gctgtcctcc 1920
cacaactcca ggagggacaa cgtgttcaac gccctgtggt cctgcaagtc catcaagaac 1980
atgctgggca tcatggccga gcagcacaac atcatcatct ccgaggtgga cccgaaccac 2040
acctccaaga tcgactgcga gaccggcaac ttcggctaca ggtactcctc cgacttctac 2100
tccgtgatcg acggccagct ggtgaggagg cacgccgacg agaacgccgc catcaacatc 2160
ggcaacaggt gggcctccag gcacaccgac ctgaagtcct tcaactgcag gcagatctcc 2220
atcgacggca ggaaggtggc cttcccgtac gccaagggca agaggaagtc cgccctgttc 2280
ggctacctgt tcggcaactg caagaccgtg ttcgtgtccg acgacggcga ctcctacacc 2340
ccgatcccgt actccaagtt caggaagtcc atctccaagg acgaccacga cgtggtgaac 2400
tacctgcacg acctgaccat gaacaagaac gtgatcaggg tggagtacaa caagtccatc 2460
aagtccgcct ccgtggagct gtacctgaac gacgacaggg tgatctccag gtccctgagg 2520
gacaaggagg tggacgccat cgagaagctg gtgtccaggg gctccctgat caacgagtcc 2580
ggcccgtccc tggagcacga cgaggtgaag tccgtgaccc actga 2625

<210> SEQ ID NO 23
<211> LENGTH: 2613
<212> TYPE: DNA
<213> ORGANISM: artificial sequence
<220> FEATURE:
<223> OTHER INFORMATION: Cas12j.5 encoding nucleic acid sequence

<400> SEQUENCE: 23
atgaaggtgc acgagatccc gaggtcccag ctgctgaaga tcaagcagta cgagggctcc 60
ttcgtggagt ggtacaggga cctgcaggag gacaggaaga agttcgcctc cctgctgttc 120
aggtgggccg ccttcggcta cgccgccagg gaggacgacg gcgccaccta catctccccg 180
tcccaggccc tgctggagag gaggctgctg ctgggcgacg ccgaggacgt ggccatcaag 240
ttcctggacg tgctgttcaa gggcggcgcc ccgtcctcct cctgctactc cctgttctac 300
gaggacttcg ccctgaggga caaggccaag tactccggcg ccaagaggga gttcatcgag 360
ggcctggcca ccatgccgct ggacaagatc atcgagagga tcaggcagga cgagcagctg 420

```
tccaagatcc cggccgagga gtggctgatc ctgggcgccg agtactcccc ggaggagatc    480
tgggagcagg tggccccgag gatcgtgaac gtggacaggt ccctgggcaa gcagctgagg    540
gagaggctgg gcatcaagtg caggaggccg cacgacgccg gctactgcaa gatcctgatg    600
gaggtggtgg ccaggcagct gaggtcccac aacgagacct accacgagta cctgaaccag    660
acccacgaga tgaagaccaa ggtggccaac aacctgacca acgagttcga cctggtgtgc    720
gagttcgccg aggtgctgga ggagaagaac tacggcctgg gctggtacgt gctgtggcag    780
ggcgtgaagc aggccctgaa ggagcagaag aagccgacca agatccagat cgccgtggac    840
cagctgaggc agccgaagtt cgccggcctg ctgaccgcca agtggagggc cctgaagggc    900
gcctacgaca cctggaagct gaagaagagg ctggagaaga ggaaggcctt cccgtacatg    960
ccgaactggg acaacgacta ccagatcccg gtgggcctga ccggcctggg cgtgttcacc   1020
ctggaggtga agaggaccga ggtggtggtg gacctgaagg agcacggcaa gctgttctgc   1080
tcccactccc actacttcgg cgacctgacc gccgagaagc acccgtccag gtaccacctg   1140
aagttcaggc acaagctgaa gctgaggaag agggactcca gggtggagcc gaccatcggc   1200
ccgtggatcg aggccgccct gagggagatc accatccaga agaagccgaa cggcgtgttc   1260
tacctgggcc tgccgtacgc cctgtcccac ggcatcgaca acttccagat cgccaagagg   1320
ttcttctccg ccgccaagcc ggacaaggag gtgatcaacg gcctgccgtc cgagatggtg   1380
gtgggcgccg ccgacctgaa cctgtccaac atcgtggccc cggtgaaggc caggatcggc   1440
aagggcctgg agggcccgct gcacgccctg gactacggct acggcgagct gatcgacggc   1500
ccgaagatcc tgaccccgga cggcccgagg tgcggcgagc tgatctccct gaagagggac   1560
atcgtggaga tcaagtccgc catcaaggag ttcaaggcct gccagaggga gggcctgacc   1620
atgtccgagg agaccaccac ctggctgtcc gaggtggagt ccccgtccga ctccccgagg   1680
tgcatgatcc agtccaggat cgccgacacc tccaggaggc tgaactcctt caagtaccag   1740
atgaacaagg agggctacca ggacctggcc gaggccctga ggctgctgga cgccatggac   1800
tcctacaact ccctgctgga gtcctaccag aggatgcacc tgtccccggg cgagcagtcc   1860
ccgaaggagg ccaagttcga caccaagagg gcctccttca gggacctgct gaggaggagg   1920
gtggcccaca ccatcgtgga gtacttcgac gactgcgaca tcgtgttctt cgaggacctg   1980
gacggcccgt ccgactccga ctccaggaac aacgccctgg tgaagctgct gtccccgagg   2040
accctgctgc tgtacatcag gcaggccctg gagaagaggg gcatcggcat ggtggaggtg   2100
gccaaggacg gcacctccca gaacaacccg atctccggcc acgtgggctg gaggaacaag   2160
cagaacaagt ccgagatcta cttctacgag gacaaggagc tgctggtgat ggacgccgac   2220
gaggtgggcg ccatgaacat cctgtgcagg ggcctgaacc actccgtgtg cccgtactcc   2280
ttcgtgacca aggccccgga gaagaagaac gacgagaaga aggagggcga ctacggcaag   2340
agggtgaaga ggttcctgaa ggacaggtac ggctcctcca acgtgaggtt cctggtggcc   2400
tccatgggct tcgtgaccgt gaccaccaag aggccgaagg acgccctggt gggcaagagg   2460
ctgtactacc acggcggcga gctggtgacc cacgacctgc acaacaggat gaaggacgag   2520
atcaagtacc tggtggagaa ggaggtgctg gccaggaggg tgtccctgtc cgactccacc   2580
atcaagtcct acaagtcctt cgcccacgtg tga                                 2613
```

<210> SEQ ID NO 24
<211> LENGTH: 2895
<212> TYPE: DNA
<213> ORGANISM: artificial sequence
<220> FEATURE:
<223> OTHER INFORMATION: Cas12j.6 encoding nucleic acid sequence

<400> SEQUENCE: 24

```
atgtccgcca acagggtgtc cgccaactcc cagttcgagc tgggctaccc gatgtccctg      60
tccctgaggg gcaaggtgtt caactccagg gagatgatga aggagatcct gccggtgatg     120
aacaacatcg tgcactacca gaacaacctg ctgaagctga tgctgatcct gaggggcgag     180
aagtacaccc tggacggcca gttcttctcc cagaaggacg tggacaggca gttcggcgac     240
ctgtgcaagg agcacaacat caagggctcc atctgctccc tgaaggagaa gtccaggaag     300
ctgtacgagg tgttctcctg ctacatcgac aagaagggca acctgaagac caactccaag     360
gccaggtcct tcgccggcgt gctgctgaac ccgaaggacg tgaagctgcc gccgcagatc     420
gactccatct cctccttcgt ggtggagctg agggccaagg gcgtgctgcc gatcaagcac     480
gagggcaact acctgtccgg ccacccgtcc ctgaagtact ccgtggccca gaacgtgctg     540
gtgaagctga cctccatgga gaagctgcag aagatctact ccgacgagaa ggccggctgg     600
gagaacatcg tgtccgaggt gaggtccgac ctgccgaaga tcgagaggta cgagaggatg     660
ctgctgtcca tcaaggccgt gaaggagatg gagaagttcg gcatcaacaa ctacaggcac     720
ctgctgaaca actggaggga cgaggtggac aaggactccg gcaaggtgct gaagcagggc     780
atgaggacct acttcgtgaa catgctggag tccaagaagg actacaggtt cgaggagtcc     840
gacaggtacc tgttcggcta cgccccggag gtgatgaacc tggtgtacca cgacttcagg     900
gacctgtggc agggcgagga catcatcggc tcccagtccc cggagaagaa ggacagggac     960
tacgtggacg tgatcttcaa ctacttcaac tggaggaagg agtccatcaa catctcctcc    1020
ttcgactcct acggcaagac cgcccagatc aagctgggcg acaactacgt gccgttctcc    1080
aacttccagt acgacaagat cctggacgcc tggaccctgg agatcgccaa cgtgtccggc    1140
gagggcgaca accacaagct ggtgatcgcc aggtccccgc agttcgactc ccactcctcc    1200
gtgaaggaca tcgtgatgaa gaacctgaag ggcaaggagg cctccaagac caccctggag    1260
ttcaggtact ccggcgactc caagaagtcc acctggtaca ggggcaccct gaaggagccg    1320
accctgaggt actcctcctc caagaactgc ctgtacgtgg acttcgccct gtccaaccac    1380
atcgtggagg gcctgatctc cgacaacctg ggcatctccg acaagatgta caagttcagg    1440
ggcgagttca tgaaggcctc cccgtcctcc ggcaagcagt ccaactccat caacctgccg    1500
atcaagaagc tgagggccat gggcgtggac ttcaacctga ggaggccgtt ccaggcctcc    1560
atctacgacg tggagaacaa gaacggcaac ctggagttct ccttcgtgaa gcacgtgcag    1620
tccttctcca acgagaacga cgaggagagg gccaaggagc tgctgaacat cgagaggaac    1680
atcctggccc tgaagatcct gatctggcag accgtgggct acgtgaccgg caagaacgac    1740
accatcgacg gcgtggtgac caggaagaac aacgccgtgg acatcgagaa gaccctgggc    1800
atcaacatga aggagtacat ggcctacctg aaccagttca ggtcctacga ggacaagaac    1860
aaggccttca tggacctgag gaagagggag tacgcctgga tcgtgccgcc gctgatcttc    1920
cagtgcaggt ccaggctgat ctccttcagg tccgagtact tcaacacccc gaaggacgag    1980
aagtcccact actgccagca caggaacttc gtggactact ccaccttcct gaagaagaac    2040
gtggtgaaga agatgatgga gctgaggagg tcctactcca ccttcggcat gtcctccgag    2100
cagtccatct gggtgaccaa caacgaccac gccaaggacg gctccaagaa gaacggcaac    2160
atgttcgacg acgacctgca ccagtggtac aacggcctgg tgaggaagtg ctcctccctg    2220
```

```
gcctcctcca tcatcaacgt ggccagggac aacggcgcca tcctggtgtt catcgaggac   2280
ctggactgcc acccgtccgc cttcgactcc gaggaggaca actccctgaa gtccatctgg   2340
ggctggggct ccatcaaggc ctccctggcc caccaggcca ggaagcacaa catcgccgtg   2400
gtggccaacg acccgcacct gacctccctg gtgtcctcca ccaccggcga gctgggcatc   2460
gccaagggca gggacgtgct gttcttcgac tccaagggca agctgacctc caaggtgaac   2520
agggacgaga acgccgccca gaacatcgcc atcaggggct tcgtgaggca ctccgacctg   2580
agggagttcg tggccgagaa gatcgaggag aacaggtaca gggtggtggt gaacaagacc   2640
cacaagagga aggccggcgc catctacagg cacatcggct ccaccgagtg catcatgtcc   2700
aagcaggccg acggctccct gaagatcgac aagaccgagc tgaccccgct ggagatcaag   2760
atggagaaga agaacgacaa gaagatgtac gtgatcctgc acggcaagac ctggaggctg   2820
aggcacgagc tgaacgagaa gctggagaag gacctggaca accacctgaa gtccaagtcc   2880
tccgtgatct cctga                                                    2895
```

```
<210> SEQ ID NO 25
<211> LENGTH: 2889
<212> TYPE: DNA
<213> ORGANISM: artificial sequence
<220> FEATURE:
<223> OTHER INFORMATION: Cas12j.7 encoding nucleic acid sequence

<400> SEQUENCE: 25

atgtcctccg ccaacgacca gctgggcctg ggctacccgc tgaccctgac cctgaggggc     60
aaggtgtaca accacgacac cgccatggag gccttcgccc cggtgatgaa gggcatggtg    120
ccgtacgcca acaacctgat gaggatcctg ctgaccctga ggctggagaa gtacaccctg    180
gacggcatcc accacaccaa ggaggaggtg gagaaggacc tgaggggcct gatgaaggag    240
tacggcatca acctgtcctt cgccaagttc tccgagatgg ccggcgaggt gtacagggtg    300
ttcgtgtgct acgtggacgc caagggcaag ctgaaggtga acggcaaggc caggggcttc    360
gccaacgtgt tcttctccga ggacgacgcc accatcccgg agaactgccc gtccatggag    420
ctgctgagga agaagggcat gttcccgatc ctggtggacg gcaagccgat ctcctccatc    480
tccagggaga agaccccgct gaagtactcc gtggcccagg acgtgctgac caagctgacc    540
tccatggagg agatctccaa ggagtacgag aaggccaaga ccgactggga gaacgagtgc    600
cagaaggtga tctcccagct gccgctgatc ggcaggtacg aggccctgct gaccaccatc    660
ccgctgatcc cggagatgag gggcttcgac ggcgacaact acaggaagat gctgaacagg    720
tggagggact acgtgaacga ggacggcgag ctggtgaggg gcggcatgaa gacctacttc    780
ctggacctgc tgtccaagga cacctcccac aagttcaacg aggaggagag gtacctgttc    840
ggctactgcc cggagttcat gaacctgatc taccacgact tcagggacct gtggtccaag    900
gaggacatca tcggctccca gaggaagggc aagggcctga agggcaagga ctacgtggac    960
gtgatcttca actgcttcca ctggaggagg gagtccatca acatctcctc cttcggcaac   1020
aacgacaagg tgatgaacat ccacctgggc gacaacttcg tgccgttcga gctgaagtcc   1080
cagaacggca tctgggaggt gcacgtgcag aacctgcacg gccagaacga cccgcacagg   1140
gtgatcgtgt gcaggtgccc gcagttcaac gaggactcct ccatgaagat ggtgcacccg   1200
ctggccaaga acggcgagga gtccgacaag gagaacatcg agttcaggta ctccggcgac   1260
tccaagaggg agacctggta caccggcctg ctgaaggagc cgaccctgag gtacgacgtg   1320
gagaggaagt ccctgtacgt ggacttcatc ctgtccaacc acagggtgga gggcgtggtg   1380
```

accaacgagt acctgaagga cccgagggac ctgttcggcg tgaggggcta cttcctgtcc 1440
tcctccgtgt ccaacccgag gcagaaggac aagacctccc tgccggacgg caagttcaac 1500
gtgatgggcg tggacctggg cctgaagtgc ccgtacgagt gcgccatcta cggcatcacc 1560
gtgaagaacg gcaagatgca gcacaagtgg tcccacaacg tgtccgccga ggacaacaac 1620
aacgtgtccg agaggctggc caacctgaag aagatcgacg agaagatcct ggccacccag 1680
gtgctgatct ccctgaccaa gatgtgcgtg gtgaaggacg aggagatccc ggactcctac 1740
accctgaggg agcacagggt ggacatcgcc aagtccctgg acctggacat ggacaagtac 1800
aggaggtacg tggagaagtg caagaagaac ccggacaaga tccaggccct gaaggacatc 1860
aggaagtccg agaacaactg gatcgtggcc gagaagatca acgagatcag gtccctgatc 1920
tccgagatca ggtccgagta ctacgcctcc aaggacaaga ggaactactg caggaacctg 1980
aacggcgtgg acctgtccgt gttcctgaag aagaaggtgg tgaagaactg gatctccctg 2040
ctgaggtcct tctccacctt cggcatgacc ccgcaggagt ccgcctacat caggaaggac 2100
ttcgccaaga acctgtccaa gtggtacaag ggcctggtga ggaagtgcgg ctccatcgcc 2160
gcccacatcg tgaacatcgc cagggacaac aaggtgatgg tgatcttcat cgaggacctg 2220
gacgccagga cctccgcctt cgactccaag gaggacaacg agctgaagat cctgtggggc 2280
tggggcgaga tcaagaagtg gatcggccac caggccagga agcacaacat cgccgtggtg 2340
gccgtggacc cgcacctgac ctccctggtg aaccacgagt ccggcctgct gggcatcgcc 2400
ggctccggca acgacaggaa catctacacc ttccagaaga acaagaagta cgtggtgatc 2460
aacagggaca acaacgccgc ccacaacatc gccctgaggg gcctgtccaa gcacaccgac 2520
atcagggagt tctacgtgga gcagatcgac gtggaccact acaggctgat gtacggcccg 2580
gaggccgaga acggcaagag gaggtccggc gccatctaca agcacatcgg ctccaccgag 2640
tgcgtgttct ccaagcagaa gaacggcacc ctgaaggtgg agaagacctc cctgaccaag 2700
gacgagaagg agatgccgaa gatcaacggc aagggcgtgt acgccatcct gcacggcaac 2760
gagtggaggc tgaggcacga gctgaacgag gagctgggcg ccaagctgga cggcatctcc 2820
gtgaagaggg tggtgtccga gccgaacaag gtgaagacct ccctggtgaa gggctccgtg 2880
agggcctga 2889

<210> SEQ ID NO 26
<211> LENGTH: 2724
<212> TYPE: DNA
<213> ORGANISM: artificial sequence
<220> FEATURE:
<223> OTHER INFORMATION: Cas12j.8 encoding nucleic acid sequence

<400> SEQUENCE: 26
atgaagaagc agaccatcgt gaagaaggac tccaaggccg agaccaagga gaacaagatg 60
tacccggaca aggacaccga cttcccggtg aactcccagt tctccaggtc catctccatc 120
agggccaacg tggacccgaa ggacctgctg gtgctgaaga ggaccttcga ggagaccacc 180
aagatctccg acgagctgct gtccaccctg ctgatgctga ggggcaagga ctactgcctg 240
gacaacgtgg tgtgcaaggg cgaggaggtg ctggagaacc tgtacaagaa gctgtccaag 300
aacgccaccg tgaacaggga caagttcatc tccaccgcca aggccttcta cgagtacttc 360
cacggctgct cctaccacaa gggcttcaag tccttcttct tctcctccaa ggagatcgac 420
tccatccagt ccgagaagtt cggctacctg agggagatcg gcctgttccc gatcaagatc 480

```
gacgcccaga tctccaacga cctgcagtac tccatcgtgg cctccaacca cgccaagatc    540
aagggcttcg agaagatcga caaggagtac caggccaaca aggagaagtg gaacaagacc    600
atcggcgagt ccaccctgaa gcacctgaac aggtacggcg agatgctgaa gggcctgtcc    660
gacctgggca ccatgggcaa cttcaacggc aagaagtacg acaggttcat gggccactgg    720
aggaacgagc agaagatccc ggaccacatc tccatgctgg acttcttcag gaagatctac    780
caggagaagg gcaagtccca caggttcacc gccatcgaca acttcaccta cggctacgag    840
tccgagttca tgaaccacat ctacctgaac ttctccgacc tgtggctgaa ggaggacgtg    900
atcggcgacg aggagtacgt gtccctgatc aggggcgcct accactggca gaaggacgtg    960
gtgggcatcg cctccttctc cggctacaac aagtacgaga agctgttcat gggcgacaac   1020
aagatcaact acgccctgga cttctccaac aaggaccagt ggctgatgaa gttcaacaac   1080
gtgatctcca aggagccgga gaccatcacc ctgaggctgt gcaagaacgg ctacttcaac   1140
aacctgtccg tgctggagaa gaacgacgag aacggcaggt acaagatcag gttctccacc   1200
gagaagcagg gcaagtactt ctacgaggcc ttcatcaggg agccgttcct gaggtacaac   1260
aaggacaacg acaagatcta cgtgcacttc tgcctgtccg aggagatcaa ggagaactgc   1320
ccgaaccacc tggacaccag gtccgacaag tacctgttca agtccgccct gctgaccaac   1380
tccaggcaga agctgggcaa gctgcactac agggacttcc acatcgtggg cgtggacctg   1440
ggcatcaacc cggtggccaa gatcaccgtg tgcaaggtgc acgtggacaa gaacgagaac   1500
ctgaagatca ccaagatcat caccgaggag accaggaaga acatcgacac caactacctg   1560
gaccagctga acctgctgta caagaagatc gtgtccctga agaggctgat cagggccacc   1620
gtggccttca agaaggacgg cgaggagatc ccgaagatgt tcaagatggg caagaagtcc   1680
ccgtacttcc tgaactggac cgaggtgctg aacgtgaact acgacgacta catcaaggag   1740
atctccacct tctccgtgga caggctgtcc ggcctgaccc tgccgatgca gtgggccagg   1800
tcccagaaca agtgggtggt gaaggacctg accaagatgg tgaggaaggg catctccgac   1860
ctgatctacg ccaggtactt caactgctcc gacaagaccc agtacgtgac cgagaacaac   1920
gccgtggaca tcaccacctt caagaagcac gacatcatct ccgagatcat cggcctgcag   1980
aagatgttct ccggcggcgg caaggacgtg gccaagaagg actacctgta cctgaggggc   2040
ctgaggaagc acatcggcaa ctacaccgcc tccgccatcg tgtccatcgc ccagaagtac   2100
aacgccgtgt tcatcttcat cgaggacctg gacctgaaga tctccggcat gaacggcaag   2160
aaggagaaca aggtgaagat cctgtggggc gtgggccagc tgaagaagag gctgtccgag   2220
aaggccgaga agttcggcat cggcatcgtg ccggtgaacc cggagctgac ctcccagatg   2280
gacagggaga ccttcctgct gggctacagg aacccgacca acaagaagga gctgtacgtg   2340
aagagggacg acaagatcga gatcctggac gccgacgaga ccgcctccta caacgtggcc   2400
ctgaggggcc tgggccacca cgccaacctg atccagttca gggccgacaa gatgccgaac   2460
ggctgcttca gggtgatgcc ggacaggaag tacaagcagg gcgccctgta cggctacctg   2520
aactccaccg ccgtgctgtt caaggacaag ggcgacggcg tgctgaccat ccacaagtcc   2580
aagctgacca agaaggagag ggactccagg ccgatcaagg gcaagaagac cttcgtggtg   2640
aagaacggca agaggtggat cctgaggcac gtgctggacg aggaggtgaa gaagtacccg   2700
gagatgtaca actcccagaa ctga                                          2724
```

<210> SEQ ID NO 27
<211> LENGTH: 2739

<212> TYPE: DNA
<213> ORGANISM: artificial sequence
<220> FEATURE:
<223> OTHER INFORMATION: Cas12j.9 encoding nucleic acid sequence

<400> SEQUENCE: 27

```
atgtccgact acaagttctc caacaacggc gtgaccaaca ccggctccgc ccacatcggc     60
ctgtccccgg agaactcctc caccgtgatg gacatgttca aggtgatcac caaggacgcc    120
gacttcctgc tgaagaacct gctgatcatg gagggcggcg agtacatgct gaacagggag    180
atccacaacg gcgacaagga gttcgacaag atcatctcca agctgggcct gtccaagaag    240
gagaaggaga acctgaagat gaagtgcaag gacttcttct tcgacttcgt gaagctgcag    300
aacggcaggt ccctggccaa catcctgttc gagaccaagg gcaccaccct gatcggctgc    360
ggcaaggaca agaagggcga gaaggtggac ggcgagtacc cgaccatcta ccacgaccac    420
gagaccctga ggtccaccgg cctgctgccg ctgaagttct ccaagaacat cgacgacgtg    480
gactacaagt acctgatctg ctacctggtg cacaacgtgc tgtcctcctt catcgagaag    540
agggacgcct acaacgacaa caagaaggag tgggagtcca agctgtccaa ctccaacctg    600
ccgcagctgg agaggatgtc cgagttcctg aacggcatca accacctggg caacatcatc    660
ggctggaacg gcaagaagta catcggcttc atcaagaagt ggaccgacga ggagtcctcc    720
atgtacgact tcttcgtgca gaagctgcag gacaacccga agtacaagtt cggcaagaag    780
gaccagttcc tgtacggcta cgagccggag ttcctgaact acctgttcca cgacttcagg    840
gacctgtggc acccggacaa cctgatcggc aaggacgagt acgtggacct gatctccggc    900
aagaacaaca ccgacgccga gaccgccaac aagggcgcct accactggct gaaggacttc    960
atcaacatct cctccttcga cgcctacggc aagatggcca ccatcggcat gggcaacaac   1020
ctgatcaact actccatgaa catcgacaag gacggcaaga tcatcgtgaa catggacaac   1080
atcttcgaca ggtccaagcc gatcgtgttc aacgtgtaca ggaactccta cttcaggaac   1140
ttcaagatca tcgagtccga cgacaagaag ggcatctaca aggtggagtt ctccacctcc   1200
aacaacggcg tgatctacga gggctacatc aagtccccgt ccctgaggtt cgccaccaag   1260
ggcggcacca tcaagatcga cttcccgatc tccgacaaga ggatcaaggg cggcagggag   1320
atgaacaccg acctgatgtg gttcctgaac agggcctccc cgtgctccac caagaacaag   1380
gaggtgaact ccttcatcgg caagaacttc gtgggcctgg ccatcgacag gggcatcaac   1440
ccgctgatgg cctggtacgt ggccgagtgg acctacgaca aggacggcaa ggccaagatc   1500
gtgaggtcca tcgccaacgg cagggtggac tccggccaca acgagtccga ggtgaagttc   1560
gtgagggaga ccaccaacag gatcgtgggc atcaagtccc tggtgtggaa caccgtgaag   1620
tacaggaccg gcggctccga gggcatcgac aggtgcagga agtcccagaa cggccaggtg   1680
gacctgttcg agatgttcga catcgactac aacaactacc tgaaggaggt gaacaacctg   1740
ccgtacgacc cgaactccga gaggtccatc atccagacct gggtgtcctc cccgtggaag   1800
gtgaaggacc tggtgaagga cgccaagaac aggatggtgc agatcaagac ccagtaccac   1860
aacgccaagg acaaggagaa gtacatcacc acccagaaca gggccggctt ctacgacttc   1920
ctgaagatcg agatggagaa gcagttcacc tccctgcaga ggatgttctc cggcggccag   1980
aaggacatct gcaagaacaa cgaggagtac aggagggggcc tgaggaggag gatcaacctg   2040
tacacctcct ccgtgatcat gtccctggcc aggaagttca acgtggactg catcttcctg   2100
gaggacctgg actcctccaa gtcctcctgg gacgacgcca agaagaactc cctgaaggac   2160
```

ctgtggtcca ccggcggcgc cgacgacatc ctgggcaaga tggccaacaa gtacaagtac 2220
ccgatcgtga aggtgaactc ccacctgacc tccctggtgg acaacaagac cggcaagatc 2280
ggctacaggg acccgaagaa gaagtccaac ctgtacgtgg agaggggcaa gaagatcgag 2340
atcatcgact ccgacgagaa cgccgccatc aacatcctga agaggggcat ctccaagcac 2400
atcgacatca gggagttctt cgccgagaag atcgaggtgt ccggcaagac cctgtacagg 2460
atctccaaca agctgggcaa gcagaggatg ggctccctgt actacctgga gggcaacaag 2520
gagatcctgt tcggcctggg caagaacggc gagccgatcg tgtgcaagag gggcctgtgc 2580
aagaaggaga ggctggcccc gaggatcgcc gagaagaagt ccacctacct gatcatgaac 2640
ggctccaagt ggatgttcag gcacgaggcc aagaagatcg tggagaccta caaggacagg 2700
tactgcgcca accacaaggt ggcctccaag gacggctga 2739

<210> SEQ ID NO 28
<211> LENGTH: 3360
<212> TYPE: DNA
<213> ORGANISM: artificial sequence
<220> FEATURE:
<223> OTHER INFORMATION: Cas12j.10 encoding nucleic acid sequence

<400> SEQUENCE: 28
atgatgaaca tcaacgagat ggtgaagctg atgaagtccg agtacctgtt cgaggacgac 60
ggcatcgtga ccaagaacaa gatccaggag aggctgagga acggcttctc cgacatcggc 120
gtggacccgt ccctggtgtc ctacgcctcc aagttcctgg actccatgtt catctgcttc 180
tccagggtga agggcgagaa gaacttcaag gccaagaacg tgaggaagaa catgtcctcc 240
gccgagaaga aggcccagaa gaagaaggag taccaggagt actaccaggg cgtgatggcc 300
cagcaggacg cctacgccca gctgctgtcc gacccgaccc aggagaacct ggacaagctg 360
aacgagctga tctccatgtc cgtgaacggc tccctggtgg aggacttctt cccggccctg 420
aagaacatga tccagaaggc cgactactcc atcgacaaga agggcctgct ggacttctcc 480
tgctgcatga tggacaggta cgaggacagg tccctgacca gggccatctc catctccgcc 540
ttcaacatcc actccggcgg cctgaggaag gccctgtccg acatctccga gaaggtgcag 600
gacctgtcca acaccctgct gatcaggatc ctgtacatga agggcgagga gctgtccatc 660
gacggcgaga agatctccaa ggaggaggtg cagaggcagc tgaaggccga ctacgaggag 720
cacaaggagt acttcgagga cttcgaggac ttcgccaaga agtgcaggtt cttctacaac 780
aagttctcca agaagaagaa gaccaggggc ttcggcacct acttcttcgg cgacaagaag 840
aaggagatct cctccgccga gtacaaggcc cacaaggagc tgagggactc cggctacctg 900
tggttcgaca tcggctggtc cgagtcctcc gacttcaagt acgtgatcgt gggcaacgtg 960
tccggcaagc tgaagtcctt cgaggagacc tccgaggagt accagaagtc caagaactgc 1020
tgggaggccg agagggtgaa gctgtacgag caggactccg acttcgtgct gttcgtggag 1080
gacatgatcg agtccaagta cggcccgatc gagaagatga agctgaggac cttcaagacc 1140
atcgtgaaga agctggacaa ggagttcggc aagagggggcg acaagacccc gtccatccac 1200
gactacttcg agtccctgga cccgaaccac accttctccc agtccgagca gttcatgtac 1260
ggcctggacg tgaccctgat gcagttcctg ttcaacaaca agaagcagtt ctacaagctg 1320
tgcaaggacc acgacggcaa gaggaccttc gccaaggtgg tggaggagtc ctaccactgg 1380
ggcaagaact ccatcaacgt gtccaccttc cagaactcca cctccatcct gctgggcggc 1440
aactacctga actactccat gtccatcgag ggcgagggcc tggtgatcaa gttcgacaac 1500
ccgctgtccg gcaaggaggt gcacttcgtg gtgtgcaaca acaagtacct gtccgacctg 1560
gagatcctgt ccggcaaccc gaacaggaag gacaacaact acaccatctc ctactccacc 1620
ggcggcaagg ccaggttcat cgccaagtcc aaggagccga ggatcttctt caacaggaag 1680
accaagaagt gggagatcgc cttccagctg tccgacgtgt ccccgctgaa cggcaagttc 1740
ggcaagcagg gcgagttcct gtccaacctg aggaagttcg tgtacaacca cgtggccaag 1800
tccccgtcca agctgaacat ctccgacaac aactgcaggg ccgtggccta cgacctgggc 1860
atcaggaacg tgggcgcctg gtcctccttc gacttctcct acaaggacgg cgtgctgggc 1920
ggctacaagt acctgacctc cggctccctg aggtccaagt ccgagtcctc cgagatggac 1980
cagggctact acttcgtgct gaacctgaag aagatcgtga agctgatccc ggtggtgaag 2040
aagtccatca tcgacgaccc ggagctgaag aggcagttca tcggcgtgct gaacgagaac 2100
ggcaacaccg tgggcctggg caacatcggc aagctggaca tcgcctccag gaaggccgtg 2160
cagtccttcc acaactgcat ccagcagatc aactactacg tggacaccta cgccgaccac 2220
atcgacaaga tctccgccaa ggacttcgtg gacgacatcg acggcatcaa ggtgctggac 2280
gaggacgacc cgtacgtggt gaagatcctg tcccacctgc cggaggacgt ggagggcaac 2340
caggacgaca tcctgaacat ctccctgctg aagtggaaga cctccaacgc ccagttcgtg 2400
ccgccgctga tccaggaggc caaggccatc atgtccagga tcaagaggga gaacctggac 2460
aacatcaggg gcaagaagac ccaggtggtg acccagaaga ccttccacaa gatcaagttc 2520
gccaaggccc tgctgtccct gatgaagtcc tggtcctcca tcggcaccgt gagggtggtg 2580
aagaccgacc agatctacgg caagaagatc tgggactaca tcaacggcct gaggaggaac 2640
gtgctgacct acctgtcctc cgccatcgtg aacaacgccc tggacctggg cgcccacatg 2700
atcatcctgg aggacctgga ctcctccgtg tccaagtaca gggagaagga caagaacgcc 2760
atccagtccc tgtggggctc cggcgagctg aagaagagga tcgaggagaa ggccgagaag 2820
cacagggtgg tggtgcagta cgtgtccccg tacctgacct cccagctgga caacgagacc 2880
aaggacatcg gctacaggaa gggcggcagg ctgtacgtgg tgaggaacgg caagatcaag 2940
tccatcgacg ccgacatcaa cgcctccaag aacatcggcg agaggttctt cgacagggac 3000
ctgatccaga ccctgtccgg cgtggtggtg gaggaccagt ccaccgtgta catcctgcag 3060
aagaggaacg tgtcctccga caacaggaag aggttctaca agaagttcct ggaggacgtg 3120
ggcggcaagt ccaagaagga cgccgtgctg aagatgggcg accacggcga gctggaggtg 3180
gagaggctga tcgacggcaa gaagctggac atcgacggca agaagatcct ggtggacggc 3240
gagaaggtgc cgttcaggaa cacctccgtg tactactccc cgaagaagaa gaagtgggtg 3300
tccaaggagc tgaggtgcaa ccacatcaag ctgaccgtgg aggagcagga catcaagtga 3360

<210> SEQ ID NO 29
<211> LENGTH: 3408
<212> TYPE: DNA
<213> ORGANISM: artificial sequence
<220> FEATURE:
<223> OTHER INFORMATION: Cas12j.11 encoding nucleic acid sequence

<400> SEQUENCE: 29
atgaacaact acgacaacta cctgtccgac tacctggcca tgctgccgca caccaagagg 60
accgagatca agaagaccgc ctccaagatc tccaggaagc tgaaccagaa ggaggtgaag 120
aagcagatcg agaggtccga gtacatcagg tccaactgcg gctacatcaa catcgagagg 180

-continued

```
ccgcagaagt ccctgtcctt cctgtcctac tccaccatca agtccgcctg catgtccgtg    240
aacttcaggg ccttccagaa cccgatcaac gactacgaga ccgccatctg caacggcatc    300
aacgagtgcg agaggttctt ctaccagcag atcgactcca tctacatgtc ccagatcatc    360
gagcagctgt tcgacttcta catcgcctcc aggcagcacg acatgttcat caacaacacc    420
gtggtgccgt acgacgtgaa caagctgaag tcctactaca ccgccaacga gaagtactcc    480
ttcgagcagt tctgcgacga catcaaggag ttcaccaaca agggcttcac ctccggcggc    540
gtgtcctgca tcctgaacct gttctacaag ggctccgtga aggactccaa gaacaagaag    600
gactacatca agtccgtgaa gaggctggag accaacggcc tgttcaagaa gctgaacatc    660
ttcgagaaga acggcatctc caagtacttc gccgcctcca ccctgtccac cttcttcgcc    720
accatctcct cctggaagaa gcagaacgac gactggaccg gcgtggccaa ggacggcacc    780
tccctgctgt ccaagctgga gaacaagacc atcaccctgc agtccatcat caagcaccac    840
agggtgatca acgagctggc cgtgctgatc gtgaaggcct acaaggaccc ggtgaagacc    900
ctgaacaacc tgttcgagga gaggtccgac aacaacaacg acttcaagta cacctgctcc    960
gacgacgagg acaagtaccc gatgtacatc aagagggaga tcgccgagtt cgtgaagaag   1020
cacaagaccg tgtgggagga gatcaggtac ttcgacgagt ccgacaccaa gaagaagaag   1080
agggacaaga aggagtcctc ctccgacgac aagtcctacc tgtgctgcgg cgactcctgg   1140
gactacctga agacctgggt gaggctgtac ggcgagtact acttcttcga caacgccctg   1200
aaccagttcc tgaggaagcc gtccgcctcc atgcacctgt acacctccct ggactggatc   1260
aacaagaaga ccatctgcat cgtgggcgcc aactactaca agatcggcaa ggtggaggtg   1320
gtggagagga acaaccagag gttcctgctg gtgtacgtgt ccgtgccgga gatggagaac   1380
tacatcatca tcccgctgca gctgaacaag tacttcggca acttccagtg caagatcttc   1440
gagggcaggc tgcaggccat cttcaagagg tacgccaact tcaacgccct gaagaacaac   1500
aagccgcagc cgtccccgaa catctccgtg aggatcaacg agttccactt cgccctgagg   1560
tcctacagga agcagcagat ctccgccgag gacttctcca agggcaggtt ctccctgatc   1620
tccaagatcg gcttccagat gaccaacgac gaggtgttcg gcaggacccc gagggagatc   1680
gccctggtga aggaccacct gtccaagggc tacgtgcact tcggctccca gatcatcgag   1740
gactccagga aggaggtgga gcaggtgctg aagaagccga tgatcctgat gggcgtggac   1800
ttcggctact ccccgctggc ctcctacaac atcaagccgc tgcagaccgg caagccggcc   1860
accgactggg tgaagaacct gcacggcaac ttcctgtgcc agaacgtgtc cctgggcgag   1920
accatcaccg agggcgagat cggcgacgtg ccgaccgaca cctacacctc ctccaacgag   1980
atctactcca tcgccaccct gaccttcagg aacgccgacg gcaagctgga gaacaggtcc   2040
ttctccaggt tctaccacga gctgaacaac accctgaaca tcatcgagca gatcaagggc   2100
accttcaact tcatccactc catcaacacc cagttcaagg agatcaaggc cctgaagacc   2160
accgaggagt tctcctccta cgtgtccacc ctgacctggg accagttcat cgaggactcc   2220
aggaagaccg ccaggtactc caagtactgg atccacatca tcaacgagaa cccgaagagg   2280
aggaccatcg ccaccctgaa cgagaccctg aagctggtgg acgagaagca caggttcacc   2340
gtgaccatcc aggagatctt cgacctggtg aagtactgcc agcagcacgg ctactacccg   2400
aagtccaacg tgatgtccaa gctgaggaac ctggccatca agctgatcaa cgacctgatc   2460
aggtaccaga agatcggcat ccactcctgc tacctggact tctgcgtgct gatcaagaac   2520
cacatcgccc tgctgaactc ctccaccgcc ttcatcatca acttctccag gaacaaggag   2580
```

```
aacatcatca ggaacaacac ctccaagatc cactccctgt gggtgtacag ggacaacttc   2640

aggaggcaga tgatcaagaa cctgtgctcc cagatcctga agatcgccgc caagaacaag   2700

gtgcacatcg tggtggtgga gaagctgaac aacatgagga ccaacaacag gaacaacgag   2760

gacaagaaca acatgatcga cctgctggcc accggccagt tcaggaagca gctgtccgac   2820

caggccaagt ggtacggcat cgccgtggtg gacaccgccg agtacaacac ctccaaggtg   2880

gacttcatga ccggcgagta cggctacagg gacgagaaca acaagaggca cttctactgc   2940

aggaagcagg acaagaccgt gctgctggac tgcgacaaga aggcctccga gaacatcctg   3000

ctggccttcg tgacccagtc cctgctgctg aaccacctga aggtgctgat caccgaggac   3060

ggcaagaccg ccgtgatcga cctgtccgag aggaccaccg agccgcagaa gatcaggtcc   3120

aagatctgga ccaactccga cgtgcagaag atcatcttct gcaagcagga gaacggctcc   3180

tacgtgctga agaagggctc caccgacatc aaggagaaga tgcacaaggc cgtgctgcac   3240

aggcacggct ccctgtggta cgactacctg aaccacaaga acatgatcga ggacatcaag   3300

aacctgcacc tgtccaactg ctccctgacc acctccacca actccgacgt gatcaactcc   3360

cactccggct cctccaggtc cctggacaag accaagacct acgcctga                 3408
```

<210> SEQ ID NO 30
<211> LENGTH: 3042
<212> TYPE: DNA
<213> ORGANISM: artificial sequence
<220> FEATURE:
<223> OTHER INFORMATION: Cas12j.12 encoding nucleic acid sequence

<400> SEQUENCE: 30

```
atggcctcct ccgacgccca gaagttcccg cagacccaca acaaggtgat gtccttcagg     60

ctgaccgcct ccaacatcgg ctccgtgctg tccctgcact ccaacctgca cgacgccgcc    120

gagatcggca tcaacgagtg caggtggtgg atcggcgacg gcgagatcta cgagagggac    180

ccggcctgca ggtccatcaa gaagggcaac gacatcagga ccgtgacctc cgagaagatc    240

aaggagctgt ggaccaagca caccgaccac tccgtgccgc tggtggactt catcgacatg    300

ctgaagttcg tggcccagtg cgccatctac ggcgactcca gggccctggc ctccaccctg    360

ttcggcaagt ccaaggccga gaccaggggc gtgtccaccg aggacatgac cgtgatcagg    420

gcctggatcg ccgagaccga cgccgtgctg gcctccggcc tgtccccgaa gaagaagaag    480

aagaaggaga aggaggccgg caagaaggag aggaagccgg acgtgaagat ggagatgtgc    540

aggaggatca ggtgcaccat ggtgcagtgc ggctacttca ggaggttccc gttcgaggcc    600

aagatcgaca acggcggcga gaggggcaag atggactccg agctgtccta cgtgtccgcc    660

aggaacctgc tgaggtgcct gtccacctgg agggcctcct ccgtgatgag gagggactcc    720

tacctgatcg aggaggagag gatcaaggag gccgagtcca agatgacccc ggagatcatc    780

gacggcctga ggaggctgta caggtactgc gccgtggacc acgacttcct gaagtggttc    840

ggcggcagga tcatcaggca catcgactcc tgcctggccc cggccatcgc cggcaacacc    900

ggcaggccga ccggcggcga gtccttcacc gtgatctacg acaggaggaa gaagagggac    960

gtgaagatca cctactccgt gccggaggag atctacggct acctgtcctc ccacccggag   1020

ctggtggcca tcggcaagga cggcatgacc ccgatctcca ggcacgccga ctacctggag   1080

atgatcgcct cccacgagaa gcacaggtgg tacgccacct tcccgaccgt gggcaaggag   1140

gacggctaca ggacctccgt gctgctgggc aagaactacc tgacctacga cctgtcctac   1200
```

```
gacggcgagt ccgtgccgga caagaagatc aacgtgatct ccaagggcca gccggtgtgc   1260
ctggacctgc acgacggcag gagggtgtcc tccctgtacc tgaccgtggg cgagtccgcc   1320
gcctacgaca tcgccgtgag gaagaacaag aggcaccacg gcaagccggc cgactactgc   1380
aggatgaggg tgcacctgac ccaggagagg gaggacaaga cctacaacga cccgtacttc   1440
tccaacatgg agatctggag ggccggcgac caggtgtacg ccatcgagtt cgacaggcac   1500
ggcgccaggt acaccgccat cgtgaaggag ccgtccgtgg agtacaggaa caagaagctg   1560
tacctgaggg tgaacatggt gctggactcc ccgtccaggc aggacgacaa ggacatgtac   1620
tacgcctaca tgaccgccta cccgtcctcc aacccgccgg tggagacctc cgacaacaag   1680
aagaggttcg agaggctggg cccgggcagg agggccatcg gcggcatcga catcggcatc   1740
ggcaggccgt acgtggccgt ggtggcctcc tacgaggtgg gcccggccgg caccgagcag   1800
aagttccaga tcgaggacag gctgatcgag gacgacggct cctccccgta cgactccctg   1860
tacaacgact tcctgaccga catcaggacc gtgtccagga tcatcgaggc cgccaagaag   1920
atctccgagg gcgacctgga ggacatcccg tccgacatgt ccgtggacga ggacggctcc   1980
atcgccgcca ccatgaagag gatgtccgcc aggatcgccg agaggcacca cctgtacggc   2040
gagaggaagt ccgaggccta cgccaccttc ctgaagatga accacaagca gaggctggac   2100
atcctgctga cccagaaggc ctccaacgcc accctgaagc agctggtgga ggaggacccg   2160
tccttcctgc cgaggatctg cgtgtactac gtgatctccg tggagaggga gctgaagaac   2220
aagcacagga acgcctacct ggacggcctg accgtggacg agaagtactc cggcgagacc   2280
aagaggggct acgcccagaa gaggctgaac tccatgctga gggcctactc cgccctgggc   2340
gaggaggaga ccgacgaggt gaggaccttc tccaccaggt ccgagaaggt gaggaacatg   2400
gccaagaacg ccatcaagag gaacgccagg aagctggtga acttctacgt gggcaagggc   2460
atcaggacca tcgtggccga ggacaccgac ccgaccaagt ccaggaacga cggcaagaag   2520
tccaacagga tcaaggccgc ctggtccccg aagcagttcc tggccgccgt gaagaacgcc   2580
gcccagtggc acggcctgga gatcgccgag gtggacccga ggatgacctc ccaggtgcac   2640
ccggagaccg gcctgatcgg ctacagggac ggcgacaccc tgcactgccc ggacggctcc   2700
aagatcgacg ccgacgtggc cggcgccgcc aacgtgtgca gggtgttcgc cggcaggggc   2760
ctgtggaggt tctccatcaa caccaacatc gacatctcca acaaggacga gaagaagagg   2820
ctgagggcct acatcgtgca ccacttcggc tccgagtcca actgggagaa gttcaggaag   2880
cagtacccgt ccggcaccac cctgtacctg cacggcaggg agtggctgac cgccgaggag   2940
cacaagtccg ccatcgacag gatcagggac gacgtgggca gggacgccga gaacgaccac   3000
gtggccatcg tgaccgccgc cgagaaggtg gagatcttct ga                      3042
```

<210> SEQ ID NO 31
<211> LENGTH: 3159
<212> TYPE: DNA
<213> ORGANISM: artificial sequence
<220> FEATURE:
<223> OTHER INFORMATION: Cas12j.13 encoding nucleic acid sequence

<400> SEQUENCE: 31

```
atgtcccacg acctgaagcc gcagaggctg atcaggtcca acatcaccaa gacccactcc     60
gaccagaacg ccaagcaggt ggccgaggag gtgaagaagg agcacctgaa ctacctgctg    120
atcaagaacg agatgctgat ctccatcgtg ccggaggcca aggacgacga cggcaacgac    180
atcgacttca agaagcagct gaagtccctg tacaaggaga ccgaccagtc cgtgtccttc    240
```

```
tccgtgttct gccagatgat gaagttcagg aacatcgccc tgctgtacgc caagggccag    300
tccaggtggg ccgtgtcctc ctacttcacc ggcaacagga ggaaggacga ctacgccaag    360
gacctgtccc tgctggacga ggccatcgag ctgctggagt gcaagaggag gaagaaggcc    420
gaggaggaga acgaggagga gaacgagacc ccgaagaaga aggaggacaa cccgtccaac    480
atctccgagg agcagatcat gaagctgttc tacgccgtga acaagaagct gaaggagatc    540
ggctacctgg acaggtactc ccacatcgag aagcaggagc agtacgccat catcggcgtg    600
acctccagga ccgtgaaggc ctgggactac gccaacttcg ccaccaggaa ccactaccag    660
tccgtgcaga acgagtacca gaagaagctg aaggccctgc cgggcaccaa gaaggacaag    720
gtgtgcctgg agaagttctt cgaccacctg aacgagaaca acatcgccgc cgactgggac    780
aagtggaggc tgaagaagca catcctgcag tgcatcatcc cggccgccaa gatcggcctg    840
aaggagctga agcagtcctt ctacgtggac aacaagggca acaagcacaa ctacttcgtg    900
aacggcctgt acgaggagat cctgaagagg ccgttcctgt actccgccga ggacccggag    960
gagtccatcc tgtacctggg cgtggaggtg gcctccctgc actccaagct gaaccacctg   1020
aggtccgagg ccaggttctc cttcgagacc ccggacgaca tctgcaagta catgaccatc   1080
tgcggcgaca actaccacaa cttcaccatg tccgccatcg gcgaggacgt ggaggacatc   1140
gaggtggagg tgtacgacta caaccactcc aagaagtacg agaccatgag gttcatcaac   1200
ggcaagagga ccaccgacct gtccctgaac ttcaagggca tcccggtgag gctgtgcctg   1260
gagggcaaga ggaacaactc ctacttcgcc gacgccatcg tgtgggagct ggacaacaag   1320
gacaagaccg gctacctgat cgagtacggc aagtccaaca acaggctgta catgctggtg   1380
aaggagccgc tgatcggctg caggaggaag ttcggcaagg acgtgctgtt cgtgtccctg   1440
tccggcaccc tggtgaacaa gtacatcgag gacgacatcg tgtccgccag gtacctgatg   1500
cagaccgccg ccccgatctt caagacctcc agggccaaga agcaggacaa gatcggcgac   1560
aagtggttcg agcactgcca gggctccacc atcaagatcg ccggcatcga catcggcatc   1620
aacccgatcg ccgccatcac cgtggccaac gtgaccttcg acagggccct gggcaacaag   1680
atcaagaacc agaagcagat cgtgatcgac tgctacgccg aggactacaa gatcgacccg   1740
gtggtggtga agaggatgga ggacatcagg cacatcaagt acaccatcaa ctcctggtac   1800
cacctggccg actgctgcag gctgaaggcc gccaacaagg agtacgtggt gaacgagagg   1860
aagcagggct tcttcaggga gaacatcgag tacctgaagg aggtggccaa gaaggccatc   1920
accgagtccg accagcagat caaggagcag aaggccgccc tgaagaggtt cgacggcgag   1980
aagaagaagg agatccaggc caccatcaac ggcttcaacc tgaagatcaa gatcctgaag   2040
aagttcgtga ggcagtccgc caagaagatc ttcgactcca ccctggagac cctggagaag   2100
tacgacaaca acatcgagca ggccaagagg gacagggagt tcggcctgaa gatcatctac   2160
gacctgatca tcaagtacta caagaggtcc aagaaggaga gggagatgaa ccagaggatc   2220
tacgtggacg actacaacca ggaggagatc gacaccgaga ggaccaagaa gatcaggaag   2280
gagaccatca ccttctgcga caacgactgg aactccctga ccaagaggat ccacgacctg   2340
gagaagaaga tgaagaagat cggcatctcc gagccgggca gggtggagca ggagatcaac   2400
gacagggact actacaacaa catccaggac aacaccaaga agaggcaggc caagatcatc   2460
gtggacgccc tgaaggagga gggcgtgtcc atcatcgtgg tggaggacct gaccggcggc   2520
ggctccgaga acaccaagga gatcaacaag tccttcgacg ccttcgcccc gatcaggttc   2580
```

```
ctgaacgccc tgaagaactg cgccgagacc aacggcatcc aggtgaccga ggtgctgtcc   2640

ccgatgtcct ccaagatggt gccgtccacc ggcgagatcg gccacaggga caagagggac   2700

aagcagctgt actacaagga cggcgaggag ctgaagtcca tcgacggcga catctccgcc   2760

tccgagatcc tgctgaggag gggcgtgtcc aggcacaccg agctgatcgg caccatgaac   2820

gtggaggacg tgctggacaa gaacaacaac aagaacaagt gcatcaaggg ctacgtgtgc   2880

aacaggtggg gcaacatcca gaacttcgag aagatcctga aggagaaggg catcggcgag   2940

agggagatca tctacctgca cggcgacaag atcctgacca tggacgagaa gaggaccctg   3000

caggcctcca tcaggaagga gctgaaggag atgagggaga gggagtccgg cgaggagaac   3060

gccggcaccg ccaggaagaa gtccaagccg aagaagaaga agaagatcaa gaggaacaac   3120

gaccaggacc tgtccaacaa caggccggcc gcctcctga                          3159
```

<210> SEQ ID NO 32
<211> LENGTH: 3138
<212> TYPE: DNA
<213> ORGANISM: artificial sequence
<220> FEATURE:
<223> OTHER INFORMATION: Cas12j.14 encoding nucleic acid sequence

<400> SEQUENCE: 32

```
atgaaggaga acaagatgaa ggagaacggc tccatgacca cccactccaa ggtgatcgcc     60

ctgaagatga agtccgagaa cgtggagttc gacaccttct acaaggagtc cttcgagctg    120

ttcaagcagt tcaccaacga gttcgtggcc tggggcaacg acgagatcta ccagtacggc    180

tcctccaaga ggaagaagga cgaccagaag atctccctga tcccggtgat cgaggacatc    240

tacaagtccg tggagaagaa ggccaccgcc gagggcatct ccaagaccga cttcagggcc    300

gtgctgaagt acctgtacca ccagatcatc aacgtgggca actccggcag gtcctacggc    360

acctccctgt tcggcggctg cgaggtgaag gagaagctgt ccaagcagga catctccaac    420

atcgtggagt gcgtgaagga gctggagctg tgcaagtcca agcaggagga gtccgacgcc    480

tacgacaaga tcctgctgaa ggagaagatc acccacatcg tgaagtccgg cgagaccgcc    540

ggcgacatca ccaagaagta caaccaggcc accaccggca ggaagacctc ctccaagggc    600

ttcttcgaca agtccaccaa gaccgaggtg aagtacaagg acatcaagga cgacaccctg    660

ctgcaggacg gctccaccat cttcatcaag tcctccgtgg acctgttcgt gaagaaggtg    720

tgcaacaccc tgagggagat caacttcttc gacaggctgc cgttcaagaa caaccactcc    780

aacaactacg gcctgctgtt ctccatgctg tcccagatcg agtcctggaa gaccatctcc    840

gagaccacca agaagtccca cgaggagcac ggcgagaaga tcgcctccat ggtgaagaag    900

ctggacctga cccagaccga gctgatgaag gacttcgccg ccttctgcat cgagaacaac    960

atcaccaaga agttcgacca caagttcaag aggcacatgg aggactgcgt gatcccgtcc   1020

ttcaagaacg gcaagatccc ggacaagctg ttctacttca acatcatcct ggccaagaag   1080

accgacgagc agatcgacta ctccctgtcc tccgagttct acaccaagct gttctccatg   1140

ccgaacctgt ggcaggagga ggaggccttc atcgtgaaga acatcaacct gatcgaggag   1200

atcaccatct tcaacaagag gaggaactac gcctgctgcc cgctgatcaa ggagaaggag   1260

tacgacaggt tccagatcca gctgaacgag accaacttcc tgaagttcca gttcgacccg   1320

aagaacgtgg tgaacatcga cgagaacacc accgaggcca ccgtgggctt cgacgagaag   1380

ctgaagctgg tggtgtgcgc cgacaagaag tacgccttct ccatcttcac ccagtgcaag   1440

taccacggca acaagcacaa gccgaacacc tacttcaaca acctgaagat catcaaggtg   1500
```

```
atcgagtcca agtccaactc cgtgaagtcc atgaagtaca ccttcgagtt caccaagagg   1560

aacgagctga agagggccga gatcaagcag ccgtccatcg tgtacaagaa caacaactac   1620

tacatcagga tcaacatgaa cgtgatcctg gacgccgacc agacctccta caagatcatc   1680

aacaacaacc agaccgcctc cctgccgtcc tacttccagt cctccctgcc gttcgagaac   1740

aacaggggca agatccacga caagggcatc gtgcactggg agaagatcaa gaacaggaag   1800

atcatcgcca tgggcgtgga cctgggcgtg aggaggccgt tctcctacgc catcggcaac   1860

ttcaccctga acaaggacat cctggacaag aacgacgtga acatcgtggc ctccggcttc   1920

aacctgtgct ccgactccga cgtgtacttc caggtgttca accagatcaa gaccctggcc   1980

aagttcatcg gcaagctgaa gtcccacaac aagggcctga aggtggactt cgagaaggac   2040

aagaagtaca tcttcgacct ggtgaacgac gccaaggcct acttcaagga catgtccgcc   2100

aagaggatca acgacaccaa ggacaacatc tccaacaccg tgaccaacaa ggagaggatc   2160

tacggctcct tcgtgtccga gtccgccgag tccgccatcc agtgcgccat cgacaggtcc   2220

gagaaggagt ccggcctgac cctgaagaag gacatctcct ggctggtgaa cgtgctgtcc   2280

aagtacctgg agaggaagtt caaggaggtg aagaacaaca ggaagtacac caacgtgaac   2340

aagtgcgaca actgcttcaa ctggctgagg gtgatcgaga acatcaagag gctgaagagg   2400

tccatctcct acctgggcga ggacctgcag aagaacccgg agctgaagat cgagctgaag   2460

aacctgaacg agtacggcaa caacgtgaag tccgacttcc tgaagcagat cgcctccaac   2520

atcatcaagg tggccatcga gcacaagtgc gacatcgtgt tcatcgagaa gctgggcaag   2580

gccgactcca ggtccaggaa gctgaacgag atgttctcct tctggtcccc gaaggccatc   2640

aagaaggcca tcgagaacgc cgcctcctgg cacggcatcc cggtggtgga ggtggacccg   2700

tcctgcacct ccaaggtgca ctacgagacc aacctgttcg gccacaggat cggcaacgac   2760

ctgtactacg tggaggacca gtgcctgaag aaggtggacg ccgacatcaa cgccgccaag   2820

cagatcctgg tgaggggcgc caccaggcac ggcaacatct cctccatcaa catcaagtac   2880

ctgcaggcca agatcgccga gctgaactcc gaggccaact ccgaggagga caaggaggag   2940

atcaagcagg gcggcaagag gatccagggc ttcctgtgga agaagtacgg caacatcacc   3000

aacatcacca accagctgac cgccgcccac aaggagaggg agtccaagtt cgactacatc   3060

tacctgcaca acgacaagtg gatcgcctac gaggacagga acgagatcaa gaaggacatc   3120

gagaagaggc tggagtga                                                 3138
```

<210> SEQ ID NO 33
<211> LENGTH: 2688
<212> TYPE: DNA
<213> ORGANISM: artificial sequence
<220> FEATURE:
<223> OTHER INFORMATION: Cas12j.15 encoding nucleic acid sequence

<400> SEQUENCE: 33

```
atgaccgcca agaagaccgc caagaagtac ttcccgccga agtgcctgag gtcctcccac     60

ttcaagatct acggcatccc gaccgccatc agggccctgg aggagaccaa caccttcgtg    120

aacaaggccg ccgccgacct gatggagatg ttcttcctga tgaggggcca gccgtacagg    180

aggaggatcg gctccgagga gaagcaggtg acccaggagc acatcgacgc caggctgagg    240

gtgctggtgg gcgactactc cctgaacgag gtgaagccgc tgctgaggca gctgtacgac    300

ggcatcaagg ccaagcagaa ctacgccccg acccacttcg tgaggttctt catccagccg    360
```

-continued

```
accaagggcg ccatcgacaa gaagtccccg gtgtcccaga gggccaagaa ggccggccag    420
aagctgcaga agatgggcgt gctgccgatc ctgccgctgt ccccgggctt caagttctgg    480
accgccgcca tgatgatggc ctgctccagg atgaactcct gggaggcctg caacgagaag    540
accatcgaga accacaaggc cttcctggag ggcatcgaga actacaagaa ggagatcagg    600
ttcgaggacc tgtgcgagga gtggtccctg ttctccgact ggctgaccga ggccgagtcc    660
gacaacgagg gcggctgcaa gttcaagctg accccgaggt tcctgcagag gtgggagagg    720
atctacctga agcagatgag gaagggcaag atcccggcca ggcacaacct gggcccggtg    780
atggaggccc tggccggcga caagtacagg cagctgtggg acaacggcga ggagagggac    840
tacatcaccg agctgggcga cctggtgacc tcccagagga aggccgtgag gctgtccagg    900
gactccgccg tgaccttccc ggacgaggag ctgtccccgg tgggcaccga gttcggccac    960
aactacatgt ccttctccat cgaccaggag aactccccacc tggtgaccct ggaggtgatc   1020
ggcggcaagt accagttcga gatctccaag tccgactact tcagggacct gatcgtggag   1080
gaggccggca agcagtccaa gttctacaac gtgtcctaca ggaagggcaa cgtgagggag   1140
gagaacctgg ccggcgactt caaggaggcc accgtgagga acaggaggtc cctgaagacc   1200
ggcaagagga ggctgtactt ctacatgtcc cactccatcc cgaccaggtt cgacgacgac   1260
ctgtacgccc agttcaccga gaagggccag ccggacttct ccaagctgta caaggccgtg   1320
acctacttcc agtgctccct gggcaacaag aaggccgaca cctacagggt gtacgtgaag   1380
atgggcacca ggttcctggg cgtggacatc ggcgtgtcca ggctgttcgg cttctccctg   1440
ttcgagctga gggaggagaa gccggagaag aacccgttct tcgagctgcc ggacgacctg   1500
ggctacgccg tgtgcctgga gtcctgggtg gacggcgtgg agaagaacca caaggtggcc   1560
caggagatga aggactggag gagggagtgc ctggccgccc agaggctgat ccactacgcc   1620
aagttcctga agaagaggga caagaacgag gagatcgact acaagcacga ggagtccctg   1680
gagaccatcg ccggcctgct gggcatcgag atcgacccgg agcagatcat cgacgtgccg   1740
ctgaagctgc tggacctggt gggccaggcc atcggcgccc tgaggaagaa gtacctggtg   1800
ctgaagaaga acgaggtgag gcagggcagg atcacctccg agctgttcct gtggccggag   1860
tgcgtggaca cctacatcag gctgctgaag tcctggacct acaaggacaa gaagccgtac   1920
cagaagggcg agaccaacaa ggacgccttc aagaagctga agggctacct ggccaggctg   1980
aggaaggacc tggccccgaa gtacgccgcc gtgatcgccg acgccgccat caggcacaag   2040
gtgcacgtgg tggtggccga gaacctggag cagttcggcc tgtccatgaa gaacgagaag   2100
gacctgaaca gggtgctggc ccactggtcc caccagaaga tctggtccat ggtggaggag   2160
cagctgaggc cgtacggcat catggtggtg tacgtggacc cgaggcacac ctccaagctg   2220
gacttcgcca ccgacgagtt cggcggcagg tgcttcacct ccctgtacgt gatgagggac   2280
ggcaagaaga ccaccaccga caccgagaag aacgcctccc agaacatccc gaagaagttc   2340
ctgaccaggc acaggaacgt gtcctggctg ctggcctacg ccgtggacct gtccgactcc   2400
cagaagaaga agctgggcat cggcgacgag aaggtgtggc tgccgaacat gggcctgatg   2460
atctccggcg ccctgaaggc caagcacggc aagaactccg ccctgctggt ggaggacggc   2520
gagaactaca ggctgctgcc gatcaccgcc gcccaggcca agaagttcgt ggtgaagagg   2580
aagaaggagg agttctacag gcacggcgag atctggctga ccaaggaggc ccacaaggcc   2640
aggatcgagt acctgttccc ggagtccaag aagggcagga agtcctga                 2688
```

```
<210> SEQ ID NO 34
<211> LENGTH: 2871
<212> TYPE: DNA
<213> ORGANISM: artificial sequence
<220> FEATURE:
<223> OTHER INFORMATION: Cas12j.16 encoding nucleic acid sequence

<400> SEQUENCE: 34

atgaagaaga ccaactacaa gacctcccac ctgctgatcg acaacccgcc gcagtccatc     60

atcgacctgc acagggacgt gatcgagatc ggctcctacc tgaccaagtt cttcctggcc    120

tgcctgggca ggccggtgga ctccaccatc ctgtccgagc cggccctgca cttccagttc    180

gtgaacggca tcctgccggt gaagaacggc ccgggcgccg acgactcctc ctggaggcac    240

tccgagaact gctactccat gctgttcgag aagaactcca agtccggcaa gtccgacggc    300

aaggtgaggc aggtgaggga gctgaaggtg gccctgttcg gcaagaagga gaagggcaag    360

ggcatcgtgg gcaagaagac ctgggacgag ctgaaggtgg tgctggaggc cctgccggag    420

gagcaccaga tcctgtccct ggagatctgc cagaggcact acgagtccag ggacgtgaag    480

gccttcggca agctggccct gtcctccaag tccaggccgt ccgtggaggc cggcctgaag    540

ctgagggagc tgggcctgct gccgctggac tccaggggcc tggacaagaa caagctgctg    600

ggcatcctgg ccgccgtgac cggcaggctg aagtcctgga gggacaggga ctgcgcctgc    660

aaggccgaca agcaggccct gagggtgaag ttcgaggaga ggctgtccaa ggtggaccag    720

tccgcctacc agcagttcaa gcagttcgcc gacgagctgc tgacccagga gggctacagg    780

atctccggca gggtgctgag ggccgtggag aagaaggact ccgactactc cccggtgctg    840

accgtgctgg ccaagtaccc ggacctgcag gacaacttcg aggagctgtg cagggcctgc    900

ctggccgagc aggccttcaa caagaagaag gccgacgcca gggtgaccgt gtgctccgag    960

acctccccgc tgcagttccc gttcggcatg accggcaacg gctacccgtt caccctgtcc   1020

gcctgcgagg gcaggatcaa cgccaccatc cacttcccgg gcggcgacct gccgctgagg   1080

ctgaggaagt ccaagtactt ccagaacccg gagatcctgc cggtgaagga cggcttccag   1140

atcaccttca ccaggggcaa gaccccgctg gtgggcacca tcaaggagcc gtccctgctg   1200

aagaagaaca accactacta cctgtccctg agggtgaacg tgccgtccgt gaagatcccg   1260

aaggaggtga gggacaccag ggcctactac tcctccgccg tgggcggcga cgagaccacc   1320

ccggtgccgg tgaaggccgt ggccatcgac ctgggcgtga ccaccctggc cgactactcc   1380

atcatcgaca cctgcctgcc gggcgactgc aaggtgttcg gcggcgagac cgccgccttc   1440

accgcccacg gcaagatcgg ccagtgcgcc aacaagtccc tgagggacag gctgtacaag   1500

aacaccgagg aggccctgtt cctgggcaag ttcatcaggc tgtccaagaa gctgagggac   1560

ggcgagggcc tgaacaggtg ggaggtggag aagctgccgg gctacgccga gaggctgggc   1620

atcacccagc acctggacaa cgcctacacc aggaaggacg agatcgccag gaagttcaag   1680

cagatcaagg gcaacttcga caagctggtg tccgagttcg ccctgaggga ccacccgtcc   1740

aagaagggcg agtcctggga gaccatctcc gccgagacca tccaggtgct ggccgccctg   1800

aagaggatcc agtccctgct gaagtcctgg acctactact cctggaccgc cgaggactac   1860

gtgctggccc tgaccgccga cggcccggtg tgcatcgacg gcgagcacgt gaaggccgtg   1920

accgccacct ccaggaggtc cttcgccccg tgcggcaagg ccgccctgct gaggctgatc   1980

gagtccggcg agatcgtgga gaccggcggc cagtaccagc tggccaccgg cgtgaagcac   2040

aggaaccacc cggtgaactt cctgtcctcc tacatcaagc acttcaacgg cctgaggagg   2100
```

```
gacctgacca acaagctggt gagggccatc gtgaacaagg cccaggagta cagggtgcag   2160

atcgtgatcg tggaggactt cggcatcgcc gacctggagg acaggatcaa ggacgcctac   2220

gagaactaca ggtggaacct gttcgccccg gccaccatcg tgaagaagct ggaggccgcc   2280

ctgctggagg tgggcatcgc catggcccag gtggacccga ggcacacctc ccagatcgcc   2340

ccgaccggcg ccttcggctt cagggaccac gccttcctgt actaccagga cgacggcctg   2400

tgcaggatcg acgccaacac caacgcctcc atgaggatcg ccgagaggtt cttcatgagg   2460

cactccgtgc tgacccagct gagggccgcc aagatcggcg agaccgagta cctgatcccg   2520

gagtccgcct ccaagaggct gaacgccttc gtgaagctgc agaccggcaa gccgttcgcc   2580

aagctgatca tgaactgctc cggcttcgtg ctggagggcc tgaccaagaa gcagtacgcc   2640

aagctggccg agaccgccgg caagaaggag tccttctacc agtacgacga caggtggttc   2700

gacaagggcc accacttcgc ctgcagggcc accctggaga acaaggtgca ggtgtgcctg   2760

aacggcggcg gcaggatcaa ggacaccacc ccggacttca acccgaagtc cctgctgagg   2820

tccgacctgc agaccccgct ggaccagctg ttcggcaact ccggcgcctg a            2871
```

```
<210> SEQ ID NO 35
<211> LENGTH: 2841
<212> TYPE: DNA
<213> ORGANISM: artificial sequence
<220> FEATURE:
<223> OTHER INFORMATION: Cas12j.17 encoding nucleic acid sequence

<400> SEQUENCE: 35
```

```
atgtccaaca ccacctacaa gacctcccac ctgctgatcg acctgccgca gcaggagctg     60

atcgacctgc acagggactc caacgagatg ggctcctacc tgaccaagtt cttcctggcc    120

gccctgggca ggccggtgga caactccatc gtgctgccgc cggagctggc cgacctgtac    180

ttccagttcg ccaacggcat cctgccggtg gacaagggcc cgggctccga cgacccgtcc    240

tggctgcact ccgagaactg ctactccatg ttcttcgaga aggactccat gtccggcaac    300

tgcaccaaca agatcaagca gtaccaggag ctgaagaccg ccctgtgcgg ccagaaggtg    360

aagggccaga agggcctggt gggcaagaag acctgggccc agctgaagaa ggtgctgacc    420

gccctgccgc agaagtacca gatcctgtcc ccgaagatct gccagaagta cttcaagtcc    480

ggcaacctgg agggcttcgg caagctggcc ctggccggca agaacaggcc gtccatgtcc    540

gccggcctgc agctgaggga gctgggcctg ctgccgctgg actccagggg catcgacaag    600

aacaagctgc tgggcatcct ggtgggcatc accggcaggc tgaagtcctg gagggacagg    660

gactgggcct gcaagaccgt gaaggaggag ctgagggtga ccttcgagaa gggcctgggc    720

gaggtggacc cgaccgccta cccgcagttc aagcagttcg ccgaccagct gttcaagcag    780

gagggctaca agatctccgg cagggtgctg agggccgtgg agggcaagga cgccgactac    840

cagccggtgc tgtccctgct gacccagtac ccggacctgc agggcgactt cgaggagctg    900

ggcagggtgt acctggccga ggccgagtac ctgaggaaga aggtggacgc cagggtgacc    960

gtgtgcgacg ccgagacctc cccgctgcag ttcccgttcg gcctgaccgg caacggctac   1020

tccatcaccc tgaccgtggt gaagggccag atcgccgcca ccctgcacct gccgggcggc   1080

gacatcaccc cgaggctgag gaggtccaag tacttccaga acccggagat cgccccggtg   1140

aaggacggca agggcaaggt gaacggcttc cagatctcct tcaagagggg caagaccccg   1200

ctggtgggca tcatcaagga gccgaagctg ctgaagaaga acggcaacta ctacctgtcc   1260

ctggccgtgg gcatcaacaa gaccgagatc ccgaaggaga tctgcgacgc cagggcctac   1320
```

```
tactcctcca cctccaggac cgacaccccg ccggccgtga aggccatgtc catcgacctg   1380
ggcgtgacca ccctggccga ctactccatc atcgacaccg gcctgccggg cgactgcggc   1440
gtgttcggcg gctccaccgc cgccttcacc gagcacggca agatcggcag gtgcggctcc   1500
aagtccctga gggacggcct gtacaagaac accgaggccg gctacttcct ggccaagtac   1560
atcaggctgt ccaagaacct gaggggcggc gtgggcctga acaagctgga gaaggagaag   1620
ctgctggagc acgtggagag gctgggcatc gagcactgcg ccgacgactt cgccaggaag   1680
gacgagatcc acaggaagtt ctccgagatc aagtccaagc tggagaagtc catctccgag   1740
ttcgccctga gggacaggcc ggacaagaag ggcgcctcct gggagggcat ctgcgccgag   1800
accgtgcagg tgctgggcgc cgtgaagagg tggcagtccc tggccaagtc ctggacctac   1860
tactcctgga ccgccgagga ctacgtgctg gccctgaccg gcgagggcag gaccagggtg   1920
tccgacgagc acgtggagtc cgtggtgaag accggcagga ggcagttcgc cccgtgcggc   1980
aaggccgccc tgctgaggct gctggagaag ggcaagatcg tggaggtgtg cccgggccag   2040
ttccagctgg ccgagggcgt ggactacaag aggcacccga ccgagttcct ggccgcccac   2100
atcaggcact tcaacggcct gaggagggac ctgaccaaca agctggtgag ggccatcgtg   2160
gagaaggccc agcagcacag ggtgcagatc gtgatcgtgg aggacttcgg catcccggac   2220
atcgagggca ggatcatgga ccactacgac aactacaggt ggaacctgtt cgccccggcc   2280
aaggtgatcg agaagctgga ggaggccctg tccgaggtgg gcatcgccat ggccgaggtg   2340
gacccgaggc acacctccca gctggccccg accggcgact tcggcttcag ggaccacgag   2400
aacctgtact tctgggagaa gggcctgtgc aggaccgacg ccaacaccaa cgcctccatg   2460
aggatcgccg agaggttctt caccaggcac tccgtgctgt cccagctgag ggccgtgaag   2520
atctccgaga ccgagttcct gatcccggtg tccaccggca agagggagaa cgccttcatc   2580
aagtcccaga ccggcaagct gttcgccaag ctggtggccg actccaacgg cttcgtgatg   2640
gtgggcctga ccgagaagca gcacggcgcc accgtgaccg tgggcaagaa ggtgtccttc   2700
tacaaccacg ccggcaggtg gctgggcaag gcccaccaca tcgcccacag ggacaggatc   2760
aagaacgagg tgaaccaggt gctgacctcc ggcaggggca ggatcaggaa catcgccccg   2820
gagctgtccc cgaagacctg a                                             2841
```

<210> SEQ ID NO 36
<211> LENGTH: 2793
<212> TYPE: DNA
<213> ORGANISM: artificial sequence
<220> FEATURE:
<223> OTHER INFORMATION: Cas12j.18 encoding nucleic acid sequence

<400> SEQUENCE: 36

```
atgaccaacc agaagccgaa gttcaagtcc tccgacatcc agatcaagca catctccccg     60
accgacaaga agaggctgaa gaccttctac caccagctgt acgagcaggt gaacttcatc    120
ctggagagga tgatcgtgat gaggggcagg ccgaggacca tcaggaacat cgacggcacc    180
gagatcttcg tgtcccagga ggaggccgac cagcagctgc tgtccctggc cggcggctcc    240
cacgagggcg tgaagtacct gaagcagtac tacgagtcct gcgtggacgc cggcaagccg    300
gccaagtacg ccgccaacat gttcctgacc aagaccatct ccggcaccaa cccgctgcag    360
tgccacaccg ccgtgtacaa gctgtacaag aaggtgcagg ccaagcagat caccaagaag    420
gagttcatcg acaagctgta ctccaagacc aagaagaaga agtccctgaa gccggcctac    480
```

-continued

```
aaggtgttca ccgagaacga gcacatcgag ttctaccaca aggtgaggtc cggcaagctg    540
ccggcctccg aggtgaggct ggaggagtcc aggagggccc cggacgtggg cctggaggtg    600
ggcctgctgc tgagggagct gggcatcttc ccgttcaact tcccgcactt caccgagaag    660
aagtacctgg acctggcctg gaccatcgcc atcaggtggc tgaagaactg gaacgagaac    720
aacaagaaca ccgccaagga gaaggccaag cagaaggcca tcgtggacaa gctgaggacc    780
tccctggacc agaaggaggt ggacctgttc gaggagttcg ccgaggagtg ctcccaggag    840
cagttcggca tcagggaggg cttcgtgaag gccaagaaga ggctgaagtc cttcccgaag    900
ggcatcgaga agtcctccta caaggagggc atgaggatcc tggtgcagaa caagcacggc    960
tccatctggg acaacttcga gaacctggcc taccaccaca tcgccctgaa cgagtacaac   1020
aggctgaggg acgaggcctc cttctccttc ccggacccga tctaccaccc gatcagggcc   1080
gagttcggcc tgacctccct gccgaagttc aacgtgggcc tgaacgacag gggcaactac   1140
gagttcacca tcaacctgcc ggacggcccg ctgatgatgc tgggcaagaa gtccaggtac   1200
tacctgaagc cgatcatcca gggcccgctg aacaacgcct tctccttcga gttcatcaag   1260
ggcaacaaga agaggccgaa gatctccgcc aagctgaagt ccatcaccgt ggtgttcgcc   1320
aagtcctcca tctacgtggg cctgccgtac aggccgatct ccatcccgat cccgcaggcc   1380
gtgaccaact ccacctacta cttcaagaag aacctgtcct ccacctccaa gttcgacaag   1440
gacgtgttca tgggcctgac cgccgtgtcc gtggacctgg gcctgaaccc ggtgttctcc   1500
atgtccgcct gcaggctgga cgagatgaag gccgacgagc actactcctg cgaggtgccg   1560
ggcttcggct gggccaacca gatctggtcc aagagggccg gcggcgtgtg gaacaggtcc   1620
ttcagggaca agatcagggg cttcgtgccg ggcaacctgt ccgacaggat cttctgctgc   1680
aagaagtcca tcatcgtgtc caagaagctg agggacgaga agccgctgac ccagtacgag   1740
gaggagaact tcgagaggtg gatgcaggtg gtgggcgtgg acccgaacga ggaccactac   1800
aagcagctga ggatcgccat cagggacatc aagaccgagt acgagaccgt gaggtccgag   1860
ttcgccctga gggaccaccc gaacaactcc aacaagacca ccgagaacat ctgcaccgag   1920
tgcttcgaca tgctgttcgt gatcaagaac ctgatctccc tgctgaagtc ctggaacagg   1980
tggcacagga ccaccggcga catcgaggag aggggcaagg acccgaacga gtgctccacc   2040
tactggaggc actacaacgg cctgaagacc gacctgctga agaagctgac caacatcctg   2100
atcgagtccg ccaagtccat cggcgcccac atcatcatcc tggaggacct gaccctgtcc   2160
cagaggtcct ccaggtccag gagggagaac tccctggtgg ccatcttcgg cgcccagacc   2220
atcatcaaga ccatctccga ggaggccgag atcaacggca tcctggtgta cctggaggac   2280
ccgaggcact cctcccagat ctccatcgtg accaacgagt tcggctacag gccgaaggag   2340
gacaaggcca agctgtactt catggacgag gagaccgtgt gcgtgaccaa ctgcgacgac   2400
tccgccgccc tgatgctgca gcagtccttc tggtccaggc acaaggacgt ggtgaaggtg   2460
aagggcacca aggtgtccga caccgagtac ctggtgtcct ccgaggacaa ggacggcacc   2520
aagatgaggc tgaggtccta cctgaagagg aacgtgggca ccgccaacgc catcctgcag   2580
aagaactgcg acggctacga cctgaagaag atctccccgc agaagaagaa gaagatcgag   2640
gagttcggca aggacgagta cttctacagg cacggcgagc agtggttcac cgccgacgcc   2700
cacttcgaca agctgaggga gttcggcaac caggtgttcc tgaccccgca gtcccagatc   2760
aagaggatca acctgcaggt ggagggcacc tga                                2793
```

<210> SEQ ID NO 37
<211> LENGTH: 2727
<212> TYPE: DNA
<213> ORGANISM: artificial sequence
<220> FEATURE:
<223> OTHER INFORMATION: Cas12j.19 encoding nucleic acid sequence

<400> SEQUENCE: 37
atgccgtcct acaagtcctc cagggtgctg gtgagggacg tgccggagga gctggtggac 60
cactacgaga ggtcccacag ggtggccgcc ttcttcatga ggctgctgct ggccatgagg 120
agggagccgt actccctgag gatgagggac ggcaccgaga gggaggtgga cctggacgag 180
accgacgact tcctgaggtc cgccggctgc gaggagccgg acgccgtgtc cgacgacctg 240
aggtccttcg ccctggccgt gctgcaccag gacaacccga agaagagggc cttcctggag 300
tccgagaact gcgtgtccat cctgtgcctg gagaagtccg cctccggcac caggtactac 360
aagaggccgg gctaccagct gctgaagaag gccatcgagg aggagtgggg ctgggacaag 420
ttcgaggcct ccctgctgga cgagaggacc ggcgaggtgg ccgagaagtt cgccgccctg 480
tccatggagg actggaggag gttcttcgcc gccagggacc cggacgacct gggcagggag 540
ctgctgaaga ccgacaccag ggagggcatg gccgccgccc tgaggctgag ggagaggggc 600
gtgttcccgg tgtccgtgcc ggagcacctg gacctggact ccctgaaggc cgccatggcc 660
tccgccgccg agaggctgaa gtcctggctg gcctgcaacc agagggccgt ggacgagaag 720
tccgagctga ggaagaggtt cgaggaggcc ctggacggcg tggacccgga gaagtacgcc 780
ctgttcgaga agttcgccgc cgagctgcag caggccgact acaacgtgac caagaagctg 840
gtgctggccg tgtccgccaa gttcccggcc accgagccgt ccgagttcaa gaggggcgtg 900
gagatcctga aggaggacgg ctacaagccg ctgtgggagg acttcaggga gctgggcttc 960
gtgtacctgg ccgagaggaa gtgggagagg aggaggggcg gcgccgccgt gaccctgtgc 1020
gacgccgacg actccccgat caaggtgagg ttcggcctga ccggcagggg caggaagttc 1080
gtgctgtccg ccgccggctc caggttcctg atcaccgtga agctgccgtg cggcgacgtg 1140
ggcctgaccg ccgtgccgtc caggtacttc tggaacccgt ccgtgggcag gaccacctcc 1200
aactccttca ggatcgagtt caccaagagg accaccgaga acaggaggta cgtgggcgag 1260
gtgaaggaga tcggcctggt gaggcagagg ggcaggtact acttcttcat cgactacaac 1320
ttcgacccgg aggaggtgtc cgacgagacc aaggtgggca gggccttctt cagggccccg 1380
ctgaacgagt ccaggccgaa gccgaaggac aagctgaccg tgatgggcat cgacctgggc 1440
atcaacccgg ccttcgcctt cgccgtgtgc accctgggcg agtgccagga cggcatcagg 1500
tccccggtgg ccaagatgga ggacgtgtcc ttcgactcca ccggcctgag gggcggcatc 1560
ggctcccaga agctgcacag ggagatgcac aacctgtccg acaggtgctt ctacggcgcc 1620
aggtacatca ggctgtccaa gaagctgagg gacaggggcg ccctgaacga catcgaggcc 1680
aggctgctgg aggagaagta catcccgggc ttcaggatcg tgcacatcga ggacgccgac 1740
gagaggagga ggaccgtggg caggaccgtg aaggagatca agcaggagta caagaggatc 1800
aggcaccagt tctacctgag gtaccacacc tccaagaggg acaggaccga gctgatctcc 1860
gccgagtact tcaggatgct gttcctggtg aagaacctga ggaacctgct gaagtcctgg 1920
aacaggtacc actggaccac cggcgacagg gagaggaggg gcggcaaccc ggacgagctg 1980
aagtcctacg tgaggtacta caacaacctg aggatggaca ccctgaagaa gctgacctgc 2040
gccatcgtga ggaccgccaa ggagcacggc gccaccctgg tggccatgga gaacatccag 2100
agggtggaca gggacgacga ggtgaagagg aggaaggaga actccctgct gtccctgtgg 2160
gccccgggca tggtgctgga gagggtggag caggagctga agaacgaggg catcctggcc 2220
tgggaggtgg acccgaggca cacctcccag acctcctgca tcaccgacga gttcggctac 2280
aggtccctgg tggccaagga caccttctac ttcgagcagg acaggaagat ccacaggatc 2340
gacgccgacg tgaacgccgc catcaacatc gccaggaggt tcctgaccag gtacaggtcc 2400
ctgacccagc tgtgggcctc cctgctggac gacggcaggt acctggtgaa cgtgaccagg 2460
cagcacgaga gggcctacct ggagctgcag accggcgccc cggccgccac cctgaacccg 2520
accgccgagg cctcctacga gctggtgggc ctgtccccgg aggaggagga gctggcccag 2580
accaggatca agaggaagaa gagggagccg ttctacaggc acgagggcgt gtggctgacc 2640
agggagaagc acagggagca ggtgcacgag ctgaggaacc aggtgctggc cctgggcaac 2700
gccaagatcc cggagatcag gacctga 2727

<210> SEQ ID NO 38
<211> LENGTH: 2466
<212> TYPE: DNA
<213> ORGANISM: artificial sequence
<220> FEATURE:
<223> OTHER INFORMATION: Cas12j.20 encoding nucleic acid sequence

<400> SEQUENCE: 38
atggccttcc agtccaagag gaggatcgtg ggcaacttcg tgaaggagca gtgcctgaag 60
gccgtggacg gcaaggtgat cctgaccgac caggagaaga gggagctgat caagaggtac 120
gagctgcacc tggagccgca caagtggctg ctgaggctgt tcctgtccgg ctacgagggc 180
agggacgacg gcttctacga ggagctgggc aacaccaacc tggacaagga gaagttcttc 240
gaggtgaccg ccggcctgag ggacgccctg ctgaggcagt ccggctcctc cagggccctg 300
aagtcctcca tgctgggcaa gtgcccgccg tccgccgccg tgggcaaggc cgccaagcac 360
atccagaccc tgagggacgc cggcatcctg ccgttcaaga ccggcctgac ctccggcgag 420
gactacaacg tgctgcagca ggccgtgcag cagctgaggt cctgggtggc ctgcgaccac 480
aggaccaggg aggcctacgc cgagcagcag gagaagacct cccaggccga ggaggccgcc 540
aagaaggccg ccaacgaggt gaagccggag gacgccaagt ccctggagag gcacgagagg 600
gtgctgacca agctgaggaa gcaggagagg aggctggaga ggatgaagtc ccacgcccag 660
ttctccctgg acgagatgga ctgcaccggc tactccctgt gcatgggcgc caactacctg 720
aaggactact gcctggagaa ggagggcagg ggcctgaggc tgaccctgaa gaactccacc 780
atggccggct cctactacgt gtccgtgggc gacggccagc acgccggcat gaagaacccg 840
ggcaccccgg ccggcggctc ccggagaag ggcaggagga ggaacatcct gttcgacttc 900
accgtggaga agtgcggcga caactacctg ttcaggtacg acgagaacgg caagaggccg 960
agggccggcg tggtgaagga gccgaggttc tgctggagga ggaagggcaa ctccgtggag 1020
ctgtacctgg ccatgccgat caacatcgag aactccatga ggaacatctt cgtgggcaag 1080
cagaagtccg gcaagcactc cgccttcacc aggcagtggc cgaaggaggt ggagggcctg 1140
gacgagctga gggacgccgt ggtgctgggc gtggacatcg gcatcaacag ggccgccttc 1200
tgcgccgccc tgaagacctc caggttcgag aacggcctgc cggccgacgt gcaggtgatg 1260
gacaccacct gcgacgccct gaccgagaag ggccaggagt acaggcagct gaggaaggac 1320
gccacctgcc tggcctggct gatcaggacc accaggaggt tcaaggccga cccgggcaac 1380
aagcacaacc agatcaagga gaaggacgtg gagaggttcg actccgccga cggcgcctac 1440

```
aggaggtaca tggacgccat cgccgagatg ccgtccgacc cgctgcaggt gtgggaggcc   1500

gccaggatca ccggctacgg cgagtgggcc aaggagatct tcgccaggtt caaccactac   1560

aagcacgagc acgcctgctg cgccgtgtcc ctgtccctgt ccgacaggct ggtgtggtgc   1620

aggctgatcg acaggatcct gtccctgaag aagtgcctgc acttcggcgg ctacgagtcc   1680

aagcacagga agggcttctg caagtccctg tacaggctga ggcacaacgc caggaacgac   1740

gtgaggaaga agctggccag gttcatcgtg gacgccgccg tggacgccgg cgcctccgtg   1800

atcgccatgg agaagctgcc gtcctccggc ggcaagcagt ccaaggacga caacaggatc   1860

tgggacctga tggccccgaa caccctggcc accaccgtgt gcctgatggc caaggtggag   1920

ggcatcggct tcgtgcaggt ggacccggag ttcacctccc agtgggtgtt cgagcagagg   1980

gtgatcggcg acagggaggg caggatcgtg tcctgcctgg acgccgaggg cgtgaggagg   2040

gactacgacg ccgacgagaa cgccgccaag aacatcgcct ggctggccct gaccagggag   2100

gccgagccgt tctgcatggc cttcgagaag aggaacggcg tggtggagcc gaagggcctg   2160

aggttcgaca tcccggagga gccgaccagg gagcaggacg agtccgacca ggacttcaag   2220

aagaggctgg aggagaggga caagctgatc gagaggctgc aggccaaggc cgacaggatg   2280

caggccatcg tgcagaggct gttcggcgac aggaggccgt gggacgcctt cgccgacagg   2340

atcccggagg gcaagtccaa gaggctgttc aggcacaggg acggcctggt gctgaacaag   2400

ccgttcaagg gcctgtgcgg ctccgagaac tccgagcaga aggcctccgc caggaactcc   2460

aggtga                                                              2466
```

<210> SEQ ID NO 39
<211> LENGTH: 2514
<212> TYPE: DNA
<213> ORGANISM: artificial sequence
<220> FEATURE:
<223> OTHER INFORMATION: Cas12j.21 encoding nucleic acid sequence

<400> SEQUENCE: 39

```
atgggcaggt tcggcaagaa gaagatcgcc gtgaacggct acgtggagca ggactgcatc     60

aagaccatct ccgccaagtg cctgctgacc agggcccaga tcgacgagct gagggccaag    120

tacgacgccg tgctggacac catgaggccg ctgatcaggc tgatcctggc cggctacgag    180

ggcagggacg acggcatcta cgaggagatc gccccggaga tgtccaagaa gaagttcttc    240

gaggccgcca ccgagtggag ggagtccatc gtgaagaacg cctccccgag ggccatgaag    300

gcctccgtgt tcggcgacaa ggagccgtgc aagtccaccg gcggcgccag ggccgtgatc    360

ggcaagctga ggaagtccgg cgtgttcccg atcgagaccg gcctgtccgg cggcgacgag    420

tacaacctga tcgagcaggc catcgagtac gccaagtcct ggctgaagtc cgacgaggcc    480

accagggagg cctacgccga ccagcagaag gacatcaaga ggctgatcgg cgaggccaag    540

aagctggccc tgaagatcga gaaggccgag aagaagctgg aggccaccaa cccgcagacc    600

aagtcctgga agaagaccac cgagatcatc aagaagtcca agagggagtt cggctccgtg    660

accaccaaga ccgagaaggc cgagaagagg ttcgagagga tgaagccgtt ctccaagctg    720

gagctgcaga acatggactg caccaagtac tccacctacc tgggcaccaa ctactccccg    780

ttcaagctga agaaggaggg cgacctgctg cagatcaccg tgacctcctc cgtgatgaag    840

ggcacctacc tggcctccta cggcgacggc cagtacggct ccaggaggaa caacggccag    900

tccaggaggg acgacttcgt gccgaacatg aaccagaaga ggaggaggaa cctgatgttc    960
```

```
gactgcaccg tggagccgtt cggcgacggc tccctgctga ggtacgagga gaacggcctg   1020
aggccgaggg tggccgagct gaaggagccg aggctgtgct ggaggaggag gaacggcaac   1080
tacgagctgt acctgatgat gccggtgaag atgcacgtga agtccccgga gatgttcgcc   1140
ggcgaccacc tggccttctc caggtactgg ccgaaggagg tggagggcct ggactccgac   1200
accaagatca ccgccctggg cgtggacgtg ggcatcatca ggtccgccta ctgcgtggcc   1260
gtgaccgccg agaggttcgt ggacggcctg ccgaccgaga tgaccgtggg caaggcctcc   1320
ttcgacgccc agaccgagaa gggcagggag tacttcgagc tgggcaggag ggccaccatg   1380
ctgggctggc tgatcaagac caccaggagg tacaagaagg acccgaagaa cgagcacaac   1440
cagatcaagg agtccgacgt ggccgccttc gacggctccc cgggcgcctt cgagcactac   1500
atcctggccg tggacgagat gtccgacgac ccgctggacg tgtggggcca cgccaacatc   1560
accggctacg gcaagtggac caagcagatc ttcaaggagt tcaaccagct gaagagggag   1620
agggccgagg gccaggtgga gccgaacatg accgacgacc tgacctggtg ctccctgatc   1680
gactacatca tctccctgaa gaagaccctg cacttcggcg gctacgagac caaggagagg   1740
gagtccttct gcccggccct gtacaacgag agggccaact gcagggacgt ggtgaggaag   1800
aggctggcca ggtacgtggt ggagagggcc atcgccgccg aggcccaggt gatctccgtg   1860
gagaacctgt ccaagtgcag gagggacgac aagaggaaga acagggtgtg ggacctgatg   1920
tcccagcagt cctggatcgg cgtgctgacc aacatggcca ggatggagaa catcgccgtg   1980
gtgtccgtga acccggacct gacctcccag tgggtggagc agtgcggcgc catcggcgac   2040
aggaaggcca ggaccatcgc ctgcagggac gtgaacggca agttcgtgtc cctggacgcc   2100
gacctgaacg ccgcctacaa catcgcctcc agggccctga ccaggcacgc cgagccgttc   2160
tccatcacct tcaagaagaa ggacggcatc ctggagcaga aggacgtgtg cttcgacccg   2220
ggcgtgatcc cggtgctgga gaagaacgag aacgaggaga agttcaggga gagggtggag   2280
aagtacgaga agtccctggt gatcaagcag gagagggccg tgaggtggag ggccatcctg   2340
cagcacctgt tcggcaacga gaggccgtgg gacgagttca ccgacgaggt gaaggagggc   2400
aggcacgtgt ccctgtacag gcaccacggc aagctggtga ggaccaagca gtacgccggc   2460
ctggtgaagg aggccaacaa cgagctggtg ccggtgtgcg ccgtggccag gtga         2514
```

<210> SEQ ID NO 40
<211> LENGTH: 2907
<212> TYPE: DNA
<213> ORGANISM: artificial sequence
<220> FEATURE:
<223> OTHER INFORMATION: Cas12j.22 encoding nucleic acid sequence

<400> SEQUENCE: 40

```
atgtccaagg ccaccaggaa gaccaagacc accgtgccgg agtccaccga caccgagtcc     60
ccggccgccg acacccaggt gagggtgcac tggctggccg cctcccacag ggcctccccg    120
ggcctgcagc aggtgaagga gatgatccag cagcacgccg acgtggcctc cgtgctgttc    180
cagggcctgg tgaggaccgc cccgatcgtg ttcaggaacg acgacggctc cccggtgaag    240
ccgctggacc tgctgctggc ctccctgagg ccgacctaca aggtgcagag ggacaccgag    300
accgtgctgg tgaccaagga cgacgtgatc aggtgcctga ccctggccac caccgccgtg    360
aacggcggcc aggccaccaa cgtggccgtg ttcgcctccg ccgacccggc cctgtccgcc    420
ccgctggcca ccctgctggc ccagctgagg gccctggagt ccgtggactc ctcctggtcc    480
gtggtgggca agctggacat caacctgagg aagttcgtgt ggctggtgct gtccgccgcc    540
```

```
ggcgtgctgc cggccctggc cgacctggag ggctacgccg ccaagtccgt gctggccaac    600
gtgcagggca agtacaagtc cctgcaggcc tgcgccgaca cccacgccgc cctgtacaag    660
cagcaccaga ccaacaagga gcagctggag aagctgatcg ccgacccggg cttcgtggcc    720
ctgtgctccg ccctgctgca ggacccggac ctgaggtccg tggactccag gaggctggcc    780
gccctggagg agatgctggg cttcgtggcc gccgacaaga actactccga gtacacctcc    840
accaggaagt gcgacggctg ggccccgccg gccaacatgt tcgacctgct gtgcgagcac    900
aaggaggccg tgaggaggaa catcgtggtg gacaactcca agtgcctgtc caggaggatc    960
tccctggtgg ccgacggcga cgtgaacgag gtgtccgtgt tcgagctgct gaacgagatg   1020
aggtggctgt ccgtgcactc ctccggcatc aggatgccga actacccgaa gcacgcctac   1080
gccctgaagt tcggcgacaa ctacatctcc gtgaagtcct tcgagaccgt ggtggacggc   1140
ggctgctccc tgctgaggat gaccgccagg gtgggcaaga acgacctggt gtgcgacttc   1200
gtgctgggca ggggcaacga gtactggaac aacctgaaga tcaccccgat gggcaagggc   1260
atcttcgccg tggtgaagac cgtgaggagg ttcaccgcca ccggcgccaa gctggtggag   1320
ctgaggggcg tgtgcaagga gccggagatc aggtacgaga ggggcgtgct gggcctgagg   1380
ctgccgatct ccttcgacgt gtacggcaag gtggaggagg actccatcgc cttcggcaag   1440
aacagggtgt ccctgaggac caccccgttc gtggagaagg ccgacaagtt ccagggcctg   1500
ctggactaca ggaacaccac cgccagggac ggctacatct actacgccgg cttcgaccag   1560
ggcgagaacg accaggtggt gggcatctac aggaccagga cctacaagaa cgccaccatg   1620
ctggagttct tcaacgtgtc cgacaccctg gaggaggtgg cctcctgcag gttctccgac   1680
taccaggaga ggaagaggag gctgaggggc gacaccggcg tgctggacat caactccatc   1740
aacgtgctgg ccgacaaggt gcagaggctg aggaggctga tctccaccct gagggcctgc   1800
gcctcccaca ccgactggta cccgaagctg aaggagagga ggaggctgga gtgggccgtg   1860
ctggcccagg gcgtgggcgt gtccgacttc gacaccgaga tcgagagggc cgagaccgcc   1920
ctgtccgccg tggccgccgt ggacttcgtg agggacccga cctgcatcat caacgtgatg   1980
gacaagcaca tctacgccca gttcaagcag ctgaggtccg agaggaacga gaagtacagg   2040
tcccagcacc agcacgacta caagtggctg cagctggtgg actccgtgat ctccctgagg   2100
aagtccatct acaggttcgg caaggccccg gagccgaggg gcgccggcga gctgtacccg   2160
cagaacctgt acacctacag ggacaacctg atgcagcagt acaggaagga ggtggccgcc   2220
ttcatcaggg acgtgtgcct ggagcacggc gtgaggcagc tggccgtgga ggccctgaac   2280
ccgacctcct acatcggcga ggactccgac gccaacagga agagggccct gttcgccccg   2340
tccgagctgc acaacgacat cgtgctggcc tgctccctgc actccatcgc cgtggtggcc   2400
gtggacgaga ccatgacctc cagggtggcc ccgaacaaca ggctgggctt caggtcccac   2460
ggcgactacc agaagttctc cgagaccgcc cagggcaggt tcaactggaa gcacctgcac   2520
tacttcggcg acaacgacgt gtccgagcac tgcgacgccg acgagaacgc ctgcaggaac   2580
atcgtgctga gggccctgac ctgcggcgcc tccaagccga ggttctccag gcagtccctg   2640
ctgggcaaga tcaagggccc ggtgctgagg acccagctgg cctacctggc ccacaagagg   2700
ggcctgctga ccgcctccac cgagccgaag aaggccgccg agaccggctt cgagctggtg   2760
gaggccgacc tgggcggcgc cctgagggtg ggcaagggct tcatctacgt ggacgccggc   2820
atctgcatca acgccaccac caggaaggag aggtcccaca aggtgggcga ggccgtggtg   2880
```

```
tccaggtccc tggcctcccc gttctga                                    2907


<210> SEQ ID NO 41
<211> LENGTH: 36
<212> TYPE: RNA
<213> ORGANISM: artificial sequence
<220> FEATURE:
<223> OTHER INFORMATION: Cas12j.3 prototype
      direct repeat

<400> SEQUENCE: 41

ggugauauag uaacuggucu guuccagcac uucacc                            36


<210> SEQ ID NO 42
<211> LENGTH: 36
<212> TYPE: RNA
<213> ORGANISM: artificial sequence
<220> FEATURE:
<223> OTHER INFORMATION: Cas12j.4 prototype direct repeat

<400> SEQUENCE: 42

gugucaaugc gaugcugaac aucgcaugag uaacac                            36


<210> SEQ ID NO 43
<211> LENGTH: 36
<212> TYPE: RNA
<213> ORGANISM: artificial sequence
<220> FEATURE:
<223> OTHER INFORMATION: Cas12j.5 prototype direct repeat

<400> SEQUENCE: 43

gugcuggccg cucucgcuag agggagguca gagcac                            36


<210> SEQ ID NO 44
<211> LENGTH: 37
<212> TYPE: RNA
<213> ORGANISM: artificial sequence
<220> FEATURE:
<223> OTHER INFORMATION: Cas12j.6 prototype direct repeat

<400> SEQUENCE: 44

guugcaaucu aguagagaaa cuacagguaa uugcaac                           37


<210> SEQ ID NO 45
<211> LENGTH: 37
<212> TYPE: RNA
<213> ORGANISM: artificial sequence
<220> FEATURE:
<223> OTHER INFORMATION: Cas12j.7 prototype direct repeat

<400> SEQUENCE: 45

auuacaaccu acugaugaua caguagguga uuguaac                           37


<210> SEQ ID NO 46
<211> LENGTH: 36
<212> TYPE: RNA
<213> ORGANISM: artificial sequence
<220> FEATURE:
<223> OTHER INFORMATION: Cas12j.8 prototype direct repeat

<400> SEQUENCE: 46

gugcaauuaa guagaaauac ugcuagugau ugcaac                            36


<210> SEQ ID NO 47
<211> LENGTH: 37
<212> TYPE: RNA
```

<213> ORGANISM: artificial sequence
<220> FEATURE:
<223> OTHER INFORMATION: Cas12j.9 prototype direct repeat

<400> SEQUENCE: 47
ggugcaauca ucuggaaaua ccagagauaa uugcaac 37

<210> SEQ ID NO 48
<211> LENGTH: 36
<212> TYPE: RNA
<213> ORGANISM: artificial sequence
<220> FEATURE:
<223> OTHER INFORMATION: Cas12j.10 prototype direct repeat

<400> SEQUENCE: 48
gguacaggcu caagaaaaac uugagccaaa ugugac 36

<210> SEQ ID NO 49
<211> LENGTH: 36
<212> TYPE: RNA
<213> ORGANISM: artificial sequence
<220> FEATURE:
<223> OTHER INFORMATION: Cas12j.11 prototype direct repeat

<400> SEQUENCE: 49
guuguaauac auuauguuaa aguaauguua uacaac 36

<210> SEQ ID NO 50
<211> LENGTH: 37
<212> TYPE: RNA
<213> ORGANISM: artificial sequence
<220> FEATURE:
<223> OTHER INFORMATION: Cas12j.12 prototype direct repeat

<400> SEQUENCE: 50
gagguagugu ggaaguccag cagggcuucg uugacac 37

<210> SEQ ID NO 51
<211> LENGTH: 36
<212> TYPE: RNA
<213> ORGANISM: artificial sequence
<220> FEATURE:
<223> OTHER INFORMATION: Cas12j.13 prototype direct repeat

<400> SEQUENCE: 51
cuaucagugu aaaacccauc gaggguuuau cuacac 36

<210> SEQ ID NO 52
<211> LENGTH: 36
<212> TYPE: RNA
<213> ORGANISM: artificial sequence
<220> FEATURE:
<223> OTHER INFORMATION: Cas12j.14 prototype direct repeat

<400> SEQUENCE: 52
auaucagugu ggguccgcaa aacggaucaa ugacac 36

<210> SEQ ID NO 53
<211> LENGTH: 37
<212> TYPE: RNA
<213> ORGANISM: artificial sequence
<220> FEATURE:
<223> OTHER INFORMATION: Cas12j.15 prototype direct repeat

<400> SEQUENCE: 53
gugcagccua uugggaucgc ccauaggcau gagacac 37

<210> SEQ ID NO 54
<211> LENGTH: 36
<212> TYPE: RNA
<213> ORGANISM: artificial sequence
<220> FEATURE:
<223> OTHER INFORMATION: Cas12j.16 prototype direct repeat

<400> SEQUENCE: 54
gugccgucac cgccuuaguu gagcggggguc aagcac 36

<210> SEQ ID NO 55
<211> LENGTH: 37
<212> TYPE: RNA
<213> ORGANISM: artificial sequence
<220> FEATURE:
<223> OTHER INFORMATION: Cas12j.17 prototype direct repeat

<400> SEQUENCE: 55
gugccaaccu caccggagac gaguggggca ccagcac 37

<210> SEQ ID NO 56
<211> LENGTH: 36
<212> TYPE: RNA
<213> ORGANISM: artificial sequence
<220> FEATURE:
<223> OTHER INFORMATION: Cas12j.18 prototype direct repeat

<400> SEQUENCE: 56
gugccgcugg ccuuucgaag aggggccuuu aagcac 36

<210> SEQ ID NO 57
<211> LENGTH: 36
<212> TYPE: RNA
<213> ORGANISM: artificial sequence
<220> FEATURE:
<223> OTHER INFORMATION: Cas12j.19 prototype direct repeat

<400> SEQUENCE: 57
gugcugcugu cucccagacg ggaggcagaa cugcac 36

<210> SEQ ID NO 58
<211> LENGTH: 36
<212> TYPE: RNA
<213> ORGANISM: artificial sequence
<220> FEATURE:
<223> OTHER INFORMATION: Cas12j.20 prototype direct repeat

<400> SEQUENCE: 58
guguaggccu ccucugaaug ggguggcuaa ugacac 36

<210> SEQ ID NO 59
<211> LENGTH: 36
<212> TYPE: RNA
<213> ORGANISM: artificial sequence
<220> FEATURE:
<223> OTHER INFORMATION: Cas12j.21 prototype direct repeat

<400> SEQUENCE: 59
guguugaucc guucugaaug gauggauugc ugacac 36

<210> SEQ ID NO 60
<211> LENGTH: 36
<212> TYPE: RNA
<213> ORGANISM: artificial sequence
<220> FEATURE:

<223> OTHER INFORMATION: Cas12j.22 prototype direct repeat

<400> SEQUENCE: 60
auuucagugc uggccugugg aagcaggcuc ugucac 36

<210> SEQ ID NO 61
<211> LENGTH: 36
<212> TYPE: DNA
<213> ORGANISM: artificial sequence
<220> FEATURE:
<223> OTHER INFORMATION: coding nucleic acid sequence of Cas12j.3 prototype direct repeat

<400> SEQUENCE: 61
ggtgatatag taactggtct gttccagcac ttcacc 36

<210> SEQ ID NO 62
<211> LENGTH: 36
<212> TYPE: DNA
<213> ORGANISM: artificial sequence
<220> FEATURE:
<223> OTHER INFORMATION: coding nucleic acid sequence of Cas12j.4 prototype direct repeat

<400> SEQUENCE: 62
gtgtcaatgc gatgctgaac atcgcatgag taacac 36

<210> SEQ ID NO 63
<211> LENGTH: 36
<212> TYPE: DNA
<213> ORGANISM: artificial sequence
<220> FEATURE:
<223> OTHER INFORMATION: coding nucleic acid sequence of Cas12j.5 prototype direct repeat

<400> SEQUENCE: 63
gtgctggccg ctctcgctag agggaggtca gagcac 36

<210> SEQ ID NO 64
<211> LENGTH: 37
<212> TYPE: DNA
<213> ORGANISM: artificial sequence
<220> FEATURE:
<223> OTHER INFORMATION: coding nucleic acid sequence of Cas12j.6 prototype direct repeat

<400> SEQUENCE: 64
gttgcaatct agtagagaaa ctacaggtaa ttgcaac 37

<210> SEQ ID NO 65
<211> LENGTH: 37
<212> TYPE: DNA
<213> ORGANISM: artificial sequence
<220> FEATURE:
<223> OTHER INFORMATION: coding nucleic acid sequence of Cas12j.7 prototype direct repeat

<400> SEQUENCE: 65
attacaacct actgatgata cagtaggtga ttgtaac 37

<210> SEQ ID NO 66
<211> LENGTH: 36
<212> TYPE: DNA
<213> ORGANISM: artificial sequence
<220> FEATURE:
<223> OTHER INFORMATION: coding nucleic acid sequence of Cas12j.8 prototype direct repeat

<400> SEQUENCE: 66
gtgcaattaa gtagaaatac tgctagtgat tgcaac 36

<210> SEQ ID NO 67
<211> LENGTH: 37
<212> TYPE: DNA
<213> ORGANISM: artificial sequence
<220> FEATURE:
<223> OTHER INFORMATION: coding nucleic acid sequence of Cas12j.9
prototype direct repeat

<400> SEQUENCE: 67
ggtgcaatca tctggaaata ccagagataa ttgcaac 37

<210> SEQ ID NO 68
<211> LENGTH: 36
<212> TYPE: DNA
<213> ORGANISM: artificial sequence
<220> FEATURE:
<223> OTHER INFORMATION: coding nucleic acid sequence of Cas12j.10
prototype direct repeat

<400> SEQUENCE: 68
ggtacaggct caagaaaaac ttgagccaaa tgtgac 36

<210> SEQ ID NO 69
<211> LENGTH: 36
<212> TYPE: DNA
<213> ORGANISM: artificial sequence
<220> FEATURE:
<223> OTHER INFORMATION: coding nucleic acid sequence of Cas12j.11
prototype direct repeat

<400> SEQUENCE: 69
gttgtaatac attatgttaa agtaatgtta tacaac 36

<210> SEQ ID NO 70
<211> LENGTH: 37
<212> TYPE: DNA
<213> ORGANISM: artificial sequence
<220> FEATURE:
<223> OTHER INFORMATION: coding nucleic acid sequence of Cas12j.12
prototype direct repeat

<400> SEQUENCE: 70
gaggtagtgt ggaagtccag cagggcttcg ttgacac 37

<210> SEQ ID NO 71
<211> LENGTH: 36
<212> TYPE: DNA
<213> ORGANISM: artificial sequence
<220> FEATURE:
<223> OTHER INFORMATION: coding nucleic acid sequence of Cas12j.13
prototype direct repeat

<400> SEQUENCE: 71
ctatcagtgt aaaacccatc gagggtttat ctacac 36

<210> SEQ ID NO 72
<211> LENGTH: 36
<212> TYPE: DNA
<213> ORGANISM: artificial sequence
<220> FEATURE:
<223> OTHER INFORMATION: coding nucleic acid sequence of Cas12j.14
prototype direct repeat

<400> SEQUENCE: 72
atatcagtgt gggtccgcaa aacggatcaa tgacac 36

<210> SEQ ID NO 73
<211> LENGTH: 37
<212> TYPE: DNA
<213> ORGANISM: artificial sequence
<220> FEATURE:
<223> OTHER INFORMATION: coding nucleic acid sequence of Cas12j.15
prototype direct repeat

<400> SEQUENCE: 73
gtgcagccta ttgggatcgc ccataggcat gagacac 37

<210> SEQ ID NO 74
<211> LENGTH: 36
<212> TYPE: DNA
<213> ORGANISM: artificial sequence
<220> FEATURE:
<223> OTHER INFORMATION: coding nucleic acid sequence of Cas12j.16
prototype direct repeat

<400> SEQUENCE: 74
gtgccgtcac cgccttagtt gagcggggtc aagcac 36

<210> SEQ ID NO 75
<211> LENGTH: 37
<212> TYPE: DNA
<213> ORGANISM: artificial sequence
<220> FEATURE:
<223> OTHER INFORMATION: coding nucleic acid sequence of Cas12j.17
prototype direct repeat

<400> SEQUENCE: 75
gtgccaacct caccggagac gagtggggca ccagcac 37

<210> SEQ ID NO 76
<211> LENGTH: 36
<212> TYPE: DNA
<213> ORGANISM: artificial sequence
<220> FEATURE:
<223> OTHER INFORMATION: coding nucleic acid sequence of Cas12j.18
prototype direct repeat

<400> SEQUENCE: 76
gtgccgctgg cctttcgaag aggggccttt aagcac 36

<210> SEQ ID NO 77
<211> LENGTH: 36
<212> TYPE: DNA
<213> ORGANISM: artificial sequence
<220> FEATURE:
<223> OTHER INFORMATION: coding nucleic acid sequence of Cas12j.19
prototype direct repeat

<400> SEQUENCE: 77
gtgctgctgt ctcccagacg ggaggcagaa ctgcac 36

<210> SEQ ID NO 78
<211> LENGTH: 36
<212> TYPE: DNA
<213> ORGANISM: artificial sequence
<220> FEATURE:
<223> OTHER INFORMATION: coding nucleic acid sequence of Cas12j.20
prototype direct repeat

<400> SEQUENCE: 78
gtgtaggcct cctctgaatg gggtggctaa tgacac 36

<210> SEQ ID NO 79
<211> LENGTH: 36
<212> TYPE: DNA
<213> ORGANISM: artificial sequence
<220> FEATURE:
<223> OTHER INFORMATION: coding nucleic acid sequence of Cas12j.21 prototype direct repeat

<400> SEQUENCE: 79
gtgttgatcc gttctgaatg gatggattgc tgacac 36

<210> SEQ ID NO 80
<211> LENGTH: 36
<212> TYPE: DNA
<213> ORGANISM: artificial sequence
<220> FEATURE:
<223> OTHER INFORMATION: coding nucleic acid sequence of Cas12j.22 prototype direct repeat

<400> SEQUENCE: 80
atttcagtgc tggcctgtgg aagcaggctc tgtcac 36

<210> SEQ ID NO 81
<211> LENGTH: 11
<212> TYPE: PRT
<213> ORGANISM: artificial sequence
<220> FEATURE:
<223> OTHER INFORMATION: NLS sequence

<400> SEQUENCE: 81

Ser Arg Ala Asp Pro Lys Lys Lys Arg Lys Val
1               5                   10

<210> SEQ ID NO 82
<211> LENGTH: 1014
<212> TYPE: PRT
<213> ORGANISM: artificial sequence
<220> FEATURE:
<223> OTHER INFORMATION: amino acid sequence of Cas12j.3-NLS fusion protein

<400> SEQUENCE: 82

Met Thr Lys Glu Lys Ile Lys Lys Thr Lys Lys Ala Lys Val Glu Lys
1               5                   10                  15

Asp Ser Val Thr Arg Ala Gly Ile Leu Arg Ile Leu Leu Asn Pro Asp
            20                  25                  30

Gln His Gln Glu Leu Asp Thr Leu Ile Ser Asp His Gln Glu Ala Ala
        35                  40                  45

Arg Glu Ile Gln Thr Ala Thr Tyr Lys Leu Ser Gly Leu Lys Leu Tyr
    50                  55                  60

Asp Lys Thr Asn Asn Met Val Val Asp Gly Ser Lys Ala Thr Pro Glu
65                  70                  75                  80

Glu Gln Glu Ala Tyr Tyr Lys Ile Ile Asn Trp Glu Gly Gln Pro Ile
                85                  90                  95

Ser Ile Ser Asn Pro Met Val Arg Ala Thr Phe Lys Ser Ile Ala Lys
            100                 105                 110

Val Lys Glu Asp Ile Arg Arg Lys Gln Glu Glu Tyr Ala Lys Leu Glu
        115                 120                 125

Glu Ala Asp Leu Thr Lys Met Ser Thr Gly Asp Val Lys Lys His Lys
    130                 135                 140

```
Asn Glu Leu Arg Lys Ala Ala Asn Arg Ile Lys His Ser Glu Glu Ile
145                 150                 155                 160

Leu Gln Phe Ala Lys Trp Arg Leu Ala Asp Ile Phe Pro Leu Pro Leu
                165                 170                 175

Ser His Asn Ser Gln Leu His Leu Lys Asn Asn Tyr His Gln Asn Val
            180                 185                 190

Phe Ser Gly Phe His Ala Arg Val Lys Gly Trp Asn Ala Cys Asp Ile
        195                 200                 205

Ala Ala Gln Ala Asn Tyr Ala Glu Ile Asp Asn Arg Leu Thr Glu Leu
    210                 215                 220

Ser Ser Glu Leu Ser Gly Asp Tyr Gly Ser Glu Val Ile Thr Asp Leu
225                 230                 235                 240

Met Gly Leu Leu Gln Tyr Thr Lys Glu Leu Gly Glu Gly Tyr Thr Asp
                245                 250                 255

Thr Ser Tyr Leu Asn Tyr Lys Phe Leu Ser Phe Phe Lys Glu Cys Trp
            260                 265                 270

Arg Pro Asn Ala Ile Ala Asn Asn Thr Gly Leu Leu Glu Gly Phe Trp
        275                 280                 285

Leu Ala Asn Asn Lys His Thr Asn Lys Lys Asn Gln Val Ala Tyr Ser
    290                 295                 300

Phe Asn Pro Lys Ile Ser Glu Glu Leu Phe Arg Arg Arg Ser Leu Trp
305                 310                 315                 320

Glu Ser Asp Lys Cys Leu Leu Ser Asp Pro Arg Phe Glu Lys Tyr Val
                325                 330                 335

Glu Leu Phe Asp Lys His Gly Arg Tyr Arg Lys Gly Ala Ser Leu Thr
            340                 345                 350

Leu Ile Ser Lys Glu Ser Pro Ile Pro Ile Gly Phe Ser Met Asp Arg
        355                 360                 365

Asn Ala Ala Lys Leu Val Arg Ile Asp Asn Asp Thr Ala Asn Arg Gln
    370                 375                 380

Leu Thr Ile Thr Ile Glu Leu Pro Asn Lys Glu Glu Arg Ser Tyr Val
385                 390                 395                 400

Ala Ala Tyr Gly Arg Lys His Glu Thr Lys Cys Tyr Tyr Asn Gly Leu
                405                 410                 415

Thr Thr Arg Leu Pro Arg Ser Glu Lys Glu Leu Leu Ala Leu Ala Lys
            420                 425                 430

Ala Glu Asn Arg Glu Leu Thr Asp Lys Glu Ile His Glu Ala Ser Leu
        435                 440                 445

Glu Lys Cys Tyr Ile Phe Glu Tyr Ala Arg Ala Gly Lys Ile Pro Val
    450                 455                 460

Phe Ala Val Val Lys Thr Leu Tyr Phe Arg Arg Asn Pro Ser Asn Gly
465                 470                 475                 480

Glu Tyr Tyr Val Ile Leu Pro Thr Asn Ile Phe Val Glu Tyr His Ala
                485                 490                 495

Asn Asn Glu Phe Asn Ser Lys Glu Leu Phe Lys Ile Arg Ser Glu Leu
            500                 505                 510

Gln Lys Ala Trp Asp Glu Val Arg Thr Pro Lys Arg Asn Val Gln Ser
        515                 520                 525

Cys Val Leu Asp Lys Asp Leu Ser Lys Arg Phe Ala Gly Arg Thr Leu
    530                 535                 540

Lys Tyr Ala Gly Ile Asp Leu Gly Tyr Ser Asn Pro Tyr Thr Val Ser
545                 550                 555                 560
```

```
Tyr Tyr Asn Val Val Gly Thr Glu Glu Gly Ile Gln Ile Lys Glu Thr
                565                 570                 575

Gly Asn Glu Ile Val Ser Thr Val Phe Asn Glu Gln Tyr Ile Gln Leu
            580                 585                 590

Lys Gly Asn Ile Tyr Gln Leu Ile Asn Ile Ile Arg Ala Ser Arg Arg
        595                 600                 605

Tyr Leu Gln Glu Ser Gly Glu Leu Lys Leu Ser Lys Asp Asp Ile Lys
    610                 615                 620

Ser Phe Asp Gln Leu Met Glu Leu Leu Pro Ser Glu Gln Arg Ile Thr
625                 630                 635                 640

Ile Asp Gln Phe Ile Lys Asp Ile Lys Lys Ala Lys Gln Glu Gly Lys
                645                 650                 655

Leu Ile Arg Asp Ile Lys Gly Lys Leu Pro Val Glu Gly Lys Lys Lys
            660                 665                 670

Glu Tyr Trp Val Ile Ser Asn Leu Met Tyr Val Ile Thr Gln Thr Met
        675                 680                 685

Asn Gly Ile Arg Gly Asn Arg Asp Ser Asn Asn His Leu Thr Glu Lys
    690                 695                 700

Lys Asn Trp Leu Ser Ala Pro Pro Leu Ile Glu Leu Ile Asp Ala Tyr
705                 710                 715                 720

Tyr Asn Leu Lys Lys Thr Phe Asn Asp Ser Gly Asp Gly Ile Lys Met
                725                 730                 735

Leu Pro Lys Asp His Val Tyr Ala Glu Gly Glu Lys Gln Arg Cys Thr
            740                 745                 750

Leu Arg Glu Glu Asn Phe Cys Lys Gly Ile Leu Glu Trp Arg Asp Asn
        755                 760                 765

Val Lys Asp Tyr Phe Ile Lys Lys Leu Phe Ser Gln Ile Ala His Arg
    770                 775                 780

Cys Tyr Glu Leu Gly Ile Gly Ile Val Ala Met Glu Asn Leu Asp Ile
785                 790                 795                 800

Met Gly Ser Ser Lys Asn Thr Lys Gln Ser Asn Arg Met Phe Asn Ile
                805                 810                 815

Trp Pro Arg Gly Gln Met Lys Lys Ser Ala Glu Asp Ala Phe Ser Tyr
            820                 825                 830

Met Gly Ile Leu Ile Gln Tyr Val Asp Glu Asn Gly Thr Ser Arg His
        835                 840                 845

Asp Ala Asp Ser Gly Ile Tyr Gly Cys Arg Asp Gly Ala Asn Leu Trp
    850                 855                 860

Leu Pro Asn Lys Lys Leu His Ala Asp Val Asn Ala Ser Arg Met Ile
865                 870                 875                 880

Ala Leu Arg Gly Leu Thr His His Thr Asn Leu Tyr Cys Arg Ser Leu
                885                 890                 895

Thr Glu Ile Glu Asn Gly Lys Tyr Val Asn Thr Tyr Glu Leu Phe Asp
            900                 905                 910

Thr Thr Lys Asn Asp Gln Ser Gly Ala Ala Lys Arg Leu Arg Gly Ala
        915                 920                 925

Glu Thr Leu Leu His Gly Tyr Ser Ala Thr Val Tyr Gln Ile His Thr
    930                 935                 940

Thr Asn Thr Gly Ala Gly Val Ala Leu Leu Pro Asp Leu Thr Ala Thr
945                 950                 955                 960

Asp Val Ile Lys Asn Lys Lys Ile Thr Ala Thr Lys Glu Asn Thr Ala
                965                 970                 975

Lys Tyr Tyr Lys Leu Asp Asn Thr Asn Thr Tyr Tyr Pro Trp Ser Val
```

```
            980                 985                 990

Cys Glu Lys Leu His Lys Asn Trp  Lys Leu Ser Ser Arg  Ala Asp Pro
        995                 1000                1005

Lys Lys  Lys Arg Lys Val
    1010


<210> SEQ ID NO 83
<211> LENGTH: 885
<212> TYPE: PRT
<213> ORGANISM: artificial sequence
<220> FEATURE:
<223> OTHER INFORMATION: amino acid sequence of Cas12j.4-NLS fusion
      protein

<400> SEQUENCE: 83

Met Lys Lys Lys Lys Asn Phe Ser Val Ser Ala Thr Gly Val Phe Ser
1               5                   10                  15

Phe Pro Thr Thr Glu Ala Lys Met Asp Phe Phe His Arg Phe Ile Glu
            20                  25                  30

Leu Asn Gly Leu Ala Ala Glu Ile Glu Thr His Phe Leu Asn Leu Lys
        35                  40                  45

Asn Asp Lys Asn Gly Glu Ser Val Tyr Asn Lys Val Leu Ser Asn Ser
    50                  55                  60

Asn His Ser Arg Pro Phe Ser Thr Pro Leu Leu Gly Thr Met Thr Gly
65                  70                  75                  80

Ser Thr Lys Val Thr Asp Lys Asn Ala Leu Tyr Gly Asn Asp Leu Asp
                85                  90                  95

His Cys Arg Lys Lys Lys Ile Val Pro Phe Ser Ser Ser Ser Pro Leu
            100                 105                 110

Ser Ser Gln Glu Lys Phe Phe Cys Ile Glu Ala Val Phe Arg Arg Ala
        115                 120                 125

Lys Ser His Met Glu Cys Lys Lys Leu Phe Gln Asp Glu Thr Asn Arg
    130                 135                 140

Met Asp Ser Gln Ile Asn Gly Ile Leu Asn Glu Leu Pro Tyr Gly Val
145                 150                 155                 160

Glu Leu Ser Asn Met Leu Ser Glu Leu Ile Ala Ile Pro Phe Ala Ile
                165                 170                 175

Gly Trp Lys Leu Glu Gly Tyr Leu Gly Gln Val Phe Phe Pro Ser Ile
            180                 185                 190

Ala Glu Gly Leu Thr Pro Pro Lys Ser Ala Lys Ile Lys Gly Arg Arg
        195                 200                 205

Arg Ser Ile Asp Tyr Ser Val Thr Asp Glu Ala Tyr Asp Ile Leu Met
    210                 215                 220

Lys Tyr Ser Asn Leu His Ser Ser Phe Glu Thr Gly Leu Lys Met Ser
225                 230                 235                 240

Asn Leu Phe Ser Ala Phe Tyr Lys Lys Ser Asn Arg Lys Asp Glu Ile
                245                 250                 255

Gln Phe Thr Pro Ile Ser Met Glu Ser Arg Cys Asp Leu Leu Leu Gly
            260                 265                 270

Lys Asn Phe Leu Lys Phe Asp Leu Lys Asn Cys Asp His Arg Ser Gly
        275                 280                 285

Ser Leu Met Leu Thr Ile Asn Asp Lys Asn Arg Leu Asn Gly Asp Tyr
    290                 295                 300

Glu Ile Arg Val Gly Ser Asp Lys Lys Asp Ser Tyr Leu Thr Gly Val
305                 310                 315                 320
```

```
Asn Val Thr Asn Leu Gly Asp Asn Val Phe Asn Leu Asn Tyr Lys Val
                325                 330                 335

Asn Gly Lys Arg Glu Tyr Asn Met Leu Leu Lys Glu Pro Ser Ile His
            340                 345                 350

Ile Lys Met His Arg Met Arg Asp Asp Gly Asn Tyr Leu Ser Ser Asp
        355                 360                 365

Phe Asp Phe Tyr Met Ile Phe Ser Met Ser Ser Glu Lys Asp Glu Glu
    370                 375                 380

Lys Leu Ala Arg Ser Trp Asp Met Arg Ala Ala Met Ser Thr Ala Tyr
385                 390                 395                 400

Gly Thr Asp Ile Lys Lys Tyr His Ser Ser Phe Pro Cys Arg Ile Leu
                405                 410                 415

Ala Cys Asp Leu Gly Val Lys His Pro Tyr Ser Ala Ala Val Met Asp
            420                 425                 430

Ile Gly Gln Leu Asn Glu Asn Gly Met Pro Val Ser Val Asp Lys Val
        435                 440                 445

His Cys Met His Ser Glu Gly Val Ser Glu Ile Gly Gln Gly Tyr Asn
    450                 455                 460

His Leu Ile Gln Lys Ile Leu Ala Leu Asn Tyr Ile Leu Ala Tyr Cys
465                 470                 475                 480

Arg Glu Phe Val Ser Gly Thr Val Asp Asp Phe Asp Lys Ile Asp Tyr
                485                 490                 495

Lys Leu Ser Gln Leu Ser Tyr Lys Gln Glu Asp Leu Leu Ile Asn Leu
            500                 505                 510

Gln Glu Met Lys Asp His Phe Gly Asn Asp Met Gln Ala Trp Lys Lys
        515                 520                 525

Ser Arg Thr Trp Val Val Ser Thr Leu Phe Phe Glu Leu Arg Gln Glu
    530                 535                 540

Phe Asn Gln Leu Arg Asn Gln Arg Pro Gly Lys Lys Thr Val Ser Leu
545                 550                 555                 560

Ala Asp Glu Phe Gln Tyr Ile Asp Met Arg Arg Lys Phe Ile Ser Leu
                565                 570                 575

Ser Arg Ser Tyr Thr Asn Val Gly Arg Gln Ser Ser Lys His Arg His
            580                 585                 590

Asp Ser Tyr Gln Thr His Tyr Asp Val Ile Asn Arg Cys Lys Lys Asn
        595                 600                 605

Leu Leu Arg Asn Ile Cys Arg Arg Met Ile Asp Met Ala Val Gln Asn
    610                 615                 620

Lys Cys Asp Ile Ile Val Val Glu Asp Leu Ser Phe Gln Leu Ser Ser
625                 630                 635                 640

His Asn Ser Arg Arg Asp Asn Val Phe Asn Ala Leu Trp Ser Cys Lys
                645                 650                 655

Ser Ile Lys Asn Met Leu Gly Ile Met Ala Glu Gln His Asn Ile Ile
            660                 665                 670

Ile Ser Glu Val Asp Pro Asn His Thr Ser Lys Ile Asp Cys Glu Thr
        675                 680                 685

Gly Asn Phe Gly Tyr Arg Tyr Ser Ser Asp Phe Tyr Ser Val Ile Asp
    690                 695                 700

Gly Gln Leu Val Arg Arg His Ala Asp Glu Asn Ala Ala Ile Asn Ile
705                 710                 715                 720

Gly Asn Arg Trp Ala Ser Arg His Thr Asp Leu Lys Ser Phe Asn Cys
                725                 730                 735

Arg Gln Ile Ser Ile Asp Gly Arg Lys Val Ala Phe Pro Tyr Ala Lys
```

```
            740                 745                 750

Gly Lys Arg Lys Ser Ala Leu Phe Gly Tyr Leu Phe Gly Asn Cys Lys
        755                 760                 765

Thr Val Phe Val Ser Asp Asp Gly Asp Ser Tyr Thr Pro Ile Pro Tyr
    770                 775                 780

Ser Lys Phe Arg Lys Ser Ile Ser Lys Asp Asp His Asp Val Val Asn
785                 790                 795                 800

Tyr Leu His Asp Leu Thr Met Asn Lys Asn Val Ile Arg Val Glu Tyr
                805                 810                 815

Asn Lys Ser Ile Lys Ser Ala Ser Val Glu Leu Tyr Leu Asn Asp Asp
            820                 825                 830

Arg Val Ile Ser Arg Ser Leu Arg Asp Lys Glu Val Asp Ala Ile Glu
        835                 840                 845

Lys Leu Val Ser Arg Gly Ser Leu Ile Asn Glu Ser Gly Pro Ser Leu
    850                 855                 860

Glu His Asp Glu Val Lys Ser Val Thr His Ser Arg Ala Asp Pro Lys
865                 870                 875                 880

Lys Lys Arg Lys Val
                885


<210> SEQ ID NO 84
<211> LENGTH: 881
<212> TYPE: PRT
<213> ORGANISM: artificial sequence
<220> FEATURE:
<223> OTHER INFORMATION: amino acid sequence of Cas12j.5-NLS fusion
      protein

<400> SEQUENCE: 84

Met Lys Val His Glu Ile Pro Arg Ser Gln Leu Leu Lys Ile Lys Gln
1               5                   10                  15

Tyr Glu Gly Ser Phe Val Glu Trp Tyr Arg Asp Leu Gln Glu Asp Arg
            20                  25                  30

Lys Lys Phe Ala Ser Leu Leu Phe Arg Trp Ala Ala Phe Gly Tyr Ala
        35                  40                  45

Ala Arg Glu Asp Asp Gly Ala Thr Tyr Ile Ser Pro Ser Gln Ala Leu
    50                  55                  60

Leu Glu Arg Arg Leu Leu Leu Gly Asp Ala Glu Asp Val Ala Ile Lys
65                  70                  75                  80

Phe Leu Asp Val Leu Phe Lys Gly Gly Ala Pro Ser Ser Ser Cys Tyr
                85                  90                  95

Ser Leu Phe Tyr Glu Asp Phe Ala Leu Arg Asp Lys Ala Lys Tyr Ser
            100                 105                 110

Gly Ala Lys Arg Glu Phe Ile Glu Gly Leu Ala Thr Met Pro Leu Asp
        115                 120                 125

Lys Ile Ile Glu Arg Ile Arg Gln Asp Glu Gln Leu Ser Lys Ile Pro
    130                 135                 140

Ala Glu Glu Trp Leu Ile Leu Gly Ala Glu Tyr Ser Pro Glu Glu Ile
145                 150                 155                 160

Trp Glu Gln Val Ala Pro Arg Ile Val Asn Val Asp Arg Ser Leu Gly
                165                 170                 175

Lys Gln Leu Arg Glu Arg Leu Gly Ile Lys Cys Arg Arg Pro His Asp
            180                 185                 190

Ala Gly Tyr Cys Lys Ile Leu Met Glu Val Val Ala Arg Gln Leu Arg
        195                 200                 205
```

```
Ser His Asn Glu Thr Tyr His Glu Tyr Leu Asn Gln Thr His Glu Met
    210                 215                 220

Lys Thr Lys Val Ala Asn Asn Leu Thr Asn Glu Phe Asp Leu Val Cys
225                 230                 235                 240

Glu Phe Ala Glu Val Leu Glu Glu Lys Asn Tyr Gly Leu Gly Trp Tyr
                245                 250                 255

Val Leu Trp Gln Gly Val Lys Gln Ala Leu Lys Glu Gln Lys Lys Pro
            260                 265                 270

Thr Lys Ile Gln Ile Ala Val Asp Gln Leu Arg Gln Pro Lys Phe Ala
        275                 280                 285

Gly Leu Leu Thr Ala Lys Trp Arg Ala Leu Lys Gly Ala Tyr Asp Thr
    290                 295                 300

Trp Lys Leu Lys Lys Arg Leu Glu Lys Arg Lys Ala Phe Pro Tyr Met
305                 310                 315                 320

Pro Asn Trp Asp Asn Asp Tyr Gln Ile Pro Val Gly Leu Thr Gly Leu
                325                 330                 335

Gly Val Phe Thr Leu Glu Val Lys Arg Thr Glu Val Val Val Asp Leu
            340                 345                 350

Lys Glu His Gly Lys Leu Phe Cys Ser His Ser His Tyr Phe Gly Asp
        355                 360                 365

Leu Thr Ala Glu Lys His Pro Ser Arg Tyr His Leu Lys Phe Arg His
    370                 375                 380

Lys Leu Lys Leu Arg Lys Arg Asp Ser Arg Val Glu Pro Thr Ile Gly
385                 390                 395                 400

Pro Trp Ile Glu Ala Ala Leu Arg Glu Ile Thr Ile Gln Lys Lys Pro
                405                 410                 415

Asn Gly Val Phe Tyr Leu Gly Leu Pro Tyr Ala Leu Ser His Gly Ile
            420                 425                 430

Asp Asn Phe Gln Ile Ala Lys Arg Phe Phe Ser Ala Ala Lys Pro Asp
        435                 440                 445

Lys Glu Val Ile Asn Gly Leu Pro Ser Glu Met Val Val Gly Ala Ala
    450                 455                 460

Asp Leu Asn Leu Ser Asn Ile Val Ala Pro Val Lys Ala Arg Ile Gly
465                 470                 475                 480

Lys Gly Leu Glu Gly Pro Leu His Ala Leu Asp Tyr Gly Tyr Gly Glu
                485                 490                 495

Leu Ile Asp Gly Pro Lys Ile Leu Thr Pro Asp Gly Pro Arg Cys Gly
            500                 505                 510

Glu Leu Ile Ser Leu Lys Arg Asp Ile Val Glu Ile Lys Ser Ala Ile
        515                 520                 525

Lys Glu Phe Lys Ala Cys Gln Arg Glu Gly Leu Thr Met Ser Glu Glu
    530                 535                 540

Thr Thr Thr Trp Leu Ser Glu Val Glu Ser Pro Ser Asp Ser Pro Arg
545                 550                 555                 560

Cys Met Ile Gln Ser Arg Ile Ala Asp Thr Ser Arg Arg Leu Asn Ser
                565                 570                 575

Phe Lys Tyr Gln Met Asn Lys Glu Gly Tyr Gln Asp Leu Ala Glu Ala
            580                 585                 590

Leu Arg Leu Leu Asp Ala Met Asp Ser Tyr Asn Ser Leu Leu Glu Ser
        595                 600                 605

Tyr Gln Arg Met His Leu Ser Pro Gly Glu Gln Ser Pro Lys Glu Ala
    610                 615                 620

Lys Phe Asp Thr Lys Arg Ala Ser Phe Arg Asp Leu Leu Arg Arg Arg
```

625 630 635 640

Val Ala His Thr Ile Val Glu Tyr Phe Asp Asp Cys Asp Ile Val Phe
645 650 655

Phe Glu Asp Leu Asp Gly Pro Ser Asp Ser Asp Ser Arg Asn Asn Ala
660 665 670

Leu Val Lys Leu Leu Ser Pro Arg Thr Leu Leu Leu Tyr Ile Arg Gln
675 680 685

Ala Leu Glu Lys Arg Gly Ile Gly Met Val Glu Val Ala Lys Asp Gly
690 695 700

Thr Ser Gln Asn Asn Pro Ile Ser Gly His Val Gly Trp Arg Asn Lys
705 710 715 720

Gln Asn Lys Ser Glu Ile Tyr Phe Tyr Glu Asp Lys Glu Leu Leu Val
725 730 735

Met Asp Ala Asp Glu Val Gly Ala Met Asn Ile Leu Cys Arg Gly Leu
740 745 750

Asn His Ser Val Cys Pro Tyr Ser Phe Val Thr Lys Ala Pro Glu Lys
755 760 765

Lys Asn Asp Glu Lys Lys Glu Gly Asp Tyr Gly Lys Arg Val Lys Arg
770 775 780

Phe Leu Lys Asp Arg Tyr Gly Ser Ser Asn Val Arg Phe Leu Val Ala
785 790 795 800

Ser Met Gly Phe Val Thr Val Thr Thr Lys Arg Pro Lys Asp Ala Leu
805 810 815

Val Gly Lys Arg Leu Tyr Tyr His Gly Gly Glu Leu Val Thr His Asp
820 825 830

Leu His Asn Arg Met Lys Asp Glu Ile Lys Tyr Leu Val Glu Lys Glu
835 840 845

Val Leu Ala Arg Arg Val Ser Leu Ser Asp Ser Thr Ile Lys Ser Tyr
850 855 860

Lys Ser Phe Ala His Val Ser Arg Ala Asp Pro Lys Lys Lys Arg Lys
865 870 875 880

Val

<210> SEQ ID NO 85
<211> LENGTH: 975
<212> TYPE: PRT
<213> ORGANISM: artificial sequence
<220> FEATURE:
<223> OTHER INFORMATION: amino acid sequence of Cas12j.6-NLS fusion protein

<400> SEQUENCE: 85

Met Ser Ala Asn Arg Val Ser Ala Asn Ser Gln Phe Glu Leu Gly Tyr
1 5 10 15

Pro Met Ser Leu Ser Leu Arg Gly Lys Val Phe Asn Ser Arg Glu Met
20 25 30

Met Lys Glu Ile Leu Pro Val Met Asn Asn Ile Val His Tyr Gln Asn
35 40 45

Asn Leu Leu Lys Leu Met Leu Ile Leu Arg Gly Glu Lys Tyr Thr Leu
50 55 60

Asp Gly Gln Phe Phe Ser Gln Lys Asp Val Asp Arg Gln Phe Gly Asp
65 70 75 80

Leu Cys Lys Glu His Asn Ile Lys Gly Ser Ile Cys Ser Leu Lys Glu
85 90 95

Lys Ser Arg Lys Leu Tyr Glu Val Phe Ser Cys Tyr Ile Asp Lys Lys

-continued

```
            100                 105                 110

Gly Asn Leu Lys Thr Asn Ser Lys Ala Arg Ser Phe Ala Gly Val Leu
        115                 120                 125

Leu Asn Pro Lys Asp Val Lys Leu Pro Pro Gln Ile Asp Ser Ile Ser
    130                 135                 140

Ser Phe Val Val Glu Leu Arg Ala Lys Gly Val Leu Pro Ile Lys His
145                 150                 155                 160

Glu Gly Asn Tyr Leu Ser Gly His Pro Ser Leu Lys Tyr Ser Val Ala
                165                 170                 175

Gln Asn Val Leu Val Lys Leu Thr Ser Met Glu Lys Leu Gln Lys Ile
            180                 185                 190

Tyr Ser Asp Glu Lys Ala Gly Trp Glu Asn Ile Val Ser Glu Val Arg
        195                 200                 205

Ser Asp Leu Pro Lys Ile Glu Arg Tyr Glu Arg Met Leu Leu Ser Ile
    210                 215                 220

Lys Ala Val Lys Glu Met Glu Lys Phe Gly Ile Asn Asn Tyr Arg His
225                 230                 235                 240

Leu Leu Asn Asn Trp Arg Asp Glu Val Asp Lys Asp Ser Gly Lys Val
                245                 250                 255

Leu Lys Gln Gly Met Arg Thr Tyr Phe Val Asn Met Leu Glu Ser Lys
            260                 265                 270

Lys Asp Tyr Arg Phe Glu Glu Ser Asp Arg Tyr Leu Phe Gly Tyr Ala
        275                 280                 285

Pro Glu Val Met Asn Leu Val Tyr His Asp Phe Arg Asp Leu Trp Gln
    290                 295                 300

Gly Glu Asp Ile Ile Gly Ser Gln Ser Pro Glu Lys Lys Asp Arg Asp
305                 310                 315                 320

Tyr Val Asp Val Ile Phe Asn Tyr Phe Asn Trp Arg Lys Glu Ser Ile
                325                 330                 335

Asn Ile Ser Ser Phe Asp Ser Tyr Gly Lys Thr Ala Gln Ile Lys Leu
            340                 345                 350

Gly Asp Asn Tyr Val Pro Phe Ser Asn Phe Gln Tyr Asp Lys Ile Leu
        355                 360                 365

Asp Ala Trp Thr Leu Glu Ile Ala Asn Val Ser Gly Glu Gly Asp Asn
    370                 375                 380

His Lys Leu Val Ile Ala Arg Ser Pro Gln Phe Asp Ser His Ser Ser
385                 390                 395                 400

Val Lys Asp Ile Val Met Lys Asn Leu Lys Gly Lys Glu Ala Ser Lys
                405                 410                 415

Thr Thr Leu Glu Phe Arg Tyr Ser Gly Asp Ser Lys Lys Ser Thr Trp
            420                 425                 430

Tyr Arg Gly Thr Leu Lys Glu Pro Thr Leu Arg Tyr Ser Ser Ser Lys
        435                 440                 445

Asn Cys Leu Tyr Val Asp Phe Ala Leu Ser Asn His Ile Val Glu Gly
    450                 455                 460

Leu Ile Ser Asp Asn Leu Gly Ile Ser Asp Lys Met Tyr Lys Phe Arg
465                 470                 475                 480

Gly Glu Phe Met Lys Ala Ser Pro Ser Ser Gly Lys Gln Ser Asn Ser
                485                 490                 495

Ile Asn Leu Pro Ile Lys Lys Leu Arg Ala Met Gly Val Asp Phe Asn
            500                 505                 510

Leu Arg Arg Pro Phe Gln Ala Ser Ile Tyr Asp Val Glu Asn Lys Asn
        515                 520                 525
```

```
Gly Asn Leu Glu Phe Ser Phe Val Lys His Val Gln Ser Phe Ser Asn
    530                 535                 540

Glu Asn Asp Glu Glu Arg Ala Lys Glu Leu Leu Asn Ile Glu Arg Asn
545                 550                 555                 560

Ile Leu Ala Leu Lys Ile Leu Ile Trp Gln Thr Val Gly Tyr Val Thr
                565                 570                 575

Gly Lys Asn Asp Thr Ile Asp Gly Val Val Thr Arg Lys Asn Asn Ala
            580                 585                 590

Val Asp Ile Glu Lys Thr Leu Gly Ile Asn Met Lys Glu Tyr Met Ala
        595                 600                 605

Tyr Leu Asn Gln Phe Arg Ser Tyr Glu Asp Lys Asn Lys Ala Phe Met
    610                 615                 620

Asp Leu Arg Lys Arg Glu Tyr Ala Trp Ile Val Pro Pro Leu Ile Phe
625                 630                 635                 640

Gln Cys Arg Ser Arg Leu Ile Ser Phe Arg Ser Glu Tyr Phe Asn Thr
                645                 650                 655

Pro Lys Asp Glu Lys Ser His Tyr Cys Gln His Arg Asn Phe Val Asp
            660                 665                 670

Tyr Ser Thr Phe Leu Lys Lys Asn Val Val Lys Lys Met Met Glu Leu
        675                 680                 685

Arg Arg Ser Tyr Ser Thr Phe Gly Met Ser Ser Glu Gln Ser Ile Trp
    690                 695                 700

Val Thr Asn Asn Asp His Ala Lys Asp Gly Ser Lys Lys Asn Gly Asn
705                 710                 715                 720

Met Phe Asp Asp Asp Leu His Gln Trp Tyr Asn Gly Leu Val Arg Lys
                725                 730                 735

Cys Ser Ser Leu Ala Ser Ser Ile Ile Asn Val Ala Arg Asp Asn Gly
            740                 745                 750

Ala Ile Leu Val Phe Ile Glu Asp Leu Asp Cys His Pro Ser Ala Phe
        755                 760                 765

Asp Ser Glu Glu Asp Asn Ser Leu Lys Ser Ile Trp Gly Trp Gly Ser
    770                 775                 780

Ile Lys Ala Ser Leu Ala His Gln Ala Arg Lys His Asn Ile Ala Val
785                 790                 795                 800

Val Ala Asn Asp Pro His Leu Thr Ser Leu Val Ser Ser Thr Thr Gly
                805                 810                 815

Glu Leu Gly Ile Ala Lys Gly Arg Asp Val Leu Phe Phe Asp Ser Lys
            820                 825                 830

Gly Lys Leu Thr Ser Lys Val Asn Arg Asp Glu Asn Ala Ala Gln Asn
        835                 840                 845

Ile Ala Ile Arg Gly Phe Val Arg His Ser Asp Leu Arg Glu Phe Val
    850                 855                 860

Ala Glu Lys Ile Glu Glu Asn Arg Tyr Arg Val Val Val Asn Lys Thr
865                 870                 875                 880

His Lys Arg Lys Ala Gly Ala Ile Tyr Arg His Ile Gly Ser Thr Glu
                885                 890                 895

Cys Ile Met Ser Lys Gln Ala Asp Gly Ser Leu Lys Ile Asp Lys Thr
            900                 905                 910

Glu Leu Thr Pro Leu Glu Ile Lys Met Glu Lys Lys Asn Asp Lys Lys
        915                 920                 925

Met Tyr Val Ile Leu His Gly Lys Thr Trp Arg Leu Arg His Glu Leu
    930                 935                 940
```

Asn Glu Lys Leu Glu Lys Asp Leu Asp Asn His Leu Lys Ser Lys Ser
945 950 955 960

Ser Val Ile Ser Ser Arg Ala Asp Pro Lys Lys Lys Arg Lys Val
965 970 975

<210> SEQ ID NO 86
<211> LENGTH: 973
<212> TYPE: PRT
<213> ORGANISM: artificial sequence
<220> FEATURE:
<223> OTHER INFORMATION: amino acid sequence of Cas12j.7-NLS fusion protein

<400> SEQUENCE: 86

Met Ser Ser Ala Asn Asp Gln Leu Gly Leu Gly Tyr Pro Leu Thr Leu
1 5 10 15

Thr Leu Arg Gly Lys Val Tyr Asn His Asp Thr Ala Met Glu Ala Phe
20 25 30

Ala Pro Val Met Lys Gly Met Val Pro Tyr Ala Asn Asn Leu Met Arg
35 40 45

Ile Leu Leu Thr Leu Arg Leu Glu Lys Tyr Thr Leu Asp Gly Ile His
50 55 60

His Thr Lys Glu Glu Val Glu Lys Asp Leu Arg Gly Leu Met Lys Glu
65 70 75 80

Tyr Gly Ile Asn Leu Ser Phe Ala Lys Phe Ser Glu Met Ala Gly Glu
85 90 95

Val Tyr Arg Val Phe Val Cys Tyr Val Asp Ala Lys Gly Lys Leu Lys
100 105 110

Val Asn Gly Lys Ala Arg Gly Phe Ala Asn Val Phe Phe Ser Glu Asp
115 120 125

Asp Ala Thr Ile Pro Glu Asn Cys Pro Ser Met Glu Leu Leu Arg Lys
130 135 140

Lys Gly Met Phe Pro Ile Leu Val Asp Gly Lys Pro Ile Ser Ser Ile
145 150 155 160

Ser Arg Glu Lys Thr Pro Leu Lys Tyr Ser Val Ala Gln Asp Val Leu
165 170 175

Thr Lys Leu Thr Ser Met Glu Glu Ile Ser Lys Glu Tyr Glu Lys Ala
180 185 190

Lys Thr Asp Trp Glu Asn Glu Cys Gln Lys Val Ile Ser Gln Leu Pro
195 200 205

Leu Ile Gly Arg Tyr Glu Ala Leu Leu Thr Thr Ile Pro Leu Ile Pro
210 215 220

Glu Met Arg Gly Phe Asp Gly Asp Asn Tyr Arg Lys Met Leu Asn Arg
225 230 235 240

Trp Arg Asp Tyr Val Asn Glu Asp Gly Glu Leu Val Arg Gly Gly Met
245 250 255

Lys Thr Tyr Phe Leu Asp Leu Leu Ser Lys Asp Thr Ser His Lys Phe
260 265 270

Asn Glu Glu Glu Arg Tyr Leu Phe Gly Tyr Cys Pro Glu Phe Met Asn
275 280 285

Leu Ile Tyr His Asp Phe Arg Asp Leu Trp Ser Lys Glu Asp Ile Ile
290 295 300

Gly Ser Gln Arg Lys Gly Lys Gly Leu Lys Gly Lys Asp Tyr Val Asp
305 310 315 320

Val Ile Phe Asn Cys Phe His Trp Arg Arg Glu Ser Ile Asn Ile Ser
325 330 335

```
Ser Phe Gly Asn Asn Asp Lys Val Met Asn Ile His Leu Gly Asp Asn
            340                 345                 350

Phe Val Pro Phe Glu Leu Lys Ser Gln Asn Gly Ile Trp Glu Val His
        355                 360                 365

Val Gln Asn Leu His Gly Gln Asn Asp Pro His Arg Val Ile Val Cys
    370                 375                 380

Arg Cys Pro Gln Phe Asn Glu Asp Ser Ser Met Lys Met Val His Pro
385                 390                 395                 400

Leu Ala Lys Asn Gly Glu Glu Ser Asp Lys Glu Asn Ile Glu Phe Arg
                405                 410                 415

Tyr Ser Gly Asp Ser Lys Arg Glu Thr Trp Tyr Thr Gly Leu Leu Lys
            420                 425                 430

Glu Pro Thr Leu Arg Tyr Asp Val Glu Arg Lys Ser Leu Tyr Val Asp
        435                 440                 445

Phe Ile Leu Ser Asn His Arg Val Glu Gly Val Val Thr Asn Glu Tyr
    450                 455                 460

Leu Lys Asp Pro Arg Asp Leu Phe Gly Val Arg Gly Tyr Phe Leu Ser
465                 470                 475                 480

Ser Ser Val Ser Asn Pro Arg Gln Lys Asp Lys Thr Ser Leu Pro Asp
                485                 490                 495

Gly Lys Phe Asn Val Met Gly Val Asp Leu Gly Leu Lys Cys Pro Tyr
            500                 505                 510

Glu Cys Ala Ile Tyr Gly Ile Thr Val Lys Asn Gly Lys Met Gln His
        515                 520                 525

Lys Trp Ser His Asn Val Ser Ala Glu Asp Asn Asn Asn Val Ser Glu
    530                 535                 540

Arg Leu Ala Asn Leu Lys Lys Ile Asp Glu Lys Ile Leu Ala Thr Gln
545                 550                 555                 560

Val Leu Ile Ser Leu Thr Lys Met Cys Val Val Lys Asp Glu Glu Ile
                565                 570                 575

Pro Asp Ser Tyr Thr Leu Arg Glu His Arg Val Asp Ile Ala Lys Ser
            580                 585                 590

Leu Asp Leu Asp Met Asp Lys Tyr Arg Arg Tyr Val Glu Lys Cys Lys
        595                 600                 605

Lys Asn Pro Asp Lys Ile Gln Ala Leu Lys Asp Ile Arg Lys Ser Glu
    610                 615                 620

Asn Asn Trp Ile Val Ala Glu Lys Ile Asn Glu Ile Arg Ser Leu Ile
625                 630                 635                 640

Ser Glu Ile Arg Ser Glu Tyr Tyr Ala Ser Lys Asp Lys Arg Asn Tyr
                645                 650                 655

Cys Arg Asn Leu Asn Gly Val Asp Leu Ser Val Phe Leu Lys Lys Lys
            660                 665                 670

Val Val Lys Asn Trp Ile Ser Leu Leu Arg Ser Phe Ser Thr Phe Gly
        675                 680                 685

Met Thr Pro Gln Glu Ser Ala Tyr Ile Arg Lys Asp Phe Ala Lys Asn
    690                 695                 700

Leu Ser Lys Trp Tyr Lys Gly Leu Val Arg Lys Cys Gly Ser Ile Ala
705                 710                 715                 720

Ala His Ile Val Asn Ile Ala Arg Asp Asn Lys Val Met Val Ile Phe
                725                 730                 735

Ile Glu Asp Leu Asp Ala Arg Thr Ser Ala Phe Asp Ser Lys Glu Asp
            740                 745                 750
```

Asn Glu Leu Lys Ile Leu Trp Gly Trp Gly Glu Ile Lys Lys Trp Ile
755 760 765

Gly His Gln Ala Arg Lys His Asn Ile Ala Val Val Ala Val Asp Pro
770 775 780

His Leu Thr Ser Leu Val Asn His Glu Ser Gly Leu Leu Gly Ile Ala
785 790 795 800

Gly Ser Gly Asn Asp Arg Asn Ile Tyr Thr Phe Gln Lys Asn Lys Lys
805 810 815

Tyr Val Val Ile Asn Arg Asp Asn Asn Ala Ala His Asn Ile Ala Leu
820 825 830

Arg Gly Leu Ser Lys His Thr Asp Ile Arg Glu Phe Tyr Val Glu Gln
835 840 845

Ile Asp Val Asp His Tyr Arg Leu Met Tyr Gly Pro Glu Ala Glu Asn
850 855 860

Gly Lys Arg Arg Ser Gly Ala Ile Tyr Lys His Ile Gly Ser Thr Glu
865 870 875 880

Cys Val Phe Ser Lys Gln Lys Asn Gly Thr Leu Lys Val Glu Lys Thr
885 890 895

Ser Leu Thr Lys Asp Glu Lys Glu Met Pro Lys Ile Asn Gly Lys Gly
900 905 910

Val Tyr Ala Ile Leu His Gly Asn Glu Trp Arg Leu Arg His Glu Leu
915 920 925

Asn Glu Glu Leu Gly Ala Lys Leu Asp Gly Ile Ser Val Lys Arg Val
930 935 940

Val Ser Glu Pro Asn Lys Val Lys Thr Ser Leu Val Lys Gly Ser Val
945 950 955 960

Arg Ala Ser Arg Ala Asp Pro Lys Lys Lys Arg Lys Val
965 970

<210> SEQ ID NO 87
<211> LENGTH: 918
<212> TYPE: PRT
<213> ORGANISM: artificial sequence
<220> FEATURE:
<223> OTHER INFORMATION: amino acid sequence of Cas12j.8-NLS fusion protein

<400> SEQUENCE: 87

Met Lys Lys Gln Thr Ile Val Lys Lys Asp Ser Lys Ala Glu Thr Lys
1 5 10 15

Glu Asn Lys Met Tyr Pro Asp Lys Asp Thr Asp Phe Pro Val Asn Ser
20 25 30

Gln Phe Ser Arg Ser Ile Ser Ile Arg Ala Asn Val Asp Pro Lys Asp
35 40 45

Leu Leu Val Leu Lys Arg Thr Phe Glu Glu Thr Thr Lys Ile Ser Asp
50 55 60

Glu Leu Leu Ser Thr Leu Leu Met Leu Arg Gly Lys Asp Tyr Cys Leu
65 70 75 80

Asp Asn Val Val Cys Lys Gly Glu Glu Val Leu Glu Asn Leu Tyr Lys
85 90 95

Lys Leu Ser Lys Asn Ala Thr Val Asn Arg Asp Lys Phe Ile Ser Thr
100 105 110

Ala Lys Ala Phe Tyr Glu Tyr Phe His Gly Cys Ser Tyr His Lys Gly
115 120 125

Phe Lys Ser Phe Phe Phe Ser Ser Lys Glu Ile Asp Ser Ile Gln Ser
130 135 140

```
Glu Lys Phe Gly Tyr Leu Arg Glu Ile Gly Leu Phe Pro Ile Lys Ile
145                 150                 155                 160

Asp Ala Gln Ile Ser Asn Asp Leu Gln Tyr Ser Ile Val Ala Ser Asn
                165                 170                 175

His Ala Lys Ile Lys Gly Phe Glu Lys Ile Asp Lys Glu Tyr Gln Ala
            180                 185                 190

Asn Lys Glu Lys Trp Asn Lys Thr Ile Gly Glu Ser Thr Leu Lys His
        195                 200                 205

Leu Asn Arg Tyr Gly Glu Met Leu Lys Gly Leu Ser Asp Leu Gly Thr
    210                 215                 220

Met Gly Asn Phe Asn Gly Lys Lys Tyr Asp Arg Phe Met Gly His Trp
225                 230                 235                 240

Arg Asn Glu Gln Lys Ile Pro Asp His Ile Ser Met Leu Asp Phe Phe
                245                 250                 255

Arg Lys Ile Tyr Gln Glu Lys Gly Lys Ser His Arg Phe Thr Ala Ile
            260                 265                 270

Asp Asn Phe Thr Tyr Gly Tyr Glu Ser Glu Phe Met Asn His Ile Tyr
        275                 280                 285

Leu Asn Phe Ser Asp Leu Trp Leu Lys Glu Asp Val Ile Gly Asp Glu
    290                 295                 300

Glu Tyr Val Ser Leu Ile Arg Gly Ala Tyr His Trp Gln Lys Asp Val
305                 310                 315                 320

Val Gly Ile Ala Ser Phe Ser Gly Tyr Asn Lys Tyr Glu Lys Leu Phe
                325                 330                 335

Met Gly Asp Asn Lys Ile Asn Tyr Ala Leu Asp Phe Ser Asn Lys Asp
            340                 345                 350

Gln Trp Leu Met Lys Phe Asn Asn Val Ile Ser Lys Glu Pro Glu Thr
        355                 360                 365

Ile Thr Leu Arg Leu Cys Lys Asn Gly Tyr Phe Asn Asn Leu Ser Val
    370                 375                 380

Leu Glu Lys Asn Asp Glu Asn Gly Arg Tyr Lys Ile Arg Phe Ser Thr
385                 390                 395                 400

Glu Lys Gln Gly Lys Tyr Phe Tyr Glu Ala Phe Ile Arg Glu Pro Phe
                405                 410                 415

Leu Arg Tyr Asn Lys Asp Asn Asp Lys Ile Tyr Val His Phe Cys Leu
            420                 425                 430

Ser Glu Glu Ile Lys Glu Asn Cys Pro Asn His Leu Asp Thr Arg Ser
        435                 440                 445

Asp Lys Tyr Leu Phe Lys Ser Ala Leu Leu Thr Asn Ser Arg Gln Lys
    450                 455                 460

Leu Gly Lys Leu His Tyr Arg Asp Phe His Ile Val Gly Val Asp Leu
465                 470                 475                 480

Gly Ile Asn Pro Val Ala Lys Ile Thr Val Cys Lys Val His Val Asp
                485                 490                 495

Lys Asn Glu Asn Leu Lys Ile Thr Lys Ile Ile Thr Glu Glu Thr Arg
            500                 505                 510

Lys Asn Ile Asp Thr Asn Tyr Leu Asp Gln Leu Asn Leu Leu Tyr Lys
        515                 520                 525

Lys Ile Val Ser Leu Lys Arg Leu Ile Arg Ala Thr Val Ala Phe Lys
    530                 535                 540

Lys Asp Gly Glu Glu Ile Pro Lys Met Phe Lys Met Gly Lys Lys Ser
545                 550                 555                 560
```

```
Pro Tyr Phe Leu Asn Trp Thr Glu Val Leu Asn Val Asn Tyr Asp Asp
                565                 570                 575

Tyr Ile Lys Glu Ile Ser Thr Phe Ser Val Asp Arg Leu Ser Gly Leu
            580                 585                 590

Thr Leu Pro Met Gln Trp Ala Arg Ser Gln Asn Lys Trp Val Val Lys
        595                 600                 605

Asp Leu Thr Lys Met Val Arg Lys Gly Ile Ser Asp Leu Ile Tyr Ala
    610                 615                 620

Arg Tyr Phe Asn Cys Ser Asp Lys Thr Gln Tyr Val Thr Glu Asn Asn
625                 630                 635                 640

Ala Val Asp Ile Thr Thr Phe Lys Lys His Asp Ile Ile Ser Glu Ile
                645                 650                 655

Ile Gly Leu Gln Lys Met Phe Ser Gly Gly Gly Lys Asp Val Ala Lys
            660                 665                 670

Lys Asp Tyr Leu Tyr Leu Arg Gly Leu Arg Lys His Ile Gly Asn Tyr
        675                 680                 685

Thr Ala Ser Ala Ile Val Ser Ile Ala Gln Lys Tyr Asn Ala Val Phe
    690                 695                 700

Ile Phe Ile Glu Asp Leu Asp Leu Lys Ile Ser Gly Met Asn Gly Lys
705                 710                 715                 720

Lys Glu Asn Lys Val Lys Ile Leu Trp Gly Val Gly Gln Leu Lys Lys
                725                 730                 735

Arg Leu Ser Glu Lys Ala Glu Lys Phe Gly Ile Gly Ile Val Pro Val
            740                 745                 750

Asn Pro Glu Leu Thr Ser Gln Met Asp Arg Glu Thr Phe Leu Leu Gly
        755                 760                 765

Tyr Arg Asn Pro Thr Asn Lys Lys Glu Leu Tyr Val Lys Arg Asp Asp
    770                 775                 780

Lys Ile Glu Ile Leu Asp Ala Asp Glu Thr Ala Ser Tyr Asn Val Ala
785                 790                 795                 800

Leu Arg Gly Leu Gly His His Ala Asn Leu Ile Gln Phe Arg Ala Asp
                805                 810                 815

Lys Met Pro Asn Gly Cys Phe Arg Val Met Pro Asp Arg Lys Tyr Lys
            820                 825                 830

Gln Gly Ala Leu Tyr Gly Tyr Leu Asn Ser Thr Ala Val Leu Phe Lys
        835                 840                 845

Asp Lys Gly Asp Gly Val Leu Thr Ile His Lys Ser Lys Leu Thr Lys
    850                 855                 860

Lys Glu Arg Asp Ser Arg Pro Ile Lys Gly Lys Lys Thr Phe Val Val
865                 870                 875                 880

Lys Asn Gly Lys Arg Trp Ile Leu Arg His Val Leu Asp Glu Glu Val
                885                 890                 895

Lys Lys Tyr Pro Glu Met Tyr Asn Ser Gln Asn Ser Arg Ala Asp Pro
            900                 905                 910

Lys Lys Lys Arg Lys Val
        915
```

<210> SEQ ID NO 88
<211> LENGTH: 923
<212> TYPE: PRT
<213> ORGANISM: artificial sequence
<220> FEATURE:
<223> OTHER INFORMATION: amino acid sequence of Cas12j.9-NLS fusion protein

<400> SEQUENCE: 88

```
Met Ser Asp Tyr Lys Phe Ser Asn Asn Gly Val Thr Asn Thr Gly Ser
1               5                   10                  15

Ala His Ile Gly Leu Ser Pro Glu Asn Ser Ser Thr Val Met Asp Met
            20                  25                  30

Phe Lys Val Ile Thr Lys Asp Ala Asp Phe Leu Leu Lys Asn Leu Leu
        35                  40                  45

Ile Met Glu Gly Gly Glu Tyr Met Leu Asn Arg Glu Ile His Asn Gly
    50                  55                  60

Asp Lys Glu Phe Asp Lys Ile Ile Ser Lys Leu Gly Leu Ser Lys Lys
65                  70                  75                  80

Glu Lys Glu Asn Leu Lys Met Lys Cys Lys Asp Phe Phe Phe Asp Phe
                85                  90                  95

Val Lys Leu Gln Asn Gly Arg Ser Leu Ala Asn Ile Leu Phe Glu Thr
            100                 105                 110

Lys Gly Thr Thr Leu Ile Gly Cys Gly Lys Asp Lys Lys Gly Glu Lys
        115                 120                 125

Val Asp Gly Glu Tyr Pro Thr Ile Tyr His Asp His Glu Thr Leu Arg
    130                 135                 140

Ser Thr Gly Leu Leu Pro Leu Lys Phe Ser Lys Asn Ile Asp Asp Val
145                 150                 155                 160

Asp Tyr Lys Tyr Leu Ile Cys Tyr Leu Val His Asn Val Leu Ser Ser
                165                 170                 175

Phe Ile Glu Lys Arg Asp Ala Tyr Asn Asp Asn Lys Lys Glu Trp Glu
            180                 185                 190

Ser Lys Leu Ser Asn Ser Asn Leu Pro Gln Leu Glu Arg Met Ser Glu
        195                 200                 205

Phe Leu Asn Gly Ile Asn His Leu Gly Asn Ile Ile Gly Trp Asn Gly
    210                 215                 220

Lys Lys Tyr Ile Gly Phe Ile Lys Lys Trp Thr Asp Glu Glu Ser Ser
225                 230                 235                 240

Met Tyr Asp Phe Phe Val Gln Lys Leu Gln Asp Asn Pro Lys Tyr Lys
                245                 250                 255

Phe Gly Lys Lys Asp Gln Phe Leu Tyr Gly Tyr Glu Pro Glu Phe Leu
            260                 265                 270

Asn Tyr Leu Phe His Asp Phe Arg Asp Leu Trp His Pro Asp Asn Leu
        275                 280                 285

Ile Gly Lys Asp Glu Tyr Val Asp Leu Ile Ser Gly Lys Asn Asn Thr
    290                 295                 300

Asp Ala Glu Thr Ala Asn Lys Gly Ala Tyr His Trp Leu Lys Asp Phe
305                 310                 315                 320

Ile Asn Ile Ser Ser Phe Asp Ala Tyr Gly Lys Met Ala Thr Ile Gly
                325                 330                 335

Met Gly Asn Asn Leu Ile Asn Tyr Ser Met Asn Ile Asp Lys Asp Gly
            340                 345                 350

Lys Ile Ile Val Asn Met Asp Asn Ile Phe Asp Arg Ser Lys Pro Ile
        355                 360                 365

Val Phe Asn Val Tyr Arg Asn Ser Tyr Phe Arg Asn Phe Lys Ile Ile
    370                 375                 380

Glu Ser Asp Asp Lys Lys Gly Ile Tyr Lys Val Glu Phe Ser Thr Ser
385                 390                 395                 400

Asn Asn Gly Val Ile Tyr Glu Gly Tyr Ile Lys Ser Pro Ser Leu Arg
                405                 410                 415
```

```
Phe Ala Thr Lys Gly Gly Thr Ile Lys Ile Asp Phe Pro Ile Ser Asp
            420                 425                 430

Lys Arg Ile Lys Gly Gly Arg Glu Met Asn Thr Asp Leu Met Trp Phe
        435                 440                 445

Leu Asn Arg Ala Ser Pro Cys Ser Thr Lys Asn Lys Glu Val Asn Ser
    450                 455                 460

Phe Ile Gly Lys Asn Phe Val Gly Leu Ala Ile Asp Arg Gly Ile Asn
465                 470                 475                 480

Pro Leu Met Ala Trp Tyr Val Ala Glu Trp Thr Tyr Asp Lys Asp Gly
                485                 490                 495

Lys Ala Lys Ile Val Arg Ser Ile Ala Asn Gly Arg Val Asp Ser Gly
            500                 505                 510

His Asn Glu Ser Glu Val Lys Phe Val Arg Glu Thr Thr Asn Arg Ile
        515                 520                 525

Val Gly Ile Lys Ser Leu Val Trp Asn Thr Val Lys Tyr Arg Thr Gly
    530                 535                 540

Gly Ser Glu Gly Ile Asp Arg Cys Arg Lys Ser Gln Asn Gly Gln Val
545                 550                 555                 560

Asp Leu Phe Glu Met Phe Asp Ile Asp Tyr Asn Asn Tyr Leu Lys Glu
                565                 570                 575

Val Asn Asn Leu Pro Tyr Asp Pro Asn Ser Glu Arg Ser Ile Ile Gln
            580                 585                 590

Thr Trp Val Ser Ser Pro Trp Lys Val Lys Asp Leu Val Lys Asp Ala
        595                 600                 605

Lys Asn Arg Met Val Gln Ile Lys Thr Gln Tyr His Asn Ala Lys Asp
    610                 615                 620

Lys Glu Lys Tyr Ile Thr Thr Gln Asn Arg Ala Gly Phe Tyr Asp Phe
625                 630                 635                 640

Leu Lys Ile Glu Met Glu Lys Gln Phe Thr Ser Leu Gln Arg Met Phe
                645                 650                 655

Ser Gly Gly Gln Lys Asp Ile Cys Lys Asn Asn Glu Glu Tyr Arg Arg
            660                 665                 670

Gly Leu Arg Arg Arg Ile Asn Leu Tyr Thr Ser Ser Val Ile Met Ser
        675                 680                 685

Leu Ala Arg Lys Phe Asn Val Asp Cys Ile Phe Leu Glu Asp Leu Asp
    690                 695                 700

Ser Ser Lys Ser Ser Trp Asp Asp Ala Lys Lys Asn Ser Leu Lys Asp
705                 710                 715                 720

Leu Trp Ser Thr Gly Gly Ala Asp Asp Ile Leu Gly Lys Met Ala Asn
                725                 730                 735

Lys Tyr Lys Tyr Pro Ile Val Lys Val Asn Ser His Leu Thr Ser Leu
            740                 745                 750

Val Asp Asn Lys Thr Gly Lys Ile Gly Tyr Arg Asp Pro Lys Lys Lys
        755                 760                 765

Ser Asn Leu Tyr Val Glu Arg Gly Lys Lys Ile Glu Ile Ile Asp Ser
    770                 775                 780

Asp Glu Asn Ala Ala Ile Asn Ile Leu Lys Arg Gly Ile Ser Lys His
785                 790                 795                 800

Ile Asp Ile Arg Glu Phe Phe Ala Glu Lys Ile Glu Val Ser Gly Lys
                805                 810                 815

Thr Leu Tyr Arg Ile Ser Asn Lys Leu Gly Lys Gln Arg Met Gly Ser
            820                 825                 830

Leu Tyr Tyr Leu Glu Gly Asn Lys Glu Ile Leu Phe Gly Leu Gly Lys
```

```
        835                 840                 845

Asn Gly Glu Pro Ile Val Cys Lys Arg Gly Leu Cys Lys Lys Glu Arg
    850                 855                 860

Leu Ala Pro Arg Ile Ala Glu Lys Lys Ser Thr Tyr Leu Ile Met Asn
865                 870                 875                 880

Gly Ser Lys Trp Met Phe Arg His Glu Ala Lys Lys Ile Val Glu Thr
                885                 890                 895

Tyr Lys Asp Arg Tyr Cys Ala Asn His Lys Val Ala Ser Lys Asp Gly
            900                 905                 910

Ser Arg Ala Asp Pro Lys Lys Lys Arg Lys Val
        915                 920


<210> SEQ ID NO 89
<211> LENGTH: 1130
<212> TYPE: PRT
<213> ORGANISM: artificial sequence
<220> FEATURE:
<223> OTHER INFORMATION: amino acid sequence of Cas12j.10-NLS fusion
      protein

<400> SEQUENCE: 89

Met Met Asn Ile Asn Glu Met Val Lys Leu Met Lys Ser Glu Tyr Leu
1               5                   10                  15

Phe Glu Asp Asp Gly Ile Val Thr Lys Asn Lys Ile Gln Glu Arg Leu
            20                  25                  30

Arg Asn Gly Phe Ser Asp Ile Gly Val Asp Pro Ser Leu Val Ser Tyr
        35                  40                  45

Ala Ser Lys Phe Leu Asp Ser Met Phe Ile Cys Phe Ser Arg Val Lys
    50                  55                  60

Gly Glu Lys Asn Phe Lys Ala Lys Asn Val Arg Lys Asn Met Ser Ser
65                  70                  75                  80

Ala Glu Lys Lys Ala Gln Lys Lys Lys Glu Tyr Gln Glu Tyr Tyr Gln
                85                  90                  95

Gly Val Met Ala Gln Gln Asp Ala Tyr Ala Gln Leu Leu Ser Asp Pro
            100                 105                 110

Thr Gln Glu Asn Leu Asp Lys Leu Asn Glu Leu Ile Ser Met Ser Val
        115                 120                 125

Asn Gly Ser Leu Val Glu Asp Phe Phe Pro Ala Leu Lys Asn Met Ile
    130                 135                 140

Gln Lys Ala Asp Tyr Ser Ile Asp Lys Lys Gly Leu Leu Asp Phe Ser
145                 150                 155                 160

Cys Cys Met Met Asp Arg Tyr Glu Asp Arg Ser Leu Thr Arg Ala Ile
                165                 170                 175

Ser Ile Ser Ala Phe Asn Ile His Ser Gly Gly Leu Arg Lys Ala Leu
            180                 185                 190

Ser Asp Ile Ser Glu Lys Val Gln Asp Leu Ser Asn Thr Leu Leu Ile
        195                 200                 205

Arg Ile Leu Tyr Met Lys Gly Glu Glu Leu Ser Ile Asp Gly Glu Lys
    210                 215                 220

Ile Ser Lys Glu Glu Val Gln Arg Gln Leu Lys Ala Asp Tyr Glu Glu
225                 230                 235                 240

His Lys Glu Tyr Phe Glu Asp Phe Glu Asp Phe Ala Lys Lys Cys Arg
                245                 250                 255

Phe Phe Tyr Asn Lys Phe Ser Lys Lys Lys Lys Thr Arg Gly Phe Gly
            260                 265                 270
```

```
Thr Tyr Phe Phe Gly Asp Lys Lys Lys Glu Ile Ser Ser Ala Glu Tyr
        275                 280                 285

Lys Ala His Lys Glu Leu Arg Asp Ser Gly Tyr Leu Trp Phe Asp Ile
    290                 295                 300

Gly Trp Ser Glu Ser Ser Asp Phe Lys Tyr Val Ile Val Gly Asn Val
305                 310                 315                 320

Ser Gly Lys Leu Lys Ser Phe Glu Glu Thr Ser Glu Glu Tyr Gln Lys
                325                 330                 335

Ser Lys Asn Cys Trp Glu Ala Glu Arg Val Lys Leu Tyr Glu Gln Asp
            340                 345                 350

Ser Asp Phe Val Leu Phe Val Glu Asp Met Ile Glu Ser Lys Tyr Gly
        355                 360                 365

Pro Ile Glu Lys Met Lys Leu Arg Thr Phe Lys Thr Ile Val Lys Lys
    370                 375                 380

Leu Asp Lys Glu Phe Gly Lys Arg Gly Asp Lys Thr Pro Ser Ile His
385                 390                 395                 400

Asp Tyr Phe Glu Ser Leu Asp Pro Asn His Thr Phe Ser Gln Ser Glu
                405                 410                 415

Gln Phe Met Tyr Gly Leu Asp Val Thr Leu Met Gln Phe Leu Phe Asn
            420                 425                 430

Asn Lys Lys Gln Phe Tyr Lys Leu Cys Lys Asp His Asp Gly Lys Arg
        435                 440                 445

Thr Phe Ala Lys Val Val Glu Glu Ser Tyr His Trp Gly Lys Asn Ser
    450                 455                 460

Ile Asn Val Ser Thr Phe Gln Asn Ser Thr Ser Ile Leu Leu Gly Gly
465                 470                 475                 480

Asn Tyr Leu Asn Tyr Ser Met Ser Ile Glu Gly Glu Gly Leu Val Ile
                485                 490                 495

Lys Phe Asp Asn Pro Leu Ser Gly Lys Glu Val His Phe Val Val Cys
            500                 505                 510

Asn Asn Lys Tyr Leu Ser Asp Leu Glu Ile Leu Ser Gly Asn Pro Asn
        515                 520                 525

Arg Lys Asp Asn Asn Tyr Thr Ile Ser Tyr Ser Thr Gly Gly Lys Ala
    530                 535                 540

Arg Phe Ile Ala Lys Ser Lys Glu Pro Arg Ile Phe Phe Asn Arg Lys
545                 550                 555                 560

Thr Lys Lys Trp Glu Ile Ala Phe Gln Leu Ser Asp Val Ser Pro Leu
                565                 570                 575

Asn Gly Lys Phe Gly Lys Gln Gly Glu Phe Leu Ser Asn Leu Arg Lys
            580                 585                 590

Phe Val Tyr Asn His Val Ala Lys Ser Pro Ser Lys Leu Asn Ile Ser
        595                 600                 605

Asp Asn Asn Cys Arg Ala Val Ala Tyr Asp Leu Gly Ile Arg Asn Val
    610                 615                 620

Gly Ala Trp Ser Ser Phe Asp Phe Ser Tyr Lys Asp Gly Val Leu Gly
625                 630                 635                 640

Gly Tyr Lys Tyr Leu Thr Ser Gly Ser Leu Arg Ser Lys Ser Glu Ser
                645                 650                 655

Ser Glu Met Asp Gln Gly Tyr Tyr Phe Val Leu Asn Leu Lys Lys Ile
            660                 665                 670

Val Lys Leu Ile Pro Val Val Lys Lys Ser Ile Ile Asp Asp Pro Glu
        675                 680                 685

Leu Lys Arg Gln Phe Ile Gly Val Leu Asn Glu Asn Gly Asn Thr Val
```

```
    690                 695                 700

Gly Leu Gly Asn Ile Gly Lys Leu Asp Ile Ala Ser Arg Lys Ala Val
705                 710                 715                 720

Gln Ser Phe His Asn Cys Ile Gln Gln Ile Asn Tyr Tyr Val Asp Thr
                725                 730                 735

Tyr Ala Asp His Ile Asp Lys Ile Ser Ala Lys Asp Phe Val Asp Asp
            740                 745                 750

Ile Asp Gly Ile Lys Val Leu Asp Glu Asp Asp Pro Tyr Val Val Lys
        755                 760                 765

Ile Leu Ser His Leu Pro Glu Asp Val Glu Gly Asn Gln Asp Asp Ile
    770                 775                 780

Leu Asn Ile Ser Leu Leu Lys Trp Lys Thr Ser Asn Ala Gln Phe Val
785                 790                 795                 800

Pro Pro Leu Ile Gln Glu Ala Lys Ala Ile Met Ser Arg Ile Lys Arg
                805                 810                 815

Glu Asn Leu Asp Asn Ile Arg Gly Lys Lys Thr Gln Val Val Thr Gln
            820                 825                 830

Lys Thr Phe His Lys Ile Lys Phe Ala Lys Ala Leu Leu Ser Leu Met
        835                 840                 845

Lys Ser Trp Ser Ser Ile Gly Thr Val Arg Val Val Lys Thr Asp Gln
    850                 855                 860

Ile Tyr Gly Lys Lys Ile Trp Asp Tyr Ile Asn Gly Leu Arg Arg Asn
865                 870                 875                 880

Val Leu Thr Tyr Leu Ser Ser Ala Ile Val Asn Asn Ala Leu Asp Leu
                885                 890                 895

Gly Ala His Met Ile Ile Leu Glu Asp Leu Asp Ser Ser Val Ser Lys
            900                 905                 910

Tyr Arg Glu Lys Asp Lys Asn Ala Ile Gln Ser Leu Trp Gly Ser Gly
        915                 920                 925

Glu Leu Lys Lys Arg Ile Glu Glu Lys Ala Glu Lys His Arg Val Val
    930                 935                 940

Val Gln Tyr Val Ser Pro Tyr Leu Thr Ser Gln Leu Asp Asn Glu Thr
945                 950                 955                 960

Lys Asp Ile Gly Tyr Arg Lys Gly Gly Arg Leu Tyr Val Val Arg Asn
                965                 970                 975

Gly Lys Ile Lys Ser Ile Asp Ala Asp Ile Asn Ala Ser Lys Asn Ile
            980                 985                 990

Gly Glu Arg Phe Phe Asp Arg Asp  Leu Ile Gln Thr Leu  Ser Gly Val
        995                 1000                1005

Val Val  Glu Asp Gln Ser Thr  Val Tyr Ile Leu Gln  Lys Arg Asn
    1010                1015                1020

Val Ser  Ser Asp Asn Arg Lys  Arg Phe Tyr Lys Lys  Phe Leu Glu
    1025                1030                1035

Asp Val  Gly Gly Lys Ser Lys  Lys Asp Ala Val Leu  Lys Met Gly
    1040                1045                1050

Asp His  Gly Glu Leu Glu Val  Glu Arg Leu Ile Asp  Gly Lys Lys
    1055                1060                1065

Leu Asp  Ile Asp Gly Lys Lys  Ile Leu Val Asp Gly  Glu Lys Val
    1070                1075                1080

Pro Phe  Arg Asn Thr Ser Val  Tyr Tyr Ser Pro Lys  Lys Lys Lys
    1085                1090                1095

Trp Val  Ser Lys Glu Leu Arg  Cys Asn His Ile Lys  Leu Thr Val
    1100                1105                1110
```

```
Glu Glu  Gln Asp Ile Lys Ser  Arg Ala Asp Pro Lys  Lys Lys Arg
    1115                 1120                 1125

Lys Val
    1130


<210> SEQ ID NO 90
<211> LENGTH: 1146
<212> TYPE: PRT
<213> ORGANISM: artificial sequence
<220> FEATURE:
<223> OTHER INFORMATION: amino acid sequence of Cas12j.11-NLS fusion
      protein

<400> SEQUENCE: 90

Met Asn Asn Tyr Asp Asn Tyr Leu Ser Asp Tyr Leu Ala Met Leu Pro
1               5                   10                  15

His Thr Lys Arg Thr Glu Ile Lys Lys Thr Ala Ser Lys Ile Ser Arg
            20                  25                  30

Lys Leu Asn Gln Lys Glu Val Lys Lys Gln Ile Glu Arg Ser Glu Tyr
        35                  40                  45

Ile Arg Ser Asn Cys Gly Tyr Ile Asn Ile Glu Arg Pro Gln Lys Ser
    50                  55                  60

Leu Ser Phe Leu Ser Tyr Ser Thr Ile Lys Ser Ala Cys Met Ser Val
65                  70                  75                  80

Asn Phe Arg Ala Phe Gln Asn Pro Ile Asn Asp Tyr Glu Thr Ala Ile
                85                  90                  95

Cys Asn Gly Ile Asn Glu Cys Glu Arg Phe Phe Tyr Gln Gln Ile Asp
            100                 105                 110

Ser Ile Tyr Met Ser Gln Ile Ile Glu Gln Leu Phe Asp Phe Tyr Ile
        115                 120                 125

Ala Ser Arg Gln His Asp Met Phe Ile Asn Asn Thr Val Val Pro Tyr
    130                 135                 140

Asp Val Asn Lys Leu Lys Ser Tyr Tyr Thr Ala Asn Glu Lys Tyr Ser
145                 150                 155                 160

Phe Glu Gln Phe Cys Asp Asp Ile Lys Glu Phe Thr Asn Lys Gly Phe
                165                 170                 175

Thr Ser Gly Gly Val Ser Cys Ile Leu Asn Leu Phe Tyr Lys Gly Ser
            180                 185                 190

Val Lys Asp Ser Lys Asn Lys Lys Asp Tyr Ile Lys Ser Val Lys Arg
        195                 200                 205

Leu Glu Thr Asn Gly Leu Phe Lys Lys Leu Asn Ile Phe Glu Lys Asn
    210                 215                 220

Gly Ile Ser Lys Tyr Phe Ala Ala Ser Thr Leu Ser Thr Phe Phe Ala
225                 230                 235                 240

Thr Ile Ser Ser Trp Lys Lys Gln Asn Asp Asp Trp Thr Gly Val Ala
                245                 250                 255

Lys Asp Gly Thr Ser Leu Leu Ser Lys Leu Glu Asn Lys Thr Ile Thr
            260                 265                 270

Leu Gln Ser Ile Ile Lys His His Arg Val Ile Asn Glu Leu Ala Val
        275                 280                 285

Leu Ile Val Lys Ala Tyr Lys Asp Pro Val Lys Thr Leu Asn Asn Leu
    290                 295                 300

Phe Glu Glu Arg Ser Asp Asn Asn Asn Asp Phe Lys Tyr Thr Cys Ser
305                 310                 315                 320

Asp Asp Glu Asp Lys Tyr Pro Met Tyr Ile Lys Arg Glu Ile Ala Glu
```

```
                325                 330                 335

Phe Val Lys Lys His Lys Thr Val Trp Glu Glu Ile Arg Tyr Phe Asp
            340                 345                 350

Glu Ser Asp Thr Lys Lys Lys Lys Arg Asp Lys Lys Glu Ser Ser Ser
        355                 360                 365

Asp Asp Lys Ser Tyr Leu Cys Cys Gly Asp Ser Trp Asp Tyr Leu Lys
    370                 375                 380

Thr Trp Val Arg Leu Tyr Gly Glu Tyr Tyr Phe Phe Asp Asn Ala Leu
385                 390                 395                 400

Asn Gln Phe Leu Arg Lys Pro Ser Ala Ser Met His Leu Tyr Thr Ser
                405                 410                 415

Leu Asp Trp Ile Asn Lys Lys Thr Ile Cys Ile Val Gly Ala Asn Tyr
            420                 425                 430

Tyr Lys Ile Gly Lys Val Glu Val Val Glu Arg Asn Asn Gln Arg Phe
        435                 440                 445

Leu Leu Val Tyr Val Ser Val Pro Glu Met Glu Asn Tyr Ile Ile Ile
    450                 455                 460

Pro Leu Gln Leu Asn Lys Tyr Phe Gly Asn Phe Gln Cys Lys Ile Phe
465                 470                 475                 480

Glu Gly Arg Leu Gln Ala Ile Phe Lys Arg Tyr Ala Asn Phe Asn Ala
                485                 490                 495

Leu Lys Asn Asn Lys Pro Gln Pro Ser Pro Asn Ile Ser Val Arg Ile
            500                 505                 510

Asn Glu Phe His Phe Ala Leu Arg Ser Tyr Arg Lys Gln Gln Ile Ser
        515                 520                 525

Ala Glu Asp Phe Ser Lys Gly Arg Phe Ser Leu Ile Ser Lys Ile Gly
    530                 535                 540

Phe Gln Met Thr Asn Asp Glu Val Phe Gly Arg Thr Pro Arg Glu Ile
545                 550                 555                 560

Ala Leu Val Lys Asp His Leu Ser Lys Gly Tyr Val His Phe Gly Ser
                565                 570                 575

Gln Ile Ile Glu Asp Ser Arg Lys Glu Val Glu Gln Val Leu Lys Lys
            580                 585                 590

Pro Met Ile Leu Met Gly Val Asp Phe Gly Tyr Ser Pro Leu Ala Ser
        595                 600                 605

Tyr Asn Ile Lys Pro Leu Gln Thr Gly Lys Pro Ala Thr Asp Trp Val
    610                 615                 620

Lys Asn Leu His Gly Asn Phe Leu Cys Gln Asn Val Ser Leu Gly Glu
625                 630                 635                 640

Thr Ile Thr Glu Gly Glu Ile Gly Asp Val Pro Thr Asp Thr Tyr Thr
                645                 650                 655

Ser Ser Asn Glu Ile Tyr Ser Ile Ala Thr Leu Thr Phe Arg Asn Ala
            660                 665                 670

Asp Gly Lys Leu Glu Asn Arg Ser Phe Ser Arg Phe Tyr His Glu Leu
        675                 680                 685

Asn Asn Thr Leu Asn Ile Ile Glu Gln Ile Lys Gly Thr Phe Asn Phe
    690                 695                 700

Ile His Ser Ile Asn Thr Gln Phe Lys Glu Ile Lys Ala Leu Lys Thr
705                 710                 715                 720

Thr Glu Glu Phe Ser Ser Tyr Val Ser Thr Leu Thr Trp Asp Gln Phe
                725                 730                 735

Ile Glu Asp Ser Arg Lys Thr Ala Arg Tyr Ser Lys Tyr Trp Ile His
            740                 745                 750
```

```
Ile Ile Asn Glu Asn Pro Lys Arg Arg Thr Ile Ala Thr Leu Asn Glu
        755                 760                 765

Thr Leu Lys Leu Val Asp Glu Lys His Arg Phe Thr Val Thr Ile Gln
    770                 775                 780

Glu Ile Phe Asp Leu Val Lys Tyr Cys Gln Gln His Gly Tyr Tyr Pro
785                 790                 795                 800

Lys Ser Asn Val Met Ser Lys Leu Arg Asn Leu Ala Ile Lys Leu Ile
                805                 810                 815

Asn Asp Leu Ile Arg Tyr Gln Lys Ile Gly Ile His Ser Cys Tyr Leu
            820                 825                 830

Asp Phe Cys Val Leu Ile Lys Asn His Ile Ala Leu Leu Asn Ser Ser
        835                 840                 845

Thr Ala Phe Ile Ile Asn Phe Ser Arg Asn Lys Glu Asn Ile Ile Arg
    850                 855                 860

Asn Asn Thr Ser Lys Ile His Ser Leu Trp Val Tyr Arg Asp Asn Phe
865                 870                 875                 880

Arg Arg Gln Met Ile Lys Asn Leu Cys Ser Gln Ile Leu Lys Ile Ala
                885                 890                 895

Ala Lys Asn Lys Val His Ile Val Val Val Glu Lys Leu Asn Asn Met
            900                 905                 910

Arg Thr Asn Asn Arg Asn Asn Glu Asp Lys Asn Asn Met Ile Asp Leu
        915                 920                 925

Leu Ala Thr Gly Gln Phe Arg Lys Gln Leu Ser Asp Gln Ala Lys Trp
    930                 935                 940

Tyr Gly Ile Ala Val Val Asp Thr Ala Glu Tyr Asn Thr Ser Lys Val
945                 950                 955                 960

Asp Phe Met Thr Gly Glu Tyr Gly Tyr Arg Asp Glu Asn Asn Lys Arg
                965                 970                 975

His Phe Tyr Cys Arg Lys Gln Asp Lys Thr Val Leu Leu Asp Cys Asp
            980                 985                 990

Lys Lys Ala Ser Glu Asn Ile Leu  Leu Ala Phe Val Thr  Gln Ser Leu
        995                 1000                1005

Leu Leu  Asn His Leu Lys Val  Leu Ile Thr Glu Asp  Gly Lys Thr
    1010                1015                1020

Ala Val  Ile Asp Leu Ser Glu  Arg Thr Thr Glu Pro  Gln Lys Ile
    1025                1030                1035

Arg Ser  Lys Ile Trp Thr Asn  Ser Asp Val Gln Lys  Ile Ile Phe
    1040                1045                1050

Cys Lys  Gln Glu Asn Gly Ser  Tyr Val Leu Lys Lys  Gly Ser Thr
    1055                1060                1065

Asp Ile  Lys Glu Lys Met His  Lys Ala Val Leu His  Arg His Gly
    1070                1075                1080

Ser Leu  Trp Tyr Asp Tyr Leu  Asn His Lys Asn Met  Ile Glu Asp
    1085                1090                1095

Ile Lys  Asn Leu His Leu Ser  Asn Cys Ser Leu Thr  Thr Ser Thr
    1100                1105                1110

Asn Ser  Asp Val Ile Asn Ser  His Ser Gly Ser Ser  Arg Ser Leu
    1115                1120                1125

Asp Lys  Thr Lys Thr Tyr Ala  Ser Arg Ala Asp Pro  Lys Lys Lys
    1130                1135                1140

Arg Lys  Val
    1145
```

<210> SEQ ID NO 91
<211> LENGTH: 1024
<212> TYPE: PRT
<213> ORGANISM: artificial sequence
<220> FEATURE:
<223> OTHER INFORMATION: amino acid sequence of Cas12j.12-NLS fusion protein

<400> SEQUENCE: 91

Met Ala Ser Ser Asp Ala Gln Lys Phe Pro Gln Thr His Asn Lys Val
1 5 10 15

Met Ser Phe Arg Leu Thr Ala Ser Asn Ile Gly Ser Val Leu Ser Leu
20 25 30

His Ser Asn Leu His Asp Ala Ala Glu Ile Gly Ile Asn Glu Cys Arg
35 40 45

Trp Trp Ile Gly Asp Gly Glu Ile Tyr Glu Arg Asp Pro Ala Cys Arg
50 55 60

Ser Ile Lys Lys Gly Asn Asp Ile Arg Thr Val Thr Ser Glu Lys Ile
65 70 75 80

Lys Glu Leu Trp Thr Lys His Thr Asp His Ser Val Pro Leu Val Asp
85 90 95

Phe Ile Asp Met Leu Lys Phe Val Ala Gln Cys Ala Ile Tyr Gly Asp
100 105 110

Ser Arg Ala Leu Ala Ser Thr Leu Phe Gly Lys Ser Lys Ala Glu Thr
115 120 125

Arg Gly Val Ser Thr Glu Asp Met Thr Val Ile Arg Ala Trp Ile Ala
130 135 140

Glu Thr Asp Ala Val Leu Ala Ser Gly Leu Ser Pro Lys Lys Lys Lys
145 150 155 160

Lys Lys Glu Lys Glu Ala Gly Lys Lys Glu Arg Lys Pro Asp Val Lys
165 170 175

Met Glu Met Cys Arg Arg Ile Arg Cys Thr Met Val Gln Cys Gly Tyr
180 185 190

Phe Arg Arg Phe Pro Phe Glu Ala Lys Ile Asp Asn Gly Gly Glu Arg
195 200 205

Gly Lys Met Asp Ser Glu Leu Ser Tyr Val Ser Ala Arg Asn Leu Leu
210 215 220

Arg Cys Leu Ser Thr Trp Arg Ala Ser Ser Val Met Arg Arg Asp Ser
225 230 235 240

Tyr Leu Ile Glu Glu Glu Arg Ile Lys Glu Ala Glu Ser Lys Met Thr
245 250 255

Pro Glu Ile Ile Asp Gly Leu Arg Arg Leu Tyr Arg Tyr Cys Ala Val
260 265 270

Asp His Asp Phe Leu Lys Trp Phe Gly Gly Arg Ile Ile Arg His Ile
275 280 285

Asp Ser Cys Leu Ala Pro Ala Ile Ala Gly Asn Thr Gly Arg Pro Thr
290 295 300

Gly Gly Glu Ser Phe Thr Val Ile Tyr Asp Arg Arg Lys Lys Arg Asp
305 310 315 320

Val Lys Ile Thr Tyr Ser Val Pro Glu Glu Ile Tyr Gly Tyr Leu Ser
325 330 335

Ser His Pro Glu Leu Val Ala Ile Gly Lys Asp Gly Met Thr Pro Ile
340 345 350

Ser Arg His Ala Asp Tyr Leu Glu Met Ile Ala Ser His Glu Lys His
355 360 365

```
Arg Trp Tyr Ala Thr Phe Pro Thr Val Gly Lys Glu Asp Gly Tyr Arg
    370                 375                 380

Thr Ser Val Leu Leu Gly Lys Asn Tyr Leu Thr Tyr Asp Leu Ser Tyr
385                 390                 395                 400

Asp Gly Glu Ser Val Pro Asp Lys Lys Ile Asn Val Ile Ser Lys Gly
                405                 410                 415

Gln Pro Val Cys Leu Asp Leu His Asp Gly Arg Arg Val Ser Ser Leu
            420                 425                 430

Tyr Leu Thr Val Gly Glu Ser Ala Ala Tyr Asp Ile Ala Val Arg Lys
        435                 440                 445

Asn Lys Arg His His Gly Lys Pro Ala Asp Tyr Cys Arg Met Arg Val
    450                 455                 460

His Leu Thr Gln Glu Arg Glu Asp Lys Thr Tyr Asn Asp Pro Tyr Phe
465                 470                 475                 480

Ser Asn Met Glu Ile Trp Arg Ala Gly Asp Gln Val Tyr Ala Ile Glu
                485                 490                 495

Phe Asp Arg His Gly Ala Arg Tyr Thr Ala Ile Val Lys Glu Pro Ser
            500                 505                 510

Val Glu Tyr Arg Asn Lys Lys Leu Tyr Leu Arg Val Asn Met Val Leu
        515                 520                 525

Asp Ser Pro Ser Arg Gln Asp Asp Lys Asp Met Tyr Tyr Ala Tyr Met
    530                 535                 540

Thr Ala Tyr Pro Ser Ser Asn Pro Pro Val Glu Thr Ser Asp Asn Lys
545                 550                 555                 560

Lys Arg Phe Glu Arg Leu Gly Pro Gly Arg Arg Ala Ile Gly Gly Ile
                565                 570                 575

Asp Ile Gly Ile Gly Arg Pro Tyr Val Ala Val Val Ala Ser Tyr Glu
            580                 585                 590

Val Gly Pro Ala Gly Thr Glu Gln Lys Phe Gln Ile Glu Asp Arg Leu
        595                 600                 605

Ile Glu Asp Asp Gly Ser Ser Pro Tyr Asp Ser Leu Tyr Asn Asp Phe
    610                 615                 620

Leu Thr Asp Ile Arg Thr Val Ser Arg Ile Ile Glu Ala Ala Lys Lys
625                 630                 635                 640

Ile Ser Glu Gly Asp Leu Glu Asp Ile Pro Ser Asp Met Ser Val Asp
                645                 650                 655

Glu Asp Gly Ser Ile Ala Ala Thr Met Lys Arg Met Ser Ala Arg Ile
            660                 665                 670

Ala Glu Arg His His Leu Tyr Gly Glu Arg Lys Ser Glu Ala Tyr Ala
        675                 680                 685

Thr Phe Leu Lys Met Asn His Lys Gln Arg Leu Asp Ile Leu Leu Thr
    690                 695                 700

Gln Lys Ala Ser Asn Ala Thr Leu Lys Gln Leu Val Glu Glu Asp Pro
705                 710                 715                 720

Ser Phe Leu Pro Arg Ile Cys Val Tyr Tyr Val Ile Ser Val Glu Arg
                725                 730                 735

Glu Leu Lys Asn Lys His Arg Asn Ala Tyr Leu Asp Gly Leu Thr Val
            740                 745                 750

Asp Glu Lys Tyr Ser Gly Glu Thr Lys Arg Gly Tyr Ala Gln Lys Arg
        755                 760                 765

Leu Asn Ser Met Leu Arg Ala Tyr Ser Ala Leu Gly Glu Glu Glu Thr
    770                 775                 780
```

```
Asp Glu Val Arg Thr Phe Ser Thr Arg Ser Glu Lys Val Arg Asn Met
785                 790                 795                 800

Ala Lys Asn Ala Ile Lys Arg Asn Ala Arg Lys Leu Val Asn Phe Tyr
                805                 810                 815

Val Gly Lys Gly Ile Arg Thr Ile Val Ala Glu Asp Thr Asp Pro Thr
            820                 825                 830

Lys Ser Arg Asn Asp Gly Lys Lys Ser Asn Arg Ile Lys Ala Ala Trp
        835                 840                 845

Ser Pro Lys Gln Phe Leu Ala Ala Val Lys Asn Ala Ala Gln Trp His
    850                 855                 860

Gly Leu Glu Ile Ala Glu Val Asp Pro Arg Met Thr Ser Gln Val His
865                 870                 875                 880

Pro Glu Thr Gly Leu Ile Gly Tyr Arg Asp Gly Asp Thr Leu His Cys
                885                 890                 895

Pro Asp Gly Ser Lys Ile Asp Ala Asp Val Ala Gly Ala Ala Asn Val
            900                 905                 910

Cys Arg Val Phe Ala Gly Arg Gly Leu Trp Arg Phe Ser Ile Asn Thr
        915                 920                 925

Asn Ile Asp Ile Ser Asn Lys Asp Glu Lys Lys Arg Leu Arg Ala Tyr
    930                 935                 940

Ile Val His His Phe Gly Ser Glu Ser Asn Trp Glu Lys Phe Arg Lys
945                 950                 955                 960

Gln Tyr Pro Ser Gly Thr Thr Leu Tyr Leu His Gly Arg Glu Trp Leu
                965                 970                 975

Thr Ala Glu Glu His Lys Ser Ala Ile Asp Arg Ile Arg Asp Asp Val
            980                 985                 990

Gly Arg Asp Ala Glu Asn Asp His  Val Ala Ile Val Thr  Ala Ala Glu
        995                 1000                1005

Lys Val  Glu Ile Phe Ser Arg  Ala Asp Pro Lys Lys  Lys Arg Lys
    1010                1015                1020

Val
```

<210> SEQ ID NO 92
<211> LENGTH: 1063
<212> TYPE: PRT
<213> ORGANISM: artificial sequence
<220> FEATURE:
<223> OTHER INFORMATION: amino acid sequence of Cas12j.13-NLS fusion protein

<400> SEQUENCE: 92

```
Met Ser His Asp Leu Lys Pro Gln Arg Leu Ile Arg Ser Asn Ile Thr
1               5                   10                  15

Lys Thr His Ser Asp Gln Asn Ala Lys Gln Val Ala Glu Glu Val Lys
            20                  25                  30

Lys Glu His Leu Asn Tyr Leu Leu Ile Lys Asn Glu Met Leu Ile Ser
        35                  40                  45

Ile Val Pro Glu Ala Lys Asp Asp Asp Gly Asn Asp Ile Asp Phe Lys
    50                  55                  60

Lys Gln Leu Lys Ser Leu Tyr Lys Glu Thr Asp Gln Ser Val Ser Phe
65                  70                  75                  80

Ser Val Phe Cys Gln Met Met Lys Phe Arg Asn Ile Ala Leu Leu Tyr
                85                  90                  95

Ala Lys Gly Gln Ser Arg Trp Ala Val Ser Ser Tyr Phe Thr Gly Asn
            100                 105                 110
```

```
Arg Arg Lys Asp Asp Tyr Ala Lys Asp Leu Ser Leu Leu Asp Glu Ala
        115                 120                 125

Ile Glu Leu Leu Glu Cys Lys Arg Arg Lys Lys Ala Glu Glu Glu Asn
    130                 135                 140

Glu Glu Glu Asn Glu Thr Pro Lys Lys Lys Glu Asp Asn Pro Ser Asn
145                 150                 155                 160

Ile Ser Glu Glu Gln Ile Met Lys Leu Phe Tyr Ala Val Asn Lys Lys
                165                 170                 175

Leu Lys Glu Ile Gly Tyr Leu Asp Arg Tyr Ser His Ile Glu Lys Gln
            180                 185                 190

Glu Gln Tyr Ala Ile Ile Gly Val Thr Ser Arg Thr Val Lys Ala Trp
        195                 200                 205

Asp Tyr Ala Asn Phe Ala Thr Arg Asn His Tyr Gln Ser Val Gln Asn
    210                 215                 220

Glu Tyr Gln Lys Lys Leu Lys Ala Leu Pro Gly Thr Lys Lys Asp Lys
225                 230                 235                 240

Val Cys Leu Glu Lys Phe Phe Asp His Leu Asn Glu Asn Asn Ile Ala
                245                 250                 255

Ala Asp Trp Asp Lys Trp Arg Leu Lys Lys His Ile Leu Gln Cys Ile
            260                 265                 270

Ile Pro Ala Ala Lys Ile Gly Leu Lys Glu Leu Lys Gln Ser Phe Tyr
        275                 280                 285

Val Asp Asn Lys Gly Asn Lys His Asn Tyr Phe Val Asn Gly Leu Tyr
    290                 295                 300

Glu Glu Ile Leu Lys Arg Pro Phe Leu Tyr Ser Ala Glu Asp Pro Glu
305                 310                 315                 320

Glu Ser Ile Leu Tyr Leu Gly Val Glu Val Ala Ser Leu His Ser Lys
                325                 330                 335

Leu Asn His Leu Arg Ser Glu Ala Arg Phe Ser Phe Glu Thr Pro Asp
            340                 345                 350

Asp Ile Cys Lys Tyr Met Thr Ile Cys Gly Asp Asn Tyr His Asn Phe
        355                 360                 365

Thr Met Ser Ala Ile Gly Glu Asp Val Glu Asp Ile Glu Val Glu Val
    370                 375                 380

Tyr Asp Tyr Asn His Ser Lys Lys Tyr Glu Thr Met Arg Phe Ile Asn
385                 390                 395                 400

Gly Lys Arg Thr Thr Asp Leu Ser Leu Asn Phe Lys Gly Ile Pro Val
                405                 410                 415

Arg Leu Cys Leu Glu Gly Lys Arg Asn Asn Ser Tyr Phe Ala Asp Ala
            420                 425                 430

Ile Val Trp Glu Leu Asp Asn Lys Asp Lys Thr Gly Tyr Leu Ile Glu
        435                 440                 445

Tyr Gly Lys Ser Asn Asn Arg Leu Tyr Met Leu Val Lys Glu Pro Leu
    450                 455                 460

Ile Gly Cys Arg Arg Lys Phe Gly Lys Asp Val Leu Phe Val Ser Leu
465                 470                 475                 480

Ser Gly Thr Leu Val Asn Lys Tyr Ile Glu Asp Asp Ile Val Ser Ala
                485                 490                 495

Arg Tyr Leu Met Gln Thr Ala Ala Pro Ile Phe Lys Thr Ser Arg Ala
            500                 505                 510

Lys Lys Gln Asp Lys Ile Gly Asp Lys Trp Phe Glu His Cys Gln Gly
        515                 520                 525

Ser Thr Ile Lys Ile Ala Gly Ile Asp Ile Gly Ile Asn Pro Ile Ala
```

```
    530                 535                 540

Ala Ile Thr Val Ala Asn Val Thr Phe Asp Arg Ala Leu Gly Asn Lys
545                 550                 555                 560

Ile Lys Asn Gln Lys Gln Ile Val Ile Asp Cys Tyr Ala Glu Asp Tyr
                565                 570                 575

Lys Ile Asp Pro Val Val Val Lys Arg Met Glu Asp Ile Arg His Ile
            580                 585                 590

Lys Tyr Thr Ile Asn Ser Trp Tyr His Leu Ala Asp Cys Cys Arg Leu
        595                 600                 605

Lys Ala Ala Asn Lys Glu Tyr Val Val Asn Glu Arg Lys Gln Gly Phe
    610                 615                 620

Phe Arg Glu Asn Ile Glu Tyr Leu Lys Glu Val Ala Lys Lys Ala Ile
625                 630                 635                 640

Thr Glu Ser Asp Gln Gln Ile Lys Glu Gln Lys Ala Ala Leu Lys Arg
                645                 650                 655

Phe Asp Gly Glu Lys Lys Lys Glu Ile Gln Ala Thr Ile Asn Gly Phe
            660                 665                 670

Asn Leu Lys Ile Lys Ile Leu Lys Lys Phe Val Arg Gln Ser Ala Lys
        675                 680                 685

Lys Ile Phe Asp Ser Thr Leu Glu Thr Leu Glu Lys Tyr Asp Asn Asn
    690                 695                 700

Ile Glu Gln Ala Lys Arg Asp Arg Glu Phe Gly Leu Lys Ile Ile Tyr
705                 710                 715                 720

Asp Leu Ile Ile Lys Tyr Tyr Lys Arg Ser Lys Lys Glu Arg Glu Met
                725                 730                 735

Asn Gln Arg Ile Tyr Val Asp Asp Tyr Asn Gln Glu Glu Ile Asp Thr
            740                 745                 750

Glu Arg Thr Lys Lys Ile Arg Lys Glu Thr Ile Thr Phe Cys Asp Asn
        755                 760                 765

Asp Trp Asn Ser Leu Thr Lys Arg Ile His Asp Leu Glu Lys Lys Met
    770                 775                 780

Lys Lys Ile Gly Ile Ser Glu Pro Gly Arg Val Glu Gln Glu Ile Asn
785                 790                 795                 800

Asp Arg Asp Tyr Tyr Asn Asn Ile Gln Asp Asn Thr Lys Lys Arg Gln
                805                 810                 815

Ala Lys Ile Ile Val Asp Ala Leu Lys Glu Glu Gly Val Ser Ile Ile
            820                 825                 830

Val Val Glu Asp Leu Thr Gly Gly Gly Ser Glu Asn Thr Lys Glu Ile
        835                 840                 845

Asn Lys Ser Phe Asp Ala Phe Ala Pro Ile Arg Phe Leu Asn Ala Leu
    850                 855                 860

Lys Asn Cys Ala Glu Thr Asn Gly Ile Gln Val Thr Glu Val Leu Ser
865                 870                 875                 880

Pro Met Ser Ser Lys Met Val Pro Ser Thr Gly Glu Ile Gly His Arg
                885                 890                 895

Asp Lys Arg Asp Lys Gln Leu Tyr Tyr Lys Asp Gly Glu Glu Leu Lys
            900                 905                 910

Ser Ile Asp Gly Asp Ile Ser Ala Ser Glu Ile Leu Leu Arg Arg Gly
        915                 920                 925

Val Ser Arg His Thr Glu Leu Ile Gly Thr Met Asn Val Glu Asp Val
    930                 935                 940

Leu Asp Lys Asn Asn Asn Lys Asn Lys Cys Ile Lys Gly Tyr Val Cys
945                 950                 955                 960
```

```
Asn Arg Trp Gly Asn Ile Gln Asn Phe Glu Lys Ile Leu Lys Glu Lys
                965                 970                 975

Gly Ile Gly Glu Arg Glu Ile Ile Tyr Leu His Gly Asp Lys Ile Leu
            980                 985                 990

Thr Met Asp Glu Lys Arg Thr Leu  Gln Ala Ser Ile Arg  Lys Glu Leu
        995                 1000                 1005

Lys Glu  Met Arg Glu Arg Glu  Ser Gly Glu Glu Asn  Ala Gly Thr
    1010                 1015                 1020

Ala Arg  Lys Lys Ser Lys Pro  Lys Lys Lys Lys Lys  Ile Lys Arg
    1025                 1030                 1035

Asn Asn  Asp Gln Asp Leu Ser  Asn Asn Arg Pro Ala  Ala Ser Ser
    1040                 1045                 1050

Arg Ala  Asp Pro Lys Lys Lys  Arg Lys Val
    1055                 1060


<210> SEQ ID NO 93
<211> LENGTH: 1056
<212> TYPE: PRT
<213> ORGANISM: artificial sequence
<220> FEATURE:
<223> OTHER INFORMATION: amino acid sequence of Cas12j.14-NLS fusion
      protein

<400> SEQUENCE: 93

Met Lys Glu Asn Lys Met Lys Glu Asn Gly Ser Met Thr Thr His Ser
1               5                   10                  15

Lys Val Ile Ala Leu Lys Met Lys Ser Glu Asn Val Glu Phe Asp Thr
            20                  25                  30

Phe Tyr Lys Glu Ser Phe Glu Leu Phe Lys Gln Phe Thr Asn Glu Phe
        35                  40                  45

Val Ala Trp Gly Asn Asp Glu Ile Tyr Gln Tyr Gly Ser Ser Lys Arg
    50                  55                  60

Lys Lys Asp Asp Gln Lys Ile Ser Leu Ile Pro Val Ile Glu Asp Ile
65                  70                  75                  80

Tyr Lys Ser Val Glu Lys Lys Ala Thr Ala Glu Gly Ile Ser Lys Thr
                85                  90                  95

Asp Phe Arg Ala Val Leu Lys Tyr Leu Tyr His Gln Ile Ile Asn Val
            100                 105                 110

Gly Asn Ser Gly Arg Ser Tyr Gly Thr Ser Leu Phe Gly Gly Cys Glu
        115                 120                 125

Val Lys Glu Lys Leu Ser Lys Gln Asp Ile Ser Asn Ile Val Glu Cys
    130                 135                 140

Val Lys Glu Leu Glu Leu Cys Lys Ser Lys Gln Glu Glu Ser Asp Ala
145                 150                 155                 160

Tyr Asp Lys Ile Leu Leu Lys Glu Lys Ile Thr His Ile Val Lys Ser
                165                 170                 175

Gly Glu Thr Ala Gly Asp Ile Thr Lys Lys Tyr Asn Gln Ala Thr Thr
            180                 185                 190

Gly Arg Lys Thr Ser Ser Lys Gly Phe Phe Asp Lys Ser Thr Lys Thr
        195                 200                 205

Glu Val Lys Tyr Lys Asp Ile Lys Asp Asp Thr Leu Leu Gln Asp Gly
    210                 215                 220

Ser Thr Ile Phe Ile Lys Ser Ser Val Asp Leu Phe Val Lys Lys Val
225                 230                 235                 240

Cys Asn Thr Leu Arg Glu Ile Asn Phe Phe Asp Arg Leu Pro Phe Lys
```

```
                245                 250                 255

Asn Asn His Ser Asn Asn Tyr Gly Leu Leu Phe Ser Met Leu Ser Gln
            260                 265                 270

Ile Glu Ser Trp Lys Thr Ile Ser Glu Thr Thr Lys Lys Ser His Glu
        275                 280                 285

Glu His Gly Glu Lys Ile Ala Ser Met Val Lys Lys Leu Asp Leu Thr
    290                 295                 300

Gln Thr Glu Leu Met Lys Asp Phe Ala Ala Phe Cys Ile Glu Asn Asn
305                 310                 315                 320

Ile Thr Lys Lys Phe Asp His Lys Phe Lys Arg His Met Glu Asp Cys
                325                 330                 335

Val Ile Pro Ser Phe Lys Asn Gly Lys Ile Pro Asp Lys Leu Phe Tyr
            340                 345                 350

Phe Asn Ile Ile Leu Ala Lys Lys Thr Asp Glu Gln Ile Asp Tyr Ser
        355                 360                 365

Leu Ser Ser Glu Phe Tyr Thr Lys Leu Phe Ser Met Pro Asn Leu Trp
    370                 375                 380

Gln Glu Glu Glu Ala Phe Ile Val Lys Asn Ile Asn Leu Ile Glu Glu
385                 390                 395                 400

Ile Thr Ile Phe Asn Lys Arg Arg Asn Tyr Ala Cys Cys Pro Leu Ile
                405                 410                 415

Lys Glu Lys Glu Tyr Asp Arg Phe Gln Ile Gln Leu Asn Glu Thr Asn
            420                 425                 430

Phe Leu Lys Phe Gln Phe Asp Pro Lys Asn Val Val Asn Ile Asp Glu
        435                 440                 445

Asn Thr Thr Glu Ala Thr Val Gly Phe Asp Glu Lys Leu Lys Leu Val
    450                 455                 460

Val Cys Ala Asp Lys Lys Tyr Ala Phe Ser Ile Phe Thr Gln Cys Lys
465                 470                 475                 480

Tyr His Gly Asn Lys His Lys Pro Asn Thr Tyr Phe Asn Asn Leu Lys
                485                 490                 495

Ile Ile Lys Val Ile Glu Ser Lys Ser Asn Ser Val Lys Ser Met Lys
            500                 505                 510

Tyr Thr Phe Glu Phe Thr Lys Arg Asn Glu Leu Lys Arg Ala Glu Ile
        515                 520                 525

Lys Gln Pro Ser Ile Val Tyr Lys Asn Asn Asn Tyr Tyr Ile Arg Ile
    530                 535                 540

Asn Met Asn Val Ile Leu Asp Ala Asp Gln Thr Ser Tyr Lys Ile Ile
545                 550                 555                 560

Asn Asn Asn Gln Thr Ala Ser Leu Pro Ser Tyr Phe Gln Ser Ser Leu
                565                 570                 575

Pro Phe Glu Asn Asn Arg Gly Lys Ile His Asp Lys Gly Ile Val His
            580                 585                 590

Trp Glu Lys Ile Lys Asn Arg Lys Ile Ile Ala Met Gly Val Asp Leu
        595                 600                 605

Gly Val Arg Arg Pro Phe Ser Tyr Ala Ile Gly Asn Phe Thr Leu Asn
    610                 615                 620

Lys Asp Ile Leu Asp Lys Asn Asp Val Asn Ile Val Ala Ser Gly Phe
625                 630                 635                 640

Asn Leu Cys Ser Asp Ser Asp Val Tyr Phe Gln Val Phe Asn Gln Ile
                645                 650                 655

Lys Thr Leu Ala Lys Phe Ile Gly Lys Leu Lys Ser His Asn Lys Gly
            660                 665                 670
```

Leu Lys Val Asp Phe Glu Lys Asp Lys Lys Tyr Ile Phe Asp Leu Val
675 680 685

Asn Asp Ala Lys Ala Tyr Phe Lys Asp Met Ser Ala Lys Arg Ile Asn
690 695 700

Asp Thr Lys Asp Asn Ile Ser Asn Thr Val Thr Asn Lys Glu Arg Ile
705 710 715 720

Tyr Gly Ser Phe Val Ser Glu Ser Ala Glu Ser Ala Ile Gln Cys Ala
725 730 735

Ile Asp Arg Ser Glu Lys Glu Ser Gly Leu Thr Leu Lys Lys Asp Ile
740 745 750

Ser Trp Leu Val Asn Val Leu Ser Lys Tyr Leu Glu Arg Lys Phe Lys
755 760 765

Glu Val Lys Asn Asn Arg Lys Tyr Thr Asn Val Asn Lys Cys Asp Asn
770 775 780

Cys Phe Asn Trp Leu Arg Val Ile Glu Asn Ile Lys Arg Leu Lys Arg
785 790 795 800

Ser Ile Ser Tyr Leu Gly Glu Asp Leu Gln Lys Asn Pro Glu Leu Lys
805 810 815

Ile Glu Leu Lys Asn Leu Asn Glu Tyr Gly Asn Asn Val Lys Ser Asp
820 825 830

Phe Leu Lys Gln Ile Ala Ser Asn Ile Ile Lys Val Ala Ile Glu His
835 840 845

Lys Cys Asp Ile Val Phe Ile Glu Lys Leu Gly Lys Ala Asp Ser Arg
850 855 860

Ser Arg Lys Leu Asn Glu Met Phe Ser Phe Trp Ser Pro Lys Ala Ile
865 870 875 880

Lys Lys Ala Ile Glu Asn Ala Ala Ser Trp His Gly Ile Pro Val Val
885 890 895

Glu Val Asp Pro Ser Cys Thr Ser Lys Val His Tyr Glu Thr Asn Leu
900 905 910

Phe Gly His Arg Ile Gly Asn Asp Leu Tyr Tyr Val Glu Asp Gln Cys
915 920 925

Leu Lys Lys Val Asp Ala Asp Ile Asn Ala Ala Lys Gln Ile Leu Val
930 935 940

Arg Gly Ala Thr Arg His Gly Asn Ile Ser Ser Ile Asn Ile Lys Tyr
945 950 955 960

Leu Gln Ala Lys Ile Ala Glu Leu Asn Ser Glu Ala Asn Ser Glu Glu
965 970 975

Asp Lys Glu Glu Ile Lys Gln Gly Gly Lys Arg Ile Gln Gly Phe Leu
980 985 990

Trp Lys Lys Tyr Gly Asn Ile Thr Asn Ile Thr Asn Gln Leu Thr Ala
995 1000 1005

Ala His Lys Glu Arg Glu Ser Lys Phe Asp Tyr Ile Tyr Leu His
1010 1015 1020

Asn Asp Lys Trp Ile Ala Tyr Glu Asp Arg Asn Glu Ile Lys Lys
1025 1030 1035

Asp Ile Glu Lys Arg Leu Glu Ser Arg Ala Asp Pro Lys Lys Lys
1040 1045 1050

Arg Lys Val
1055

<210> SEQ ID NO 94
<211> LENGTH: 906

<212> TYPE: PRT
<213> ORGANISM: artificial sequence
<220> FEATURE:
<223> OTHER INFORMATION: amino acid sequence of Cas12j.15-NLS fusion protein

<400> SEQUENCE: 94

Met Thr Ala Lys Lys Thr Ala Lys Lys Tyr Phe Pro Pro Lys Cys Leu
1 5 10 15

Arg Ser Ser His Phe Lys Ile Tyr Gly Ile Pro Thr Ala Ile Arg Ala
20 25 30

Leu Glu Glu Thr Asn Thr Phe Val Asn Lys Ala Ala Ala Asp Leu Met
35 40 45

Glu Met Phe Phe Leu Met Arg Gly Gln Pro Tyr Arg Arg Arg Ile Gly
50 55 60

Ser Glu Glu Lys Gln Val Thr Gln Glu His Ile Asp Ala Arg Leu Arg
65 70 75 80

Val Leu Val Gly Asp Tyr Ser Leu Asn Glu Val Lys Pro Leu Leu Arg
85 90 95

Gln Leu Tyr Asp Gly Ile Lys Ala Lys Gln Asn Tyr Ala Pro Thr His
100 105 110

Phe Val Arg Phe Phe Ile Gln Pro Thr Lys Gly Ala Ile Asp Lys Lys
115 120 125

Ser Pro Val Ser Gln Arg Ala Lys Lys Ala Gly Gln Lys Leu Gln Lys
130 135 140

Met Gly Val Leu Pro Ile Leu Pro Leu Ser Pro Gly Phe Lys Phe Trp
145 150 155 160

Thr Ala Ala Met Met Met Ala Cys Ser Arg Met Asn Ser Trp Glu Ala
165 170 175

Cys Asn Glu Lys Thr Ile Glu Asn His Lys Ala Phe Leu Glu Gly Ile
180 185 190

Glu Asn Tyr Lys Lys Glu Ile Arg Phe Glu Asp Leu Cys Glu Glu Trp
195 200 205

Ser Leu Phe Ser Asp Trp Leu Thr Glu Ala Glu Ser Asp Asn Glu Gly
210 215 220

Gly Cys Lys Phe Lys Leu Thr Pro Arg Phe Leu Gln Arg Trp Glu Arg
225 230 235 240

Ile Tyr Leu Lys Gln Met Arg Lys Gly Lys Ile Pro Ala Arg His Asn
245 250 255

Leu Gly Pro Val Met Glu Ala Leu Ala Gly Asp Lys Tyr Arg Gln Leu
260 265 270

Trp Asp Asn Gly Glu Glu Arg Asp Tyr Ile Thr Glu Leu Gly Asp Leu
275 280 285

Val Thr Ser Gln Arg Lys Ala Val Arg Leu Ser Arg Asp Ser Ala Val
290 295 300

Thr Phe Pro Asp Glu Glu Leu Ser Pro Val Gly Thr Glu Phe Gly His
305 310 315 320

Asn Tyr Met Ser Phe Ser Ile Asp Gln Glu Asn Ser His Leu Val Thr
325 330 335

Leu Glu Val Ile Gly Gly Lys Tyr Gln Phe Glu Ile Ser Lys Ser Asp
340 345 350

Tyr Phe Arg Asp Leu Ile Val Glu Glu Ala Gly Lys Gln Ser Lys Phe
355 360 365

Tyr Asn Val Ser Tyr Arg Lys Gly Asn Val Arg Glu Glu Asn Leu Ala
370 375 380

```
Gly Asp Phe Lys Glu Ala Thr Val Arg Asn Arg Arg Ser Leu Lys Thr
385                 390                 395                 400

Gly Lys Arg Arg Leu Tyr Phe Tyr Met Ser His Ser Ile Pro Thr Arg
                405                 410                 415

Phe Asp Asp Asp Leu Tyr Ala Gln Phe Thr Glu Lys Gly Gln Pro Asp
            420                 425                 430

Phe Ser Lys Leu Tyr Lys Ala Val Thr Tyr Phe Gln Cys Ser Leu Gly
        435                 440                 445

Asn Lys Lys Ala Asp Thr Tyr Arg Val Tyr Val Lys Met Gly Thr Arg
    450                 455                 460

Phe Leu Gly Val Asp Ile Gly Val Ser Arg Leu Phe Gly Phe Ser Leu
465                 470                 475                 480

Phe Glu Leu Arg Glu Glu Lys Pro Glu Lys Asn Pro Phe Phe Glu Leu
                485                 490                 495

Pro Asp Asp Leu Gly Tyr Ala Val Cys Leu Glu Ser Trp Val Asp Gly
            500                 505                 510

Val Glu Lys Asn His Lys Val Ala Gln Glu Met Lys Asp Trp Arg Arg
        515                 520                 525

Glu Cys Leu Ala Ala Gln Arg Leu Ile His Tyr Ala Lys Phe Leu Lys
    530                 535                 540

Lys Arg Asp Lys Asn Glu Glu Ile Asp Tyr Lys His Glu Glu Ser Leu
545                 550                 555                 560

Glu Thr Ile Ala Gly Leu Leu Gly Ile Glu Ile Asp Pro Glu Gln Ile
                565                 570                 575

Ile Asp Val Pro Leu Lys Leu Leu Asp Leu Val Gly Gln Ala Ile Gly
            580                 585                 590

Ala Leu Arg Lys Lys Tyr Leu Val Leu Lys Lys Asn Glu Val Arg Gln
        595                 600                 605

Gly Arg Ile Thr Ser Glu Leu Phe Leu Trp Pro Glu Cys Val Asp Thr
    610                 615                 620

Tyr Ile Arg Leu Leu Lys Ser Trp Thr Tyr Lys Asp Lys Lys Pro Tyr
625                 630                 635                 640

Gln Lys Gly Glu Thr Asn Lys Asp Ala Phe Lys Lys Leu Lys Gly Tyr
                645                 650                 655

Leu Ala Arg Leu Arg Lys Asp Leu Ala Pro Lys Tyr Ala Ala Val Ile
            660                 665                 670

Ala Asp Ala Ala Ile Arg His Lys Val His Val Val Val Ala Glu Asn
        675                 680                 685

Leu Glu Gln Phe Gly Leu Ser Met Lys Asn Glu Lys Asp Leu Asn Arg
    690                 695                 700

Val Leu Ala His Trp Ser His Gln Lys Ile Trp Ser Met Val Glu Glu
705                 710                 715                 720

Gln Leu Arg Pro Tyr Gly Ile Met Val Val Tyr Val Asp Pro Arg His
                725                 730                 735

Thr Ser Lys Leu Asp Phe Ala Thr Asp Glu Phe Gly Gly Arg Cys Phe
            740                 745                 750

Thr Ser Leu Tyr Val Met Arg Asp Gly Lys Lys Thr Thr Thr Asp Thr
        755                 760                 765

Glu Lys Asn Ala Ser Gln Asn Ile Pro Lys Lys Phe Leu Thr Arg His
    770                 775                 780

Arg Asn Val Ser Trp Leu Leu Ala Tyr Ala Val Asp Leu Ser Asp Ser
785                 790                 795                 800
```

```
Gln Lys Lys Lys Leu Gly Ile Gly Asp Glu Lys Val Trp Leu Pro Asn
                805                 810                 815

Met Gly Leu Met Ile Ser Gly Ala Leu Lys Ala Lys His Gly Lys Asn
            820                 825                 830

Ser Ala Leu Leu Val Glu Asp Gly Glu Asn Tyr Arg Leu Leu Pro Ile
        835                 840                 845

Thr Ala Ala Gln Ala Lys Lys Phe Val Val Lys Arg Lys Lys Glu Glu
    850                 855                 860

Phe Tyr Arg His Gly Glu Ile Trp Leu Thr Lys Glu Ala His Lys Ala
865                 870                 875                 880

Arg Ile Glu Tyr Leu Phe Pro Glu Ser Lys Lys Gly Arg Lys Ser Ser
                885                 890                 895

Arg Ala Asp Pro Lys Lys Lys Arg Lys Val
            900                 905
```

<210> SEQ ID NO 95
<211> LENGTH: 967
<212> TYPE: PRT
<213> ORGANISM: artificial sequence
<220> FEATURE:
<223> OTHER INFORMATION: amino acid sequence of Cas12j.16-NLS fusion protein

<400> SEQUENCE: 95

```
Met Lys Lys Thr Asn Tyr Lys Thr Ser His Leu Leu Ile Asp Asn Pro
1               5                   10                  15

Pro Gln Ser Ile Ile Asp Leu His Arg Asp Val Ile Glu Ile Gly Ser
            20                  25                  30

Tyr Leu Thr Lys Phe Phe Leu Ala Cys Leu Gly Arg Pro Val Asp Ser
        35                  40                  45

Thr Ile Leu Ser Glu Pro Ala Leu His Phe Gln Phe Val Asn Gly Ile
    50                  55                  60

Leu Pro Val Lys Asn Gly Pro Gly Ala Asp Asp Ser Ser Trp Arg His
65                  70                  75                  80

Ser Glu Asn Cys Tyr Ser Met Leu Phe Glu Lys Asn Ser Lys Ser Gly
                85                  90                  95

Lys Ser Asp Gly Lys Val Arg Gln Val Arg Glu Leu Lys Val Ala Leu
            100                 105                 110

Phe Gly Lys Lys Glu Lys Gly Lys Gly Ile Val Gly Lys Lys Thr Trp
        115                 120                 125

Asp Glu Leu Lys Val Val Leu Glu Ala Leu Pro Glu Glu His Gln Ile
    130                 135                 140

Leu Ser Leu Glu Ile Cys Gln Arg His Tyr Glu Ser Arg Asp Val Lys
145                 150                 155                 160

Ala Phe Gly Lys Leu Ala Leu Ser Ser Lys Ser Arg Pro Ser Val Glu
                165                 170                 175

Ala Gly Leu Lys Leu Arg Glu Leu Gly Leu Leu Pro Leu Asp Ser Arg
            180                 185                 190

Gly Leu Asp Lys Asn Lys Leu Leu Gly Ile Leu Ala Ala Val Thr Gly
        195                 200                 205

Arg Leu Lys Ser Trp Arg Asp Arg Asp Cys Ala Cys Lys Ala Asp Lys
    210                 215                 220

Gln Ala Leu Arg Val Lys Phe Glu Glu Arg Leu Ser Lys Val Asp Gln
225                 230                 235                 240

Ser Ala Tyr Gln Gln Phe Lys Gln Phe Ala Asp Glu Leu Leu Thr Gln
                245                 250                 255
```

```
Glu Gly Tyr Arg Ile Ser Gly Arg Val Leu Arg Ala Val Glu Lys Lys
            260                 265                 270

Asp Ser Asp Tyr Ser Pro Val Leu Thr Val Leu Ala Lys Tyr Pro Asp
        275                 280                 285

Leu Gln Asp Asn Phe Glu Glu Leu Cys Arg Ala Cys Leu Ala Glu Gln
    290                 295                 300

Ala Phe Asn Lys Lys Lys Ala Asp Ala Arg Val Thr Val Cys Ser Glu
305                 310                 315                 320

Thr Ser Pro Leu Gln Phe Pro Phe Gly Met Thr Gly Asn Gly Tyr Pro
                325                 330                 335

Phe Thr Leu Ser Ala Cys Glu Gly Arg Ile Asn Ala Thr Ile His Phe
            340                 345                 350

Pro Gly Gly Asp Leu Pro Leu Arg Leu Arg Lys Ser Lys Tyr Phe Gln
        355                 360                 365

Asn Pro Glu Ile Leu Pro Val Lys Asp Gly Phe Gln Ile Thr Phe Thr
    370                 375                 380

Arg Gly Lys Thr Pro Leu Val Gly Thr Ile Lys Glu Pro Ser Leu Leu
385                 390                 395                 400

Lys Lys Asn Asn His Tyr Tyr Leu Ser Leu Arg Val Asn Val Pro Ser
                405                 410                 415

Val Lys Ile Pro Lys Glu Val Arg Asp Thr Arg Ala Tyr Tyr Ser Ser
            420                 425                 430

Ala Val Gly Gly Asp Glu Thr Thr Pro Val Pro Val Lys Ala Val Ala
        435                 440                 445

Ile Asp Leu Gly Val Thr Thr Leu Ala Asp Tyr Ser Ile Ile Asp Thr
    450                 455                 460

Cys Leu Pro Gly Asp Cys Lys Val Phe Gly Gly Glu Thr Ala Ala Phe
465                 470                 475                 480

Thr Ala His Gly Lys Ile Gly Gln Cys Ala Asn Lys Ser Leu Arg Asp
                485                 490                 495

Arg Leu Tyr Lys Asn Thr Glu Glu Ala Leu Phe Leu Gly Lys Phe Ile
            500                 505                 510

Arg Leu Ser Lys Lys Leu Arg Asp Gly Glu Gly Leu Asn Arg Trp Glu
        515                 520                 525

Val Glu Lys Leu Pro Gly Tyr Ala Glu Arg Leu Gly Ile Thr Gln His
    530                 535                 540

Leu Asp Asn Ala Tyr Thr Arg Lys Asp Glu Ile Ala Arg Lys Phe Lys
545                 550                 555                 560

Gln Ile Lys Gly Asn Phe Asp Lys Leu Val Ser Glu Phe Ala Leu Arg
                565                 570                 575

Asp His Pro Ser Lys Lys Gly Glu Ser Trp Glu Thr Ile Ser Ala Glu
            580                 585                 590

Thr Ile Gln Val Leu Ala Ala Leu Lys Arg Ile Gln Ser Leu Leu Lys
        595                 600                 605

Ser Trp Thr Tyr Tyr Ser Trp Thr Ala Glu Asp Tyr Val Leu Ala Leu
    610                 615                 620

Thr Ala Asp Gly Pro Val Cys Ile Asp Gly Glu His Val Lys Ala Val
625                 630                 635                 640

Thr Ala Thr Ser Arg Arg Ser Phe Ala Pro Cys Gly Lys Ala Ala Leu
                645                 650                 655

Leu Arg Leu Ile Glu Ser Gly Glu Ile Val Glu Thr Gly Gly Gln Tyr
            660                 665                 670
```

```
Gln Leu Ala Thr Gly Val Lys His Arg Asn His Pro Val Asn Phe Leu
        675                 680                 685

Ser Ser Tyr Ile Lys His Phe Asn Gly Leu Arg Arg Asp Leu Thr Asn
    690                 695                 700

Lys Leu Val Arg Ala Ile Val Asn Lys Ala Gln Glu Tyr Arg Val Gln
705                 710                 715                 720

Ile Val Ile Val Glu Asp Phe Gly Ile Ala Asp Leu Glu Asp Arg Ile
                725                 730                 735

Lys Asp Ala Tyr Glu Asn Tyr Arg Trp Asn Leu Phe Ala Pro Ala Thr
            740                 745                 750

Ile Val Lys Lys Leu Glu Ala Ala Leu Leu Glu Val Gly Ile Ala Met
        755                 760                 765

Ala Gln Val Asp Pro Arg His Thr Ser Gln Ile Ala Pro Thr Gly Ala
    770                 775                 780

Phe Gly Phe Arg Asp His Ala Phe Leu Tyr Tyr Gln Asp Asp Gly Leu
785                 790                 795                 800

Cys Arg Ile Asp Ala Asn Thr Asn Ala Ser Met Arg Ile Ala Glu Arg
                805                 810                 815

Phe Phe Met Arg His Ser Val Leu Thr Gln Leu Arg Ala Ala Lys Ile
            820                 825                 830

Gly Glu Thr Glu Tyr Leu Ile Pro Glu Ser Ala Ser Lys Arg Leu Asn
        835                 840                 845

Ala Phe Val Lys Leu Gln Thr Gly Lys Pro Phe Ala Lys Leu Ile Met
    850                 855                 860

Asn Cys Ser Gly Phe Val Leu Glu Gly Leu Thr Lys Lys Gln Tyr Ala
865                 870                 875                 880

Lys Leu Ala Glu Thr Ala Gly Lys Lys Glu Ser Phe Tyr Gln Tyr Asp
                885                 890                 895

Asp Arg Trp Phe Asp Lys Gly His His Phe Ala Cys Arg Ala Thr Leu
            900                 905                 910

Glu Asn Lys Val Gln Val Cys Leu Asn Gly Gly Gly Arg Ile Lys Asp
        915                 920                 925

Thr Thr Pro Asp Phe Asn Pro Lys Ser Leu Leu Arg Ser Asp Leu Gln
    930                 935                 940

Thr Pro Leu Asp Gln Leu Phe Gly Asn Ser Gly Ala Ser Arg Ala Asp
945                 950                 955                 960

Pro Lys Lys Lys Arg Lys Val
                965


<210> SEQ ID NO 96
<211> LENGTH: 957
<212> TYPE: PRT
<213> ORGANISM: artificial sequence
<220> FEATURE:
<223> OTHER INFORMATION: amino acid sequence of Cas12j.17-NLS fusion
      protein

<400> SEQUENCE: 96

Met Ser Asn Thr Thr Tyr Lys Thr Ser His Leu Leu Ile Asp Leu Pro
1               5                   10                  15

Gln Gln Glu Leu Ile Asp Leu His Arg Asp Ser Asn Glu Met Gly Ser
            20                  25                  30

Tyr Leu Thr Lys Phe Phe Leu Ala Ala Leu Gly Arg Pro Val Asp Asn
        35                  40                  45

Ser Ile Val Leu Pro Pro Glu Leu Ala Asp Leu Tyr Phe Gln Phe Ala
    50                  55                  60
```

```
Asn Gly Ile Leu Pro Val Asp Lys Gly Pro Gly Ser Asp Asp Pro Ser
65                  70                  75                  80

Trp Leu His Ser Glu Asn Cys Tyr Ser Met Phe Phe Glu Lys Asp Ser
                85                  90                  95

Met Ser Gly Asn Cys Thr Asn Lys Ile Lys Gln Tyr Gln Glu Leu Lys
            100                 105                 110

Thr Ala Leu Cys Gly Gln Lys Val Lys Gly Gln Lys Gly Leu Val Gly
        115                 120                 125

Lys Lys Thr Trp Ala Gln Leu Lys Lys Val Leu Thr Ala Leu Pro Gln
    130                 135                 140

Lys Tyr Gln Ile Leu Ser Pro Lys Ile Cys Gln Lys Tyr Phe Lys Ser
145                 150                 155                 160

Gly Asn Leu Glu Gly Phe Gly Lys Leu Ala Leu Ala Gly Lys Asn Arg
                165                 170                 175

Pro Ser Met Ser Ala Gly Leu Gln Leu Arg Glu Leu Gly Leu Leu Pro
            180                 185                 190

Leu Asp Ser Arg Gly Ile Asp Lys Asn Lys Leu Leu Gly Ile Leu Val
        195                 200                 205

Gly Ile Thr Gly Arg Leu Lys Ser Trp Arg Asp Arg Asp Trp Ala Cys
    210                 215                 220

Lys Thr Val Lys Glu Glu Leu Arg Val Thr Phe Glu Lys Gly Leu Gly
225                 230                 235                 240

Glu Val Asp Pro Thr Ala Tyr Pro Gln Phe Lys Gln Phe Ala Asp Gln
                245                 250                 255

Leu Phe Lys Gln Glu Gly Tyr Lys Ile Ser Gly Arg Val Leu Arg Ala
            260                 265                 270

Val Glu Gly Lys Asp Ala Asp Tyr Gln Pro Val Leu Ser Leu Leu Thr
        275                 280                 285

Gln Tyr Pro Asp Leu Gln Gly Asp Phe Glu Glu Leu Gly Arg Val Tyr
    290                 295                 300

Leu Ala Glu Ala Glu Tyr Leu Arg Lys Lys Val Asp Ala Arg Val Thr
305                 310                 315                 320

Val Cys Asp Ala Glu Thr Ser Pro Leu Gln Phe Pro Phe Gly Leu Thr
                325                 330                 335

Gly Asn Gly Tyr Ser Ile Thr Leu Thr Val Val Lys Gly Gln Ile Ala
            340                 345                 350

Ala Thr Leu His Leu Pro Gly Gly Asp Ile Thr Pro Arg Leu Arg Arg
        355                 360                 365

Ser Lys Tyr Phe Gln Asn Pro Glu Ile Ala Pro Val Lys Asp Gly Lys
    370                 375                 380

Gly Lys Val Asn Gly Phe Gln Ile Ser Phe Lys Arg Gly Lys Thr Pro
385                 390                 395                 400

Leu Val Gly Ile Ile Lys Glu Pro Lys Leu Leu Lys Lys Asn Gly Asn
                405                 410                 415

Tyr Tyr Leu Ser Leu Ala Val Gly Ile Asn Lys Thr Glu Ile Pro Lys
            420                 425                 430

Glu Ile Cys Asp Ala Arg Ala Tyr Tyr Ser Ser Thr Ser Arg Thr Asp
        435                 440                 445

Thr Pro Pro Ala Val Lys Ala Met Ser Ile Asp Leu Gly Val Thr Thr
    450                 455                 460

Leu Ala Asp Tyr Ser Ile Ile Asp Thr Gly Leu Pro Gly Asp Cys Gly
465                 470                 475                 480
```

```
Val Phe Gly Gly Ser Thr Ala Ala Phe Thr Glu His Gly Lys Ile Gly
                485                 490                 495

Arg Cys Gly Ser Lys Ser Leu Arg Asp Gly Leu Tyr Lys Asn Thr Glu
            500                 505                 510

Ala Gly Tyr Phe Leu Ala Lys Tyr Ile Arg Leu Ser Lys Asn Leu Arg
        515                 520                 525

Gly Gly Val Gly Leu Asn Lys Leu Glu Lys Glu Lys Leu Leu Glu His
    530                 535                 540

Val Glu Arg Leu Gly Ile Glu His Cys Ala Asp Asp Phe Ala Arg Lys
545                 550                 555                 560

Asp Glu Ile His Arg Lys Phe Ser Glu Ile Lys Ser Lys Leu Glu Lys
                565                 570                 575

Ser Ile Ser Glu Phe Ala Leu Arg Asp Arg Pro Asp Lys Lys Gly Ala
            580                 585                 590

Ser Trp Glu Gly Ile Cys Ala Glu Thr Val Gln Val Leu Gly Ala Val
        595                 600                 605

Lys Arg Trp Gln Ser Leu Ala Lys Ser Trp Thr Tyr Tyr Ser Trp Thr
    610                 615                 620

Ala Glu Asp Tyr Val Leu Ala Leu Thr Gly Glu Gly Arg Thr Arg Val
625                 630                 635                 640

Ser Asp Glu His Val Glu Ser Val Val Lys Thr Gly Arg Arg Gln Phe
                645                 650                 655

Ala Pro Cys Gly Lys Ala Ala Leu Leu Arg Leu Leu Glu Lys Gly Lys
            660                 665                 670

Ile Val Glu Val Cys Pro Gly Gln Phe Gln Leu Ala Glu Gly Val Asp
        675                 680                 685

Tyr Lys Arg His Pro Thr Glu Phe Leu Ala Ala His Ile Arg His Phe
    690                 695                 700

Asn Gly Leu Arg Arg Asp Leu Thr Asn Lys Leu Val Arg Ala Ile Val
705                 710                 715                 720

Glu Lys Ala Gln Gln His Arg Val Gln Ile Val Ile Val Glu Asp Phe
                725                 730                 735

Gly Ile Pro Asp Ile Glu Gly Arg Ile Met Asp His Tyr Asp Asn Tyr
            740                 745                 750

Arg Trp Asn Leu Phe Ala Pro Ala Lys Val Ile Glu Lys Leu Glu Glu
        755                 760                 765

Ala Leu Ser Glu Val Gly Ile Ala Met Ala Glu Val Asp Pro Arg His
    770                 775                 780

Thr Ser Gln Leu Ala Pro Thr Gly Asp Phe Gly Phe Arg Asp His Glu
785                 790                 795                 800

Asn Leu Tyr Phe Trp Glu Lys Gly Leu Cys Arg Thr Asp Ala Asn Thr
                805                 810                 815

Asn Ala Ser Met Arg Ile Ala Glu Arg Phe Phe Thr Arg His Ser Val
            820                 825                 830

Leu Ser Gln Leu Arg Ala Val Lys Ile Ser Glu Thr Glu Phe Leu Ile
        835                 840                 845

Pro Val Ser Thr Gly Lys Arg Glu Asn Ala Phe Ile Lys Ser Gln Thr
    850                 855                 860

Gly Lys Leu Phe Ala Lys Leu Val Ala Asp Ser Asn Gly Phe Val Met
865                 870                 875                 880

Val Gly Leu Thr Glu Lys Gln His Gly Ala Thr Val Thr Val Gly Lys
                885                 890                 895

Lys Val Ser Phe Tyr Asn His Ala Gly Arg Trp Leu Gly Lys Ala His
```

```
            900                 905                 910

His Ile Ala His Arg Asp Arg Ile Lys Asn Glu Val Asn Gln Val Leu
        915                 920                 925

Thr Ser Gly Arg Gly Arg Ile Arg Asn Ile Ala Pro Glu Leu Ser Pro
    930                 935                 940

Lys Thr Ser Arg Ala Asp Pro Lys Lys Lys Arg Lys Val
945                 950                 955


<210> SEQ ID NO 97
<211> LENGTH: 941
<212> TYPE: PRT
<213> ORGANISM: artificial sequence
<220> FEATURE:
<223> OTHER INFORMATION: amino acid sequence of Cas12j.18-NLS fusion
      protein

<400> SEQUENCE: 97

Met Thr Asn Gln Lys Pro Lys Phe Lys Ser Ser Asp Ile Gln Ile Lys
1               5                   10                  15

His Ile Ser Pro Thr Asp Lys Lys Arg Leu Lys Thr Phe Tyr His Gln
            20                  25                  30

Leu Tyr Glu Gln Val Asn Phe Ile Leu Glu Arg Met Ile Val Met Arg
        35                  40                  45

Gly Arg Pro Arg Thr Ile Arg Asn Ile Asp Gly Thr Glu Ile Phe Val
    50                  55                  60

Ser Gln Glu Glu Ala Asp Gln Gln Leu Leu Ser Leu Ala Gly Gly Ser
65                  70                  75                  80

His Glu Gly Val Lys Tyr Leu Lys Gln Tyr Tyr Glu Ser Cys Val Asp
                85                  90                  95

Ala Gly Lys Pro Ala Lys Tyr Ala Ala Asn Met Phe Leu Thr Lys Thr
            100                 105                 110

Ile Ser Gly Thr Asn Pro Leu Gln Cys His Thr Ala Val Tyr Lys Leu
        115                 120                 125

Tyr Lys Lys Val Gln Ala Lys Gln Ile Thr Lys Lys Glu Phe Ile Asp
    130                 135                 140

Lys Leu Tyr Ser Lys Thr Lys Lys Lys Lys Ser Leu Lys Pro Ala Tyr
145                 150                 155                 160

Lys Val Phe Thr Glu Asn Glu His Ile Glu Phe Tyr His Lys Val Arg
                165                 170                 175

Ser Gly Lys Leu Pro Ala Ser Glu Val Arg Leu Glu Glu Ser Arg Arg
            180                 185                 190

Ala Pro Asp Val Gly Leu Glu Val Gly Leu Leu Leu Arg Glu Leu Gly
        195                 200                 205

Ile Phe Pro Phe Asn Phe Pro His Phe Thr Glu Lys Lys Tyr Leu Asp
    210                 215                 220

Leu Ala Trp Thr Ile Ala Ile Arg Trp Leu Lys Asn Trp Asn Glu Asn
225                 230                 235                 240

Asn Lys Asn Thr Ala Lys Glu Lys Ala Lys Gln Lys Ala Ile Val Asp
                245                 250                 255

Lys Leu Arg Thr Ser Leu Asp Gln Lys Glu Val Asp Leu Phe Glu Glu
            260                 265                 270

Phe Ala Glu Glu Cys Ser Gln Glu Gln Phe Gly Ile Arg Glu Gly Phe
        275                 280                 285

Val Lys Ala Lys Lys Arg Leu Lys Ser Phe Pro Lys Gly Ile Glu Lys
    290                 295                 300
```

```
Ser Ser Tyr Lys Glu Gly Met Arg Ile Leu Val Gln Asn Lys His Gly
305                 310                 315                 320

Ser Ile Trp Asp Asn Phe Glu Asn Leu Ala Tyr His His Ile Ala Leu
                325                 330                 335

Asn Glu Tyr Asn Arg Leu Arg Asp Glu Ala Ser Phe Ser Phe Pro Asp
            340                 345                 350

Pro Ile Tyr His Pro Ile Arg Ala Glu Phe Gly Leu Thr Ser Leu Pro
        355                 360                 365

Lys Phe Asn Val Gly Leu Asn Asp Arg Gly Asn Tyr Glu Phe Thr Ile
    370                 375                 380

Asn Leu Pro Asp Gly Pro Leu Met Met Leu Gly Lys Lys Ser Arg Tyr
385                 390                 395                 400

Tyr Leu Lys Pro Ile Ile Gln Gly Pro Leu Asn Asn Ala Phe Ser Phe
                405                 410                 415

Glu Phe Ile Lys Gly Asn Lys Lys Arg Pro Lys Ile Ser Ala Lys Leu
            420                 425                 430

Lys Ser Ile Thr Val Val Phe Ala Lys Ser Ser Ile Tyr Val Gly Leu
        435                 440                 445

Pro Tyr Arg Pro Ile Ser Ile Pro Ile Pro Gln Ala Val Thr Asn Ser
    450                 455                 460

Thr Tyr Tyr Phe Lys Lys Asn Leu Ser Ser Thr Ser Lys Phe Asp Lys
465                 470                 475                 480

Asp Val Phe Met Gly Leu Thr Ala Val Ser Val Asp Leu Gly Leu Asn
                485                 490                 495

Pro Val Phe Ser Met Ser Ala Cys Arg Leu Asp Glu Met Lys Ala Asp
            500                 505                 510

Glu His Tyr Ser Cys Glu Val Pro Gly Phe Gly Trp Ala Asn Gln Ile
        515                 520                 525

Trp Ser Lys Arg Ala Gly Gly Val Trp Asn Arg Ser Phe Arg Asp Lys
    530                 535                 540

Ile Arg Gly Phe Val Pro Gly Asn Leu Ser Asp Arg Ile Phe Cys Cys
545                 550                 555                 560

Lys Lys Ser Ile Ile Val Ser Lys Lys Leu Arg Asp Glu Lys Pro Leu
                565                 570                 575

Thr Gln Tyr Glu Glu Glu Asn Phe Glu Arg Trp Met Gln Val Val Gly
            580                 585                 590

Val Asp Pro Asn Glu Asp His Tyr Lys Gln Leu Arg Ile Ala Ile Arg
        595                 600                 605

Asp Ile Lys Thr Glu Tyr Glu Thr Val Arg Ser Glu Phe Ala Leu Arg
    610                 615                 620

Asp His Pro Asn Asn Ser Asn Lys Thr Thr Glu Asn Ile Cys Thr Glu
625                 630                 635                 640

Cys Phe Asp Met Leu Phe Val Ile Lys Asn Leu Ile Ser Leu Leu Lys
                645                 650                 655

Ser Trp Asn Arg Trp His Arg Thr Thr Gly Asp Ile Glu Glu Arg Gly
            660                 665                 670

Lys Asp Pro Asn Glu Cys Ser Thr Tyr Trp Arg His Tyr Asn Gly Leu
        675                 680                 685

Lys Thr Asp Leu Leu Lys Lys Leu Thr Asn Ile Leu Ile Glu Ser Ala
    690                 695                 700

Lys Ser Ile Gly Ala His Ile Ile Ile Leu Glu Asp Leu Thr Leu Ser
705                 710                 715                 720

Gln Arg Ser Ser Arg Ser Arg Arg Glu Asn Ser Leu Val Ala Ile Phe
```

```
                725                 730                 735

Gly Ala Gln Thr Ile Ile Lys Thr Ile Ser Glu Glu Ala Glu Ile Asn
            740                 745                 750

Gly Ile Leu Val Tyr Leu Glu Asp Pro Arg His Ser Ser Gln Ile Ser
        755                 760                 765

Ile Val Thr Asn Glu Phe Gly Tyr Arg Pro Lys Glu Asp Lys Ala Lys
    770                 775                 780

Leu Tyr Phe Met Asp Glu Glu Thr Val Cys Val Thr Asn Cys Asp Asp
785                 790                 795                 800

Ser Ala Ala Leu Met Leu Gln Gln Ser Phe Trp Ser Arg His Lys Asp
                805                 810                 815

Val Val Lys Val Lys Gly Thr Lys Val Ser Asp Thr Glu Tyr Leu Val
            820                 825                 830

Ser Ser Glu Asp Lys Asp Gly Thr Lys Met Arg Leu Arg Ser Tyr Leu
        835                 840                 845

Lys Arg Asn Val Gly Thr Ala Asn Ala Ile Leu Gln Lys Asn Cys Asp
    850                 855                 860

Gly Tyr Asp Leu Lys Lys Ile Ser Pro Gln Lys Lys Lys Lys Ile Glu
865                 870                 875                 880

Glu Phe Gly Lys Asp Glu Tyr Phe Tyr Arg His Gly Glu Gln Trp Phe
                885                 890                 895

Thr Ala Asp Ala His Phe Asp Lys Leu Arg Glu Phe Gly Asn Gln Val
            900                 905                 910

Phe Leu Thr Pro Gln Ser Gln Ile Lys Arg Ile Asn Leu Gln Val Glu
        915                 920                 925

Gly Thr Ser Arg Ala Asp Pro Lys Lys Lys Arg Lys Val
    930                 935                 940


<210> SEQ ID NO 98
<211> LENGTH: 919
<212> TYPE: PRT
<213> ORGANISM: artificial sequence
<220> FEATURE:
<223> OTHER INFORMATION: amino acid sequence of Cas12j.19-NLS fusion
      protein

<400> SEQUENCE: 98

Met Pro Ser Tyr Lys Ser Ser Arg Val Leu Val Arg Asp Val Pro Glu
1               5                   10                  15

Glu Leu Val Asp His Tyr Glu Arg Ser His Arg Val Ala Ala Phe Phe
            20                  25                  30

Met Arg Leu Leu Leu Ala Met Arg Arg Glu Pro Tyr Ser Leu Arg Met
        35                  40                  45

Arg Asp Gly Thr Glu Arg Glu Val Asp Leu Asp Glu Thr Asp Asp Phe
    50                  55                  60

Leu Arg Ser Ala Gly Cys Glu Glu Pro Asp Ala Val Ser Asp Asp Leu
65                  70                  75                  80

Arg Ser Phe Ala Leu Ala Val Leu His Gln Asp Asn Pro Lys Lys Arg
                85                  90                  95

Ala Phe Leu Glu Ser Glu Asn Cys Val Ser Ile Leu Cys Leu Glu Lys
            100                 105                 110

Ser Ala Ser Gly Thr Arg Tyr Tyr Lys Arg Pro Gly Tyr Gln Leu Leu
        115                 120                 125

Lys Lys Ala Ile Glu Glu Glu Trp Gly Trp Asp Lys Phe Glu Ala Ser
    130                 135                 140
```

```
Leu Leu Asp Glu Arg Thr Gly Glu Val Ala Glu Lys Phe Ala Ala Leu
145                 150                 155                 160

Ser Met Glu Asp Trp Arg Arg Phe Phe Ala Ala Arg Asp Pro Asp Asp
                165                 170                 175

Leu Gly Arg Glu Leu Leu Lys Thr Asp Thr Arg Glu Gly Met Ala Ala
            180                 185                 190

Ala Leu Arg Leu Arg Glu Arg Gly Val Phe Pro Val Ser Val Pro Glu
        195                 200                 205

His Leu Asp Leu Asp Ser Leu Lys Ala Ala Met Ala Ser Ala Ala Glu
    210                 215                 220

Arg Leu Lys Ser Trp Leu Ala Cys Asn Gln Arg Ala Val Asp Glu Lys
225                 230                 235                 240

Ser Glu Leu Arg Lys Arg Phe Glu Glu Ala Leu Asp Gly Val Asp Pro
                245                 250                 255

Glu Lys Tyr Ala Leu Phe Glu Lys Phe Ala Ala Glu Leu Gln Gln Ala
            260                 265                 270

Asp Tyr Asn Val Thr Lys Lys Leu Val Leu Ala Val Ser Ala Lys Phe
        275                 280                 285

Pro Ala Thr Glu Pro Ser Glu Phe Lys Arg Gly Val Glu Ile Leu Lys
    290                 295                 300

Glu Asp Gly Tyr Lys Pro Leu Trp Glu Asp Phe Arg Glu Leu Gly Phe
305                 310                 315                 320

Val Tyr Leu Ala Glu Arg Lys Trp Glu Arg Arg Arg Gly Gly Ala Ala
                325                 330                 335

Val Thr Leu Cys Asp Ala Asp Asp Ser Pro Ile Lys Val Arg Phe Gly
            340                 345                 350

Leu Thr Gly Arg Gly Arg Lys Phe Val Leu Ser Ala Ala Gly Ser Arg
        355                 360                 365

Phe Leu Ile Thr Val Lys Leu Pro Cys Gly Asp Val Gly Leu Thr Ala
    370                 375                 380

Val Pro Ser Arg Tyr Phe Trp Asn Pro Ser Val Gly Arg Thr Thr Ser
385                 390                 395                 400

Asn Ser Phe Arg Ile Glu Phe Thr Lys Arg Thr Thr Glu Asn Arg Arg
                405                 410                 415

Tyr Val Gly Glu Val Lys Glu Ile Gly Leu Val Arg Gln Arg Gly Arg
            420                 425                 430

Tyr Tyr Phe Phe Ile Asp Tyr Asn Phe Asp Pro Glu Glu Val Ser Asp
        435                 440                 445

Glu Thr Lys Val Gly Arg Ala Phe Phe Arg Ala Pro Leu Asn Glu Ser
    450                 455                 460

Arg Pro Lys Pro Lys Asp Lys Leu Thr Val Met Gly Ile Asp Leu Gly
465                 470                 475                 480

Ile Asn Pro Ala Phe Ala Phe Ala Val Cys Thr Leu Gly Glu Cys Gln
                485                 490                 495

Asp Gly Ile Arg Ser Pro Val Ala Lys Met Glu Asp Val Ser Phe Asp
            500                 505                 510

Ser Thr Gly Leu Arg Gly Gly Ile Gly Ser Gln Lys Leu His Arg Glu
        515                 520                 525

Met His Asn Leu Ser Asp Arg Cys Phe Tyr Gly Ala Arg Tyr Ile Arg
    530                 535                 540

Leu Ser Lys Lys Leu Arg Asp Arg Gly Ala Leu Asn Asp Ile Glu Ala
545                 550                 555                 560

Arg Leu Leu Glu Glu Lys Tyr Ile Pro Gly Phe Arg Ile Val His Ile
```

```
                565                 570                 575

Glu Asp Ala Asp Glu Arg Arg Arg Thr Val Gly Arg Thr Val Lys Glu
            580                 585                 590

Ile Lys Gln Glu Tyr Lys Arg Ile Arg His Gln Phe Tyr Leu Arg Tyr
        595                 600                 605

His Thr Ser Lys Arg Asp Arg Thr Glu Leu Ile Ser Ala Glu Tyr Phe
    610                 615                 620

Arg Met Leu Phe Leu Val Lys Asn Leu Arg Asn Leu Leu Lys Ser Trp
625                 630                 635                 640

Asn Arg Tyr His Trp Thr Thr Gly Asp Arg Glu Arg Arg Gly Gly Asn
                645                 650                 655

Pro Asp Glu Leu Lys Ser Tyr Val Arg Tyr Tyr Asn Asn Leu Arg Met
            660                 665                 670

Asp Thr Leu Lys Lys Leu Thr Cys Ala Ile Val Arg Thr Ala Lys Glu
        675                 680                 685

His Gly Ala Thr Leu Val Ala Met Glu Asn Ile Gln Arg Val Asp Arg
    690                 695                 700

Asp Asp Glu Val Lys Arg Arg Lys Glu Asn Ser Leu Leu Ser Leu Trp
705                 710                 715                 720

Ala Pro Gly Met Val Leu Glu Arg Val Glu Gln Glu Leu Lys Asn Glu
                725                 730                 735

Gly Ile Leu Ala Trp Glu Val Asp Pro Arg His Thr Ser Gln Thr Ser
            740                 745                 750

Cys Ile Thr Asp Glu Phe Gly Tyr Arg Ser Leu Val Ala Lys Asp Thr
        755                 760                 765

Phe Tyr Phe Glu Gln Asp Arg Lys Ile His Arg Ile Asp Ala Asp Val
    770                 775                 780

Asn Ala Ala Ile Asn Ile Ala Arg Arg Phe Leu Thr Arg Tyr Arg Ser
785                 790                 795                 800

Leu Thr Gln Leu Trp Ala Ser Leu Leu Asp Asp Gly Arg Tyr Leu Val
                805                 810                 815

Asn Val Thr Arg Gln His Glu Arg Ala Tyr Leu Glu Leu Gln Thr Gly
            820                 825                 830

Ala Pro Ala Ala Thr Leu Asn Pro Thr Ala Glu Ala Ser Tyr Glu Leu
        835                 840                 845

Val Gly Leu Ser Pro Glu Glu Glu Leu Ala Gln Thr Arg Ile Lys
    850                 855                 860

Arg Lys Lys Arg Glu Pro Phe Tyr Arg His Glu Gly Val Trp Leu Thr
865                 870                 875                 880

Arg Glu Lys His Arg Glu Gln Val His Glu Leu Arg Asn Gln Val Leu
                885                 890                 895

Ala Leu Gly Asn Ala Lys Ile Pro Glu Ile Arg Thr Ser Arg Ala Asp
            900                 905                 910

Pro Lys Lys Lys Arg Lys Val
        915
```

<210> SEQ ID NO 99
<211> LENGTH: 832
<212> TYPE: PRT
<213> ORGANISM: artificial sequence
<220> FEATURE:
<223> OTHER INFORMATION: amino acid sequence of Cas12j.20-NLS fusion protein

<400> SEQUENCE: 99

-continued

```
Met Ala Phe Gln Ser Lys Arg Arg Ile Val Gly Asn Phe Val Lys Glu
1               5                   10                  15

Gln Cys Leu Lys Ala Val Asp Gly Lys Val Ile Leu Thr Asp Gln Glu
            20                  25                  30

Lys Arg Glu Leu Ile Lys Arg Tyr Glu Leu His Leu Glu Pro His Lys
        35                  40                  45

Trp Leu Leu Arg Leu Phe Leu Ser Gly Tyr Glu Gly Arg Asp Asp Gly
    50                  55                  60

Phe Tyr Glu Glu Leu Gly Asn Thr Asn Leu Asp Lys Glu Lys Phe Phe
65                  70                  75                  80

Glu Val Thr Ala Gly Leu Arg Asp Ala Leu Leu Arg Gln Ser Gly Ser
                85                  90                  95

Ser Arg Ala Leu Lys Ser Ser Met Leu Gly Lys Cys Pro Pro Ser Ala
            100                 105                 110

Ala Val Gly Lys Ala Ala Lys His Ile Gln Thr Leu Arg Asp Ala Gly
        115                 120                 125

Ile Leu Pro Phe Lys Thr Gly Leu Thr Ser Gly Glu Asp Tyr Asn Val
    130                 135                 140

Leu Gln Gln Ala Val Gln Gln Leu Arg Ser Trp Val Ala Cys Asp His
145                 150                 155                 160

Arg Thr Arg Glu Ala Tyr Ala Glu Gln Gln Glu Lys Thr Ser Gln Ala
                165                 170                 175

Glu Glu Ala Ala Lys Lys Ala Ala Asn Glu Val Lys Pro Glu Asp Ala
            180                 185                 190

Lys Ser Leu Glu Arg His Glu Arg Val Leu Thr Lys Leu Arg Lys Gln
        195                 200                 205

Glu Arg Arg Leu Glu Arg Met Lys Ser His Ala Gln Phe Ser Leu Asp
    210                 215                 220

Glu Met Asp Cys Thr Gly Tyr Ser Leu Cys Met Gly Ala Asn Tyr Leu
225                 230                 235                 240

Lys Asp Tyr Cys Leu Glu Lys Glu Gly Arg Gly Leu Arg Leu Thr Leu
                245                 250                 255

Lys Asn Ser Thr Met Ala Gly Ser Tyr Tyr Val Ser Val Gly Asp Gly
            260                 265                 270

Gln His Ala Gly Met Lys Asn Pro Gly Thr Pro Ala Gly Gly Ser Pro
        275                 280                 285

Glu Lys Gly Arg Arg Arg Asn Ile Leu Phe Asp Phe Thr Val Glu Lys
    290                 295                 300

Cys Gly Asp Asn Tyr Leu Phe Arg Tyr Asp Glu Asn Gly Lys Arg Pro
305                 310                 315                 320

Arg Ala Gly Val Val Lys Glu Pro Arg Phe Cys Trp Arg Arg Lys Gly
                325                 330                 335

Asn Ser Val Glu Leu Tyr Leu Ala Met Pro Ile Asn Ile Glu Asn Ser
            340                 345                 350

Met Arg Asn Ile Phe Val Gly Lys Gln Lys Ser Gly Lys His Ser Ala
        355                 360                 365

Phe Thr Arg Gln Trp Pro Lys Glu Val Glu Gly Leu Asp Glu Leu Arg
    370                 375                 380

Asp Ala Val Val Leu Gly Val Asp Ile Gly Ile Asn Arg Ala Ala Phe
385                 390                 395                 400

Cys Ala Ala Leu Lys Thr Ser Arg Phe Glu Asn Gly Leu Pro Ala Asp
                405                 410                 415

Val Gln Val Met Asp Thr Thr Cys Asp Ala Leu Thr Glu Lys Gly Gln
```

```
            420                 425                 430

Glu Tyr Arg Gln Leu Arg Lys Asp Ala Thr Cys Leu Ala Trp Leu Ile
        435                 440                 445

Arg Thr Thr Arg Arg Phe Lys Ala Asp Pro Gly Asn Lys His Asn Gln
    450                 455                 460

Ile Lys Glu Lys Asp Val Glu Arg Phe Asp Ser Ala Asp Gly Ala Tyr
465                 470                 475                 480

Arg Arg Tyr Met Asp Ala Ile Ala Glu Met Pro Ser Asp Pro Leu Gln
                485                 490                 495

Val Trp Glu Ala Ala Arg Ile Thr Gly Tyr Gly Glu Trp Ala Lys Glu
            500                 505                 510

Ile Phe Ala Arg Phe Asn His Tyr Lys His Glu His Ala Cys Cys Ala
        515                 520                 525

Val Ser Leu Ser Leu Ser Asp Arg Leu Val Trp Cys Arg Leu Ile Asp
    530                 535                 540

Arg Ile Leu Ser Leu Lys Lys Cys Leu His Phe Gly Gly Tyr Glu Ser
545                 550                 555                 560

Lys His Arg Lys Gly Phe Cys Lys Ser Leu Tyr Arg Leu Arg His Asn
                565                 570                 575

Ala Arg Asn Asp Val Arg Lys Lys Leu Ala Arg Phe Ile Val Asp Ala
            580                 585                 590

Ala Val Asp Ala Gly Ala Ser Val Ile Ala Met Glu Lys Leu Pro Ser
        595                 600                 605

Ser Gly Gly Lys Gln Ser Lys Asp Asp Asn Arg Ile Trp Asp Leu Met
    610                 615                 620

Ala Pro Asn Thr Leu Ala Thr Thr Val Cys Leu Met Ala Lys Val Glu
625                 630                 635                 640

Gly Ile Gly Phe Val Gln Val Asp Pro Glu Phe Thr Ser Gln Trp Val
                645                 650                 655

Phe Glu Gln Arg Val Ile Gly Asp Arg Glu Gly Arg Ile Val Ser Cys
            660                 665                 670

Leu Asp Ala Glu Gly Val Arg Arg Asp Tyr Asp Ala Asp Glu Asn Ala
        675                 680                 685

Ala Lys Asn Ile Ala Trp Leu Ala Leu Thr Arg Glu Ala Glu Pro Phe
    690                 695                 700

Cys Met Ala Phe Glu Lys Arg Asn Gly Val Val Glu Pro Lys Gly Leu
705                 710                 715                 720

Arg Phe Asp Ile Pro Glu Glu Pro Thr Arg Glu Gln Asp Glu Ser Asp
                725                 730                 735

Gln Asp Phe Lys Lys Arg Leu Glu Glu Arg Asp Lys Leu Ile Glu Arg
            740                 745                 750

Leu Gln Ala Lys Ala Asp Arg Met Gln Ala Ile Val Gln Arg Leu Phe
        755                 760                 765

Gly Asp Arg Arg Pro Trp Asp Ala Phe Ala Asp Arg Ile Pro Glu Gly
    770                 775                 780

Lys Ser Lys Arg Leu Phe Arg His Arg Asp Gly Leu Val Leu Asn Lys
785                 790                 795                 800

Pro Phe Lys Gly Leu Cys Gly Ser Glu Asn Ser Glu Gln Lys Ala Ser
                805                 810                 815

Ala Arg Asn Ser Arg Ser Arg Ala Asp Pro Lys Lys Lys Arg Lys Val
            820                 825                 830
```

<210> SEQ ID NO 100

```
<211> LENGTH: 848
<212> TYPE: PRT
<213> ORGANISM: artificial sequence
<220> FEATURE:
<223> OTHER INFORMATION: amino acid sequence of Cas12j.21-NLS fusion
      protein

<400> SEQUENCE: 100

Met Gly Arg Phe Gly Lys Lys Lys Ile Ala Val Asn Gly Tyr Val Glu
1               5                   10                  15

Gln Asp Cys Ile Lys Thr Ile Ser Ala Lys Cys Leu Leu Thr Arg Ala
            20                  25                  30

Gln Ile Asp Glu Leu Arg Ala Lys Tyr Asp Ala Val Leu Asp Thr Met
        35                  40                  45

Arg Pro Leu Ile Arg Leu Ile Leu Ala Gly Tyr Glu Gly Arg Asp Asp
    50                  55                  60

Gly Ile Tyr Glu Glu Ile Ala Pro Glu Met Ser Lys Lys Lys Phe Phe
65                  70                  75                  80

Glu Ala Ala Thr Glu Trp Arg Glu Ser Ile Val Lys Asn Ala Ser Pro
                85                  90                  95

Arg Ala Met Lys Ala Ser Val Phe Gly Asp Lys Glu Pro Cys Lys Ser
            100                 105                 110

Thr Gly Gly Ala Arg Ala Val Ile Gly Lys Leu Arg Lys Ser Gly Val
        115                 120                 125

Phe Pro Ile Glu Thr Gly Leu Ser Gly Gly Asp Glu Tyr Asn Leu Ile
    130                 135                 140

Glu Gln Ala Ile Glu Tyr Ala Lys Ser Trp Leu Lys Ser Asp Glu Ala
145                 150                 155                 160

Thr Arg Glu Ala Tyr Ala Asp Gln Gln Lys Asp Ile Lys Arg Leu Ile
                165                 170                 175

Gly Glu Ala Lys Lys Leu Ala Leu Lys Ile Glu Lys Ala Glu Lys Lys
            180                 185                 190

Leu Glu Ala Thr Asn Pro Gln Thr Lys Ser Trp Lys Lys Thr Thr Glu
        195                 200                 205

Ile Ile Lys Lys Ser Lys Arg Glu Phe Gly Ser Val Thr Thr Lys Thr
    210                 215                 220

Glu Lys Ala Glu Lys Arg Phe Glu Arg Met Lys Pro Phe Ser Lys Leu
225                 230                 235                 240

Glu Leu Gln Asn Met Asp Cys Thr Lys Tyr Ser Thr Tyr Leu Gly Thr
                245                 250                 255

Asn Tyr Ser Pro Phe Lys Leu Lys Lys Glu Gly Asp Leu Leu Gln Ile
            260                 265                 270

Thr Val Thr Ser Ser Val Met Lys Gly Thr Tyr Leu Ala Ser Tyr Gly
        275                 280                 285

Asp Gly Gln Tyr Gly Ser Arg Arg Asn Asn Gly Gln Ser Arg Arg Asp
    290                 295                 300

Asp Phe Val Pro Asn Met Asn Gln Lys Arg Arg Arg Asn Leu Met Phe
305                 310                 315                 320

Asp Cys Thr Val Glu Pro Phe Gly Asp Gly Ser Leu Leu Arg Tyr Glu
                325                 330                 335

Glu Asn Gly Leu Arg Pro Arg Val Ala Glu Leu Lys Glu Pro Arg Leu
            340                 345                 350

Cys Trp Arg Arg Arg Asn Gly Asn Tyr Glu Leu Tyr Leu Met Met Pro
        355                 360                 365

Val Lys Met His Val Lys Ser Pro Glu Met Phe Ala Gly Asp His Leu
```

```
    370                 375                 380

Ala Phe Ser Arg Tyr Trp Pro Lys Glu Val Glu Gly Leu Asp Ser Asp
385                 390                 395                 400

Thr Lys Ile Thr Ala Leu Gly Val Asp Val Gly Ile Ile Arg Ser Ala
                405                 410                 415

Tyr Cys Val Ala Val Thr Ala Glu Arg Phe Val Asp Gly Leu Pro Thr
            420                 425                 430

Glu Met Thr Val Gly Lys Ala Ser Phe Asp Ala Gln Thr Glu Lys Gly
        435                 440                 445

Arg Glu Tyr Phe Glu Leu Gly Arg Arg Ala Thr Met Leu Gly Trp Leu
    450                 455                 460

Ile Lys Thr Thr Arg Arg Tyr Lys Lys Asp Pro Lys Asn Glu His Asn
465                 470                 475                 480

Gln Ile Lys Glu Ser Asp Val Ala Ala Phe Asp Gly Ser Pro Gly Ala
                485                 490                 495

Phe Glu His Tyr Ile Leu Ala Val Asp Glu Met Ser Asp Asp Pro Leu
            500                 505                 510

Asp Val Trp Gly His Ala Asn Ile Thr Gly Tyr Gly Lys Trp Thr Lys
        515                 520                 525

Gln Ile Phe Lys Glu Phe Asn Gln Leu Lys Arg Glu Arg Ala Glu Gly
    530                 535                 540

Gln Val Glu Pro Asn Met Thr Asp Asp Leu Thr Trp Cys Ser Leu Ile
545                 550                 555                 560

Asp Tyr Ile Ile Ser Leu Lys Lys Thr Leu His Phe Gly Gly Tyr Glu
                565                 570                 575

Thr Lys Glu Arg Glu Ser Phe Cys Pro Ala Leu Tyr Asn Glu Arg Ala
            580                 585                 590

Asn Cys Arg Asp Val Val Arg Lys Arg Leu Ala Arg Tyr Val Val Glu
        595                 600                 605

Arg Ala Ile Ala Ala Glu Ala Gln Val Ile Ser Val Glu Asn Leu Ser
    610                 615                 620

Lys Cys Arg Arg Asp Asp Lys Arg Lys Asn Arg Val Trp Asp Leu Met
625                 630                 635                 640

Ser Gln Gln Ser Trp Ile Gly Val Leu Thr Asn Met Ala Arg Met Glu
                645                 650                 655

Asn Ile Ala Val Val Ser Val Asn Pro Asp Leu Thr Ser Gln Trp Val
            660                 665                 670

Glu Gln Cys Gly Ala Ile Gly Asp Arg Lys Ala Arg Thr Ile Ala Cys
        675                 680                 685

Arg Asp Val Asn Gly Lys Phe Val Ser Leu Asp Ala Asp Leu Asn Ala
    690                 695                 700

Ala Tyr Asn Ile Ala Ser Arg Ala Leu Thr Arg His Ala Glu Pro Phe
705                 710                 715                 720

Ser Ile Thr Phe Lys Lys Lys Asp Gly Ile Leu Glu Gln Lys Asp Val
                725                 730                 735

Cys Phe Asp Pro Gly Val Ile Pro Val Leu Glu Lys Asn Glu Asn Glu
            740                 745                 750

Glu Lys Phe Arg Glu Arg Val Glu Lys Tyr Glu Lys Ser Leu Val Ile
        755                 760                 765

Lys Gln Glu Arg Ala Val Arg Trp Arg Ala Ile Leu Gln His Leu Phe
    770                 775                 780

Gly Asn Glu Arg Pro Trp Asp Glu Phe Thr Asp Glu Val Lys Glu Gly
785                 790                 795                 800
```

```
Arg His Val Ser Leu Tyr Arg His His Gly Lys Leu Val Arg Thr Lys
                805                 810                 815

Gln Tyr Ala Gly Leu Val Lys Glu Ala Asn Asn Glu Leu Val Pro Val
            820                 825                 830

Cys Ala Val Ala Arg Ser Arg Ala Asp Pro Lys Lys Lys Arg Lys Val
        835                 840                 845


<210> SEQ ID NO 101
<211> LENGTH: 979
<212> TYPE: PRT
<213> ORGANISM: artificial sequence
<220> FEATURE:
<223> OTHER INFORMATION: amino acid sequence of Cas12j.22-NLS fusion
      protein

<400> SEQUENCE: 101

Met Ser Lys Ala Thr Arg Lys Thr Lys Thr Thr Val Pro Glu Ser Thr
1               5                   10                  15

Asp Thr Glu Ser Pro Ala Ala Asp Thr Gln Val Arg Val His Trp Leu
            20                  25                  30

Ala Ala Ser His Arg Ala Ser Pro Gly Leu Gln Gln Val Lys Glu Met
        35                  40                  45

Ile Gln Gln His Ala Asp Val Ala Ser Val Leu Phe Gln Gly Leu Val
    50                  55                  60

Arg Thr Ala Pro Ile Val Phe Arg Asn Asp Asp Gly Ser Pro Val Lys
65                  70                  75                  80

Pro Leu Asp Leu Leu Leu Ala Ser Leu Arg Pro Thr Tyr Lys Val Gln
                85                  90                  95

Arg Asp Thr Glu Thr Val Leu Val Thr Lys Asp Asp Val Ile Arg Cys
            100                 105                 110

Leu Thr Leu Ala Thr Thr Ala Val Asn Gly Gly Gln Ala Thr Asn Val
        115                 120                 125

Ala Val Phe Ala Ser Ala Asp Pro Ala Leu Ser Ala Pro Leu Ala Thr
    130                 135                 140

Leu Leu Ala Gln Leu Arg Ala Leu Glu Ser Val Asp Ser Ser Trp Ser
145                 150                 155                 160

Val Val Gly Lys Leu Asp Ile Asn Leu Arg Lys Phe Val Trp Leu Val
                165                 170                 175

Leu Ser Ala Ala Gly Val Leu Pro Ala Leu Ala Asp Leu Glu Gly Tyr
            180                 185                 190

Ala Ala Lys Ser Val Leu Ala Asn Val Gln Gly Lys Tyr Lys Ser Leu
        195                 200                 205

Gln Ala Cys Ala Asp Thr His Ala Ala Leu Tyr Lys Gln His Gln Thr
    210                 215                 220

Asn Lys Glu Gln Leu Glu Lys Leu Ile Ala Asp Pro Gly Phe Val Ala
225                 230                 235                 240

Leu Cys Ser Ala Leu Leu Gln Asp Pro Asp Leu Arg Ser Val Asp Ser
                245                 250                 255

Arg Arg Leu Ala Ala Leu Glu Glu Met Leu Gly Phe Val Ala Ala Asp
            260                 265                 270

Lys Asn Tyr Ser Glu Tyr Thr Ser Thr Arg Lys Cys Asp Gly Trp Ala
        275                 280                 285

Pro Pro Ala Asn Met Phe Asp Leu Leu Cys Glu His Lys Glu Ala Val
    290                 295                 300

Arg Arg Asn Ile Val Val Asp Asn Ser Lys Cys Leu Ser Arg Arg Ile
```

```
305                 310                 315                 320

Ser Leu Val Ala Asp Gly Asp Val Asn Glu Val Ser Val Phe Glu Leu
                325                 330                 335

Leu Asn Glu Met Arg Trp Leu Ser Val His Ser Ser Gly Ile Arg Met
            340                 345                 350

Pro Asn Tyr Pro Lys His Ala Tyr Ala Leu Lys Phe Gly Asp Asn Tyr
        355                 360                 365

Ile Ser Val Lys Ser Phe Glu Thr Val Val Asp Gly Gly Cys Ser Leu
    370                 375                 380

Leu Arg Met Thr Ala Arg Val Gly Lys Asn Asp Leu Val Cys Asp Phe
385                 390                 395                 400

Val Leu Gly Arg Gly Asn Glu Tyr Trp Asn Asn Leu Lys Ile Thr Pro
                405                 410                 415

Met Gly Lys Gly Ile Phe Ala Val Val Lys Thr Val Arg Arg Phe Thr
            420                 425                 430

Ala Thr Gly Ala Lys Leu Val Glu Leu Arg Gly Val Cys Lys Glu Pro
        435                 440                 445

Glu Ile Arg Tyr Glu Arg Gly Val Leu Gly Leu Arg Leu Pro Ile Ser
    450                 455                 460

Phe Asp Val Tyr Gly Lys Val Glu Glu Asp Ser Ile Ala Phe Gly Lys
465                 470                 475                 480

Asn Arg Val Ser Leu Arg Thr Thr Pro Phe Val Glu Lys Ala Asp Lys
                485                 490                 495

Phe Gln Gly Leu Leu Asp Tyr Arg Asn Thr Thr Ala Arg Asp Gly Tyr
            500                 505                 510

Ile Tyr Tyr Ala Gly Phe Asp Gln Gly Glu Asn Asp Gln Val Val Gly
        515                 520                 525

Ile Tyr Arg Thr Arg Thr Tyr Lys Asn Ala Thr Met Leu Glu Phe Phe
    530                 535                 540

Asn Val Ser Asp Thr Leu Glu Glu Val Ala Ser Cys Arg Phe Ser Asp
545                 550                 555                 560

Tyr Gln Glu Arg Lys Arg Arg Leu Arg Gly Asp Thr Gly Val Leu Asp
                565                 570                 575

Ile Asn Ser Ile Asn Val Leu Ala Asp Lys Val Gln Arg Leu Arg Arg
            580                 585                 590

Leu Ile Ser Thr Leu Arg Ala Cys Ala Ser His Thr Asp Trp Tyr Pro
        595                 600                 605

Lys Leu Lys Glu Arg Arg Arg Leu Glu Trp Ala Val Leu Ala Gln Gly
    610                 615                 620

Val Gly Val Ser Asp Phe Asp Thr Glu Ile Glu Arg Ala Glu Thr Ala
625                 630                 635                 640

Leu Ser Ala Val Ala Ala Val Asp Phe Val Arg Asp Pro Thr Cys Ile
                645                 650                 655

Ile Asn Val Met Asp Lys His Ile Tyr Ala Gln Phe Lys Gln Leu Arg
            660                 665                 670

Ser Glu Arg Asn Glu Lys Tyr Arg Ser Gln His Gln His Asp Tyr Lys
        675                 680                 685

Trp Leu Gln Leu Val Asp Ser Val Ile Ser Leu Arg Lys Ser Ile Tyr
    690                 695                 700

Arg Phe Gly Lys Ala Pro Glu Pro Arg Gly Ala Gly Glu Leu Tyr Pro
705                 710                 715                 720

Gln Asn Leu Tyr Thr Tyr Arg Asp Asn Leu Met Gln Gln Tyr Arg Lys
                725                 730                 735
```

```
Glu Val Ala Ala Phe Ile Arg Asp Val Cys Leu Glu His Gly Val Arg
            740                 745                 750

Gln Leu Ala Val Glu Ala Leu Asn Pro Thr Ser Tyr Ile Gly Glu Asp
        755                 760                 765

Ser Asp Ala Asn Arg Lys Arg Ala Leu Phe Ala Pro Ser Glu Leu His
    770                 775                 780

Asn Asp Ile Val Leu Ala Cys Ser Leu His Ser Ile Ala Val Val Ala
785                 790                 795                 800

Val Asp Glu Thr Met Thr Ser Arg Val Ala Pro Asn Asn Arg Leu Gly
                805                 810                 815

Phe Arg Ser His Gly Asp Tyr Gln Lys Phe Ser Glu Thr Ala Gln Gly
            820                 825                 830

Arg Phe Asn Trp Lys His Leu His Tyr Phe Gly Asp Asn Asp Val Ser
        835                 840                 845

Glu His Cys Asp Ala Asp Glu Asn Ala Cys Arg Asn Ile Val Leu Arg
    850                 855                 860

Ala Leu Thr Cys Gly Ala Ser Lys Pro Arg Phe Ser Arg Gln Ser Leu
865                 870                 875                 880

Leu Gly Lys Ile Lys Gly Pro Val Leu Arg Thr Gln Leu Ala Tyr Leu
                885                 890                 895

Ala His Lys Arg Gly Leu Leu Thr Ala Ser Thr Glu Pro Lys Lys Ala
            900                 905                 910

Ala Glu Thr Gly Phe Glu Leu Val Glu Ala Asp Leu Gly Gly Ala Leu
        915                 920                 925

Arg Val Gly Lys Gly Phe Ile Tyr Val Asp Ala Gly Ile Cys Ile Asn
    930                 935                 940

Ala Thr Thr Arg Lys Glu Arg Ser His Lys Val Gly Glu Ala Val Val
945                 950                 955                 960

Ser Arg Ser Leu Ala Ser Pro Phe Ser Arg Ala Asp Pro Lys Lys Lys
                965                 970                 975

Arg Lys Val
```

<210> SEQ ID NO 102
<211> LENGTH: 3268
<212> TYPE: DNA
<213> ORGANISM: artificial sequence
<220> FEATURE:
<223> OTHER INFORMATION: plasmid expressing Cas12j.3 system

<400> SEQUENCE: 102

```
tttacacttt atgcttccgg ctcgtatgtt aggaggtctt tatcatgacc aaggagaaga     60

tcaagaagac caagaaggcc aaggtggaga aggactccgt gaccagggcc ggcatcctga    120

ggatcctgct gaacccggac cagcaccagg agctggacac cctgatctcc gaccaccagg    180

aggccgccag ggagatccag accgccacct acaagctgtc cggcctgaag ctgtacgaca    240

agaccaacaa catggtggtg gacggctcca aggccacccc ggaggagcag gaggcctact    300

acaagatcat caactgggag ggccagccga tctccatctc caacccgatg gtgagggcca    360

ccttcaagtc catcgccaag gtgaaggagg acatcaggag gaagcaggag gagtacgcca    420

agctggagga ggccgacctg accaagatgt ccaccggcga cgtgaagaag cacaagaacg    480

agctgaggaa ggccgccaac aggatcaagc actccgagga gatcctgcag ttcgccaagt    540

ggaggctggc cgacatcttc ccgctgccgc tgtcccacaa ctcccagctg cacctgaaga    600

acaactacca ccagaacgtg ttctccggct tccacgccag ggtgaagggc tggaacgcct    660
```

```
gcgacatcgc cgcccaggcc aactacgccg agatcgacaa caggctgacc gagctgtcct    720
ccgagctgtc cggcgactac ggctccgagg tgatcaccga cctgatgggc ctgctgcagt    780
acaccaagga gctgggcgag ggctacaccg acacctccta cctgaactac aagttcctgt    840
ccttcttcaa ggagtgctgg aggccgaacg ccatcgccaa caacaccggc ctgctggagg    900
gcttctggct ggccaacaac aagcacacca acaagaagaa ccaggtggcc tactccttca    960
acccgaagat ctccgaggag ctgttcagga ggaggtccct gtgggagtcc gacaagtgcc   1020
tgctgtccga cccgaggttc gagaagtacg tggagctgtt cgacaagcac ggcaggtaca   1080
ggaagggcgc ctccctgacc ctgatctcca aggagtcccc gatcccgatc ggcttctcca   1140
tggacaggaa cgccgccaag ctggtgagga tcgacaacga caccgccaac aggcagctga   1200
ccatcaccat cgagctgccg aacaaggagg agaggtccta cgtggccgcc tacggcagga   1260
agcacgagac caagtgctac tacaacggcc tgaccaccag gctgccgagg tccgagaagg   1320
agctgctggc cctggccaag gccgagaaca gggagctgac cgacaaggag atccacgagg   1380
cctccctgga gaagtgctac atcttcgagt acgccagggc cggcaagatc ccggtgttcg   1440
ccgtggtgaa gaccctgtac ttcaggagga acccgtccaa cggcgagtac tacgtgatcc   1500
tgccgaccaa catcttcgtg gagtaccacg ccaacaacga gttcaactcc aaggagctgt   1560
tcaagatcag gtccgagctg cagaaggcct gggacgaggt gaggaccccg aagaggaacg   1620
tgcagtcctg cgtgctggac aaggacctgt ccaagaggtt cgccggcagg accctgaagt   1680
acgccggcat cgacctgggc tactccaacc cgtacaccgt gtcctactac aacgtggtgg   1740
gcaccgagga gggcatccag atcaaggaga ccggcaacga gatcgtgtcc accgtgttca   1800
acgagcagta catccagctg aagggcaaca tctaccagct gatcaacatc atcagggcct   1860
ccaggaggta cctgcaggag tccggcgagc tgaagctgtc caaggacgac atcaagtcct   1920
tcgaccagct gatggagctg ctgccgtccg agcagaggat caccatcgac cagttcatca   1980
aggacatcaa gaaggccaag caggagggca agctgatcag ggacatcaag ggcaagctgc   2040
cggtggaggg caagaagaag gagtactggg tgatctccaa cctgatgtac gtgatcaccc   2100
agaccatgaa cggcatcagg ggcaacaggg actccaacaa ccacctgacc gagaagaaga   2160
actggctgtc cgccccgccg ctgatcgagc tgatcgacgc ctactacaac ctgaagaaga   2220
ccttcaacga ctccggcgac ggcatcaaga tgctgccgaa ggaccacgtg tacgccgagg   2280
gcgagaagca gaggtgcacc ctgagggagg agaacttctg caagggcatc ctggagtgga   2340
gggacaacgt gaaggactac ttcatcaaga agctgttctc ccagatcgcc cacaggtgct   2400
acgagctggg catcggcatc gtggccatgg agaacctgga catcatgggc tcctccaaga   2460
acaccaagca gtccaacagg atgttcaaca tctggccgag gggccagatg aagaagtccg   2520
ccgaggacgc cttctcctac atgggcatcc tgatccagta cgtggacgag aacggcacct   2580
ccaggcacga cgccgactcc ggcatctacg gctgcaggga cggcgccaac ctgtggctgc   2640
cgaacaagaa gctgcacgcc gacgtgaacg cctccaggat gatcgccctg aggggcctga   2700
cccaccacac caacctgtac tgcaggtccc tgaccgagat cgagaacggc aagtacgtga   2760
acacctacga gctgttcgac accaccaaga acgaccagtc cggcgccgcc aagaggctga   2820
ggggcgccga gaccctgctg cacggctact ccgccaccgt gtaccagatc cacaccacca   2880
acaccggcgc cggcgtggcc ctgctgccgg acctgaccgc caccgacgtg atcaagaaca   2940
agaagatcac cgccaccaag gagaacaccg ccaagtacta caagctggac aacaccaaca   3000
```

cctactaccc gtggtccgtg tgcgagaagc tgcacaagaa ctggaagctg tcctgacaaa 3060
taaaacgaaa ggctcagtcg aaagactggg cctttcgttt tatctgttgt ttgtcggtga 3120
acgctctcct gagtaggaca aatttgacag ctagctcagt cctaggtata atgctagcgg 3180
tgatatagta actggtctgt tccagcactt caccggtata acaacttcga cgagctctac 3240
aagaaggcca tcctgacgga tggccttt 3268

<210> SEQ ID NO 103
<211> LENGTH: 35
<212> TYPE: DNA
<213> ORGANISM: artificial sequence
<220> FEATURE:
<223> OTHER INFORMATION: PAM library sequence
<220> FEATURE:
<221> NAME/KEY: misc_feature
<222> LOCATION: (1)..(8)
<223> OTHER INFORMATION: n = a or t or c or g

<400> SEQUENCE: 103
nnnnnnnngg tataacaact tcgacgagct ctaca 35

<210> SEQ ID NO 104
<211> LENGTH: 27
<212> TYPE: RNA
<213> ORGANISM: artificial sequence
<220> FEATURE:
<223> OTHER INFORMATION: Pre-crRNA processing and PAM consumption guide RNA

<400> SEQUENCE: 104
gguauaacaa cuucgacgag cucuaca 27

<210> SEQ ID NO 105
<211> LENGTH: 24
<212> TYPE: RNA
<213> ORGANISM: artificial sequence
<220> FEATURE:
<223> OTHER INFORMATION: Cas12j.19 guide RNA

<400> SEQUENCE: 105
cuuccaucag agaaccucac ugcg 24

<210> SEQ ID NO 106
<211> LENGTH: 1020
<212> TYPE: DNA
<213> ORGANISM: artificial sequence
<220> FEATURE:
<223> OTHER INFORMATION: targeted double-stranded DNA sequence

<400> SEQUENCE: 106
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt accccctctt 420
cgctattacg ccagctggcg aaagggggat gtgctgcaag gcgattaagt tgggtaacgc 480
cagggttttc ccagtcacga cgttgtaaaa cgacggccag tgaattcgag ctcggtacca 540

```
tcgtattagg tatagcaagc cgtctcgcag tgaggttctc tgatggaagc atatcgtagc    600

ttggcgtaat catggtcata gctgtttcct gtgtgaaatt gttatccgct cacaattcca    660

cacaacatac gagccggaag cataaagtgt aaagcctggg gtgcctaatg agtgagctaa    720

ctggggatcc tctagagtcg acctgcaggc atgcaagctt ggcgtaatca tggtcatagc    780

tgtttcctgt gtgaaattgt tatccgctca caattccaca caacatacga gccggaagca    840

taaagtgtaa agcctggggt gcctaatgag tgagctaact cacattaatt gcgttgcgct    900

cactgcccgc tttccagtcg ggaaacctgt cgtgccagct gcattaatga atcggccaac    960

gcgcggggag aggcggtttg cgtattgggc gctcttccgc ttcctcgctc actgactcgc   1020


<210> SEQ ID NO 107
<211> LENGTH: 882
<212> TYPE: PRT
<213> ORGANISM: artificial sequence
<220> FEATURE:
<223> OTHER INFORMATION: Cas12j.1 amino acid sequence

<400> SEQUENCE: 107

Met Leu Tyr Thr Met Asn Val Lys Thr Ile Lys Leu Lys Val Asp Ala
1               5                   10                  15

Thr Lys Glu Val Glu Ser Arg Leu Thr Lys Met Leu Leu Val His Asn
            20                  25                  30

Asn Ile Gly Arg Glu Ile Ile Asn Phe Leu Ile Leu Cys Ser Gly Asn
        35                  40                  45

Asp Asn Ile Arg Lys Thr Lys Phe Asp Glu Phe Gly Asn Ser Tyr Asp
    50                  55                  60

Glu Phe Cys Asn Leu Lys Leu Asp Gln Phe Asn Leu Tyr Asp Arg Leu
65                  70                  75                  80

Thr Glu Ile His Asp Glu Val Thr Leu Glu Asp Phe Gln Lys Thr Leu
                85                  90                  95

Asn Asp Ile Tyr Asp Leu Val Leu Asn Ser Lys Ser Phe Ser Asn Val
            100                 105                 110

Ser Ser Thr Ile Phe Asn Lys Asn Lys Lys Val Asn Phe Asp Glu Thr
        115                 120                 125

Lys Lys Gly Asp Leu Ser Arg Lys Cys Leu Met Asn Ala Arg Asp Trp
    130                 135                 140

Gly Val Leu Pro Leu Ile Ser Val Asp Asp Asp Ile Val Thr Cys Gly
145                 150                 155                 160

Thr Leu Lys Gly Ile Leu Ser Glu Cys Gln Ser Arg Ile Leu Ser Trp
                165                 170                 175

Asn Glu Cys Asn Leu Ser Thr Lys Glu Thr Tyr Ser Glu Lys Lys Ser
            180                 185                 190

Glu Tyr Gln Ser Ile Leu Asp Asp Ser Met Thr Lys Asp Ala Asp Val
        195                 200                 205

Thr Thr Ala Met Ile Gln Phe Met Asp Asp Val Ser Asn Val Tyr Gly
    210                 215                 220

Ser Asn Asn Glu Asn Gln Leu Lys Trp Phe Asn Asn Arg Phe Leu Thr
225                 230                 235                 240

Tyr Val Arg Asn Lys Ile Arg Pro Phe Leu Leu Thr Asn Ser Pro Ile
                245                 250                 255

Asp Asn Phe Glu Gln Ser Asp Thr Ser Tyr Asn Cys Ser Ile Glu Ile
            260                 265                 270

Val Arg Ile Leu Ser Lys Tyr Glu Ile Leu Trp Lys Asp Glu Val Ser
        275                 280                 285
```

-continued

```
Val Asn Arg Tyr Lys Lys Thr Cys Asp Asp Gly Ile Asn Ile Glu Lys
    290                 295                 300

Tyr Arg Tyr Leu Val His Ala Lys Ser Asp Phe Leu Arg Tyr Lys Glu
305                 310                 315                 320

Thr Ala Ser Phe Lys Glu Ile His Ala Val Lys Ser Pro Ile Ser Leu
                325                 330                 335

Cys Phe Gly Asn Asn Tyr Gln Pro Phe Ser Leu Ser Asp Val Gly Asp
            340                 345                 350

Arg His Asn Ile Asn Phe Gly Tyr Lys Phe Gly Lys Leu Gly Lys Gln
        355                 360                 365

Arg Lys Glu Cys Ser Phe Asn Leu Asn Tyr Arg Arg Lys Lys Val Lys
    370                 375                 380

Tyr Ala Asn Thr Pro Val Arg Ser Asp Glu Asn Lys Cys Tyr Leu Asp
385                 390                 395                 400

Asn Leu Glu Ile Glu Asp Ala Lys Asn Gly Ser Tyr Lys Leu Ser Tyr
                405                 410                 415

Met Val Asn Lys Lys Tyr Lys Arg Glu Ser Phe Ile Lys Glu Pro Lys
            420                 425                 430

Met Lys Met Tyr Asn Gly Lys Leu Tyr Met Tyr Phe Pro Met Ser Asn
        435                 440                 445

Glu Phe Glu Glu Asp Arg Asp Ser Phe Ala Leu Leu Thr Tyr Phe Ser
    450                 455                 460

Arg Ser Ser Asn Ser Lys Ser Gln Ile Asp Glu Ala Ser Asn Ile Leu
465                 470                 475                 480

Gln Asn Arg Lys Ile Arg Val Cys Gly Val Asp Leu Gly Ile Asn Pro
                485                 490                 495

Thr Phe Ala Leu Ser Val Leu Glu Tyr Ser Asp Asn Lys Ile Thr Asp
            500                 505                 510

Thr Asn Ile Gly Met Lys His Glu Gly Ser Tyr Asn Asn Phe Ser Glu
        515                 520                 525

Ile Arg Lys Gln Ile Asn Asp Val Thr Asp Met Ile Ser Tyr Leu Lys
    530                 535                 540

Ser Lys Tyr Asp Asn Cys Glu Lys Asp Tyr Ser Ser Lys Ile Asp Asp
545                 550                 555                 560

His Ile Lys Ser Arg Leu Asn Glu Glu Ile Ser Asn Phe Cys Asp Leu
                565                 570                 575

Val Ser Tyr Lys Arg Asn Lys Asn Thr Ile Ile Arg Lys Glu Ile Lys
            580                 585                 590

Asn Val Glu Lys Glu Ile Asn Lys Ile Lys Asn Cys Arg Arg His Thr
        595                 600                 605

Leu Lys Lys Asp Leu Thr Glu Asn Phe Gly Trp Val Ser Ala Leu Asn
    610                 615                 620

Glu Phe Ile Ser Leu Lys His Ser Phe Asn Asp Met Gly Glu Ser Phe
625                 630                 635                 640

Asp Ser Lys Thr Asn Pro Ser Tyr Ser Tyr Phe Glu Lys Trp Lys Arg
                645                 650                 655

Tyr Ile Asp Asn Ile Lys Asp Asp Ser Leu Lys Thr Val Ser Arg Glu
            660                 665                 670

Ile Leu Asn Phe Cys Ile Glu Asn Ser Val Asp Phe Ile Ala Leu Glu
        675                 680                 685

Asp Leu Gln Thr Phe Ala Pro Ser Asp Asp Arg Thr Lys Ser His Asn
    690                 695                 700
```

Lys Leu Thr Gln Leu Trp Cys Phe Gly Lys Leu Lys Lys Cys Leu Glu
705 710 715 720

Asp Ile Ala Ser Met Tyr Gly Ile His Val Tyr Ser Ser Thr Asp Pro
725 730 735

Arg Asn Thr Ser Asp Thr His Phe Glu Ser Lys Asn Phe Gly Tyr Arg
740 745 750

Asp Glu Ser Asn Lys His Asn Leu Trp Val Asn Val Asp Gly Glu Tyr
755 760 765

Thr Val Val Asp Ser Asp Ile Asn Ala Ser Lys Asn Ile Ala Asn Arg
770 775 780

Phe Leu Thr His His Lys Asp Leu Lys Gln Leu Pro Met Ile Gly Asp
785 790 795 800

Gly Thr Leu Phe Lys Ile Asp Ser Ser Ser Lys Arg Asn Lys Ser Phe
805 810 815

Ala Val Lys Leu Asn Ile His Lys Asn Val Tyr Glu Leu Ile Asp Gly
820 825 830

Glu Phe Val Lys Ser Asn Lys Lys Pro Asn Gly Thr Ser Arg Lys Gln
835 840 845

Thr Ala Tyr Ile His Gly Asp Met Phe Ile Asp Ser Ile Ser His Lys
850 855 860

Asn Lys Lys Met Phe Leu Arg Glu Asn Leu Ile Arg Asn Gly Phe Ile
865 870 875 880

Ser Lys

<210> SEQ ID NO 108
<211> LENGTH: 935
<212> TYPE: PRT
<213> ORGANISM: artificial sequence
<220> FEATURE:
<223> OTHER INFORMATION: Cas12j.2 amino acid sequence

<400> SEQUENCE: 108

Met Asn Lys Thr Asp Thr Gln Asn Asn Glu Gln Ile Asn Lys Pro Thr
1 5 10 15

Gln Leu Leu Asn Asn Lys Asp Ile Glu Leu Thr Val Lys Thr Val Lys
20 25 30

Ser Ala Thr Val Lys Val Asp Asn Asn Ser Lys Lys Glu Leu Phe Gly
35 40 45

Leu Phe Asn Tyr Phe Thr Ser Val Ala Ser Gly Ile Lys Asp Lys Val
50 55 60

Tyr Asn Leu Gln Ser Asp Glu Lys Thr Ala Pro Ile Phe Asn Asp Tyr
65 70 75 80

Val Lys Gln Pro Gln Arg Gly Arg Ser Ala Ala Thr Thr Leu Phe Thr
85 90 95

Lys Leu Asp Ala Glu Lys Thr Tyr Thr Ser Gln His Ser Phe Pro Gly
100 105 110

Lys Trp Arg Asp Ser Gly Ile Phe Pro Leu Tyr Asn Lys Glu Ser Glu
115 120 125

Lys Tyr Asp Leu Ser Thr His Gly Tyr His Tyr Ser Ala Asn Ala Glu
130 135 140

Ile His Thr Gln Leu Asp Ser His Asp Glu Cys Asn Lys Glu Cys Glu
145 150 155 160

Lys Glu Tyr Ala Ala Leu Arg Asp Glu Val Asn Asn Tyr Lys Tyr Glu
165 170 175

Phe Thr Leu Gln Phe Lys Ala Glu Asn Ala Glu Lys Phe Tyr Asn Phe

```
            180                 185                 190

Val Glu Lys Leu Thr Leu Met Gly Trp Arg Tyr Asp Ala Thr Phe Arg
        195                 200                 205

Ser Phe Phe Glu Leu His Met His Pro Lys Leu Lys Thr Gly Glu Thr
    210                 215                 220

Thr Tyr Arg Ala Thr Tyr Lys Leu Pro Ser Gly Lys Ser Lys Arg Tyr
225                 230                 235                 240

Ser Phe Phe Arg Asp Asp Ile Ala Asp Glu Ile Ala Lys Asn Pro Glu
                245                 250                 255

Phe Trp Pro Met Leu Glu Ser Ser Asn Ala Ile Ser Trp Ile Asn Ser
            260                 265                 270

Asn Asn Leu Leu Ser Arg Lys Lys Asp Lys Ala Asn Tyr Ser Ser Thr
        275                 280                 285

Ser Leu Ile Lys Ser Gln Ile Arg Leu Tyr Leu Gly Asn Asn Gly Val
    290                 295                 300

Pro Phe Thr Ala Arg Glu His Asp Gly Arg Ile Tyr Phe Ser Phe Arg
305                 310                 315                 320

Leu Pro Ala Ile Asn Gly Glu Lys Gly Arg Met Val Glu Ile Pro Cys
                325                 330                 335

Ser Tyr Lys Lys Val Phe Asn Gly Lys Ala Arg Lys Ser Cys Tyr Leu
            340                 345                 350

Gly Gly Leu Thr Ile Glu Lys Thr Asp Ala Gly Lys His Ile Phe Lys
        355                 360                 365

Tyr Ser Val Asn Asn Lys Lys Pro Gln Val Ala Glu Leu Asn Glu Cys
    370                 375                 380

Phe Leu Arg Leu Val Val Arg Asn Arg Glu Tyr Phe Asn Asn Val Val
385                 390                 395                 400

Ala Gly Lys Ile Thr Asp Ile Asn Thr Asp His Phe Asp Phe Tyr Val
                405                 410                 415

Asp Leu Pro Leu Asn Val Lys Glu Asp Pro Ile His Asp Leu Ser Ser
            420                 425                 430

Thr Glu Val Phe Gly Lys Asn Gly Leu Arg Ser Tyr Tyr Ser Ser Ala
        435                 440                 445

Tyr Pro Glu Ile Lys Asn Leu Gly Ser Gln Ile Glu Thr Gly Lys Asn
    450                 455                 460

Leu Thr Cys Pro Ile Thr Lys Thr His Asn Ile Met Gly Ile Asp Leu
465                 470                 475                 480

Gly Gln Arg Asn Pro Phe Ala Tyr Cys Ile Lys Asp Asn Thr Gly Lys
                485                 490                 495

Leu Ile Ala Gln Gly His Met Asp Gly Ser Lys Asn Glu Thr Tyr Lys
            500                 505                 510

Lys Tyr Ile Asn Phe Gly Lys Glu Ser Thr Ser Val Ser His Leu Ile
        515                 520                 525

Lys Glu Thr Arg Ser Tyr Leu His Gly Asp Pro Glu Ala Ile Ser Lys
    530                 535                 540

Glu Leu Tyr Asn Glu Val Ala Gly Phe Cys Asn Asn Pro Val Ser Tyr
545                 550                 555                 560

Glu Glu Tyr Leu Lys Tyr Leu Asp Ser Lys Lys Phe Leu Ile Asn Lys
                565                 570                 575

Glu Asp Leu Ser Lys Asn Ala Met His Leu Leu Arg Gln Lys Asp His
            580                 585                 590

Asn Trp Ile Gly Arg Asp Trp Leu Trp Tyr Ile Ser Lys Gln Tyr Lys
        595                 600                 605
```

```
Lys His Asn Glu Asn Arg Met Gln Asp Ala Asp Trp Arg Gln Thr Leu
    610                 615                 620

Tyr Trp Ile Asp Ser Leu Tyr Arg Tyr Ile Asp Val Met Lys Ser Phe
625                 630                 635                 640

His Asn Phe Gly Ser Phe Tyr Asp Lys Asn Leu Lys Lys Lys Val Asn
                645                 650                 655

Gly Thr Val Val Gly Phe Cys Lys Thr Val His Asp Gln Ile Asn Asn
            660                 665                 670

Asn Asn Asp Asp Met Phe Lys Lys Phe Thr Asn Glu Leu Met Ser Val
        675                 680                 685

Ile Arg Glu His Lys Val Ser Val Val Ala Leu Glu Lys Met Asp Ser
    690                 695                 700

Met Leu Gly Asp Lys Ser Arg His Thr Phe Glu Asn Arg Asn Tyr Asn
705                 710                 715                 720

Leu Trp Pro Val Gly Gln Leu Lys Thr Phe Met Glu Gly Lys Leu Glu
                725                 730                 735

Ser Phe Asn Val Ala Leu Ile Glu Ile Asp Glu Arg Asn Thr Ser Gln
            740                 745                 750

Val Cys Lys Glu Asn Trp Ser Tyr Arg Glu Ala Asp Asp Leu Tyr Tyr
        755                 760                 765

Val Thr Asp Gly Glu Ser His Lys Val His Ala Asp Glu Asn Ala Ala
    770                 775                 780

Asn Asn Ile Val Asp Arg Cys Ile Ser Arg His Thr Asn Met Phe Ser
785                 790                 795                 800

Leu His Met Val Asn Pro Lys Asp Asp Tyr Tyr Val Pro Thr Cys Ile
                805                 810                 815

Trp Asp Thr Thr Glu Glu Ser Gly Lys Arg Val Arg Gly Phe Leu Thr
            820                 825                 830

Lys Leu Tyr Lys Asn Ser Asp Val Val Phe Thr Lys Lys Gly Asp Lys
        835                 840                 845

Leu Val Lys Ser Lys Thr Ser Val Lys Glu Leu Lys Lys Leu Val Gly
    850                 855                 860

Lys Thr Lys Glu Lys Arg Gly Gln Tyr Trp Tyr Arg Phe Glu Gly Lys
865                 870                 875                 880

Ser Trp Ile Asn Glu Ala Asp Arg Asp Thr Ile Ile Leu Asn Ala Lys
                885                 890                 895

Lys Ile Ser Arg Glu Arg Asp Asn Gly Glu Gln Ser Thr Asp Thr Arg
            900                 905                 910

Ser Gln Asn Val Thr Val Ser Val Leu Asp Val Cys Glu Thr Ala Glu
        915                 920                 925

Lys Lys Lys Leu Val Leu Val
    930                 935
```

<210> SEQ ID NO 109
<211> LENGTH: 50
<212> TYPE: DNA
<213> ORGANISM: Artificial Sequence
<220> FEATURE:
<223> OTHER INFORMATION: Cas12j.4 cleavage site

<400> SEQUENCE: 109

```
gctcggtacc atcgtattag gtatagcaag ccgtctcgca gtgaggttct                50
```

<210> SEQ ID NO 110
<211> LENGTH: 50

<212> TYPE: DNA
<213> ORGANISM: Artificial Sequence
<220> FEATURE:
<223> OTHER INFORMATION: Cas12j.4 cleavage site

<400> SEQUENCE: 110
agaacctcac tgcgagacgg cttgctatac ctaatacgat ggtaccgagc 50

<210> SEQ ID NO 111
<211> LENGTH: 17
<212> TYPE: DNA
<213> ORGANISM: Artificial Sequence
<220> FEATURE:
<223> OTHER INFORMATION: Cas12j.4 forward sequence
<220> FEATURE:
<221> NAME/KEY: misc_feature
<222> LOCATION: (17)..(17)
<223> OTHER INFORMATION: n is a, c, g, or t

<400> SEQUENCE: 111
aagccgtctc gcagtgn 17

<210> SEQ ID NO 112
<211> LENGTH: 17
<212> TYPE: DNA
<213> ORGANISM: Artificial Sequence
<220> FEATURE:
<223> OTHER INFORMATION: Cas12j.4 reverse sequence

<400> SEQUENCE: 112
gcagtgaggt tctctga 17

<210> SEQ ID NO 113
<211> LENGTH: 50
<212> TYPE: DNA
<213> ORGANISM: Artificial Sequence
<220> FEATURE:
<223> OTHER INFORMATION: Cas12j.22 cleavage site

<400> SEQUENCE: 113
ggtaccatcg tattaggtat agcaagccgt ctcgcagtga ggttctctga 50

<210> SEQ ID NO 114
<211> LENGTH: 50
<212> TYPE: DNA
<213> ORGANISM: Artificial Sequence
<220> FEATURE:
<223> OTHER INFORMATION: Cas12j.22 cleavage site

<400> SEQUENCE: 114
tcagagaacc tcactgcgag acggcttgct atacctaata cgatggtacc 50

<210> SEQ ID NO 115
<211> LENGTH: 17
<212> TYPE: DNA
<213> ORGANISM: Artificial Sequence
<220> FEATURE:
<223> OTHER INFORMATION: Cas12j.22 forward sequence

<400> SEQUENCE: 115
aagccgtctc gcagtga 17

<210> SEQ ID NO 116
<211> LENGTH: 17
<212> TYPE: DNA
<213> ORGANISM: Artificial Sequence
<220> FEATURE:

<223> OTHER INFORMATION: Cas12j.22 reverse sequence

<400> SEQUENCE: 116
gcagtgaggt tctctga 17

<210> SEQ ID NO 117
<211> LENGTH: 55
<212> TYPE: DNA
<213> ORGANISM: Artificial Sequence
<220> FEATURE:
<223> OTHER INFORMATION: Cas12j.19 cleavage site

<400> SEQUENCE: 117
caagctacga tatgcttcca tcagagaacc tcactgcgag acggcttgct atacc 55

<210> SEQ ID NO 118
<211> LENGTH: 55
<212> TYPE: DNA
<213> ORGANISM: Artificial Sequence
<220> FEATURE:
<223> OTHER INFORMATION: Cas12j.19 cleavage site

<400> SEQUENCE: 118
ggtatagcaa gccgtctcgc agtgaggttc tctgatggaa gcatatcgta gcttg 55

<210> SEQ ID NO 119
<211> LENGTH: 17
<212> TYPE: DNA
<213> ORGANISM: Artificial Sequence
<220> FEATURE:
<223> OTHER INFORMATION: Cas12j.19 forward sequence

<400> SEQUENCE: 119
gagaaactca ctgcgag 17

<210> SEQ ID NO 120
<211> LENGTH: 17
<212> TYPE: DNA
<213> ORGANISM: Artificial Sequence
<220> FEATURE:
<223> OTHER INFORMATION: Cas12j.19 reverse sequence
<220> FEATURE:
<221> NAME/KEY: misc_feature
<222> LOCATION: (1)..(1)
<223> OTHER INFORMATION: n is a, c, g, or t

<400> SEQUENCE: 120
nacggcttgg ctatacc 17

<210> SEQ ID NO 121
<211> LENGTH: 28
<212> TYPE: RNA
<213> ORGANISM: Artificial Sequence
<220> FEATURE:
<223> OTHER INFORMATION: CRISPR/Cas12j.19 system spacer

<400> SEQUENCE: 121
cuuccaucag agaaccucac ugcgagac 28

<210> SEQ ID NO 122
<211> LENGTH: 26
<212> TYPE: RNA
<213> ORGANISM: Artificial Sequence
<220> FEATURE:
<223> OTHER INFORMATION: CRISPR/Cas12j.19 system spacer

<400> SEQUENCE: 122
cuuccaucag agaaccucac ugcgag 26

<210> SEQ ID NO 123
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 123
cuuccaucag agaaccucac ugcg 24

<210> SEQ ID NO 124
<211> LENGTH: 22
<212> TYPE: RNA
<213> ORGANISM: Artificial Sequence
<220> FEATURE:
<223> OTHER INFORMATION: CRISPR/Cas12j.19 system spacer

<400> SEQUENCE: 124
cuuccaucag agaaccucac ug 22

<210> SEQ ID NO 125
<211> LENGTH: 20
<212> TYPE: RNA
<213> ORGANISM: Artificial Sequence
<220> FEATURE:
<223> OTHER INFORMATION: CRISPR/Cas12j.19 system spacer

<400> SEQUENCE: 125
cuuccaucag agaaccucac 20

<210> SEQ ID NO 126
<211> LENGTH: 18
<212> TYPE: RNA
<213> ORGANISM: Artificial Sequence
<220> FEATURE:
<223> OTHER INFORMATION: CRISPR/Cas12j.19 system spacer

<400> SEQUENCE: 126
cuuccaucag agaaccuc 18

<210> SEQ ID NO 127
<211> LENGTH: 16
<212> TYPE: RNA
<213> ORGANISM: Artificial Sequence
<220> FEATURE:
<223> OTHER INFORMATION: CRISPR/Cas12j.19 system spacer

<400> SEQUENCE: 127
cuuccaucag agaacc 16

<210> SEQ ID NO 128
<211> LENGTH: 14
<212> TYPE: RNA
<213> ORGANISM: Artificial Sequence
<220> FEATURE:
<223> OTHER INFORMATION: CRISPR/Cas12j.19 system spacer

<400> SEQUENCE: 128
cuuccaucag agaa 14

<210> SEQ ID NO 129
<211> LENGTH: 36
<212> TYPE: RNA

<213> ORGANISM: Artificial Sequence
<220> FEATURE:
<223> OTHER INFORMATION: CRISPR/Cas12j.19 system repeat

<400> SEQUENCE: 129
gugcugcugu cucccagacg ggaggcagaa cugcac 36

<210> SEQ ID NO 130
<211> LENGTH: 34
<212> TYPE: RNA
<213> ORGANISM: Artificial Sequence
<220> FEATURE:
<223> OTHER INFORMATION: CRISPR/Cas12j.19 system repeat

<400> SEQUENCE: 130
gcugcugucu cccagacggg aggcagaacu gcac 34

<210> SEQ ID NO 131
<211> LENGTH: 32
<212> TYPE: RNA
<213> ORGANISM: Artificial Sequence
<220> FEATURE:
<223> OTHER INFORMATION: CRISPR/Cas12j.19 system repeat

<400> SEQUENCE: 131
ugcugucucc cagacgggag gcagaacugc ac 32

<210> SEQ ID NO 132
<211> LENGTH: 30
<212> TYPE: RNA
<213> ORGANISM: Artificial Sequence
<220> FEATURE:
<223> OTHER INFORMATION: CRISPR/Cas12j.19 system repeat

<400> SEQUENCE: 132
cugucuccca gacgggaggc agaacugcac 30

<210> SEQ ID NO 133
<211> LENGTH: 28
<212> TYPE: RNA
<213> ORGANISM: Artificial Sequence
<220> FEATURE:
<223> OTHER INFORMATION: CRISPR/Cas12j.19 system repeat

<400> SEQUENCE: 133
gucucccaga cgggaggcag aacugcac 28

<210> SEQ ID NO 134
<211> LENGTH: 26
<212> TYPE: RNA
<213> ORGANISM: Artificial Sequence
<220> FEATURE:
<223> OTHER INFORMATION: CRISPR/Cas12j.19 system repeat

<400> SEQUENCE: 134
cucccagacg ggaggcagaa cugcac 26

<210> SEQ ID NO 135
<211> LENGTH: 24
<212> TYPE: RNA
<213> ORGANISM: Artificial Sequence
<220> FEATURE:
<223> OTHER INFORMATION: CRISPR/Cas12j.19 system repeat

<400> SEQUENCE: 135
cccagacggg aggcagaacu gcac 24

<210> SEQ ID NO 136
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 136
auuccaucag agaaccucac ugcg 24

<210> SEQ ID NO 137
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 137
cuaccaucag agaaccucac ugcg 24

<210> SEQ ID NO 138
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 138
cuucaaucag agaaccucac ugcg 24

<210> SEQ ID NO 139
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 139
cuuccagcag agaaccucac ugcg 24

<210> SEQ ID NO 140
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 140
cuuccaucgg agaaccucac ugcg 24

<210> SEQ ID NO 141
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 141
cuuccaucag ugaaccucac ugcg 24

<210> SEQ ID NO 142
<211> LENGTH: 24
<212> TYPE: RNA
<213> ORGANISM: Artificial Sequence
<220> FEATURE:

```
<223> OTHER INFORMATION: CRISPR/Cas12j.19 system spacer

<400> SEQUENCE: 142

cuuccaucag aggaccucac ugcg                                             24


<210> SEQ ID NO 143
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 143

cuuccaucag agaaucucac ugcg                                             24


<210> SEQ ID NO 144
<211> LENGTH: 24
<212> TYPE: RNA
<213> ORGANISM: Artificial Sequence
<220> FEATURE:
<223> OTHER INFORMATION: CRISPR/Cas12j.19 system spacer

<400> SEQUENCE: 144

cuuccaucag agaaccacac ugcg                                             24
```